(12) United States Patent
Seifermann et al.

(10) Patent No.: US 11,919,882 B2
(45) Date of Patent: *Mar. 5, 2024

(54) ORGANIC MOLECULES FOR USE IN ORGANIC OPTOELECTRONIC DEVICES

(71) Applicant: SAMSUNG DISPLAY CO., LTD., Yongin-si (KR)

(72) Inventors: Stefan Seifermann, Bühl (DE);
Michael Danz, Eggenstein-Leopoldshafen (DE);
Georgios Liaptsis, Mannheim (DE)

(73) Assignee: Samsung Display Co., Ltd., Yongin-si (KR)

( * ) Notice: Subject to any disclaimer, the term of this patent is extended or adjusted under 35 U.S.C. 154(b) by 889 days.

This patent is subject to a terminal disclaimer.

(21) Appl. No.: 16/322,760

(22) PCT Filed: Aug. 1, 2017

(86) PCT No.: PCT/EP2017/069434
§ 371 (c)(1),
(2) Date: Feb. 1, 2019

(87) PCT Pub. No.: WO2018/024725
PCT Pub. Date: Feb. 8, 2018

(65) Prior Publication Data
US 2021/0171501 A1 Jun. 10, 2021

(30) Foreign Application Priority Data

Aug. 4, 2016 (EP) .................................. 16182886
Sep. 20, 2016 (EP) .................................. 16189677
Dec. 20, 2016 (EP) .................................. 16205432

(51) Int. Cl.
*C07D 403/04* (2006.01)
*H10K 85/60* (2023.01)
(Continued)

(52) U.S. Cl.
CPC ......... *C07D 403/04* (2013.01); *H10K 85/621* (2023.02); *H10K 85/654* (2023.02);
(Continued)

(58) Field of Classification Search
CPC .............................................. H01L 51/50–56
See application file for complete search history.

(56) References Cited

U.S. PATENT DOCUMENTS 10,651,394 B2 * 5/2020 Danz .................. H01L 51/0058
2017/0263868 A1    9/2017 Tanabe et al.
(Continued)

FOREIGN PATENT DOCUMENTS

CN      104379572 A    2/2015
WO      2016/046034 A1 3/2016
(Continued)

OTHER PUBLICATIONS

STN structure search for U.S. Appl. No. 16/322,760. All Pages, 2023. (Year: 2023).*

Primary Examiner — Daniel P Malley, Jr.
(74) Attorney, Agent, or Firm — Lewis Roca Rothgerber Christie LLP

(57) ABSTRACT

An organic molecule is disclosed having a structure with:
a first chemical unit having a structure of formula A1

Formula A1

(Continued)

at least one second chemical unit having a structure of formula D

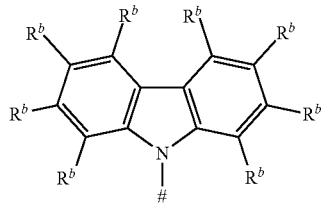

Formula D1 with

=point of attachment of the second chemical unit to the first chemical unit;

$R^N$ is a structure of the formula N1

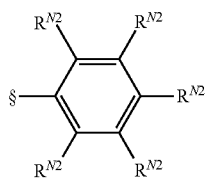

Formula N1 with

§ =point of attachment of the chemical unit of formula N1 to the first chemical unit.

20 Claims, 3 Drawing Sheets

(51) Int. Cl.
    *H10K 50/11*     (2023.01)
    *H10K 50/15*     (2023.01)
    *H10K 50/16*     (2023.01)
    *H10K 50/17*     (2023.01)
    *H10K 101/10*     (2023.01)

(52) U.S. Cl.
    CPC ......... H10K 85/6572 (2023.02); *H10K 50/11* (2023.02); *H10K 50/15* (2023.02); *H10K 50/16* (2023.02); *H10K 50/171* (2023.02); *H10K 2101/10* (2023.02)

(56) References Cited

U.S. PATENT DOCUMENTS

2019/0334097 A1* 10/2019 Sugawara ................. G09F 9/30
2021/0171501 A1* 6/2021 Seifermann .......... C07D 403/04
2021/0184134 A1* 6/2021 Seifermann ......... H01L 51/0071

FOREIGN PATENT DOCUMENTS

WO           2016042070 A1     3/2016
WO   PCT/EP2017/069431     8/2017

\* cited by examiner

ORGANIC MOLECULES FOR USE IN ORGANIC OPTOELECTRONIC DEVICES

CROSS-REFERENCE TO RELATED APPLICATIONS

This application claims priority under 35 U.S.C. § 371 to International Application No. PCDEP2017/069434 filed Aug. 1, 2017, which claims priority to European Patent Application No. 161828868.6 filed Aug. 4, 2016 and European Patent Application No. 16189677.4 filed Sep. 20, 2016, and European Patent Application No. 16205432.4 filed Dec. 20, 2016, the disclosures of which are incorporated by reference herein in their entireties.

FIELD OF INVENTION

The invention relates to purely organic molecules and to the use thereof in organic light-emitting diodes (OLEDs) and in other organic optoelectronic devices.

BACKGROUND

It is a feature of organic optoelectronic devices that either electrical energy is converted to photons (organic light-emitting diodes, OLEDs, or light-emitting electrochemical cells, LEECs) or the reverse process proceeds (organic photovoltaics, OPVs). It is important here that these processes proceed with maximum efficiency. For the field of LEDs, therefore, it is ideally necessary to use materials having maximum photoluminescent quantum yield. Limited efficiencies of OLED materials can be improved through use of efficient materials that exhibit thermally activated delayed fluorescence (TADF), since, by contrast with purely fluorescent materials, it is possible to utilize up to 100% of the excitons rather than 25% of the excitons formed in an OLED. It is also possible here to convert the triplet excitons that arise to singlet excitons, from which state photons can then be emitted. A prerequisite for such thermal repopulation is a small energy gap between the lowest excited singlet level (S1) and triplet level (T1). This can be achieved, for example, through use of copper(I) complexes (in this regard, see, for example, H. Yersin, U. Monkowius, T. Fischer, T. Hofbeck, WO 2010/149748 A1) or else by means of purely organic materials (in this regard, see, for example, Q. Zhang et al., J. Am. Chem. Soc. 2012, 134, 14706, WO 2013161437 A1).

There is still a great demand for novel materials, especially for deep blue TADF-OLEDs. Existing blue TADF materials often exhibit long exciton lifetimes, which are bad for efficient and long-lived OLEDs. As well as the properties of the materials that have been mentioned, obtainability is likewise of relevance for commercialization. This includes the availability of synthesis units, and also the complexity for the actual synthesis of the functional material, including the purification thereof.

BRIEF DESCRIPTION OF THE DRAWINGS

Exemplary embodiments of the present invention will be described below in more detail, with reference to the accompanying drawings, of which.

DETAILED DESCRIPTION OF EXEMPLARY EMBODIMENTS OF THE INVENTION

Figure 1:
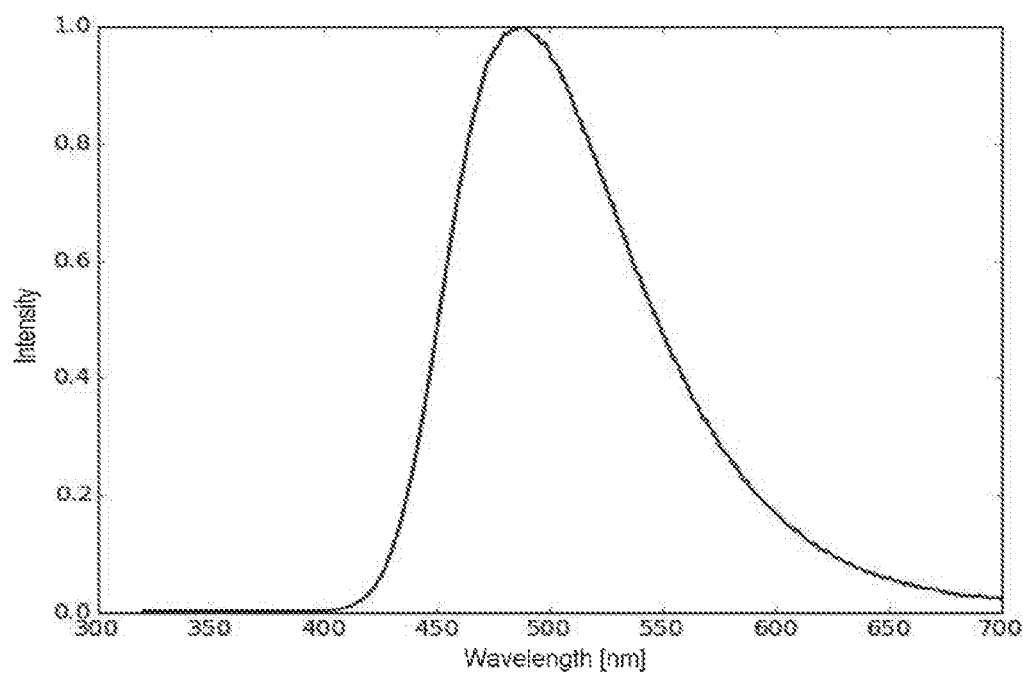
FIG. 1 is an emission spectrum of Example 1 (10% in PMMA).

Exemplary embodiments of the invention will now be discussed in further detail. This invention may, however, be embodied in many different forms and should not be construed as limited to the embodiments set forth herein.

The problem addressed by the present invention was that of providing molecules suitable for use as emitter materials in OLEDs.

Surprisingly, organic molecules having high quantum yields and short exciton lifetimes have been found.

The invention relates, in a first aspect; to organic molecules comprising a first chemical unit comprising or consisting of a structure of the formula A1

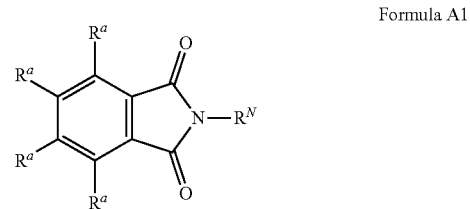

Formula A1 and
at least one second chemical unit comprising or consisting of a structure of the formula D1

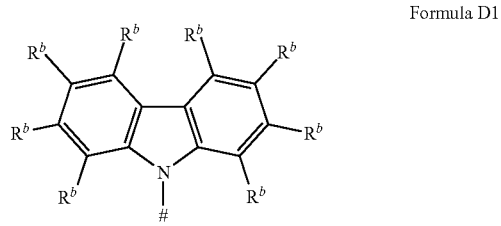

Formula D1 with
=point of attachment of the second chemical unit to the first chemical unit;
$R^N$ is a structure of the formula N1:

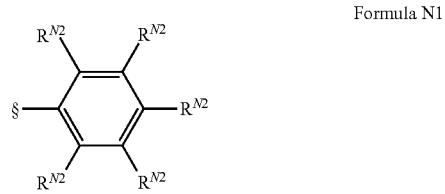

Formula N1 with
§ =point of attachment of the chemical unit $R^N$ of formula N1 to the first chemical unit;

$R^{N2}$ is the same or different at each instance and is H, phenyl or naphthyl;

$R^a$ is the same or different at each instance and is selected from the group consisting of a point of attachment of the first chemical unit to the second chemical unit and H;

$R^b$ at each instance is independently selected from the group consisting of H, deuterium, $CF_3$, $O(=O)R^1$, ON, carbazolyl which is unsubstituted or substituted by one or more $R^2$, $Si(R^4)_3$, an alkyl group which is unsubstituted or substituted by one or more $R^2$, an aryl group which is unsubstituted or substituted by one or more $R^2$, and a heteroaryl group which is unsubstituted or substituted by one or more $R^2$;

$R^1$ independently at each instance is an aryl group which is unsubstituted or substituted by one or more $R^3$;

$R^2$ at each instance is independently selected from the group consisting of $CF_3$, $O(=O)R^1$, ON, an alkyl group which is unsubstituted or substituted by one or more $R^3$, an aryl group which is unsubstituted or substituted by one or more $R^3$, and a heteroaryl group which is unsubstituted or substituted by one or more $R^3$;

$R^3$ at each instance is independently selected from the group consisting of an unsubstituted alkyl group, an unsubstituted aryl group and an unsubstituted heteroaryl group;

$R^4$ at each instance is independently selected from the group consisting of an aryl group which is unsubstituted or substituted by one or more $R^3$, and a heteroaryl group which is unsubstituted or substituted by one or more $R^3$;

where two or more of the $R^1$, $R^2$ and $R^3$ substituents together may form a monocyclic or polycyclic, aliphatic or aromatic and/or benzofused ring system;

where not less than one and not more than three $R^{N2}$ is phenyl or naphthyl.

In one embodiment, the organic molecule comprises or consists of a structure of the formula A2.

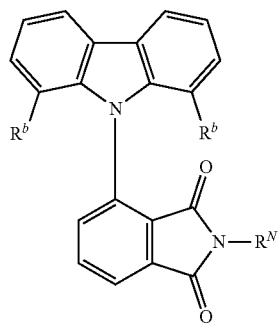

Formula A2 where the definitions given above are applicable.

In one embodiment, the organic molecule compress or consists of a structure of the formula A3.

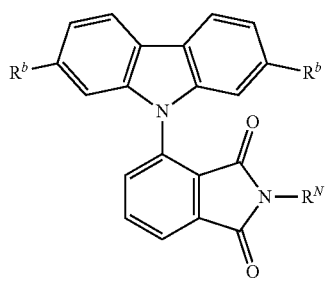

Formula A3 where the definitions given above are applicable.

In one embodiment, the organic molecule comprises or consists of a structure of the formula A4.

Formula A4

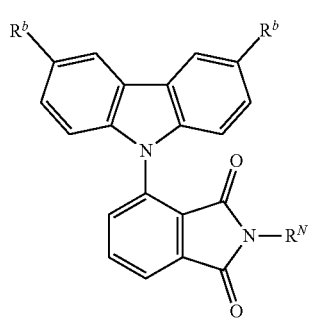

where the definitions given above are applicable.

In one embodiment, the organic molecule comprises or consists of a structure of the formula A5.

Formula A5 where the definitions given above are applicable.

In one embodiment, the organic molecule comprises a structure of the formula A3, A4 or A5 with $R^b$ at each instance independently selected from the group consisting of deuterium, $CF_3$, $C(=O)R^1$, ON, carbazolyl which is unsubstituted or substituted by one or more $R^2$, $Si(R^4)_3$, an alkyl group which is unsubstituted or substituted by one or more $R^2$, an aryl group which is unsubstituted or substituted by one or more $R^2$, and a heteroaryl group which is unsubstituted or substituted by one or more $R^2$.

In one embodiment of the organic molecule, $R^N$ is the same or different at each instance and is selected from one of the structures O1 to O10:

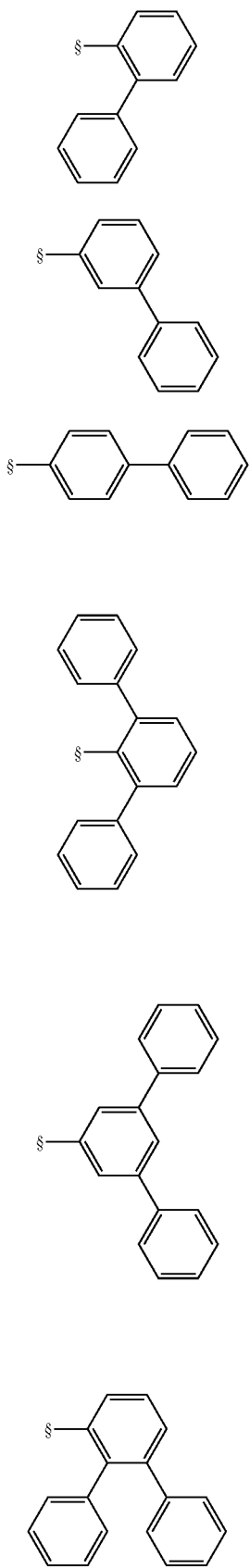
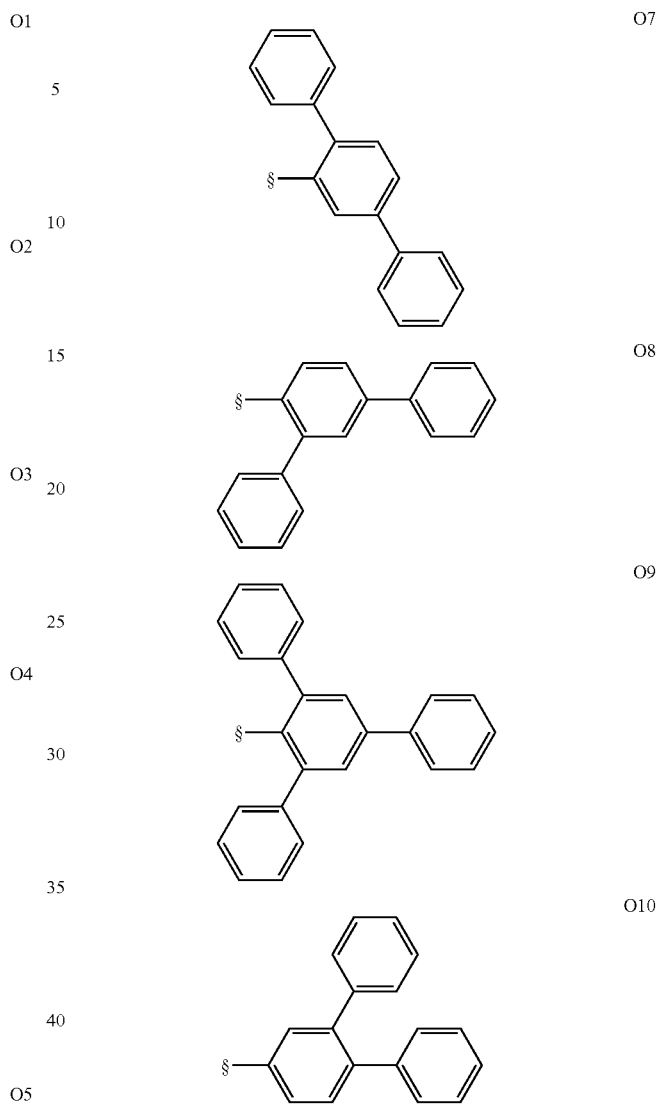
where the definitions given above are applicable.
In one embodiment of the organic molecule, $R^N$ is the same or different at each instance and is selected from one of the structures P1 to P3:
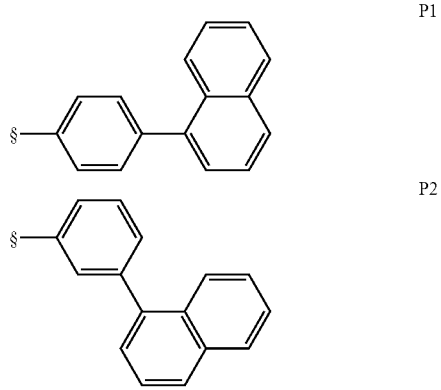

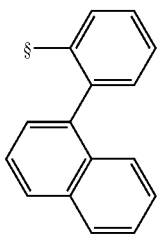

P3 where the definitions given above are applicable.

In one embodiment of the organic molecule, $R^b$ is the same or different at each instance and is selected from the group consisting of H, deuterium, methyl, isopropyl, tert-butyl, $CF_3$, ON, a phenyl group which is unsubstituted or substituted by one or more $R^6$, a pyridine group which is unsubstituted or substituted by one or more $R^5$, a pyrimidine group which is unsubstituted or substituted by one or more $R^6$, a pyrazine group which is unsubstituted or substituted by one or more $R^6$, and a triazine group which is unsubstituted or substituted by one or more $R^6$.

$R^5$ is the same or different at each instance and is selected from the group consisting of deuterium, methyl, isopropyl, tert-butyl, $CF_3$, ON and phenyl.

The organic molecule of the invention may also comprise or consist of a structure of the formula A6, A7 or A8 (where the variables that occur therein are defined above).

Formula A6

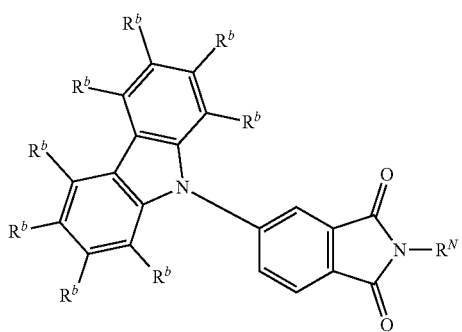

Formula A7

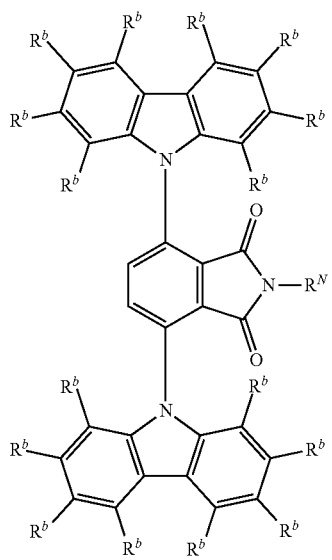

Formula A8

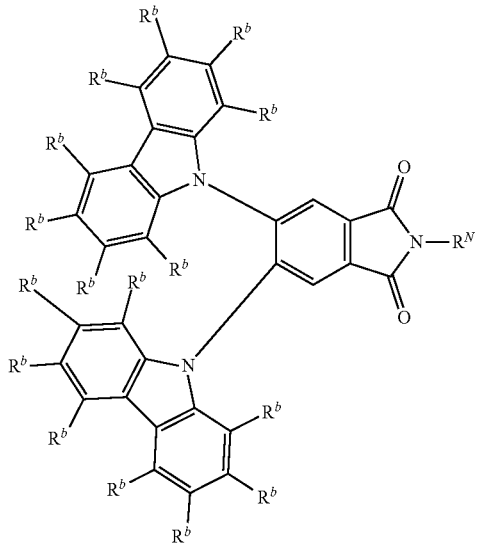

In the context of this invention, an aryl group contains 6 to 60 aromatic ring atoms; a heteroaryl group contains 5 to 60 aromatic ring atoms, of which at least one is a heteroatom. The heteroatoms are especially N, O and/or S. If, in the description of particular embodiments of the invention, other definitions departing from the definition mentioned are given, for example with regard to the number of aromatic ring atoms or of heteroatoms present, these are applicable.

An aryl group or heteroaryl group is understood to mean a simple aromatic cycle, i.e. benzene, or a simple heteroaromatic cycle, for example pyridine, pyrimidine or thiophene, or a heteroaromatic polycycle, for example phenanthrene, quinoline or carbazole. A fused (annelated) aromatic or heteroaromatic polycycle in the context of the present invention consists of two or more mutually condensed simple aromatic or heteroaromatic cycles.

An alkyl or heteroaryl group which may be joined via any desired positions to the aromatic or heteroaromatic system is especially understood to mean groups derived from benzene, naphthalene, anthracene, phenanthrene, pyrene, dihydropyrene, chrysene, perylene, fluoranthene, benzanthracene, benzphenanthrene, tetracene, pentacene, benzopyrene, furan, benzofuran, isobenzofuran, dibenzofuran, thiophene, benzothiophene, isobenzothiophene, dibenzothiophene; pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, napthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,2,3,4-tetrazine, purine, pteridine, indolizine and benzothiadiazole or combinations of the groups mentioned.

A cyclic alkyl, alkoxy or thioalkoxy group is understood here to mean a monocyclic, bicyclic or polycyclic group.

In the context of the present invention, an alkyl group is understood to mean, for example, the methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]-octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl)cyclohex-1-yl, 1-(n-hexyl)cyclohex-1-yl, 1-(n-octyl)cyclohex-1-yl and 1-(n-decyl)cyclohex-1-yl radicals. An alkenyl group is understood to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is understood to mean, for example, ethynyl, propynyl, butyryl, pentynyl, hexynyl, heptynyl or octynyl. A $C_1$- to $C_{40}$-alkoxy group is understood to mean, for example, methoxy, trifluoromethoxy, ethoxy, n-propoxy, i-propoxy, n-butoxy, i-butoxy, s-butoxy, t-butoxy or 2-methylbutoxy.

The organic molecules according to the invention show high photoluminescence quantum yields and short excitor lifetimes, and are therefore advantageous emitter materials for blue, sky blue or green OLEDs.

One embodiment of the invention relates to organic molecules with an emission maximum between 400 and 500 nm, especially between 420 and 481 nm, more preferably between 430 and 470 nm, even more preferably between 440 and 460 nm.

More particularly, the organic molecules according to the invention have a $\Delta E(S_1-T_1)$ value between the lowermost excited singlet state ($S_1$) and the triplet state ($T_1$) below it of not higher than 5000 cm$^{-1}$, especially not higher than 3000 cm$^{-1}$, or not higher than 1500 cm$^{-1}$ or 1000 cm$^{-1}$, and/or an emission lifetime of not more than 50 µs, especially of not more than 20 ρs, or of not more than 10 µs, preferably not more than 5 µs, and/or a main emission band having a half-height width of less than 120 nm, especially less than 100 mm, less than 80 nm, or less than 60 nm, and/or a photoluminescence quantum yield (PLQY) of greater than 50%, of greater than 55%, of greater than 60%, of greater than 65%, of greater than 70%, or of greater than 80%.

In a further aspect, the invention relates to the use of the organic molecules as luminescent emitters or as host material in an organic optoelectronic device, especially where the organic optoelectronic device is selected from the group consisting of:
  organic light-emitting diodes (OLEDs),
  light-emitting electrochemical cells,
  OLED sensors, especially in gas and vapour sensors not hermetically shielded from the outside,
  organic diodes,
  organic solar cells,
  organic transistors,
  organic field-effect transistors,
  organic lasers and
  down-conversion elements.

In a further aspect, the invention relates to a composition comprising or consisting of:
(a) at least one organic molecule according to the invention, especially as emitter and/or host, and
(b) at least one, i.e. one or more, emitter and/or host material(s) other than the organic molecule according to the invention, and
(c) optionally one or more dyes and/or one or more organic solvents.

In one embodiment, the composition according to the invention consists of an organic molecule according to the invention and one or more host materials. The host material(s) especially has/have triplet ($T_1$) and singlet ($S_1$) energy levels at higher energy than the triplet ($T_1$) and singlet ($S_1$) energy levels of the organic molecule according to the invention. In one embodiment, the composition, as well as the organic molecule according to the invention, comprise an electron-dominant and a hole-dominant host material. The highest occupied orbital (HOMO) and the lowest unoccupied orbital (LUMO) of the hole-dominant host material are especially at higher energy than those of the electron-dominant host material. The HOMO of the hole-dominant host material is at lower energy than the HOMO of the organic molecule according to the invention, while the LUMO of the electron-dominant host material is at higher energy than the LUMO of the organic molecule according to the invention. In order to avoid exciplex formation between emitter and host material(s), the materials should be chosen such that the energy gaps between the respective orbitals are small. The gap between the LUMO of the electron-dominant host material and the LUMO of the organic molecule according to the invention is especially less than 0.5 eV, preferably less than 0.3 eV, even more preferably less than 0.2 eV. The gap between the HOMO of the hole-dominant host material and the HOMO of the organic molecule according to the invention is especially less than 0.5 eV, preferably less than 0.3 eV, even more preferably less than 0.2 eV.

In a further aspect, the invention relates to an organic optoelectronic device comprising an organic molecule according to the invention or a composition according to the invention. The organic optoelectronic device especially takes the form of a device selected from the group consisting of organic light-emitting diode (OLED); light-emitting electrochemical cell; OLED sensor, especially gas and vapour sensors that are not hermetically shielded from the outside; organic diode; organic solar cell; organic transistor; organic field effect transistor; organic laser and down-conversion element.

An organic optoelectronic device comprising
  a substrate,
  an anode and
  a cathode, where the anode or cathode has been applied to the substrate, and
  at least one light-emitting layer which is arranged between anode and cathode and comprising an organic molecule according to the invention is a further embodiment of the invention.

In one embodiment, the optoelectronic device is an OLED. A typical OLED comprises, for example, the following layer structure:
1. Substrate (carrier material)
2. Anode
3. Hole injection layer (HIL)
4. Hole transport layer (HTL)
5. Electron blocking layer (EBL)
6. Emitting layer (EML)

7. Hole blocking layer (HBL)
8. Electron transport layer (ETL)
9. Electron injection layer (EIL)
10. Cathode.

Individual layers here are present merely in an optional manner. In addition, two or more of these layers may be combined. And it is possible for individual layers to be present more than once in the component.

In one embodiment, at least one electrode of the organic component is translucent. "Translucent" refers here to a layer which is transparent to visible light. The translucent layer here may be clear and see-through, i.e. transparent, or at least partly light-absorbing and/or partly light-scattering, such that the translucent layer, for example, may also have a diffuse or milky appearance. More particularly, a layer referred to here as translucent is very substantially transparent, such that, in particular, the absorption of light is as low as possible.

In a further embodiment, the organic component, especially an OLED, has an inverted structure. It is a feature of the inverted structure that the cathode is on the substrate and the other layers are applied in a correspondingly inverted manner.

1. Substrate (carrier material)
2. Cathode
3. Electron injection layer (EIL)
4. Electron transport layer (ETL)
5. Hole blocking layer (HBL)
6. Emission layer/emitting layer (EML)
7. Electron blocking layer (EBL)
8. Hole transport layer (HTL)
9. Hole injection layer (HIL)
10. Anode Individual layers here are present merely in an optional manner. In addition, two or more of these layers may be combined. And it is possible for individual layers to be present more than once in the component.

In one embodiment, in the inverted OLED, the anode layer of the typical structure, for example an ITO (indium tin oxide) layer, is connected as the cathode.

In a further embodiment, the organic component, especially an OLED, comprises a stacked structure. The individual OLEDs here are arranged one on top of another and not one alongside another as usual. A stacked structure can enable the generation of mixed light. For example, this structure can be used in the generation of white light, which is produced by forming the entire visible spectrum, typically by the combination of the emitted light from blue, green and red emitters. In addition, with practically the same efficiency and identical luminance, it is possible to achieve significantly longer lifetimes compared to standard OLEDs. For the stacked structure, it is optionally possible to use what is called a charge generation layer (CGL) between two OLEDs. This consists of an n-doped layer and a p-doped layer, the n-doped layer typically being applied closer to the anode.

In one embodiment—called a tandem OLED—two or more emission layers occur between the anode and cathode. In one embodiment, three emission layers are arranged one on top of another, where one emission layer emits red light, one emission layer emits green light and one emission layer emits blue light, and there are optionally further charge generation, blocker or transport layers applied between the individual emission layers. In a further embodiment, the respective emission layers are applied in a directly adjacent manner. In a further embodiment, there is one charge generation layer in each case between the emission layers. In addition, in an OLED, it is possible to combine directly adjacent emission layers and emission layers separated by charge generation layers.

It is also possible to arrange an encapsulation on top of the electrodes and the organic layers. The encapsulation may take the form, for example, of a glass lid or the form of a thin-film encapsulation.

The carrier material used in the optoelectronic device may, for example, be glass, quartz, plastic, metal, a silicon wafer or any other suitable solid or flexible, optionally transparent material.

The carrier material may comprise, for example, one or more materials in the form of a layer, a film, a sheet or a laminate.

Anodes used in the optoelectronic device may, for example, be transparent conductive metal oxides, for example ITO (indium tin oxide), zinc oxide, tin oxide, cadmium oxide, titanium oxide, indium oxide or aluminium zinc oxide (AZO), $Zn_2SnO_4$, $CdSnO_3$, $ZnSnO_3$, $MgIn_2O_4$, $GaInO_3$, $Zn_2In_2O_5$ or $In_4Sn_3O_{12}$ or mixtures of different transparent conductive oxides.

HIL materials used may, for example, be PEDOT:PSS (poly-3,4-ethylenedioxythiophene:polystyrenesulphonic acid), PEDOT (poly-3,4-ethylenedioxythiophene), m-MTDATA (4,4',4"-tris[phenyl(m-tolyl)amino]triphenylamine), spiro-TAD (2,2',7,7'-tetrakis(N,N-diphenylamino)-9,9-spirobifluorene), DNTPD (4,4'-bis[N-[4-{N,N-bis(3-methylphenyl)amino}phenyl]-N-phenylamino]biphenyl), NPB (N,N'-bis-(1-naphthalenyl)-N,N'-bisphenyl-(1,1-biphenyl)-4,4'-diamine), NPNPB (N,N'-diphenyl-N,N'-di-[4-(N,N-diphenylamino)phenyl]benzene), MeO-TPD (N,N,N',N'-tetrakis(4-methoxyphenyl)benzene), HAT-ON (1,4,5,8,9,11-hexaazatriphenylenehexacarbonitrile) or spiro-NPD (N,N'-diphenyl-N,N'-bis-(1-naphthyl)-9,9'-spirobifluorene-2,7-diamine). By way of example, the layer thickness is 10-80 nm. In addition, it is possible to use small molecules (e.g. copper phthalocyanine (CuPc, e.g. thickness 10 nm)) or metal oxides, by way of example $MoO_3$, $V_2O_5$.

HTL materials used may be tertiary amines, carbazole derivatives, polystyrenesulphonic acid-doped polyethylenedioxythiophene, camphorsulphonic acid-doped polyaniline, poly-TPD (poly(4-butylphenyldiphenylamine), [alpha]-NPD (poly(4-butylphenyldiphenylamine)), TAPC (4,4'-cyclohexylidenebis[N,N-bis(4-methylphenyl)benzeneamine]), TCTA (tris(4-carbazoyl-9-ylphenyl)amine), 2-TNATA (4,4',4"-tris[2-naphthyl(phenyl)amino]triphenylamine), spiro-TAD, DNTPD, NPB, NPNPB, MeO-TPD, HAT-ON or TrisPcz (9,9'-diphenyl-6-(9-phenyl-9H-carbazol-3-yl)-9H,9'H-3,3'-bicarbazole). By way of example, the layer thickness is 10 nm to 100 nm.

The HTL may comprise a p-doped layer comprising an inorganic or organic dopant in an organic hole-conducting matrix. Inorganic dopants used may, for example, be transition metal oxides, for instance vanadium oxide, molybdenum oxide or tungsten oxide. Organic dopants used may, for example, be tetrafluorotetracyanoquinodimethane (F4-TCNQ), copper pentafluorobenzoate (Cu(I)pFBz) or transition metal complexes. By way of example, the layer thickness is 10 nm to 100 nm.

Electron blocker layer materials used may, for example, be mCP (1,3-bis(carbazol-9-yl)benzene). TCTA, 2-TNATA, mCBP (3,3-di(9H-carbazol-9-yl)biphenyl), tris-Pcz (9,9'-diphenyl-6-(9-phenyl-9H-carbazol-3-yl)-9H,9'H-3,3'-bicarbazole), CzSi (9-(4-tert-butylphenyl)-3,6-bis(triphenylsilyl)-9H-carbazole) or DCB (N,N'-dicarbazolyl-1,4-dimethylbenzene). By way of example, the layer thickness is 10 nm to 50 nm.

The emitter layer EML or emission layer consists of or comprises emitter material or a mixture comprising at least two emitter materials and optionally one or more host materials. Suitable host materials are, for example, mCP, TCTA, 2-TNATA, mCBP, CBP (4,4'-bis-(N-carbazolyl)biphenyl), Sif87 (dibenzo[b,d]thiophen-2-yltriphenylsilane), Sif88 (dibenzo[b,d]thiophen-2-yl)diphenylsilane) or DPEPO (bis[2-((oxo)diphenylphosphino)phenyl] ether). For emitter material which emits in the green or in the red or a mixture comprising at least two emitter materials, the standard matrix materials are suitable, such as CBP. For emitter material which emits in the blue or a mixture comprising at least two emitter materials, it is possible to use UHG matrix materials (ultra-high-energy gap materials) (see, for example, M. E. Thompson et al., Chem. Mater. 2004, 16, 4743), or other so-called wide-gap matrix materials. By way of example, the layer thickness is 10 nm to 250 nm.

The hole blocker layer HBL may include, for example, BCP (2,9-dimethyl-4,7-diphenyl-1,10-phenanthroline=bathocuproin), bis(2-methyl-8-hydroxyquinolinato)-(4-phenylphenolato)aluminium(III) (BAlq), Nbphen (2,9-bis(naphthalen-2-yl)-4,7-diphenyl-1,10-phenanthroline), Alq3 (aluminium tris(8-hydroxyquinoline)), TSPO1 (diphenyl-4-triphenylsilylphenylphosphine oxide) or TCB/TCP (1,3,5-tris(N-carbazolyl)benzene/1,3,5-tris(carbazol)-9-yl)benzene), By way of example, the layer thickness is 10 nm to 50 nm.

The electron transport layer ETL may include, for example, materials based on $AlQ_3$, TSPO1, BPyTP2 (2,7-di(2,2'-bipyridin-5-yl)triphenyl), Sif87, Sif88, BmPyPhB (1,3-bis[3,5-di(pyridin-3-yl)phenyl]benzene) or BTB (4,4'-bis-[2-(4,6-diphenyl-1,3,5-triazinyl)]-1,1'-biphenyl). By way of example, the layer thickness is 10 nm to 200 nm.

Materials used in a thin electron injection layer EIL may, for example, be CsF, LiF, 8-hydroxyquinolinolatolithium (Liq), $Li_2O$, $BaF_2$, MgO or NaF.

Materials used in the cathode layer may be metals or alloys, for example Al, Al>AlF, Ag, Pt, Au, Mg, Ag:Mg. Typical layer thicknesses are 100 nm to 200 nm. In particular, one or more metals that are stable under air and/or self-passivating, for example through formation of a thin protective oxide layer, are used.

Suitable materials for encapsulation are, for example, aluminium oxide, vanadium oxide, zinc oxide, zirconium oxide, titanium oxide, hafnium oxide, lanthanum oxide, tantalum oxide.

In one embodiment of the organic optoelectronic device according to the invention, the organic molecule according to the invention is used as emission material in a light-emitting layer EML, where it is used either in the form of a pure layer or in combination with one or more host materials.

One embodiment of the invention relates to organic optoelectronic devices having an external quantum efficiency (EQE) at 1000 $cd/m^2$ of greater than 5%, especially of greater than 8%, especially of greater than 10%, or of greater than 13%, or of greater than 16% and especially of greater than 20%, and/or an emission maximum at a wavelength between 420 nm and 500 nm, especially between 430 nm and 490 nm, or between 440 nm and 480 nm and especially between 450 nm and 470 nm, and/or an LT80 value at 500 $cd/m^2$ of greater than 30 h, especially of greater than 70 h, or of greater than 100 h, or of greater than 150 h and especially of greater than 200 h.

The proportion by mass of the organic molecule according to the invention in the emitter layer EML, in a further embodiment in a light-emitting layer in optical light-emitting devices, especially in OLEDs, is between 1% and 80%. In one embodiment of the organic optoelectronic device according to the invention, the light-emitting layer is applied to a substrate, preferably with application of an anode and a cathode to the substrate and application of the light-emitting layer between the anode and cathode.

The light-emitting layer, in one embodiment, has exclusively an organic molecule according to the invention in 100% concentration, with the anode and the cathode applied to the substrate, and the light-emitting layer applied between the anode and cathode.

In one embodiment of the organic optoelectronic device according to the invention, a hole- and electron-injecting layer has been applied between the anode and cathode, and a hole- and electron-transporting layer between the hole- and electron-injecting layer, and the light-emitting layer between the hole- and electron-transporting layer.

The organic optoelectronic device, in a further embodiment of the invention, comprises: a substrate, an anode, a cathode and at least one hole- and one electron-injecting layer, and at least one hole- and one electron-transporting layer, and at least one light-emitting layer including an organic molecule according to the invention and one or more host materials, the triplet (T1) and singlet (S1) energy levels of which are at higher energy than the triplet (T1) and singlet (S1) energy levels of the organic molecule, with the anode and cathode applied to the substrate, and the hole- and electron-injecting layer applied between the anode and cathode, and the hole- and electron-transporting layer applied between the hole- and electron-injecting layer, and the light-emitting layer applied between the hole- and electron-transporting layer.

In a further aspect, the invention relates to a process for producing an optoelectronic component. This is done using an organic molecule according to the invention.

In one embodiment, the production process encompasses the processing of the organic molecule according to the invention by means of a vacuum evaporation method or from a solution.

The invention also includes a process for producing an optoelectronic device according to the invention, in which at least one layer of the optoelectronic device is coated by a sublimation method, is coated by an OVPD (organic vapour phase deposition) method, is coated by a carrier gas sublimation, and/or is produced from solution or by a printing method.

In the production of the optoelectronic device according to the invention, known methods are used. In general, the layers are applied individually to a suitable substrate in successive deposition process steps. In the gas phase deposition, it is possible to employ the commonly used methods, such as thermal evaporation, chemical gas phase deposition (CVD), physical gas phase deposition (PVD). For active-matrix OLED displays, deposition is effected on an AMOLED backplane as substrate.

Alternatively, it is possible to apply layers from solutions or dispersions in suitable solvents. Illustrative suitable coating methods are spin-coating, dip-coating and jet printing methods. The individual layers can be produced in accordance with the invention either via the same coating method or via different coating methods in each case.

EXAMPLES

General Methods
GM1:

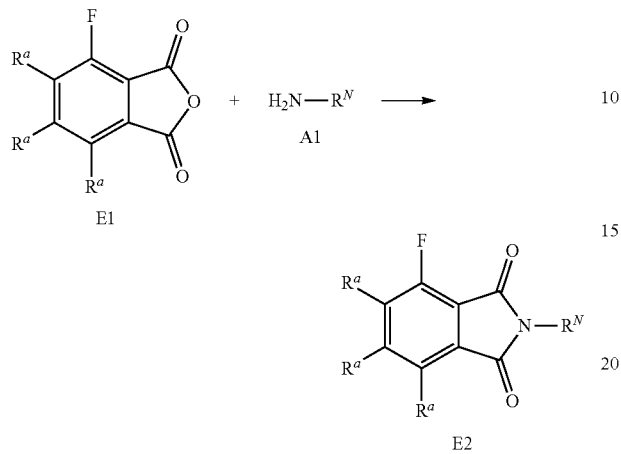

In a round-bottom flask with reflux condenser, E1 (1 equivalent) is suspended in glacial acetic acid. After addition of A1 (1.1 equivalents), the mixture is stirred at 100° C. for 3 hours. After cooling, the reaction solution is concentrated as far as possible on a rotary evaporator. The residue is taken up in $CH_2Cl_2$ and washed twice with saturated $Na_2CO_3$. The combined organic phases are dried over $MgSO_4$. The solvent is removed on a rotary evaporator. After drying under high vacuum, E2 is obtained as product, which can generally be used without further purification. If required, the product E2 can be purified further by recrystallization.

Illustrative A1 and E2 Combinations

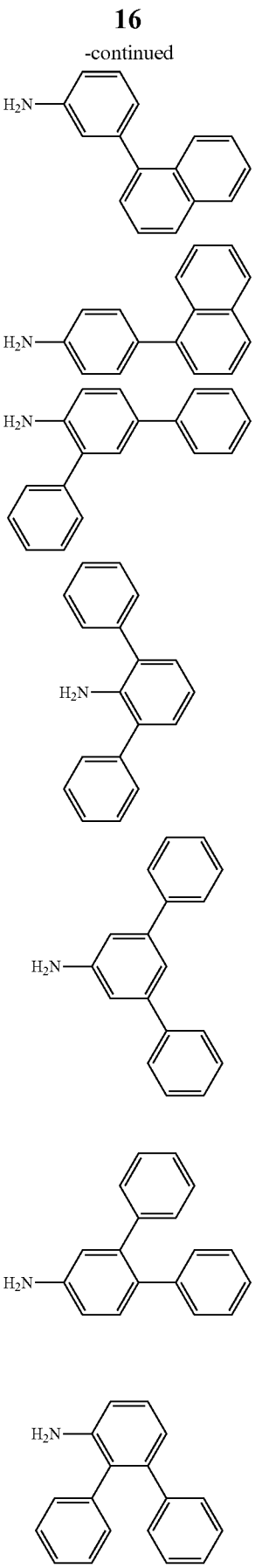

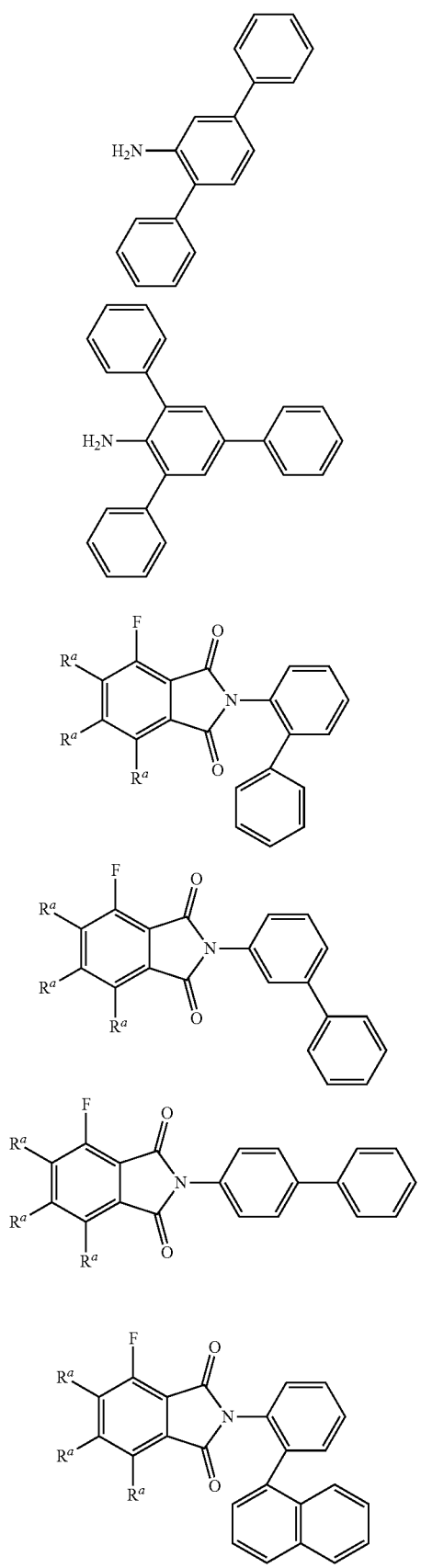
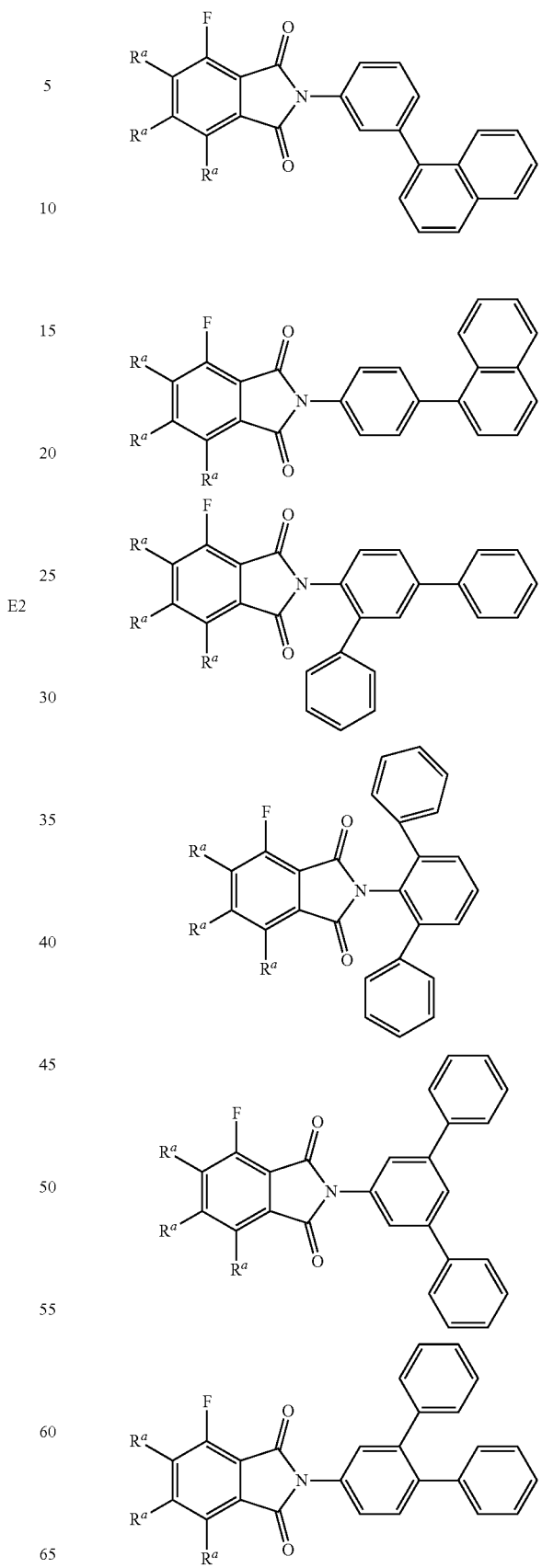
E2

-continued

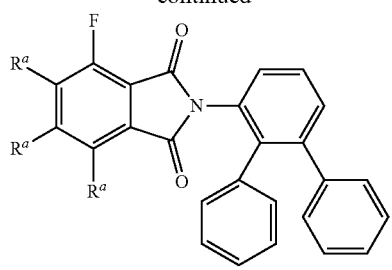

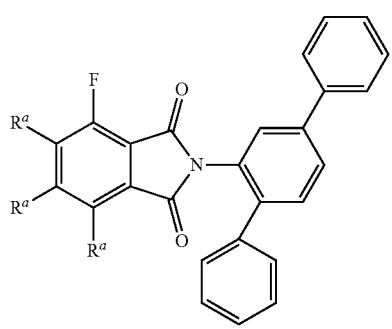

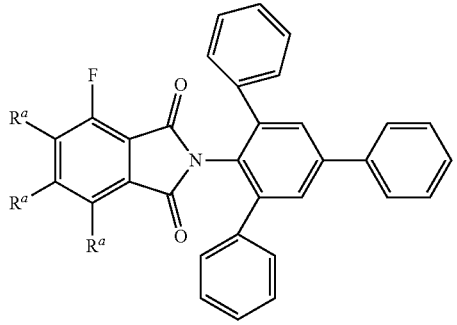

GM2:

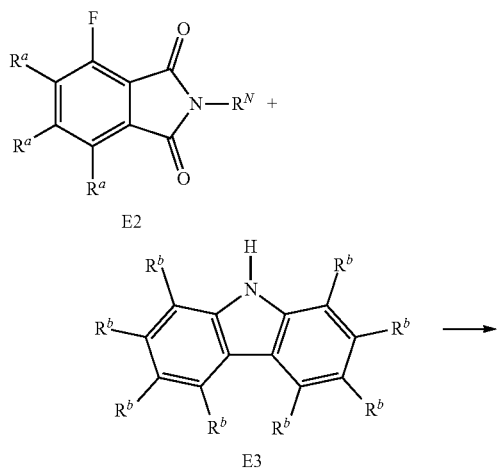

-continued

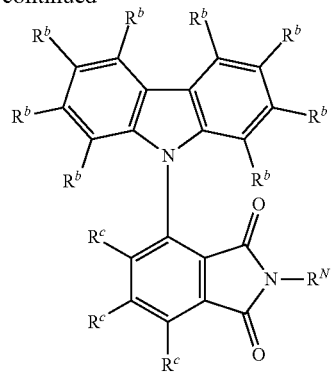

A round-bottom flask is initially charged with phthalimide E2 (1 equivalent), a carbazole derivative E3 (1 equivalent) and K₃PO₄ (2 equivalents), and evacuated for 5 min. Under inert gas atmosphere, DMSO (dry) is added and the reaction solution is stirred at 100° C. for 16 h. After cooling, the reaction solution is poured onto water and extracted with CH₂Cl₂. After extracting again with CH₂Cl₂, the combined organic phases are washed 2× with water and with saturated NaCl solution. This is followed by drying over MgSO₄ and removal of the solvent on a rotary evaporator. The respective product can be purified by recrystallization.

GM3:

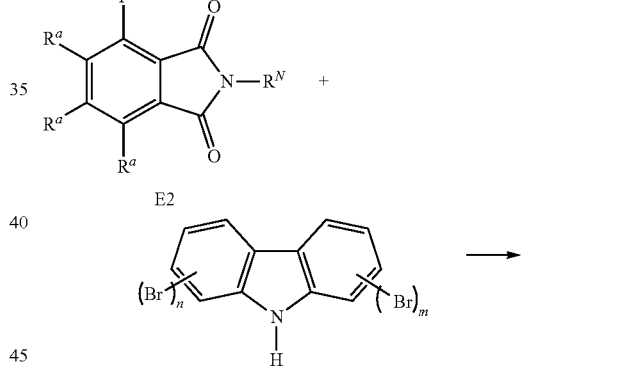

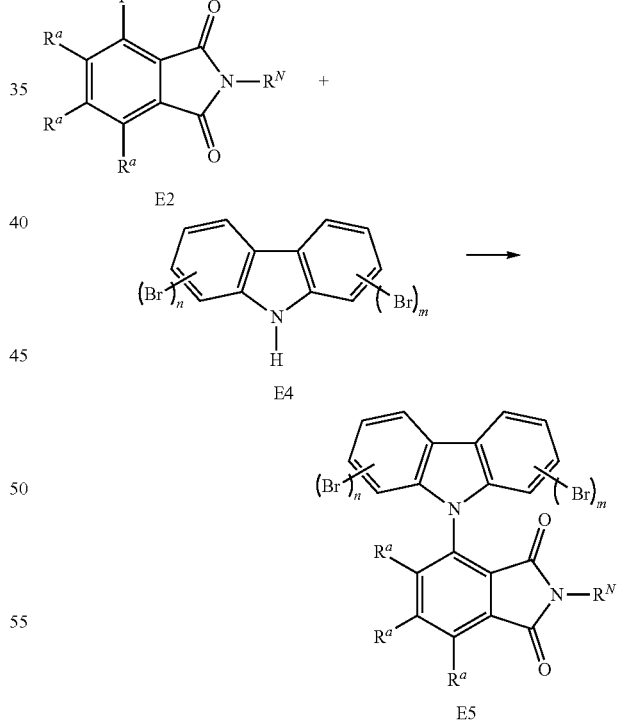

n=1 to 4, m=0 to 4

A round-bottom flask is initially charged with E2 (1.2 equivalents), a bromine-substituted carbazole E4 (1 equivalent) and K₃PO₄ (2 equivalents), and evacuated for 5 min. Under inert gas atmosphere, DMSO (dry) is added and the reaction solution is stirred at 100° C. for 16 h. After cooling, the reaction solution is poured onto water and extracted with CH$_2$Cl$_2$. After extracting again with CH$_2$Cl$_2$, the combined organic phases are washed 2× with water and with saturated NaCl solution. This is followed by drying over MgSO$_4$ and removal of the solvent on a rotary evaporator. The respective product can be purified by recrystallization. It is possible in accordance with the invention also to use chlorine- or iodine-substituted carbazole rather than bromine-substituted carbazole.

Illustrative E4 and E5 Combinations

E4

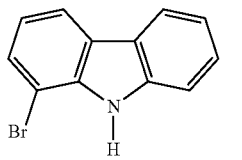
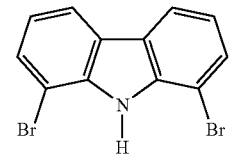
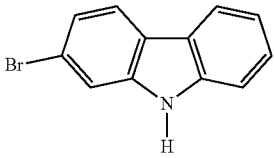
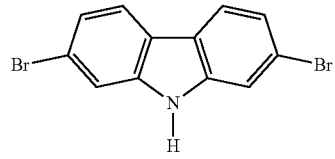
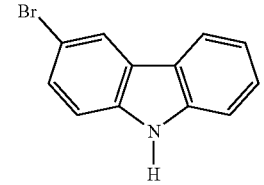
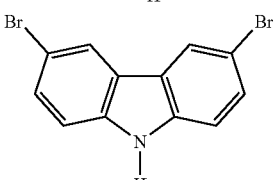
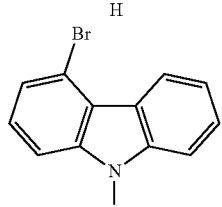
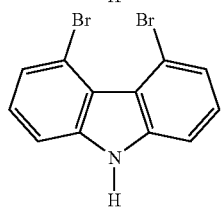

-continued

E5

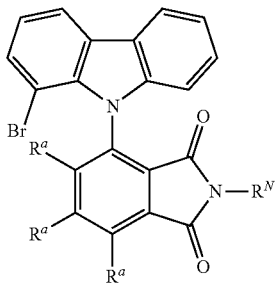
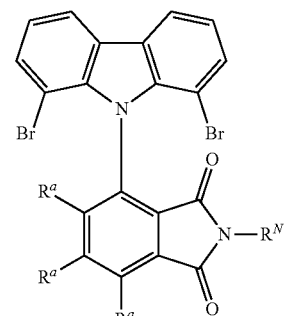
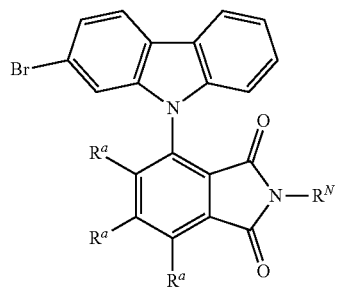
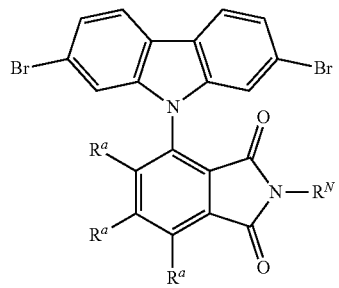
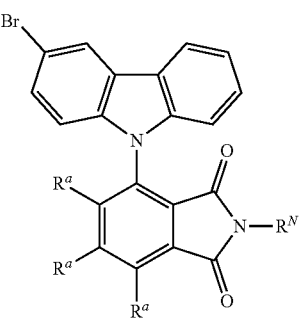

-continued

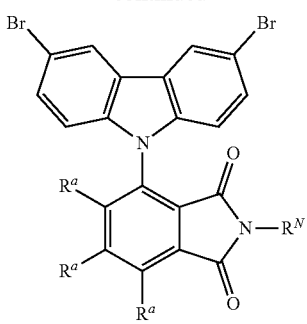

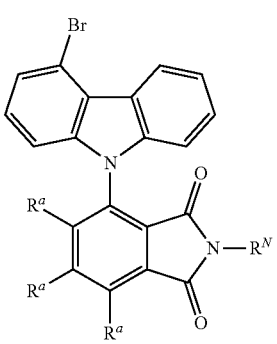

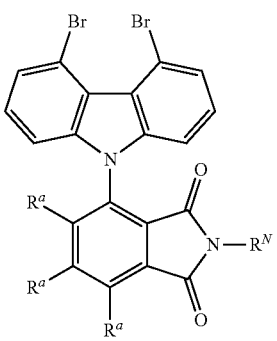

GM4:
Stage 1

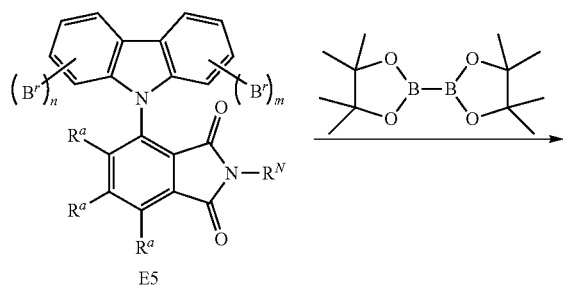

E5

-continued

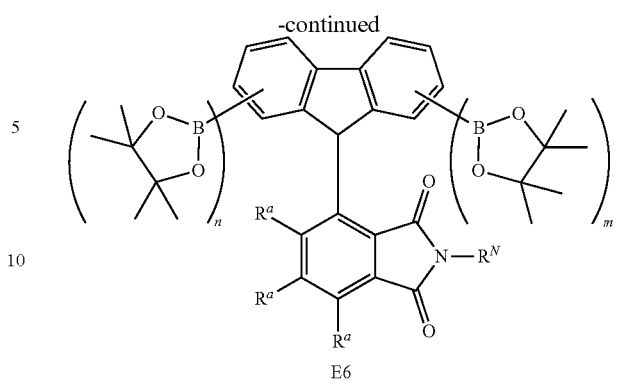

E6

E5 (1.00 equivalent), bis(pinacolato)diboron (1.5(n+m) equivalents), tris(dibenzylideneacetone)dipalladium (0.01 equivalent), 2-(dicyclohexylphosphino)-2',4',6'-triisopropyl-biphenyl (0.04 equivalent) and tribasic potassium phosphate (3n+3m equivalents) are stirred under nitrogen in dioxane at 110° C. for 12 to 24 h. The crude product obtained can be purified by recrystallization.

Stage 2:

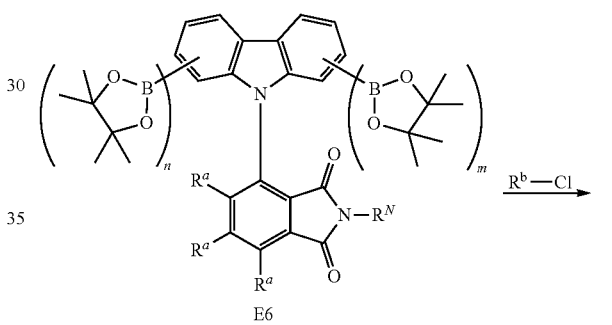

E6

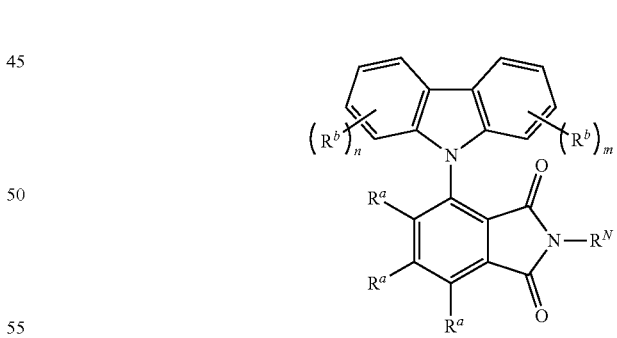

E6 (1.00 equivalent), $R^b$—Cl (1.3n+1.3m equivalents), tris(dibenzylideneacetone)dipalladium (0.01 equivalent), 2-(dicyclohexylphosphino)-2',4',6'-triisopropylbiphenyl (0.04 equivalent) and tribasic potassium phosphate (2.5n+ 2.5m equivalents) are stirred under nitrogen in a toluene/ water (10:1) mixture at 100° C. for 12 to 24 h. The crude product obtained is purified by flash chromatography or by recrystallization.

It is also possible in accordance with the invention to use $R^b$—Br or $R^b$—I rather than $R^b$—Cl.

GM5:

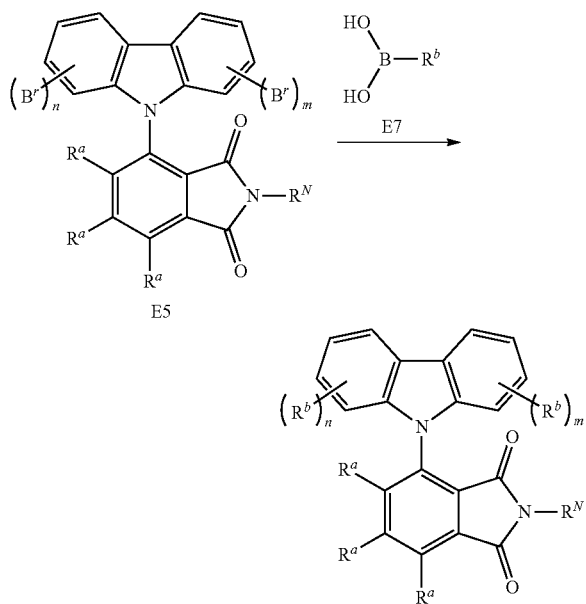

E5 (1.00 equivalent), the appropriate boronic acid of the $R^b$ radical E7 (1.3n+1.3m equivalents), tris(dibenzylideneacetone)dipalladium (0.01 equivalent), 2-(dicyclohexylphosphino)-2',4',6'-triisopropylbiphenyl (0.04 equivalent) and tribasic potassium phosphate (3n+3m equivalents) are stirred under nitrogen in dioxane/water (10:1) at 110° C. for 12 to 24 h. The crude product obtained is purified by flash chromatography or by recrystallization.

It is also possible in accordance with the invention to use a corresponding boronic ester rather than a boronic acid.

The molecules according to the invention can each be obtained according to GM2 or a combination of GM3 and GM4 or GM3 and GM5. The products from the synthesis routes differ in each case merely by the yields or purity obtained prior to the purification. After appropriate purification, the products are of equivalent quality.

Calculations by Density Functional Theory

For the optimization of the molecular structures, the BP86 functional (Becke, A. D. Phys. Rev. A1988, 38, 3098-3100; Perdew, J. P. Phys. Rev. B1986, 33, 8822-8827) was used, using the resolution-of-identity (RI) approximation (Sierka, M.; Hogekamp, A.; Ahlrichs, R. J. Chem, Phys. 2003, 118, 9136-9148; Becke, A. D., J. Chem. Phys. 98 (1993) 5648-5652; Lee, C; Yang, W; Parr, R. G. Phys. Rev. B 37 (1988) 785-789). Excitation energies were calculated in the BP86-optimized structure by the time-dependent DFT method (TD-DFT) using the B3LYP functional (Becke, A. D., J. Chem. Phys. 98 (1993) 5648-5652; Lee, C; Yang, W; Parr, R. G. Phys. Rev. B 37 (1988) 785-789; Vosko, S. H.; Wilk, L.; Nusair, M. Can. J. Phys. 58 (1980) 1200-1211; Stephens, P. J.; Devlin, F. J.; Chabalowski, C. F.; Frisch, M. J. J. Phys. Chem. 98 (1994) 11623-11627). In all calculations, deft-SV (P) basis sets (Weigend, F.; Ahlrichs, R. Phys. Chem. Chem. Phys. 2005, 7, 3297-3305; Rappoport, D.; Furche, F. J. Chem. Phys. 2010, 133, 134105/1-134105/11) and an m4 grid were used for numerical integration. All DFT calculations were conducted with the Turbomole software package (version 6.5) (TURBOMOLE V6.4 2012, a development by the University of Karlsruhe and Forschungszentrum Karlsruhe GmbH, 1989-2007, TURBOMOLE GmbH, since 2007; http://www.turbomole.com).

The frontier orbitals shown in the figures were calculated with the B3LYP functional for the optimized ground state geometries.

Photophysical Measurements

Pretreatment of Optical Glassware

All glassware (cuvettes and substrates made from quartz glass, diameter: 1 cm) was cleaned after each use: Three rinses each time with dichloromethane, acetone, ethanol, demineralized water, placing in 5% Hellmanex solution for 24 h, thorough rinsing-out with demineralized water. For drying, the optical glassware was blown dry with nitrogen.

Sample Preparation: Solutions 1-2 mg of the sample were dissolved in 100 ml of the particular solvent; concentration $10^{-5}$ mol/l. The cuvette was sealed air-tight and degassed for 10 min.

Sample Preparation, Film: Spin-Coating (Instrument: Spin150, SPS Euro.) Sample concentration corresponded to 10 mg/ml, made up in toluene or chlorobenzene. Programme: 1) 3 s at 400 rpm; 2) 20 sec at 1000 rpm at 1000 rpm/s. 3) 10 s at 4000 rpm at 1000 rpm/s. After coating, the films were dried at 70° C. under air on an LHG precision hotplate for 1 min.

Absorption Spectroscopy

Solutions: UV-vis spectra were recorded on a Thermo Scientific instrument, model: Evolution 201. (See Sample preparation: solutions)

Film: UV-vis spectra were recorded on a Thermo Scientific instrument, model: Evolution 201. (See Sample preparation, film: spin-coating)

Photoluminescence Spectroscopy and TCSPC

Steady-state emission spectroscopy was conducted with a Horiba Scientific fluorescence spectrometer, model: Fluoro-Max-4, equipped with a 150 W xenon arc lamp, excitation and emission monochromators and a Hamamatsu R928 photomultiplier tube, and also a TCSPC option. Emission and excitation spectra were corrected by means of standard correction curves.

The emission decay times were likewise measured with this system using the TCSPC method with the FM-2013 accessories and a TCSPC hub from Horiba Yvon Jobin. Excitation sources: NanoLED 370 (wavelength: 371 nm, pulse duration: 1.1 ns), NanoLED 290 (wavelength: 294 nm, pulse duration: <1 ns), SpectraLED 310 (wavelength: 314 nm), SpectraLED 355 (wavelength: 355 nm).

The evaluation (exponential fitting) was effected with the DataStation software package and the DAS 6 evaluation software. The fit was reported by the chi-squared method $$c^2 = \sum_{k=1}^{i} \frac{(e_i - o_i)^2}{e_i}$$

with $e_i$: parameter predicted by the fit and $o_i$: parameter measured.

Determination of Quantum Efficiency

The photoluminescence quantum yield (PLQY) was measured by means of an Absolute PL Quantum Yield Measurement C9920-03G system from Hamamatsu Photonics. This consists of a 150 W xenon gas discharge lamp, automatically adjustable Czerny-Turner monochromators (250-950 nm) and an Ulbricht sphere with highly reflective Spectralon coating (a Teflon derivative), connected via a glass fibre cable to a PMA-12 multichannel detector with a BT (backthinned) CCD chip having 1024×122 pixels (size 24×24 μm). The quantum efficiency and the CIE coordinates were evaluated with the aid of the U6039-05 software, version 3.6.0. for G9920-OXG (PMA-12). The emission maximum is reported in nm, the quantum yield Φ in %, and the CIE colour coordinates as x,y values.

The PLQY was determined for polymer s, solutions and powder samples by the following protocol:
1) Performance of quality assurance: The reference material used is anthracene in ethanol with known concentration.
2) Determining the excitation wavelength: First of all, the absorption maximum of the organic molecule was determined and it was excited therewith.
3) Performance of sample analysis: The absolute quantum yield of degassed solutions and films was determined under a nitrogen atmosphere. The calculation was effected within the system according to the following equation:

$$\Phi_{PL} = \frac{n_{photon}, \text{emitted}}{n_{photon}, \text{absorbed}} = \frac{\int \frac{\lambda}{hc}[Int^{Sample}_{emitted}(\lambda) - Int^{Sample}_{absorbed}(\lambda)]d\lambda}{\int \frac{\lambda}{hc}[Int^{Reference}_{emitted}(\lambda) - Int^{Reference}_{absorbed}(\lambda)]d\lambda}$$

with the photon count $n_{photon}$ and the intensity Int.

Production and Characterization of Organic Electroluminescent Devices from the Gas Phase With the organic molecules according to the invention, it is possible to create OLED devices by means of vacuum sublimation methodology. If a layer contains two or more components, the ratio of these is reported in percent by mass.

These as yet unoptimized OLEDs can be characterized in a standard manner; for this purpose, the electroluminescent spectra, the external quantum efficiency (measured in %) as a function of brightness, calculated from the light detected by the photodiode, and the current are recorded. The lifetime of the OLEDs can be determined from the plot of the electroluminescence spectra against time. The LT50 value reported corresponds here to the time at which the luminance has dropped to 50% of the starting value. Analogously, the LT70 value corresponds to the time at which the luminance has dropped to 70% of the starting value.

Example 1

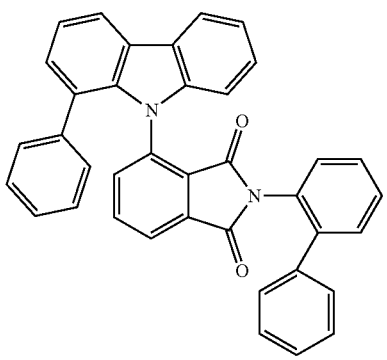 [SMILES: O=C1c2cccc(-n3c4ccccc4c4cccc(-c5ccccc5)c43)c2C(=O)N1c1ccccc1-c1ccccc1]

FIG. 1 shows the emission spectrum of Example 1 (10% in PMMA). The emission maximum is at 487 nm. The photoluminescence quantum yield (PLQY) is 61% and the full width at half maximum (FWHM) is 97 nm (0.49 eV). The emission lifetime is 3.8 μs.

Example 2

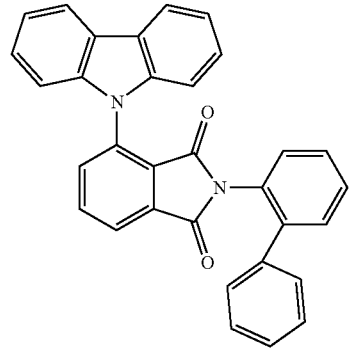 [SMILES: O=C1c2cccc(-n3c4ccccc4c4ccccc43)c2C(=O)N1c1ccccc1-c1ccccc1]

Figure 2:
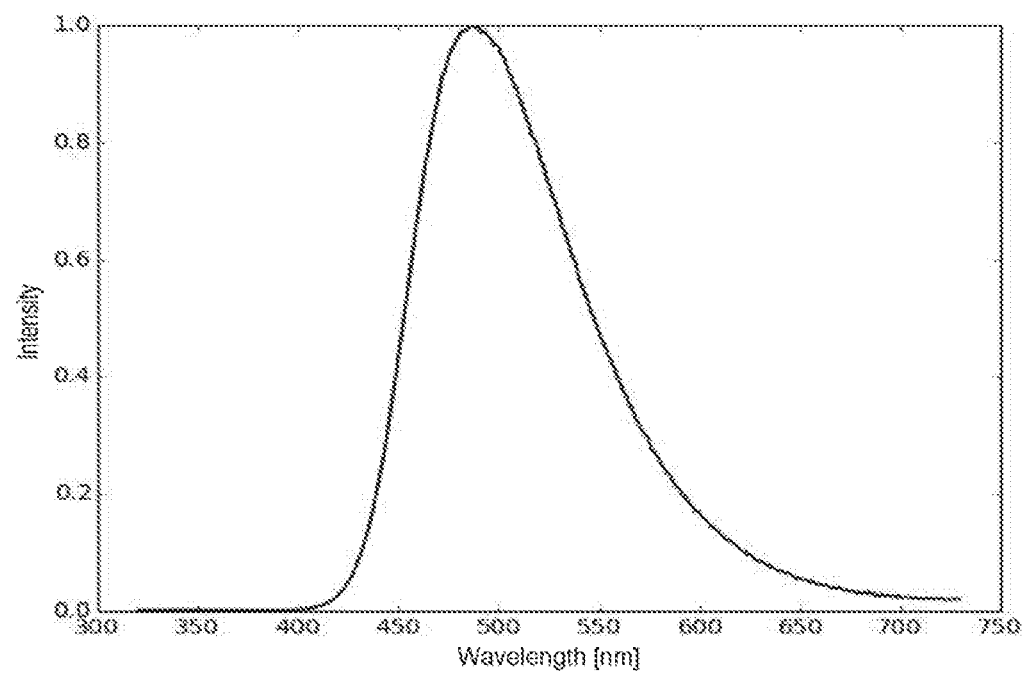
FIG. 2 is an emission spectrum of Example 2 (10% in PMMA).

FIG. 2 shows the emission spectrum of Example 2 (10% in PMMA). The emission maximum is at 487 nm. The photoluminescence quantum yield (PLQY) is 57% and the full width at half maximum (FWHM) is 95 nm (0.49 eV). The emission lifetime is 7.2 μs.

Example 3

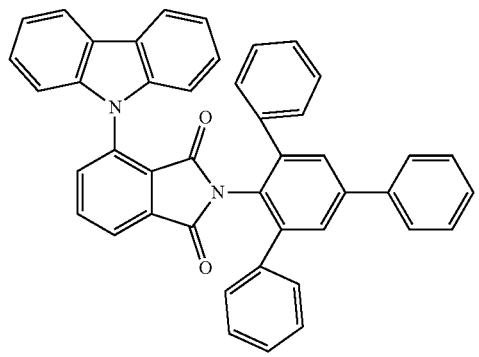 [SMILES: O=C1c2cccc(-n3c4ccccc4c4ccccc43)c2C(=O)N1c1c(-c2ccccc2)cc(-c2ccccc2)cc1-c1ccccc1]

Figure 3:
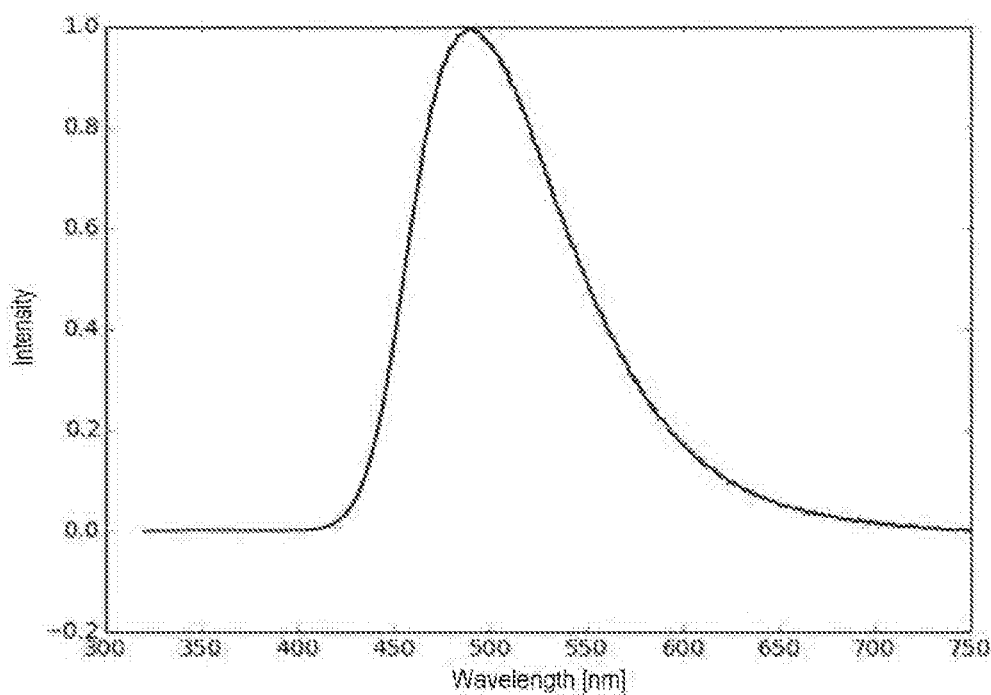
FIG. 3 is an emission spectrum of Example 3 (10% in PMMA).

FIG. 3 shows the emission spectrum of Example 3 (10% in PMMA). The emission maximum is at 490 nm. The photoluminescence quantum yield (PLQY) is 59% and the full width at half maximum (FWHM) is 96 nm (0.48 eV). The emission lifetime is 6.4 μs.

Example 4

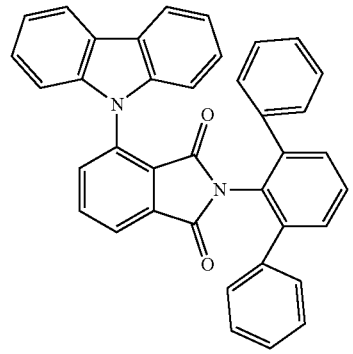 [SMILES: O=C1c2cccc(-n3c4ccccc4c4ccccc43)c2C(=O)N1c1c(-c2ccccc2)cccc1-c1ccccc1]

Figure 4:
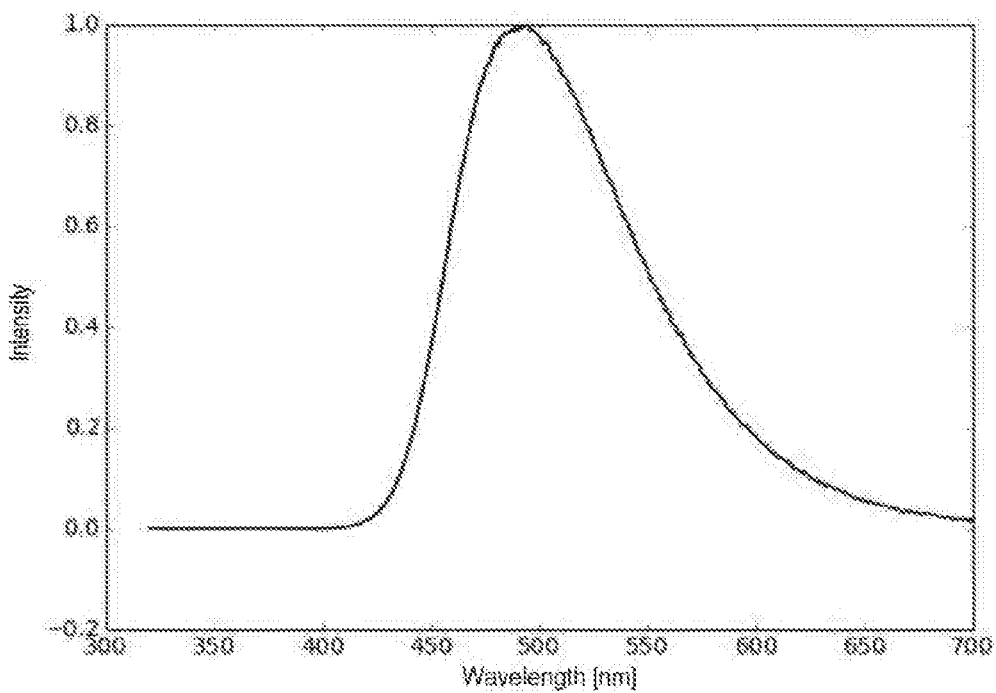
FIG. 4 is an emission spectrum of Example 4 (10% in PMMA).

FIG. 4 shows the emission spectrum of Example 4 (10% in PMMA). The emission maximum is at 494 nm. The photoluminescence quantum yield (PLQY) is 61% and the full width at half maximum (FWHM) is 95 nm (0.47 eV). The emission lifetime is 5.9 μs.

Example 5

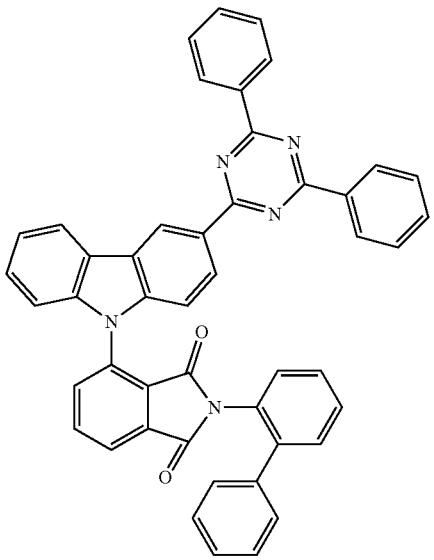 [SMILES: O=C1c2cccc(-n3c4ccccc4c4cc(-c5nc(-c6ccccc6)nc(-c6ccccc6)n5)ccc43)c2C(=O)N1c1ccccc1-c1ccccc1]

Example 5 was prepared according to GM4 proceeding from 3-(3-bromocarbazolyl)-N-(o-biphenyl)phthalimide in a yield of 66%. $^1$H NMR (500 MHz, chloroform-d): δ (ppm)=9.54 (dd, J=12.2, 1.6 Hz), 8.87-8.85 (m), 8.83-8.81 (m), 8.73 (dd, J=8.7, 1.7 Hz), 8.33-8.31 (m), 8.05 (td, J=7.5, 1.0 Hz), 7.98 (td, J=7.7, 3.1 Hz, 1H), 7.92 (dd, J=7.9, 1.1 Hz), 7.91 (dd, J=7.9, 1.1 Hz), 7.65-7.27 (m), 6.60-6.57 (m). The product consists of two rotamers, the NMR signals of which obscure one another.

Figure 5:
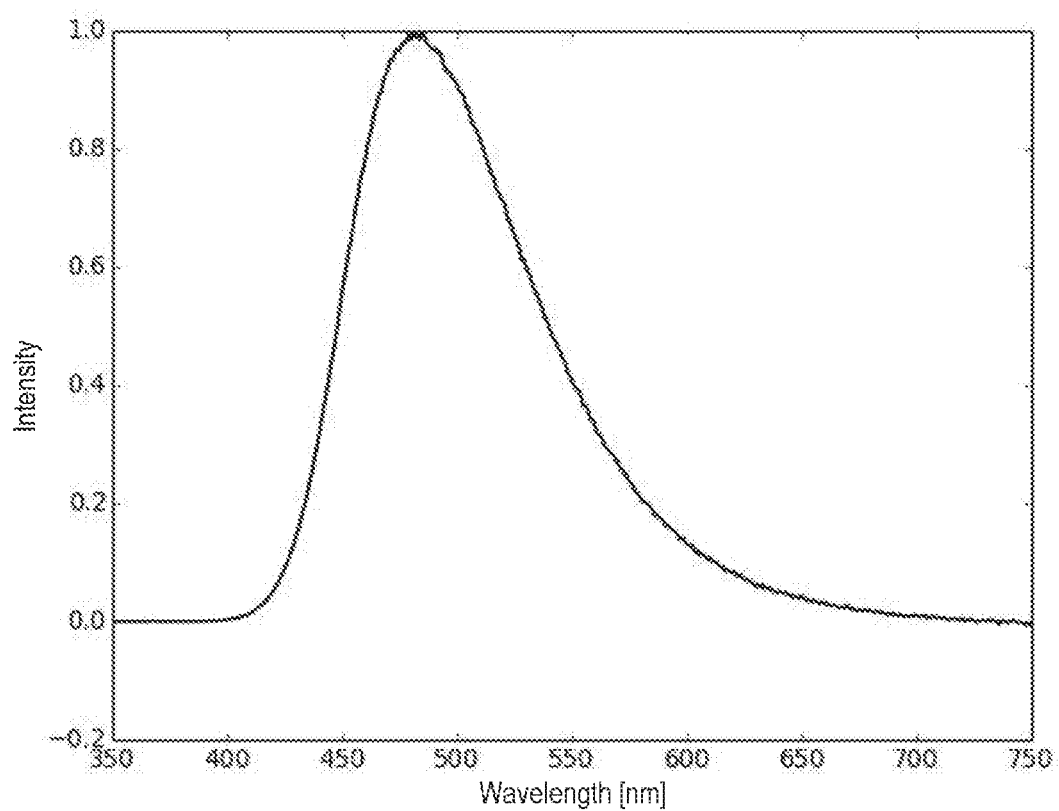
FIG. 5 is an emission spectrum of Example 5 (10% in PMMA).

FIG. 5 shows the emission spectrum of Example 5 (10% in PMMA). The emission maximum is at 481 nm. The photoluminescence quantum yield (PLQY) is 68% and the full width at half maximum (FWHM) is 92 nm (0.47 eV). The emission lifetime is 5.7 μs.

Example 6

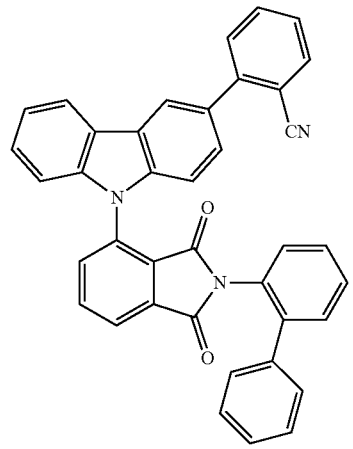 [SMILES: N#Cc1ccccc1-c1ccc2c(c1)c1ccccc1n2-c1cccc2c1C(=O)N(c1ccccc1-c1ccccc1)C2=O]

Example 6 was prepared according to GM4 proceeding from 3-(3-bromocarbazolyl)-N-(o-biphenyl)phthalimide in a yield of 42%, The emission spectrum of Example 6 (10% in PMMA) was recorded. The emission maximum is at 489 nm. The photoluminescence quantum yield (PLQY) is 62% and the full width at half maximum (FWHM) is 97 nm (0.48 eV). The emission lifetime is 5.9 μs.

Example 7

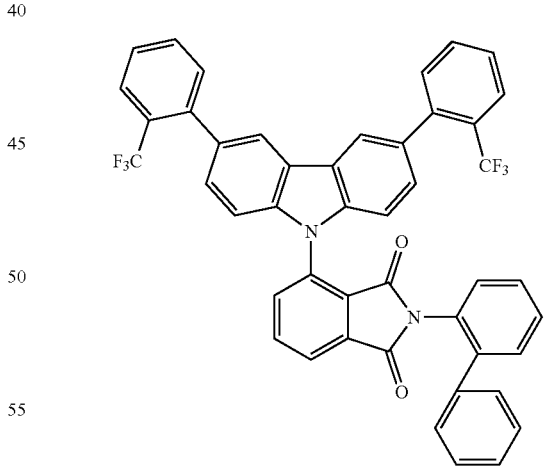

Example 7 was prepared according to GM5 from 3-(3,6-dibromocarbazolyl)-N-(o-biphenyl)phthalimide and 2-trifluoromethylphenylboronic acid in a yield of 80%.

The emission spectrum of Example 7 (10% in PMMA) was measured. The emission maximum is at 483 nm. The photoluminescence quantum yield (PLQY) is 68% and the full width at half maximum (FWHM) is 93 nm (0.47 eV),

Example 8

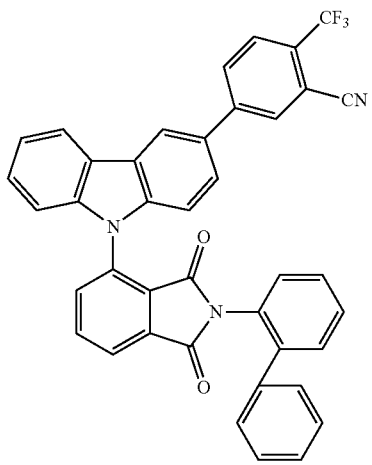 [SMILES: N#Cc1cc(-c2ccc3c(c2)c2ccccc2n3-c2cccc3c2C(=O)N(c2ccccc2-c2ccccc2)C3=O)ccc1C(F)(F)F]

Example 8 was prepared according to GM4 by the conversion of 3-(3-bromocarbazolyl)-N-(o-biphenyl)phthalimide to the corresponding bis(boronic acid pinacol ester) and subsequent reaction with 3-bromo-6-trifluoromethylbenzonitrile in a yield of 64%.

The emission spectrum of Example 8 (10% in PMMA) was measured. The emission maximum is at 491 nm. The photoluminescence quantum yield (PLQY) is 65% and the full width at half maximum (FWHM) is 96 nm (0.48 eV).

Example 9

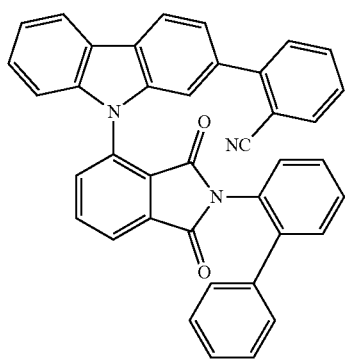 [SMILES: N#Cc1ccccc1-c1ccc2c3ccccc3n(-c3cccc4c3C(=O)N(c3ccccc3-c3ccccc3)C4=O)c2c1]

Example 9 was prepared according to GM4 by the conversion of 3-(2-bromocarbazolyl)-N-(o-biphenyl)phthalimide to the corresponding bis(boronic acid pinacol ester) and subsequent reaction with 2-bromobenzonitrile in a yield of 97%.

The emission spectrum of Example 9 (10% in PMMA) was recorded. The emission maximum is at 476 nm. The photoluminescence quantum yield (PLQY) is 61% and the full width at half maximum (FWHM) is 91 nm (0.48 eV).

Example 10

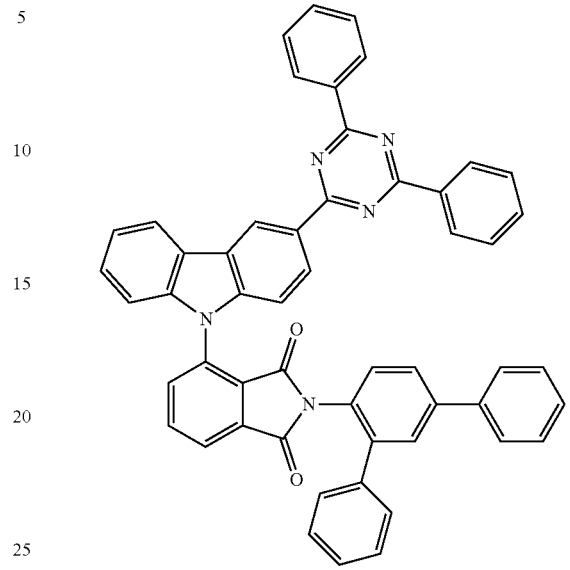

Example 10 was prepared according to GM4 by the conversion of 3-(2-bromocarbazolyl)-N-(o-(meta-terphenyl))phthalimide to the corresponding bis(boronic acid pinacol ester) and subsequent reaction with chlorodiphenyltriazine in a yield of 44%.

The emission spectrum of Example 10 (10% in PMMA) was recorded. The emission maximum is at 486 nm. The photoluminescence quantum yield (PLQY) is 65% and the full width at half maximum (FWHM) is 93 nm (0.47 eV). The emission lifetime is 5.6 μs.

Example 11

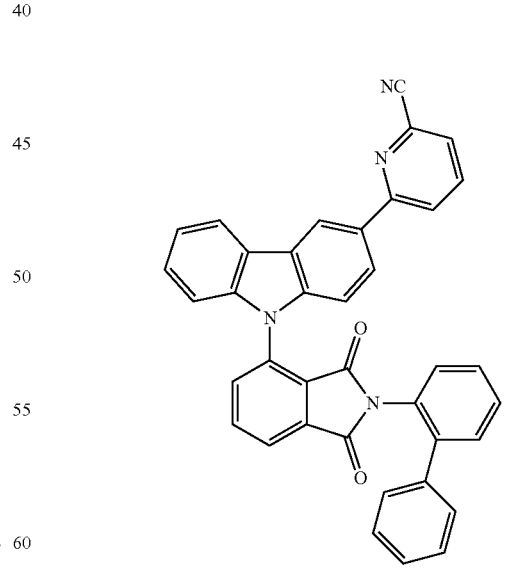

Example 11 was prepared according to GM4 by the conversion of 3-(2-bromocarbazolyl)-N-(o-biphenyl)phthalimide to the corresponding bis(boronic acid pinacol ester) and subsequent reaction with 2-bromo-6-cyanopyridine in a yield of 13%.

The emission spectrum of Example 11 (10% in PMMA) was recorded. The emission maximum is at 489 nm. The photoluminescence quantum yield (PLQY) is 61% and the full width at half maximum (FWHM) is 97 nm (0.48 eV).

Example 12

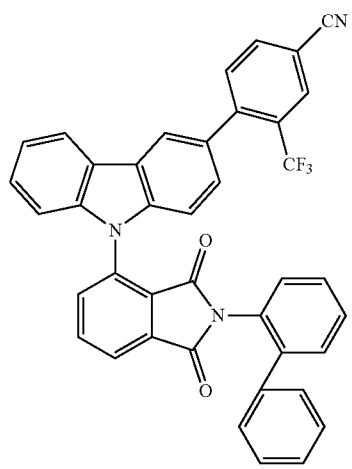 [SMILES: N#Cc1ccc(-c2ccc3c(c2)c2ccccc2n3-c2cccc3c2C(=O)N(c2ccccc2-c2ccccc2)C3=O)c(C(F)(F)F)c1]

Example 12 was prepared according to GM4 by the conversion of 3-(3-bromocarbazolyl)-N-(o-biphenyl)phthalimide to the corresponding bis(boronic acid pinacol ester) and subsequent reaction with 4-bromo-3-trifluoromethylbenzonitrile in a yield of 94%.

The emission spectrum of Example 12 (10% in PMMA) was measured. The emission maximum is at 479 nm. The photoluminescence quantum yield (PLQY) is 63% and the full width at half maximum (FWHM) is 92 nm (0.46 eV).

Example 13

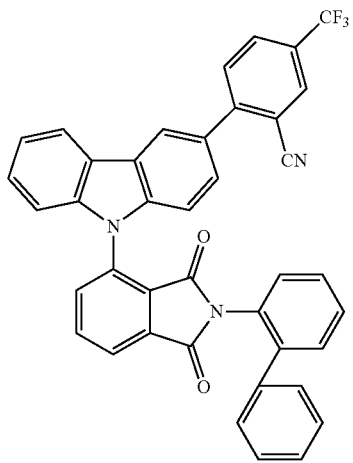 [SMILES: N#Cc1cc(C(F)(F)F)ccc1-c1ccc2c(c1)c1ccccc1n2-c1cccc2c1C(=O)N(c1ccccc1-c1ccccc1)C2=O]

Example 13 was prepared according to GM4 by the conversion of 3-(3-bromocarbazolyl)-N-(o-biphenyl)phthalimide to the corresponding bis(boronic acid pinacol ester) and subsequent reaction with 2-bromo-5-trifluoromethylbenzonitrile in a yield of 36%.

The emission spectrum of Example 13 (10% in PMMA) was measured. The emission maximum is at 475 nm. The photoluminescence quantum yield (PLQY) is 67% and the full width at half maximum (FWHM) is 91 nm (0.48 eV).

Example 14

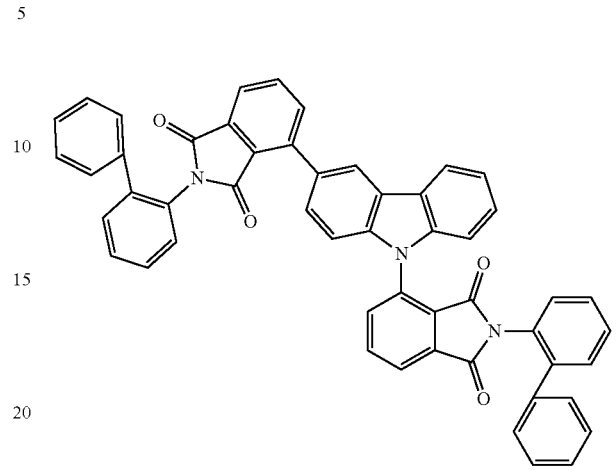

Example 14 was prepared according to GM4 by the conversion of 3-(3-bromocarbazolyl)-N-(o-biphenyl)phthalimide to the corresponding boronic acid pinacol ester and subsequent reaction with N-(o-biphenyl)phthalimido-3-chlorophthalimide in a yield of 45%.

The emission spectrum of Example 14 (10% in PMMA) was measured. The emission maximum is at 490 nm. The photoluminescence quantum yield (PLQY) is 61% and the full width at half maximum (FWHM) is 96 nm (0.48 eV).

Example 15

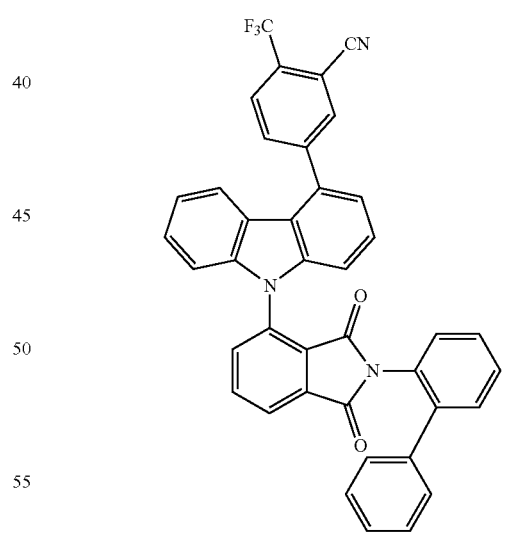

Example 15 was prepared according to GM4 by the conversion of 3-(4-bromocarbazolyl)-N-(o-biphenyl)phthalimide to the corresponding bis(boronic acid pinacol ester) and subsequent reaction with 3-bromo-6-trifluoromethylbenzonitrile in a yield of 40%.

The emission spectrum of Example 15 (10% in PMMA) was measured. The emission maximum is at 474 nm. The photoluminescence quantum yield (PLQY) is 61% and the full width at half maximum (FWHM) is 93 nm (0.48 eV).

Example 16

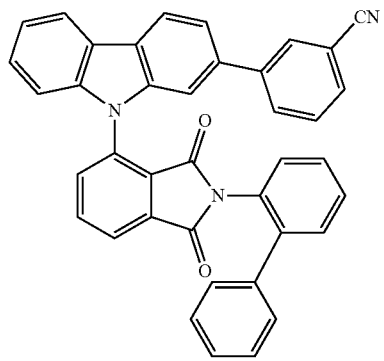 [SMILES: N#Cc1cccc(-c2ccc3c4ccccc4n(-c4cccc5c4C(=O)N(c4ccccc4-c4ccccc4)C5=O)c3c2)c1]

Example 16 was prepared according to GM5 from 3-(2-bromocarbazolyl)-N-(o-biphenyl)phthalimide and 3-cyanophenylboronic acid in a yield of 31%.

The emission spectrum of Example 16 (10% in PMMA) was measured. The emission maximum is at 474 nm. The photoluminescence quantum yield (PLAY) is 54% and the full width at half maximum (FWHM) is 93 nm (0.48 eV).

Example D1

Example 5 was tested in an OLED component ("component D1") with the following structure (proportion of the molecule according to the invention in the emission layer is reported in percent by mass):

| Layer | Thickness | D1 |
|---|---|---|
| 7 | 100 nm | Al |
| 6 | 2 nm | Liq |
| 5 | 40 nm | NBPhen |
| 4 | 20 nm | 5 (30%): mCBP |
| 3 | 10 nm | TCTA |
| 2 | 80 nm | NPB |
| 1 | 130 nm | ITO |
| Substrate | | glass |
| | Maximum values | at 1000 cd/m² | LT80 at 500 cd/m² |
| External quantum efficiency (EQE): | 8.9 ± 0.03% | 8.7 ± 0.02% | 72 h |

The emission maximum is at 486 nm; CIEx was determined as 0.24 and CIEy as 0.39 at 4.5 V.

Further Example Molecules

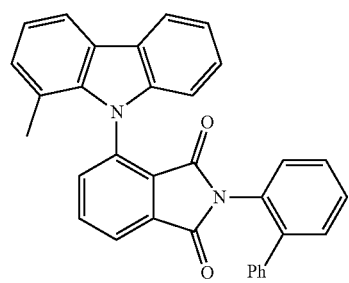

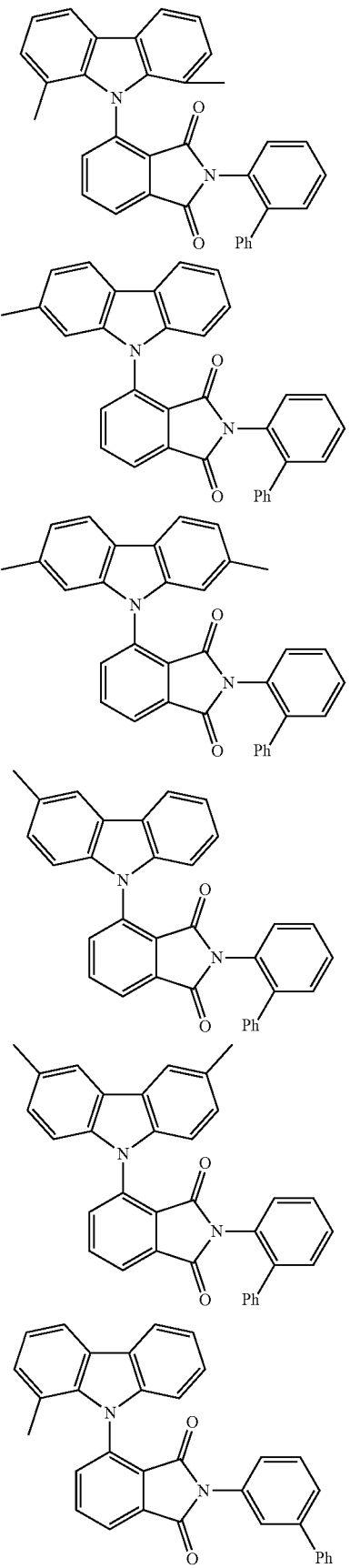

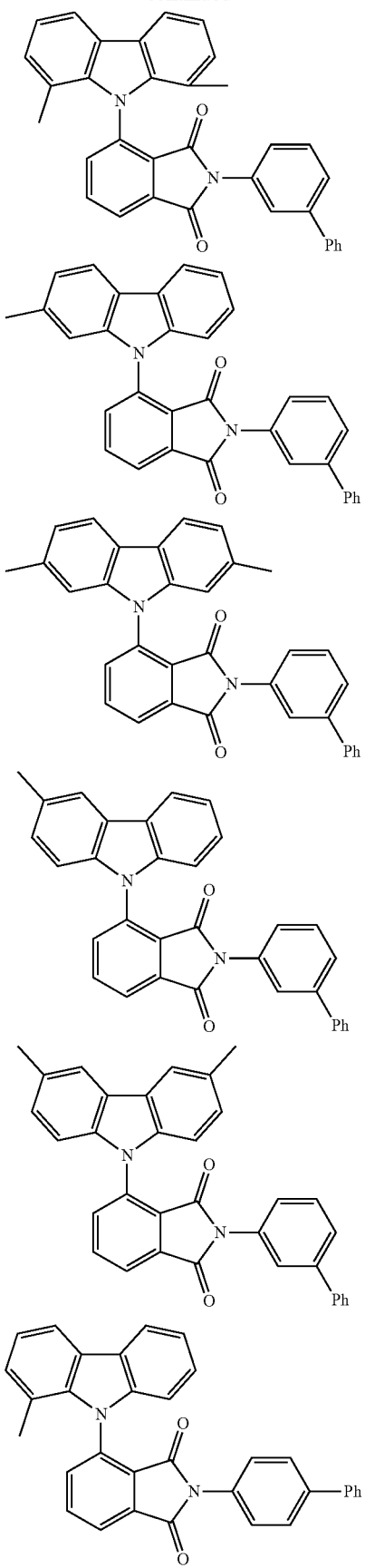
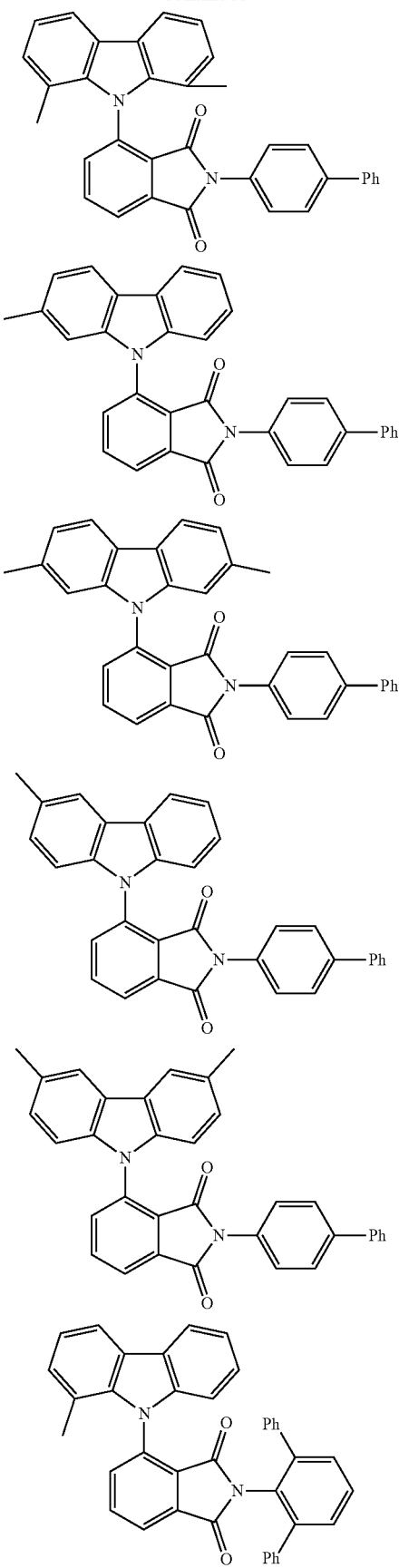

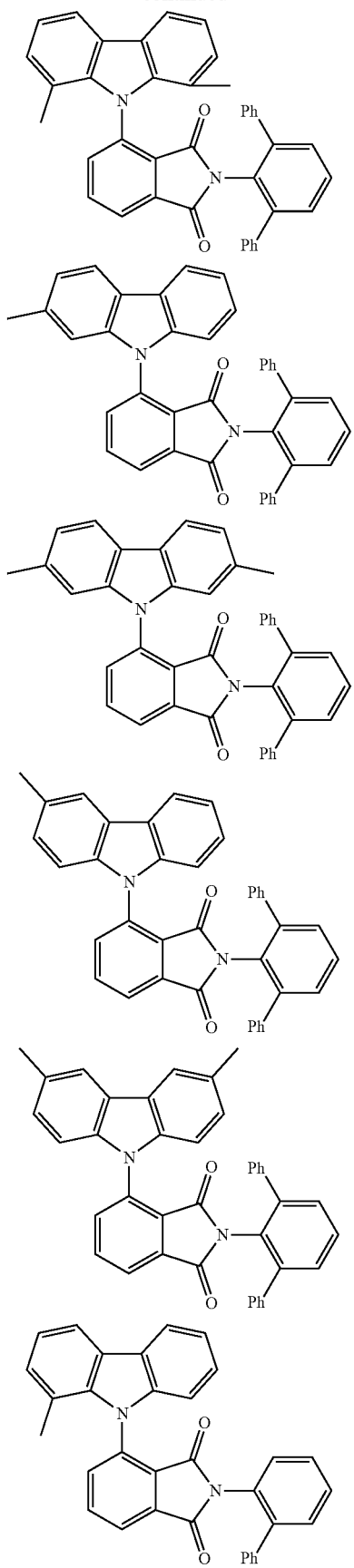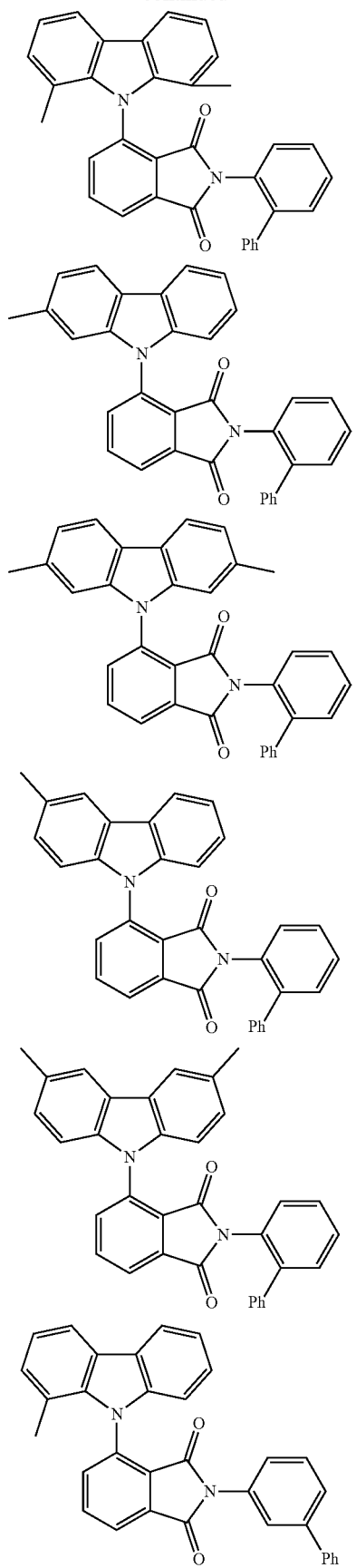

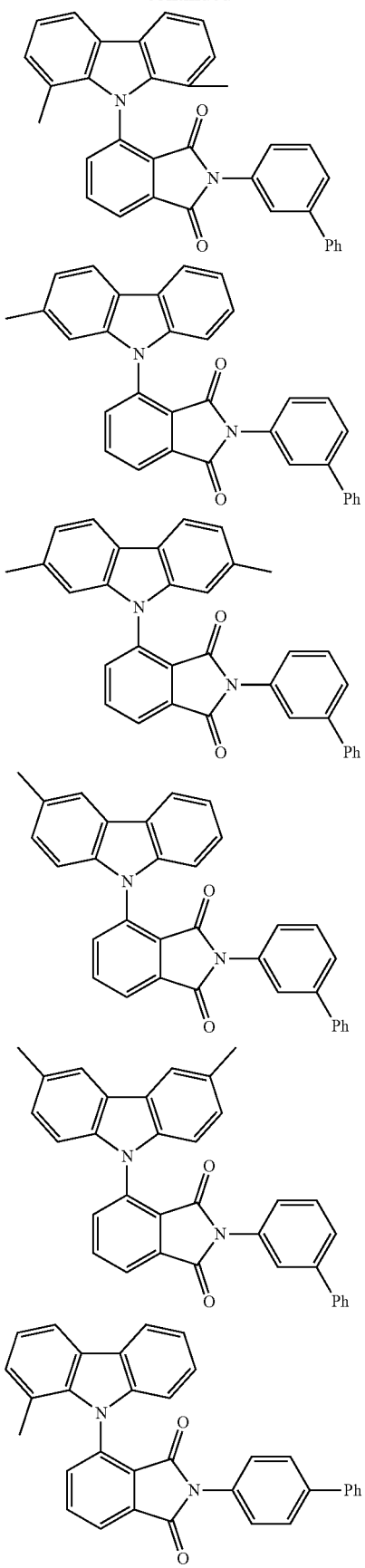
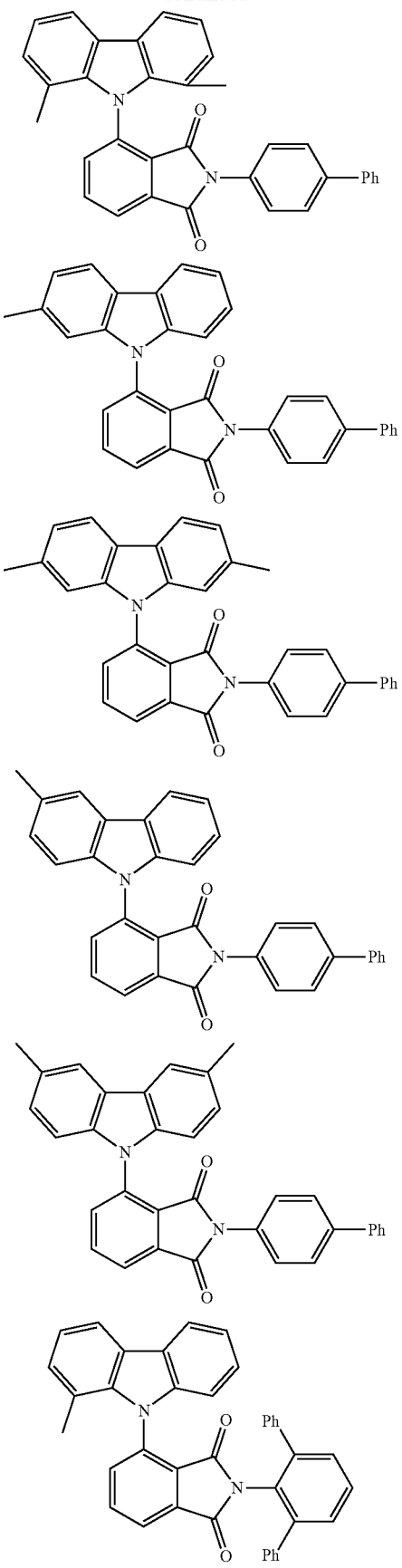

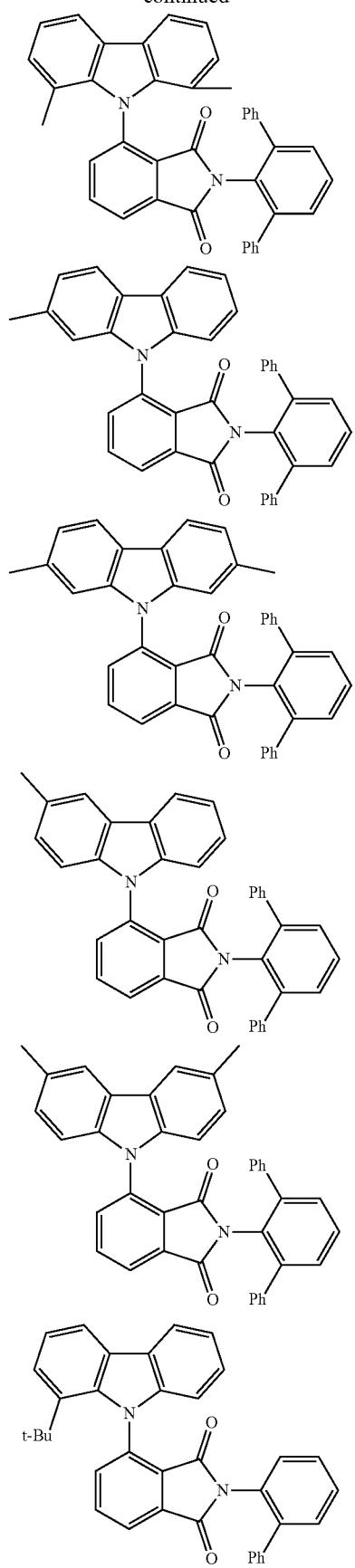
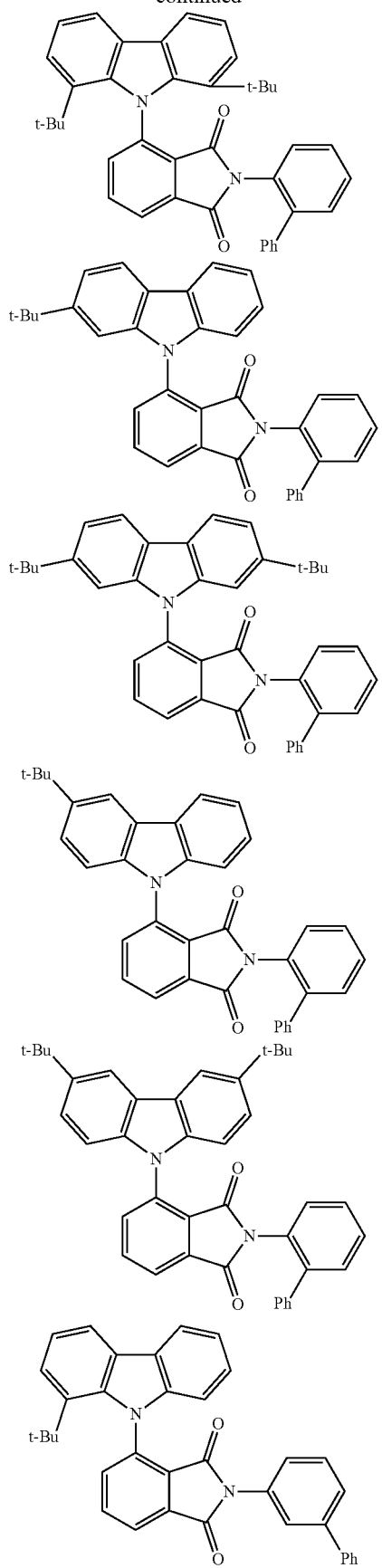

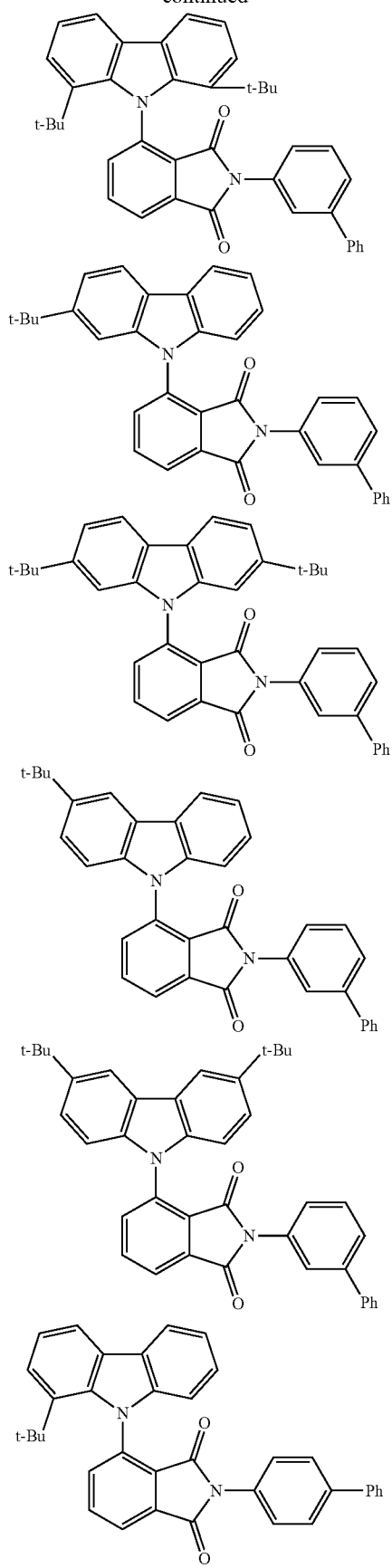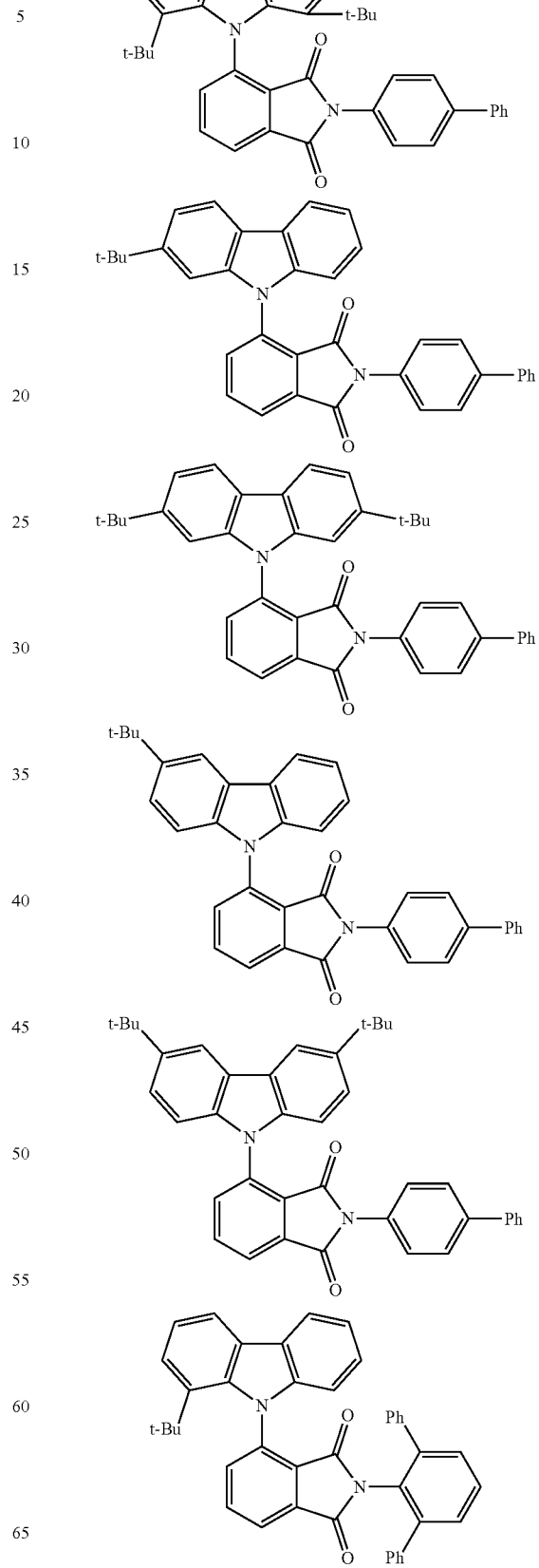

-continued
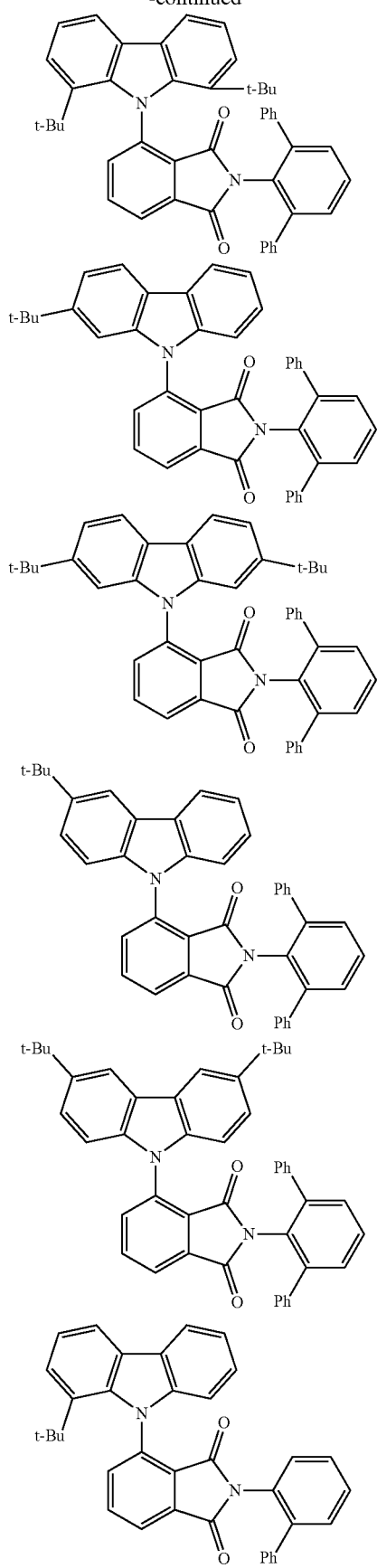
-continued
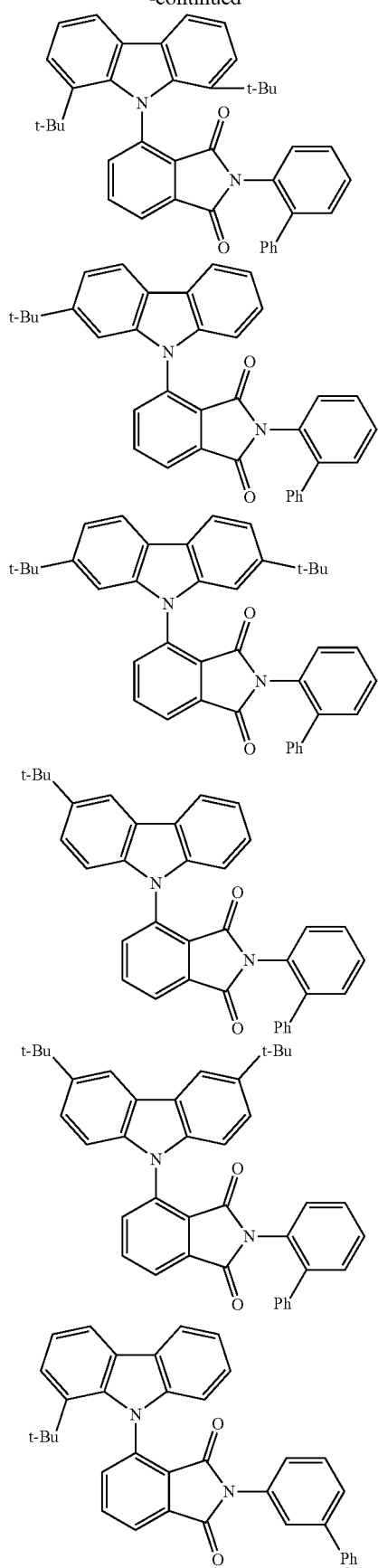

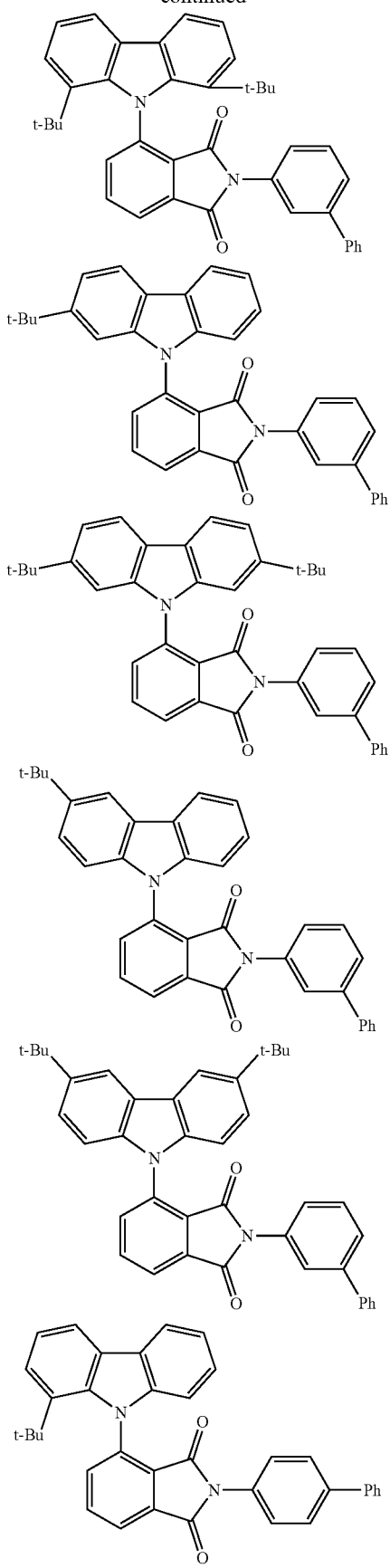
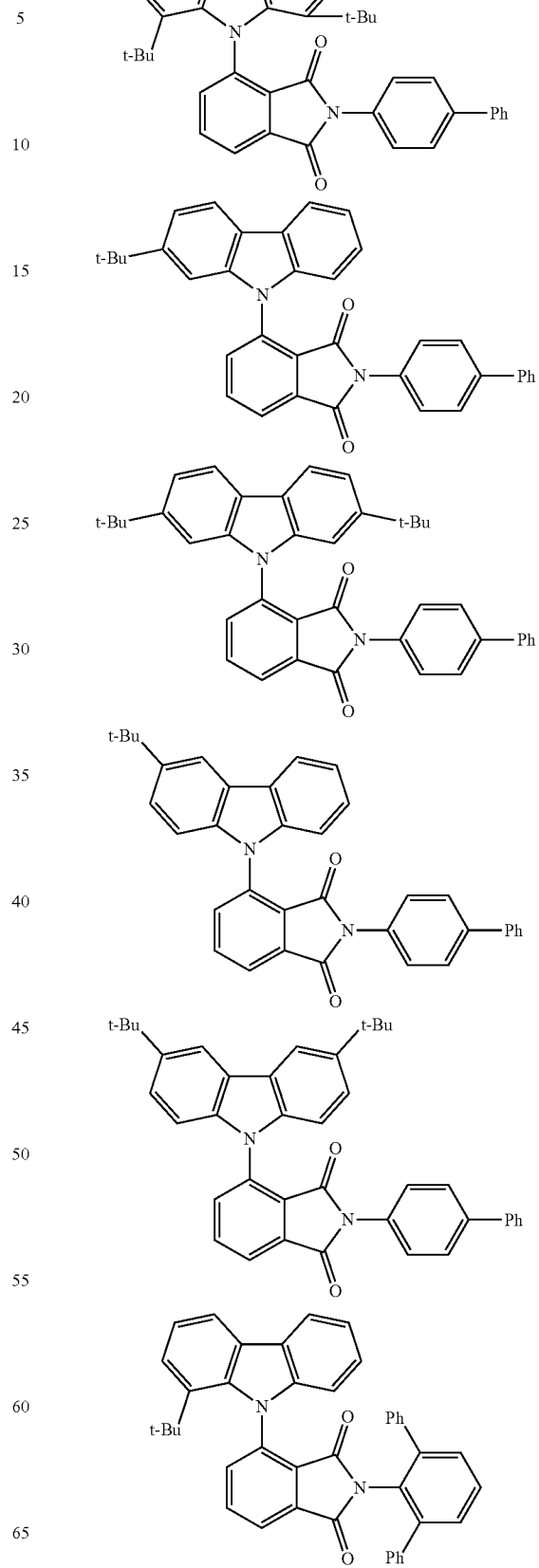

-continued
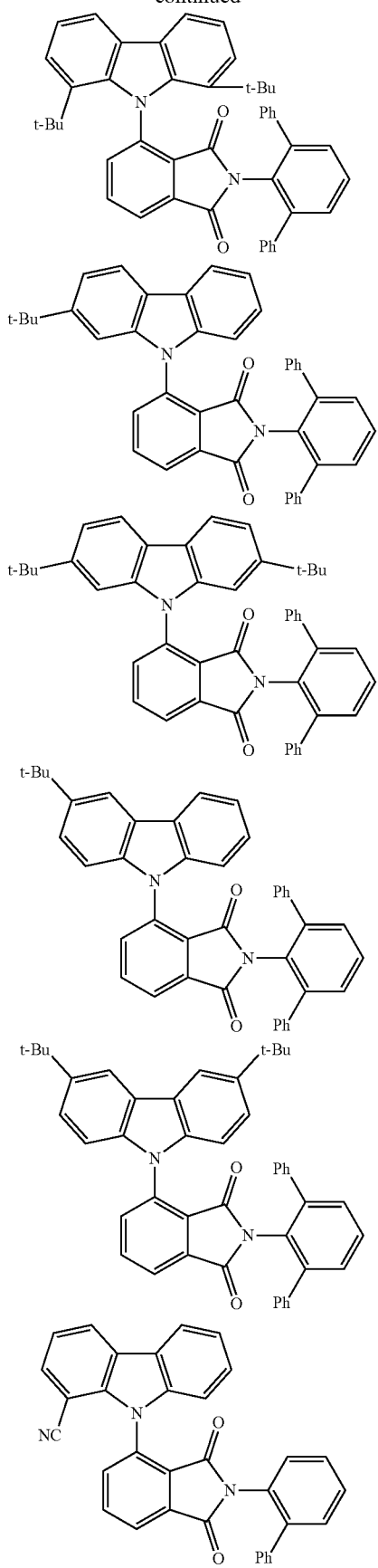
-continued
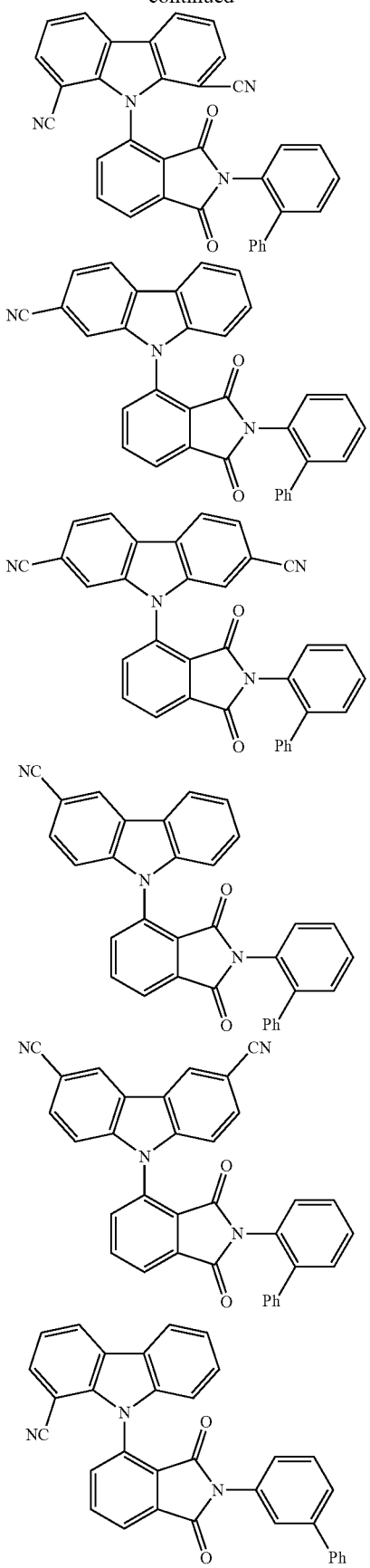

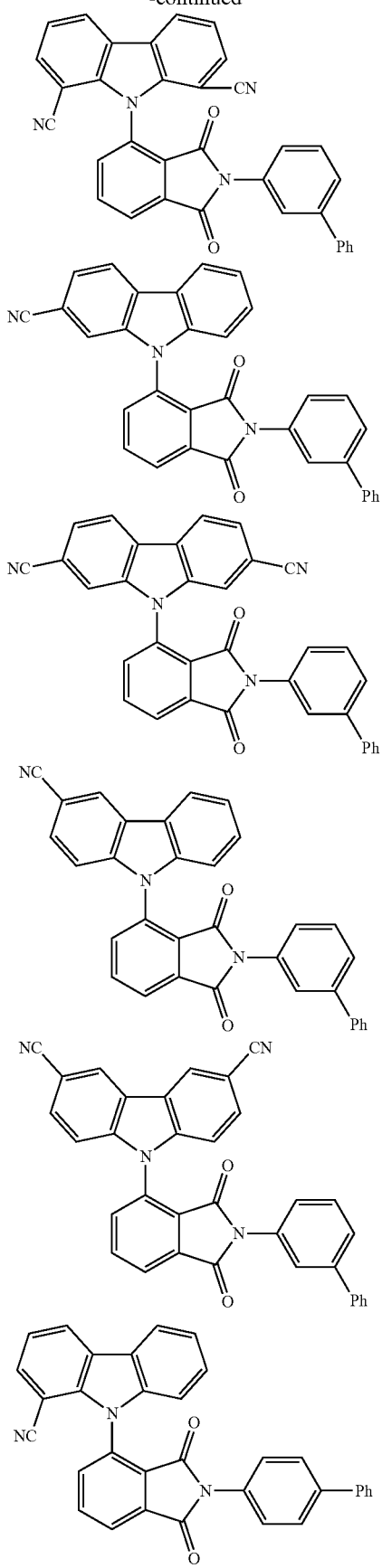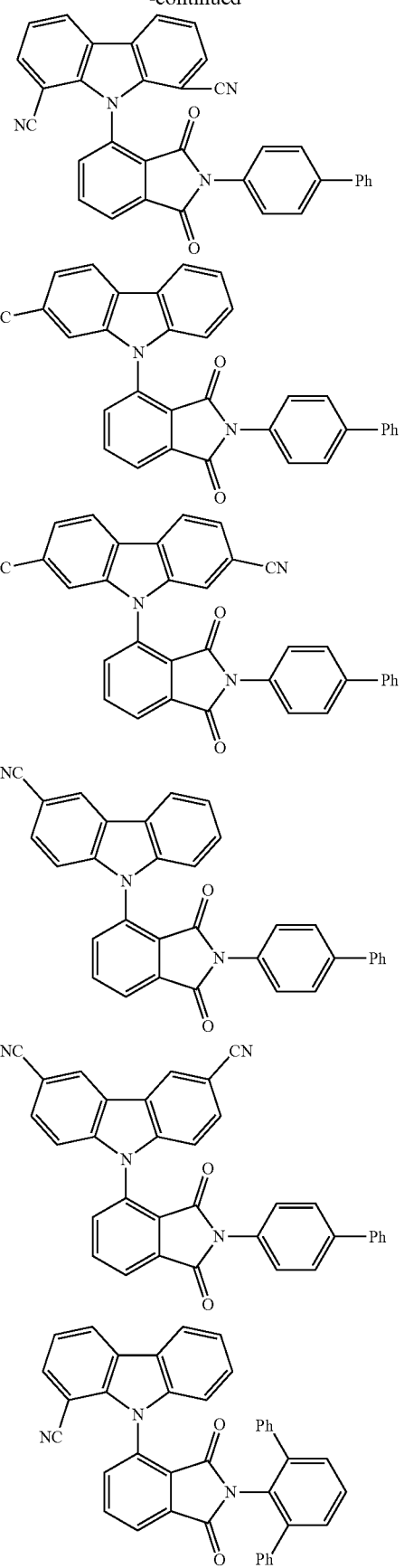

55
-continued
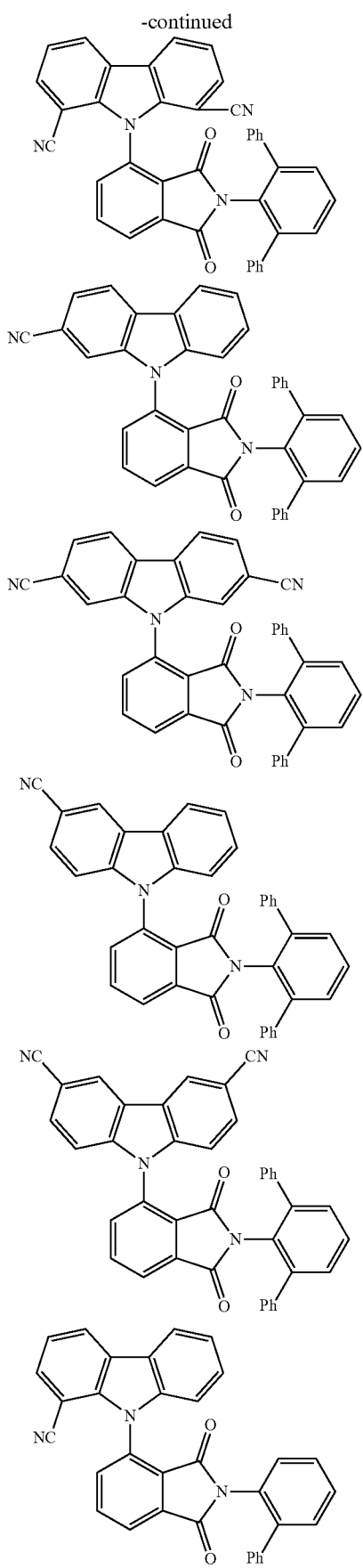
56
-continued
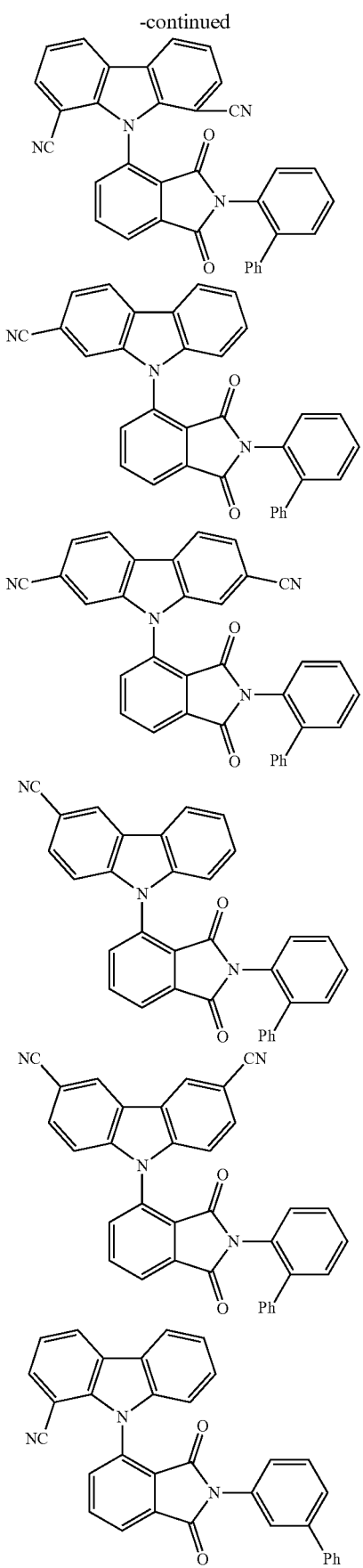

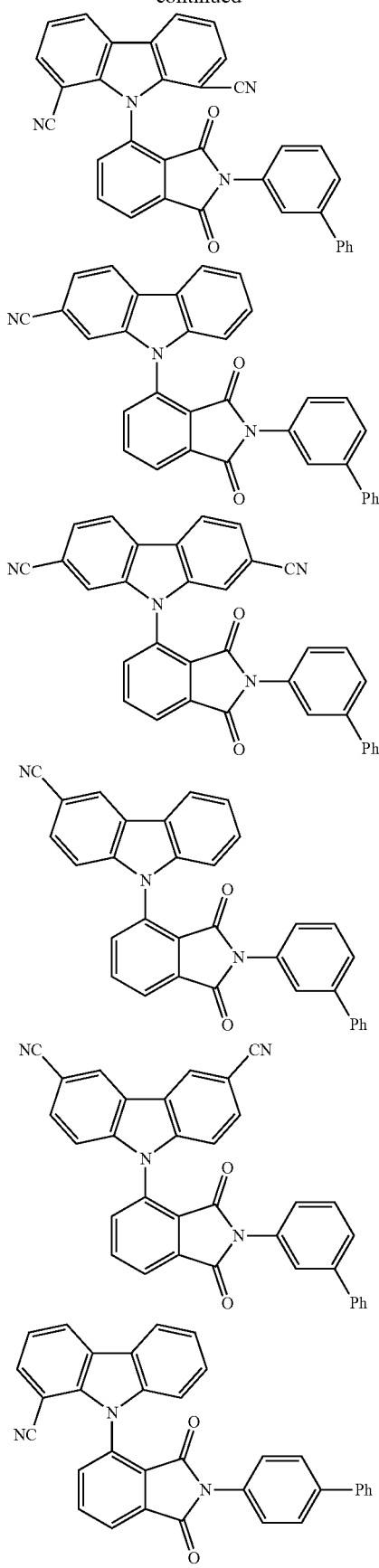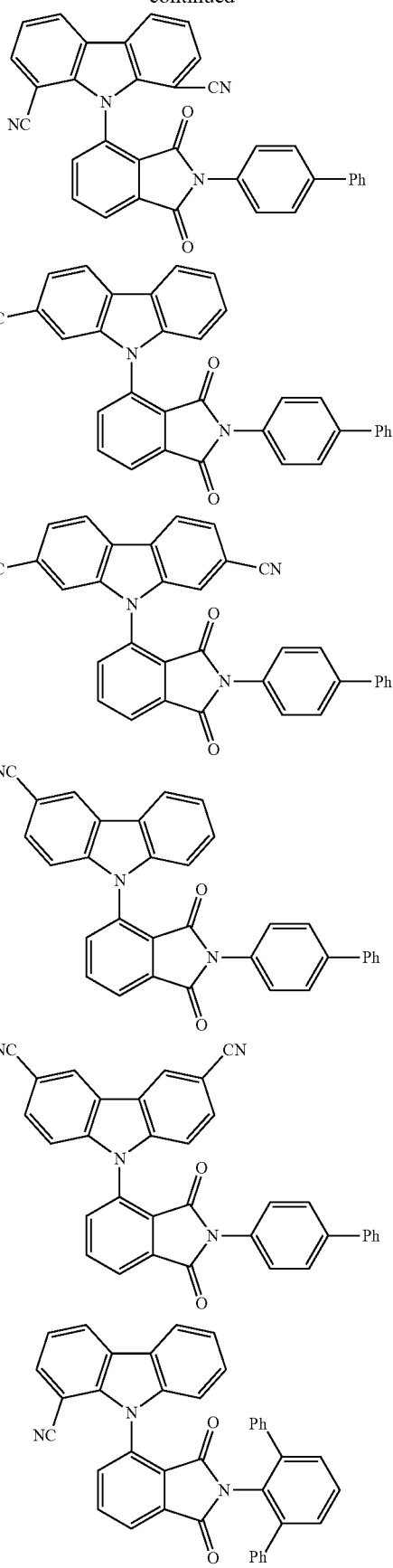

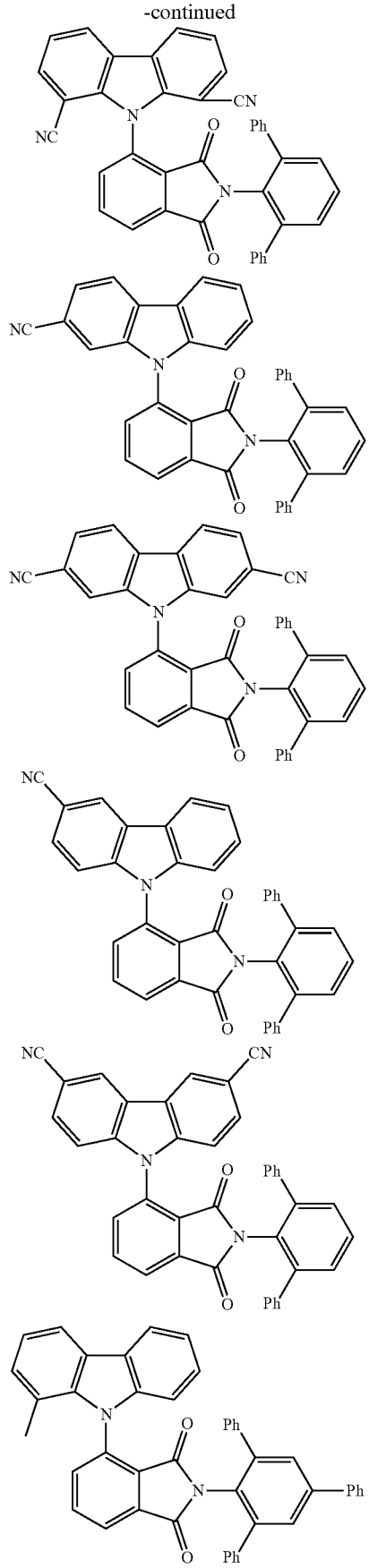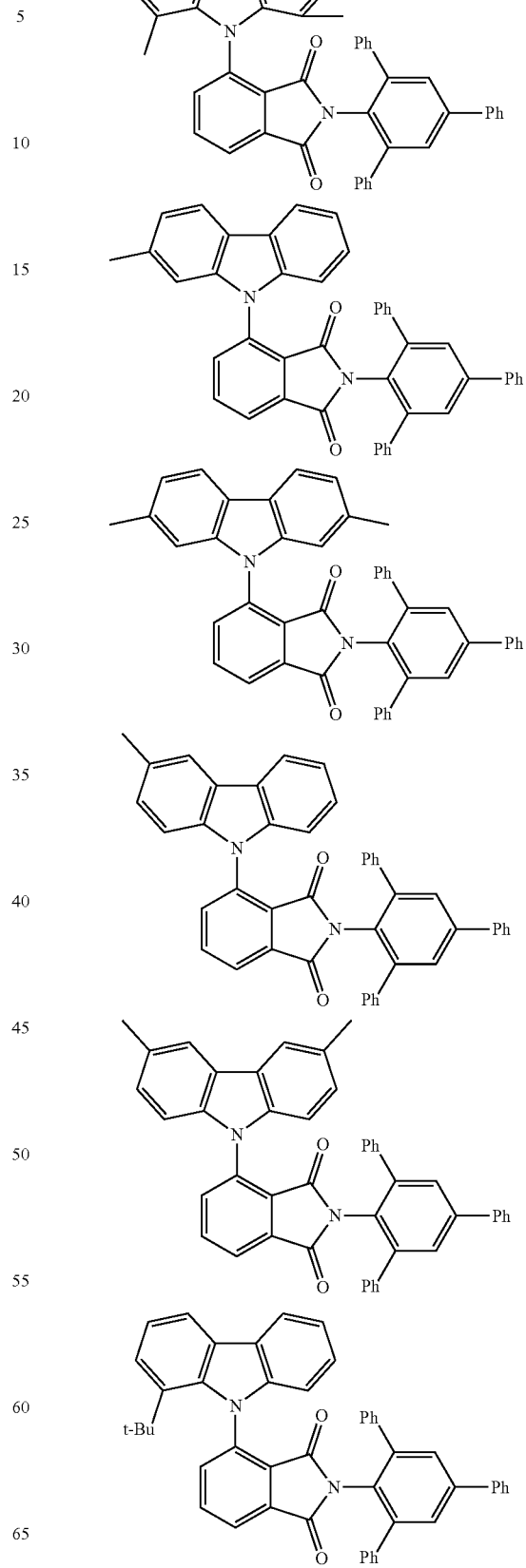

-continued
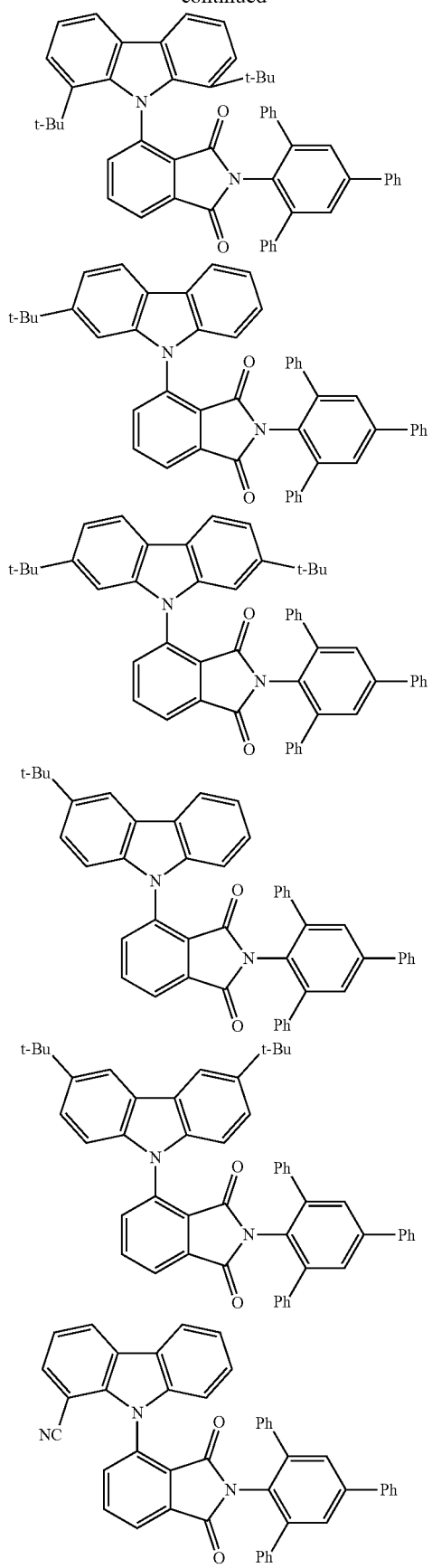
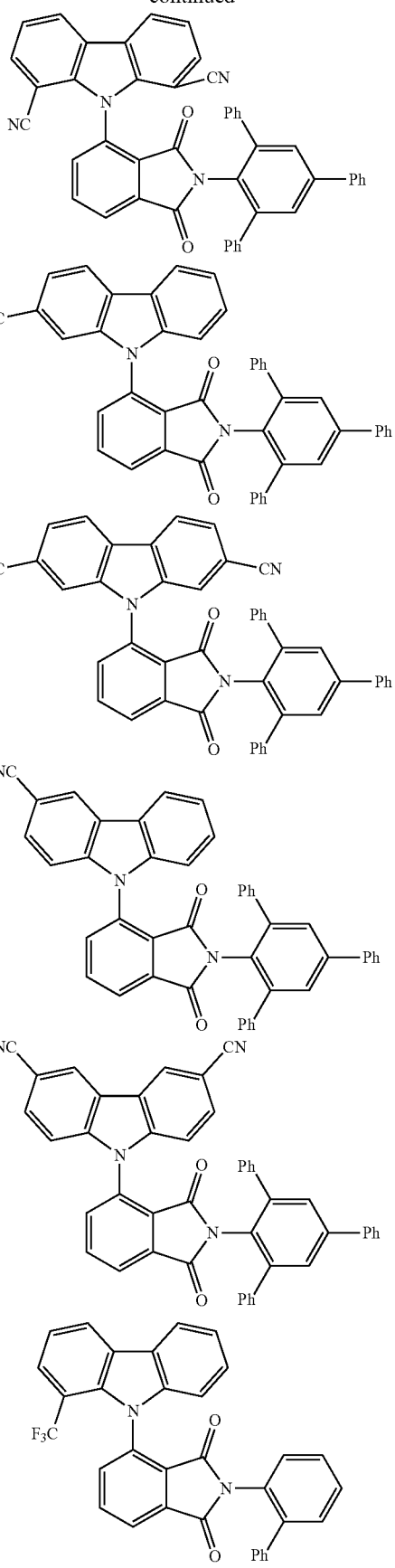

-continued
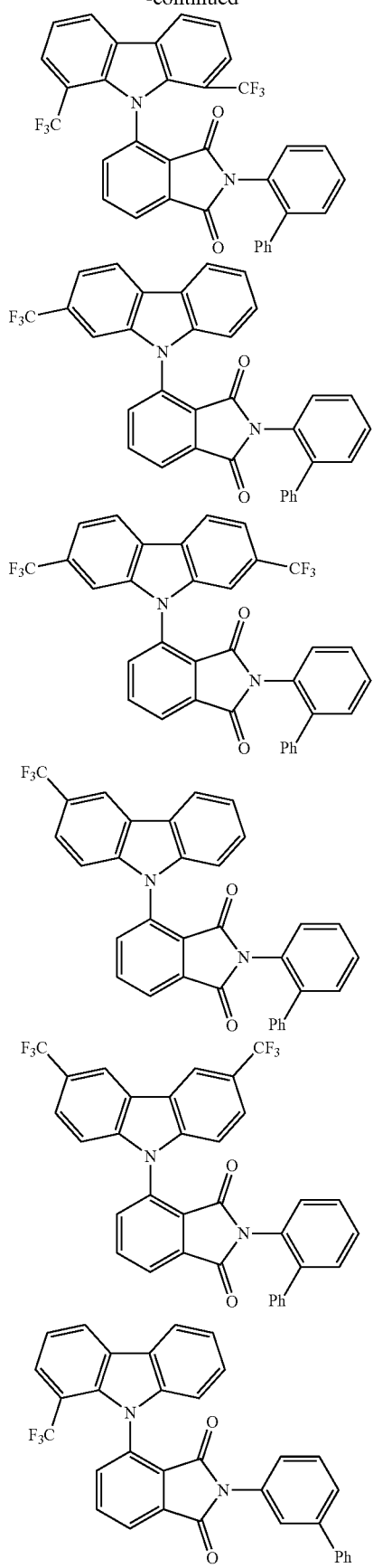
-continued
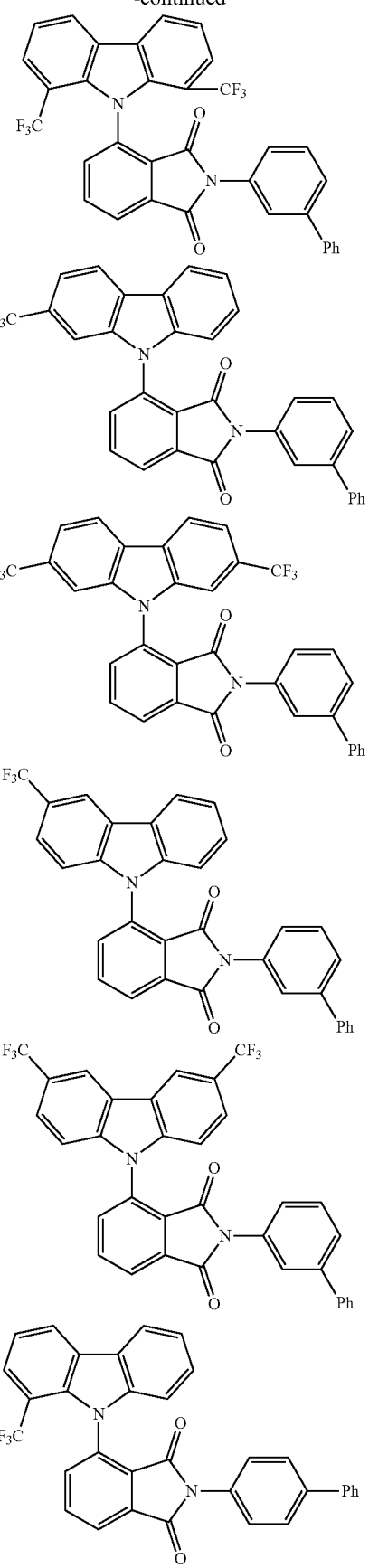

-continued
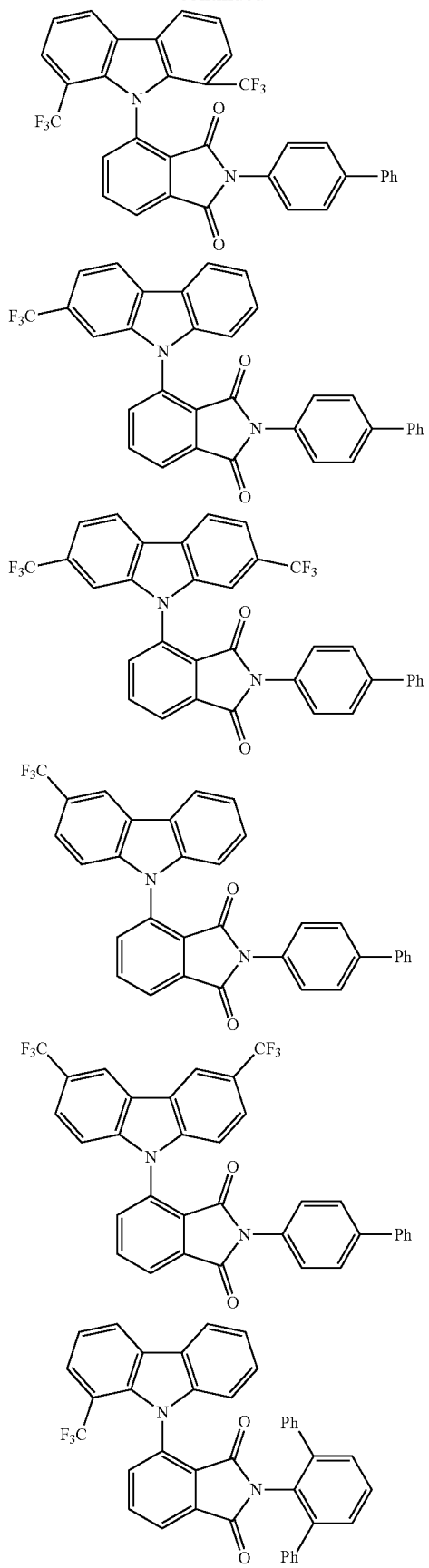
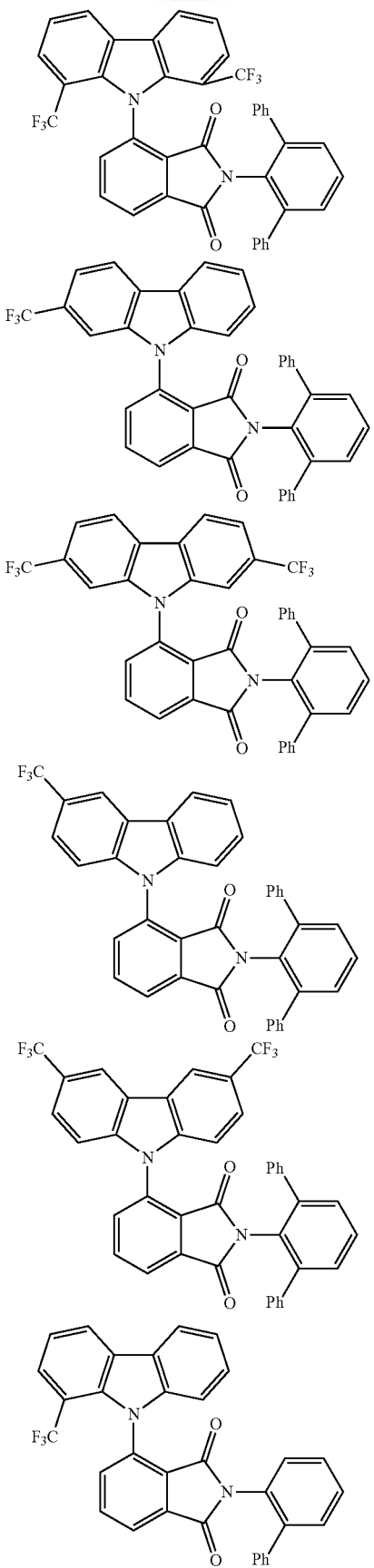

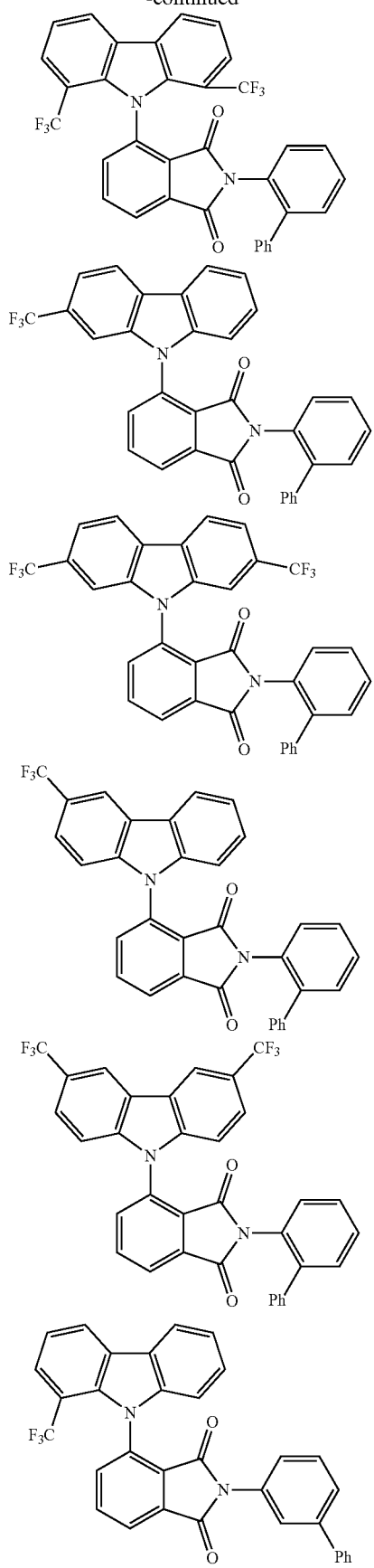
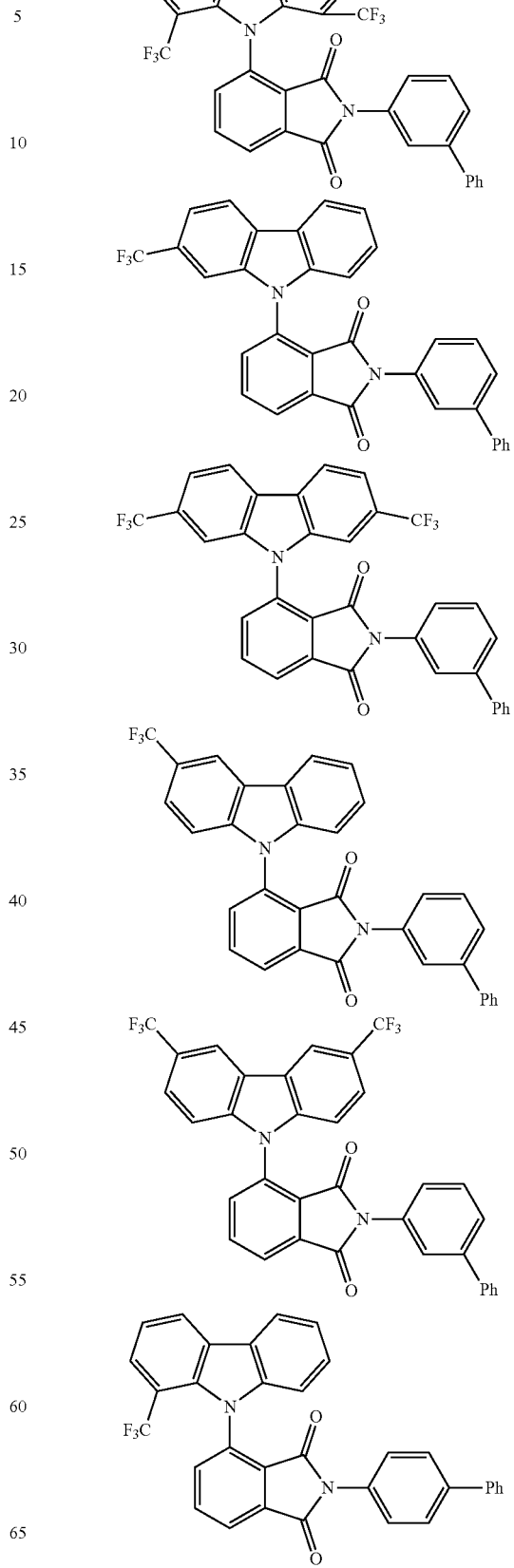

-continued
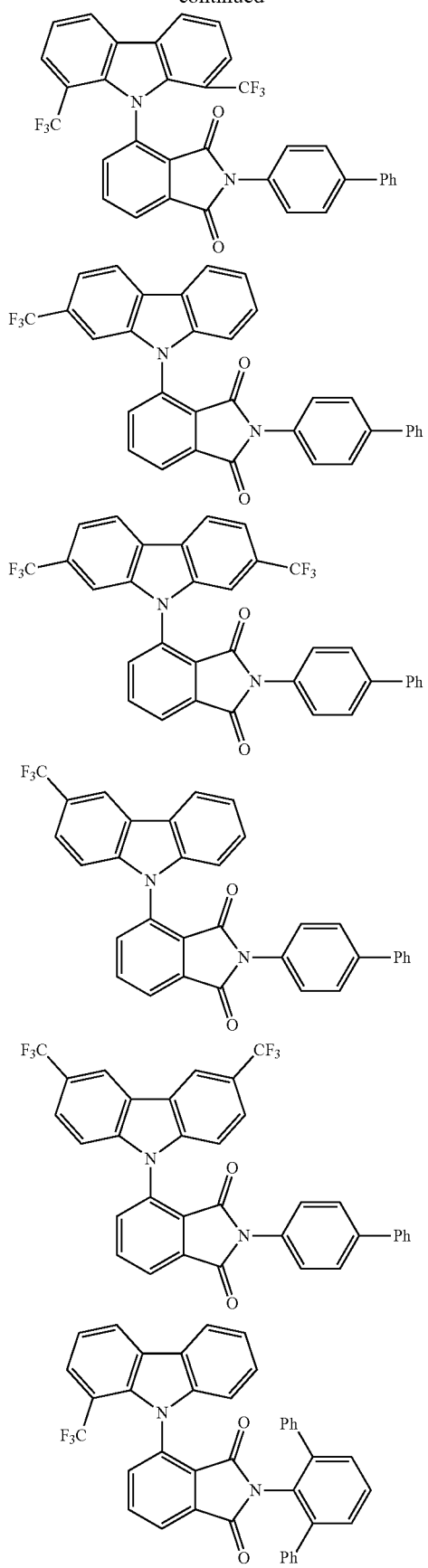
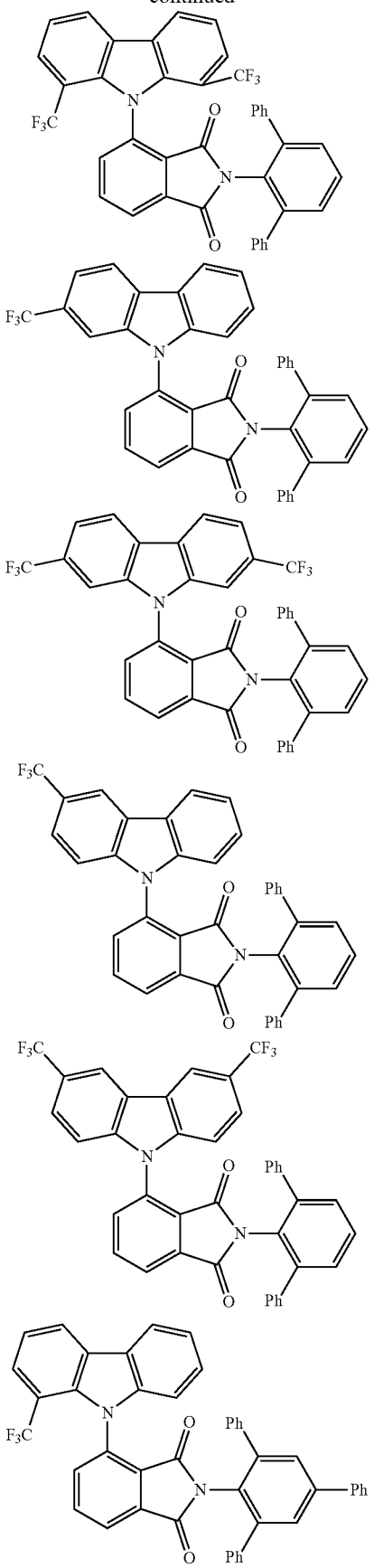

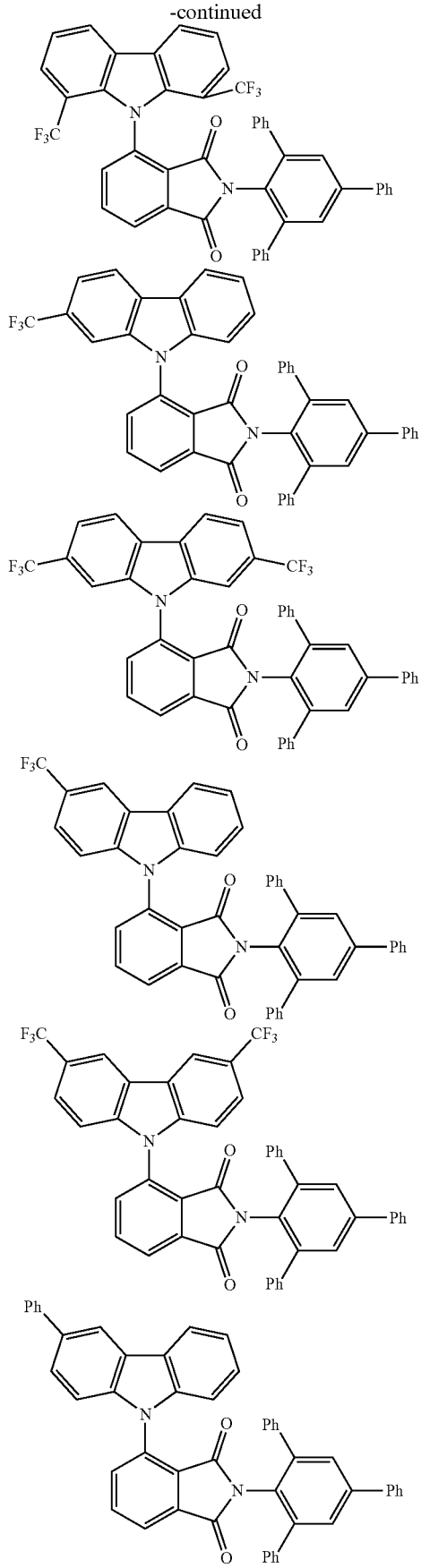
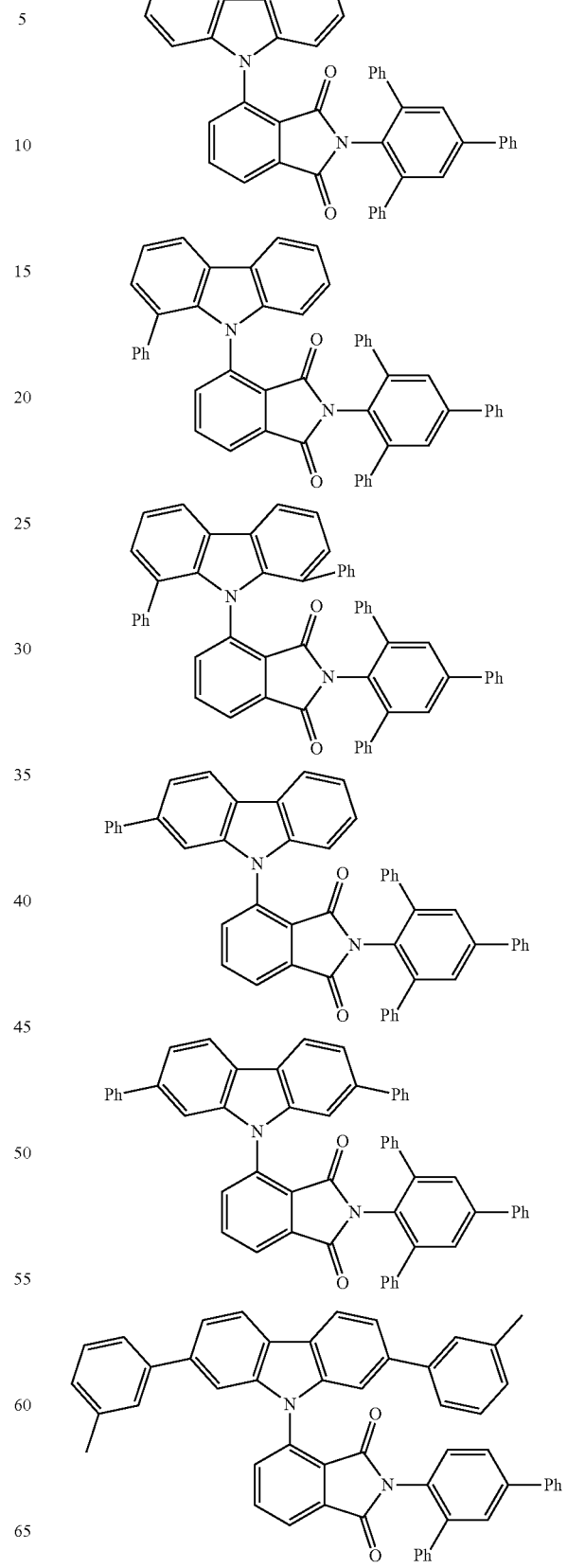

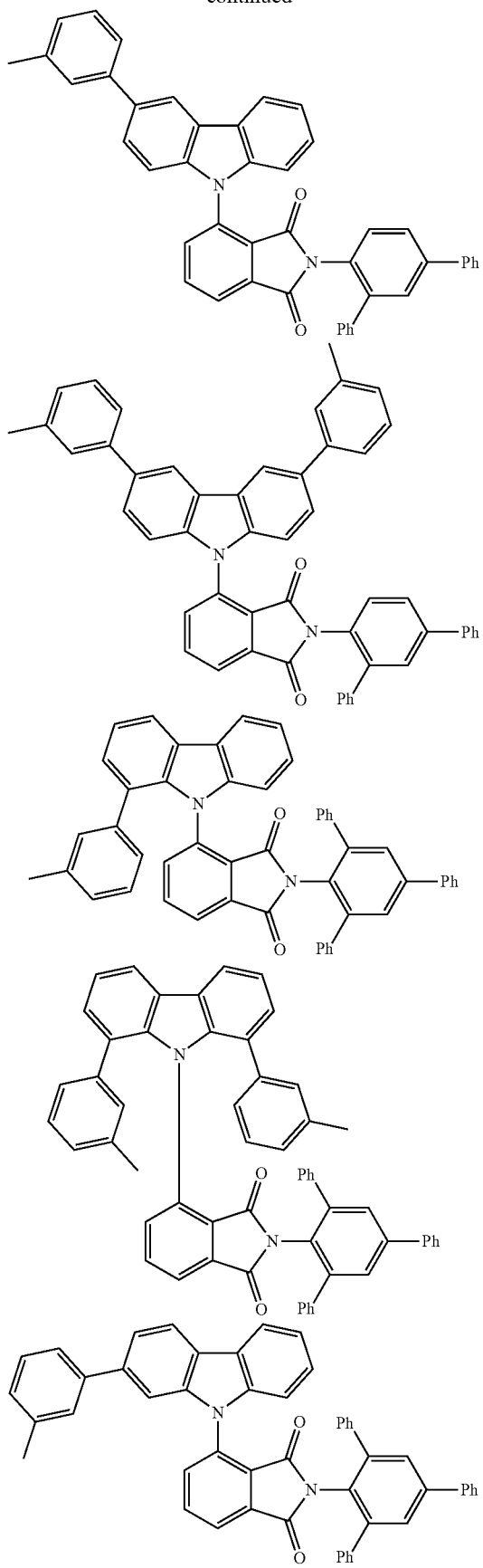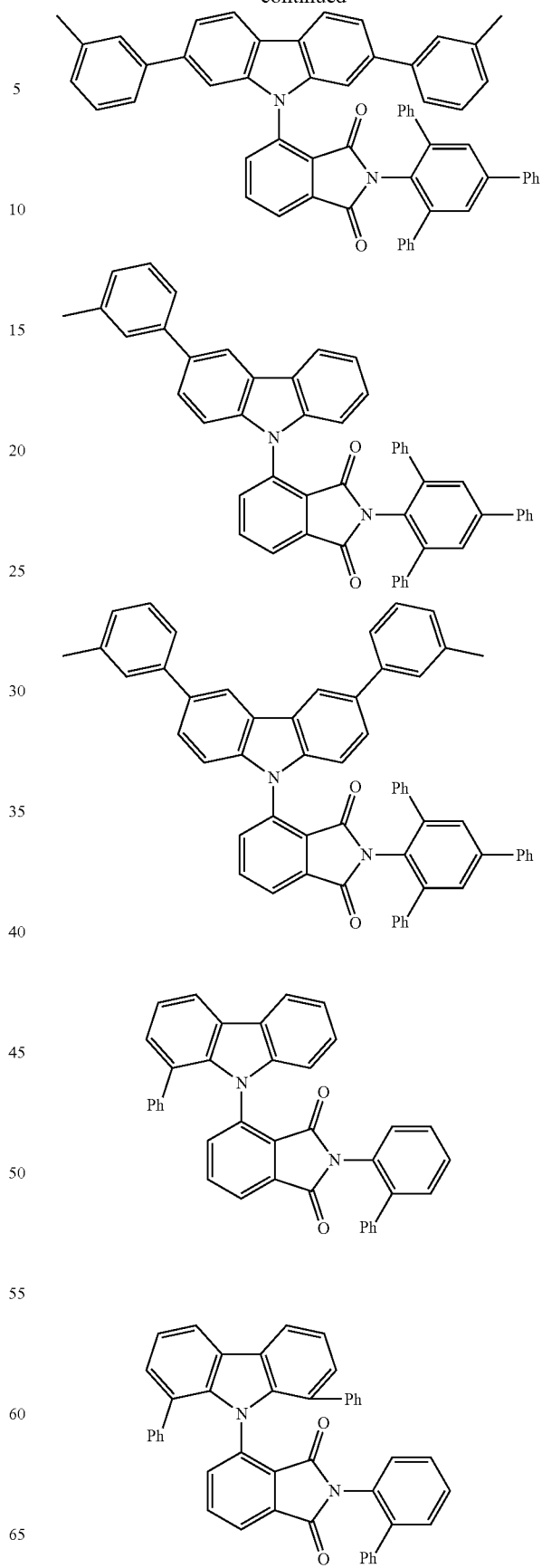

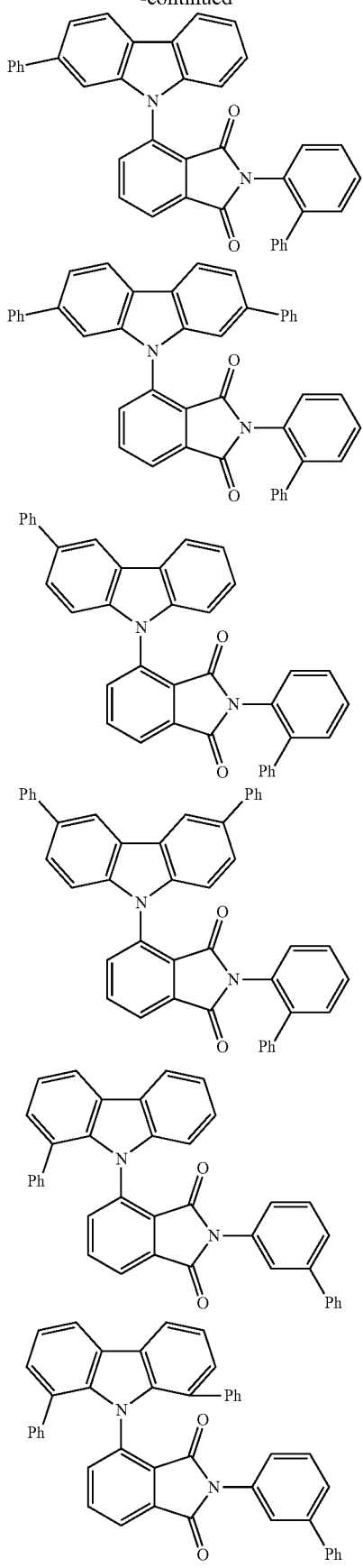
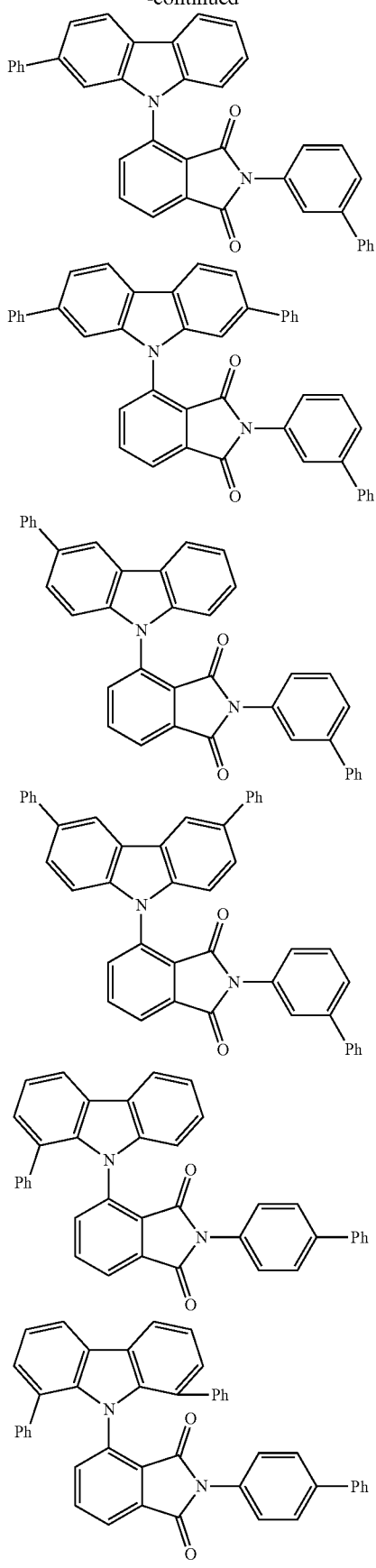

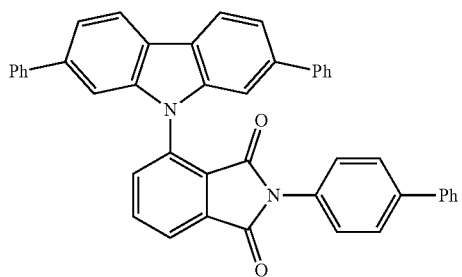
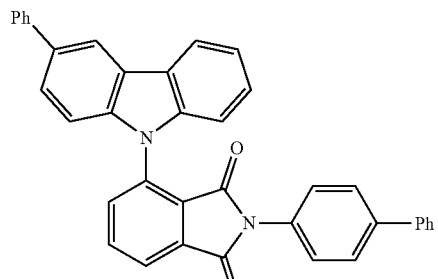
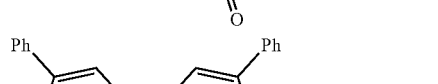
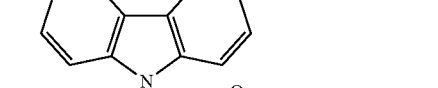
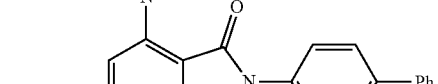
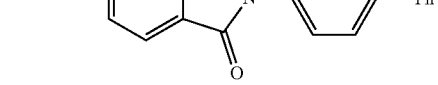
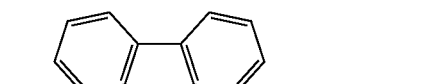
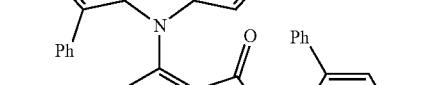
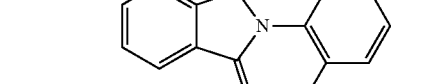
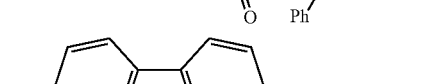
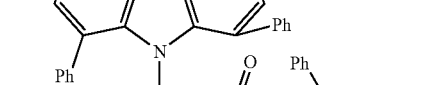
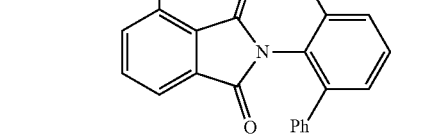
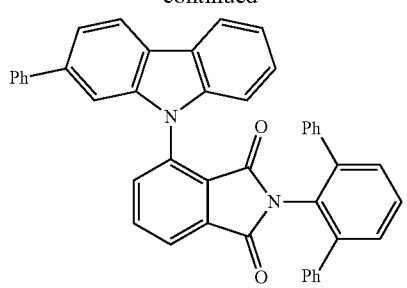
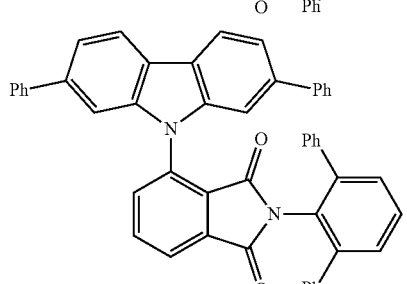
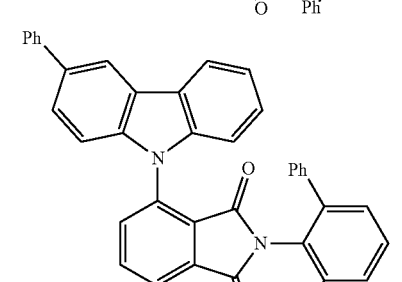
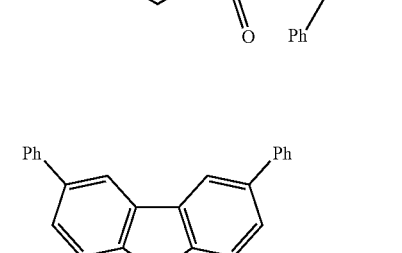
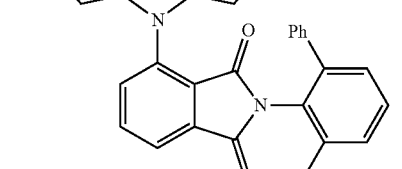
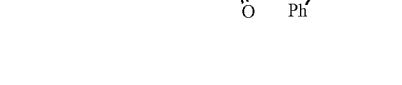
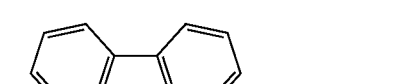
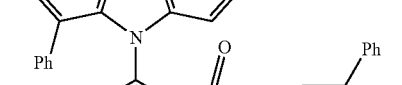
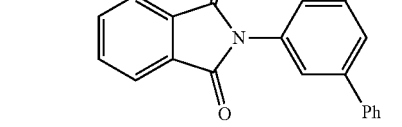

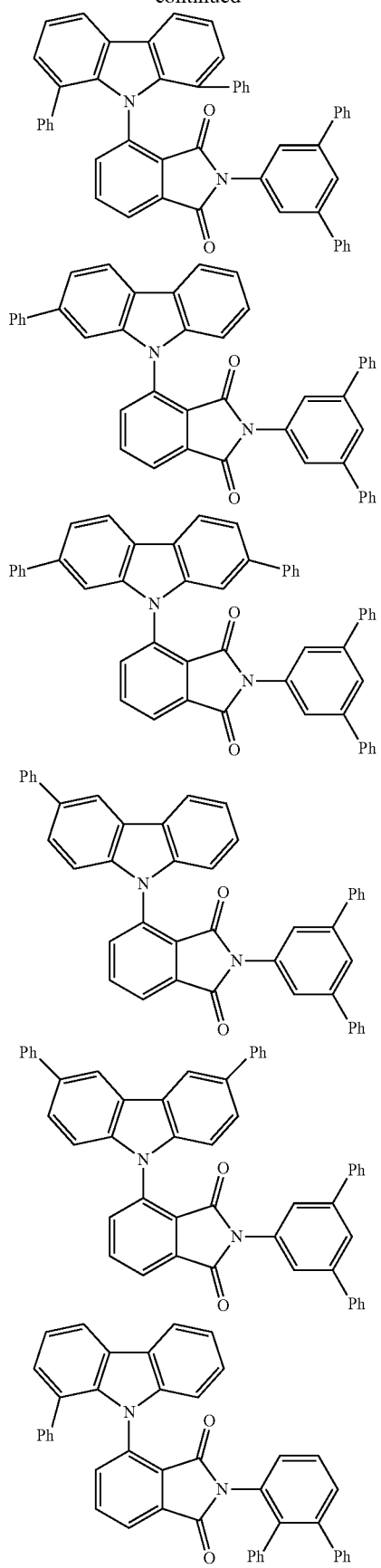
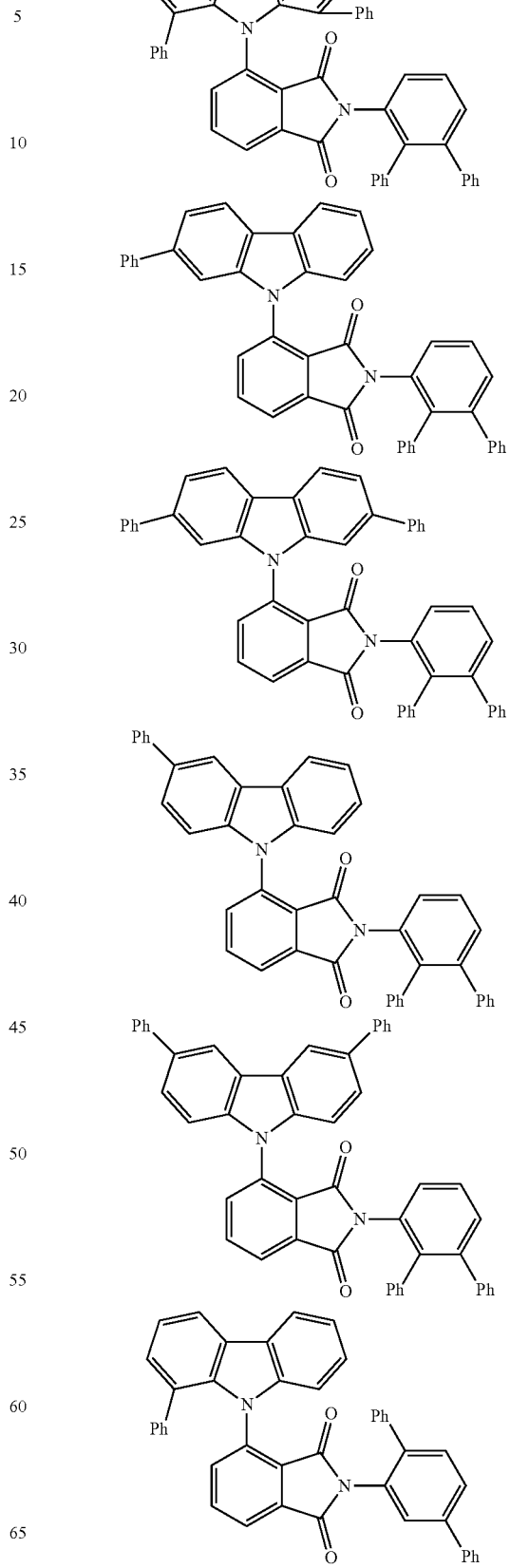

-continued
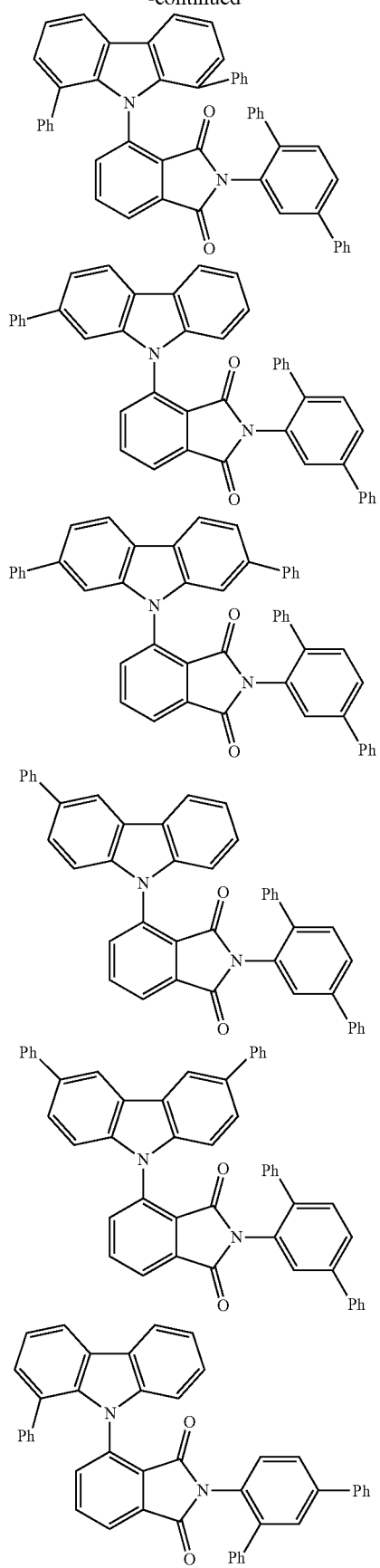
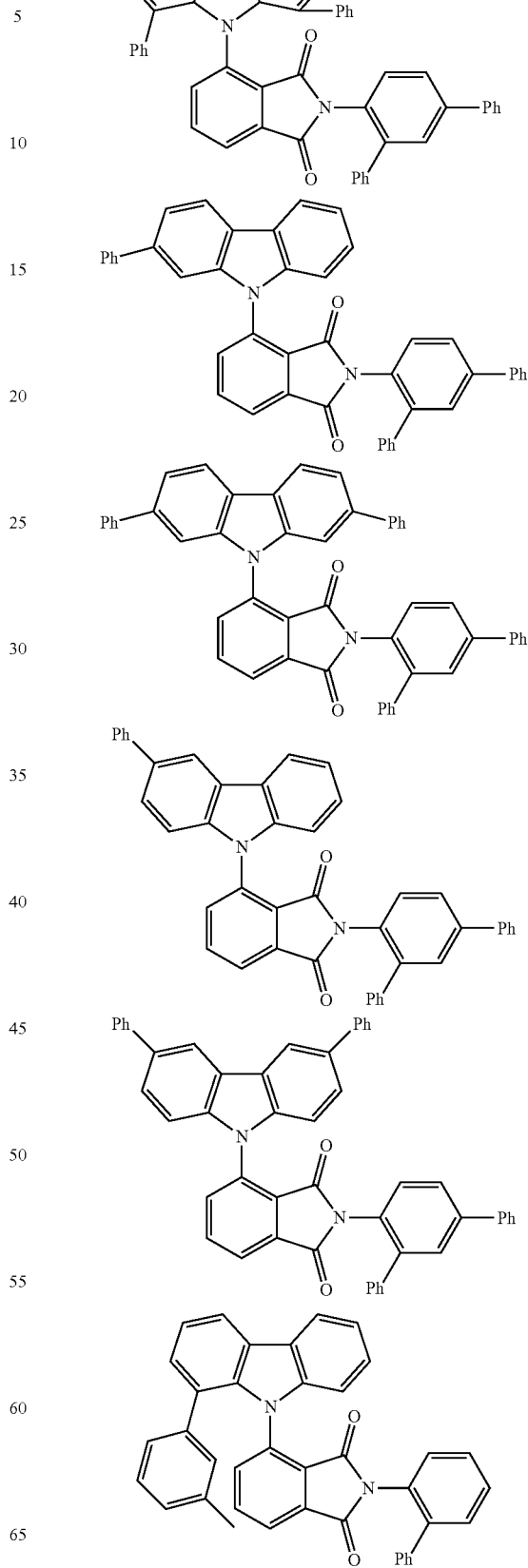

-continued
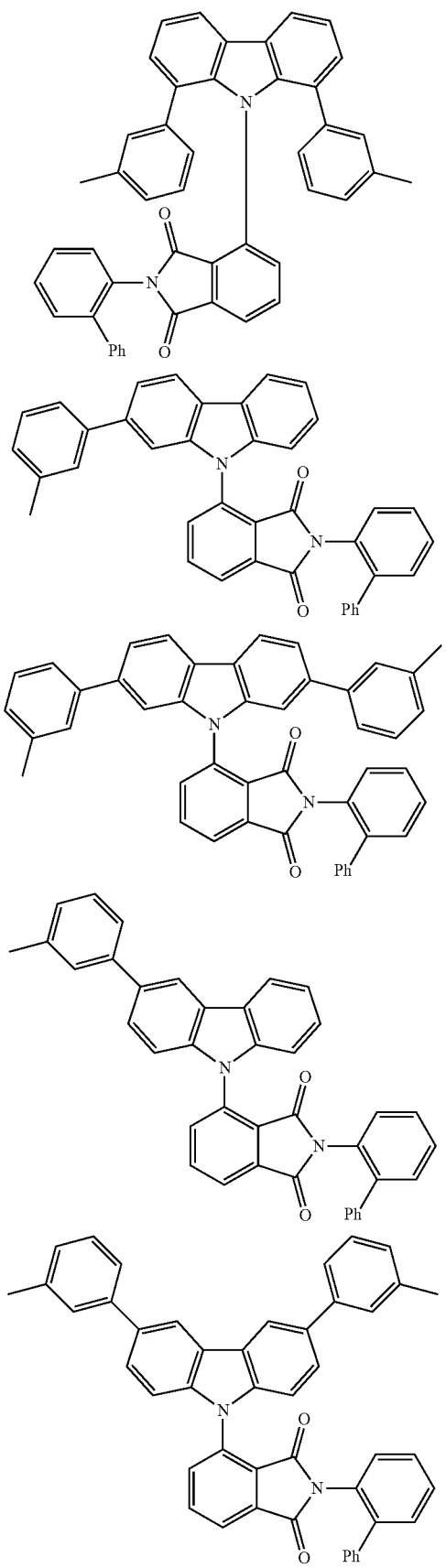
-continued
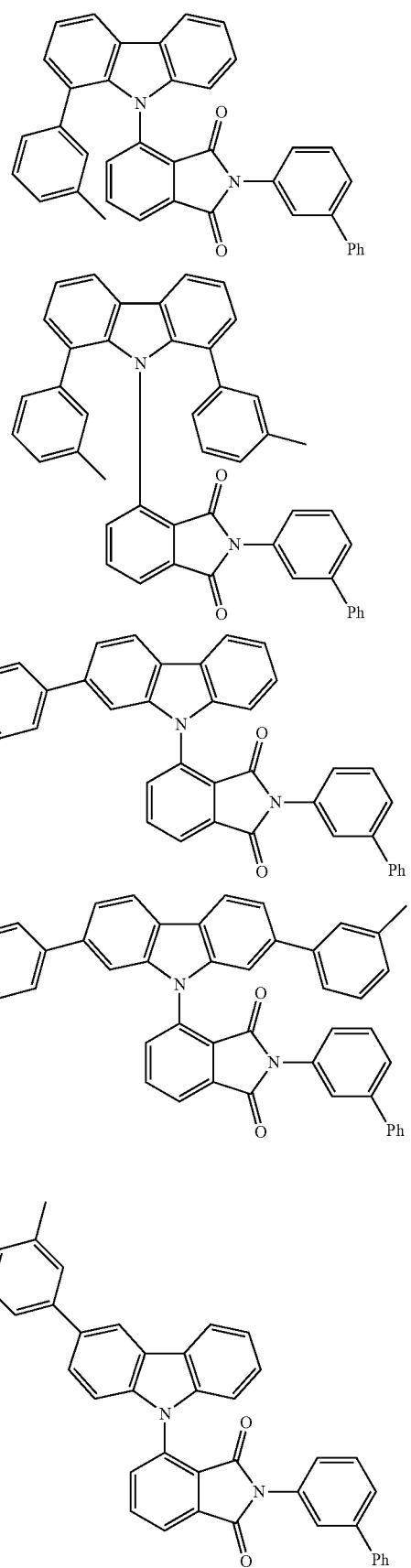

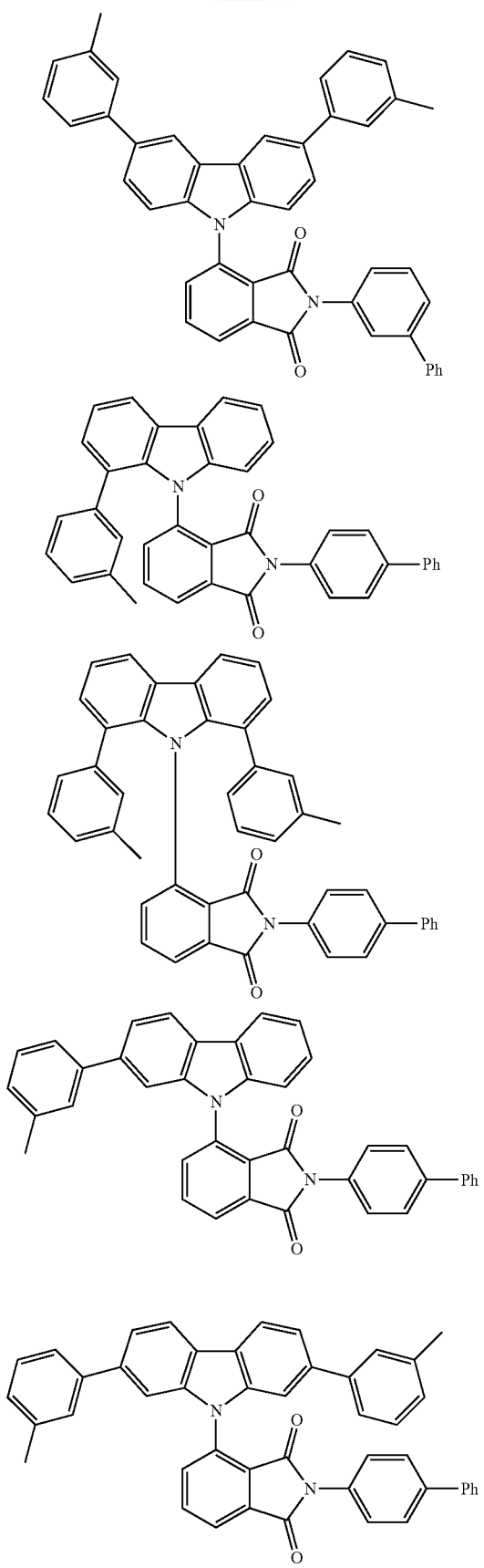
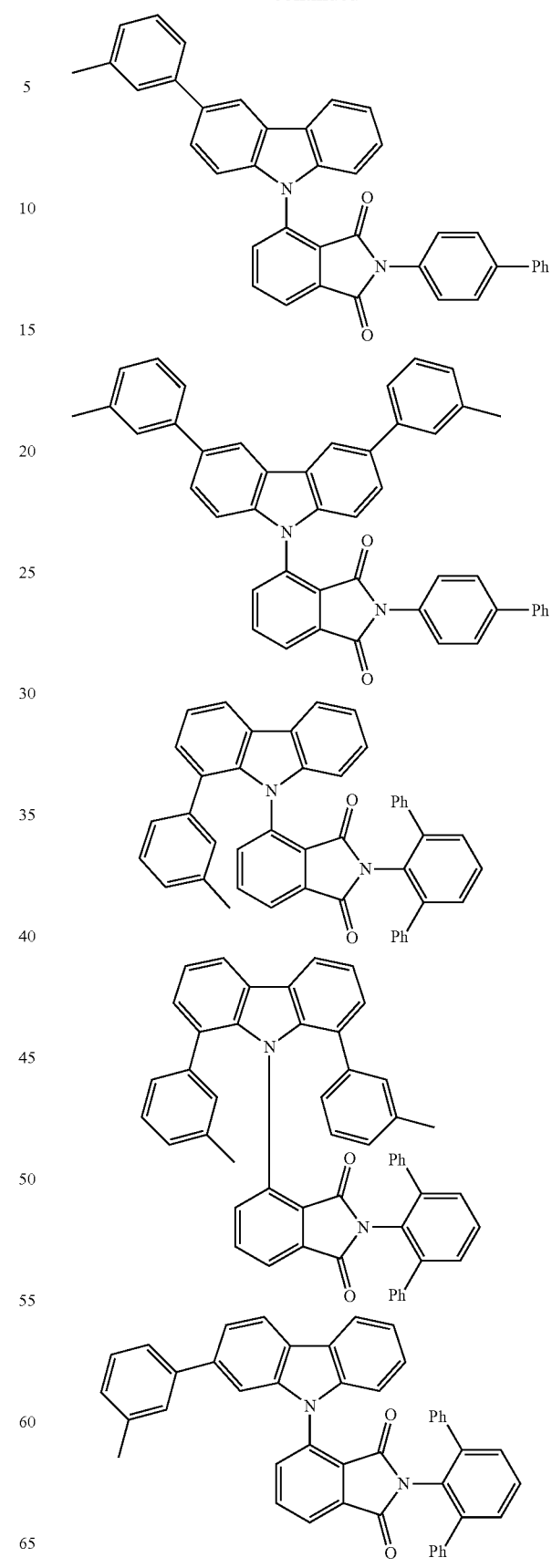

87
-continued
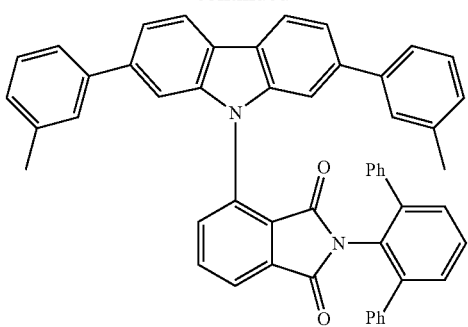
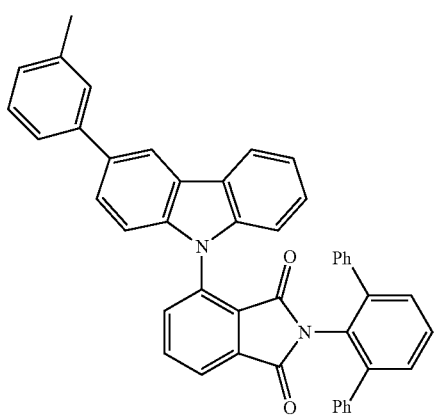
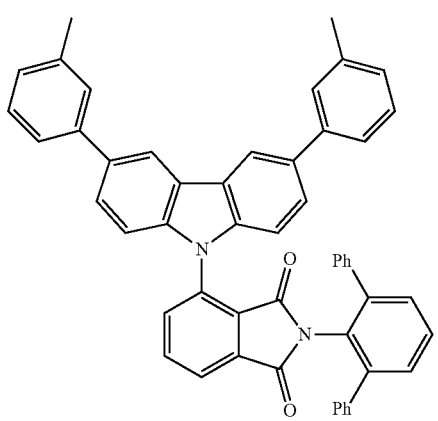
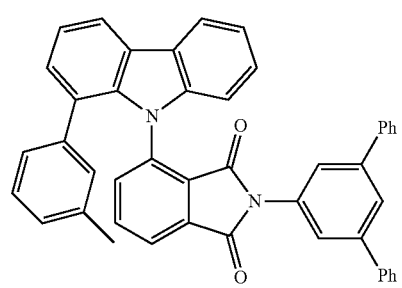
88
-continued
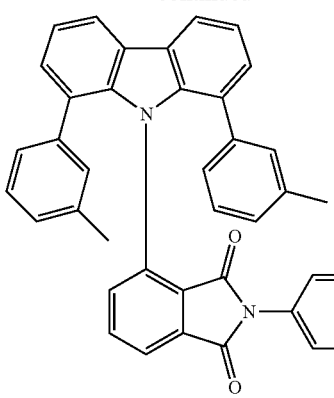
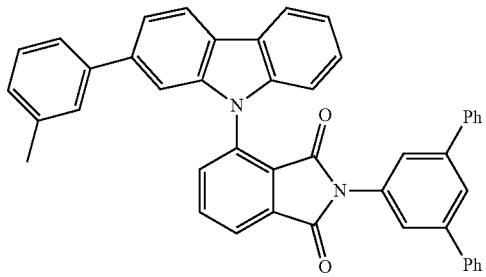
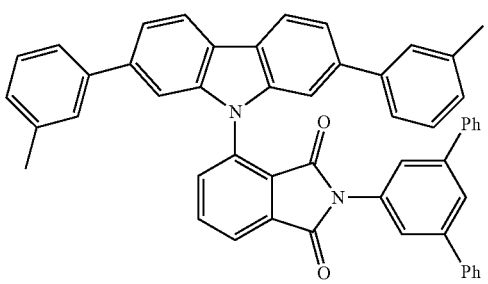
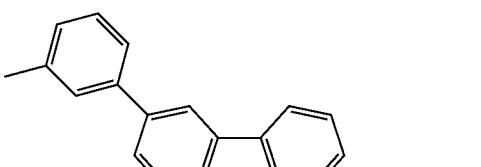
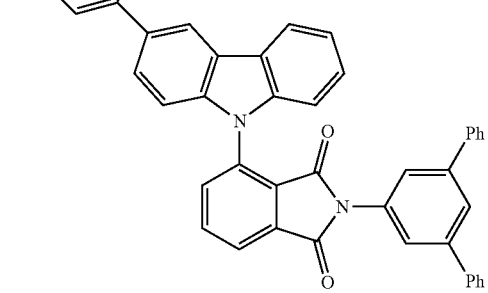
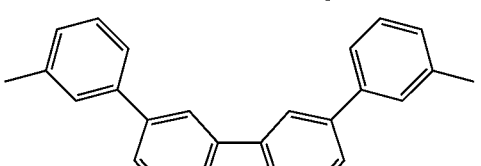
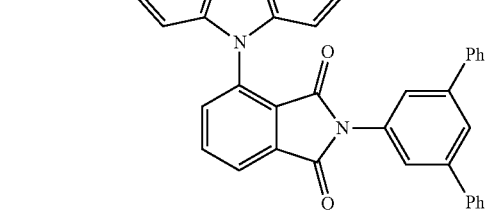

-continued
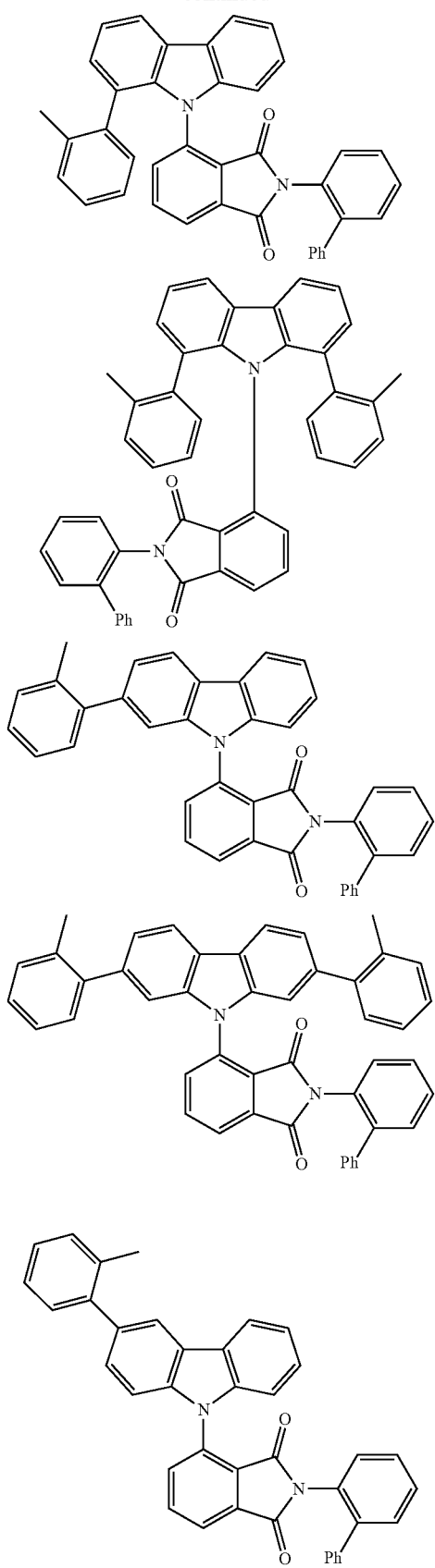
-continued
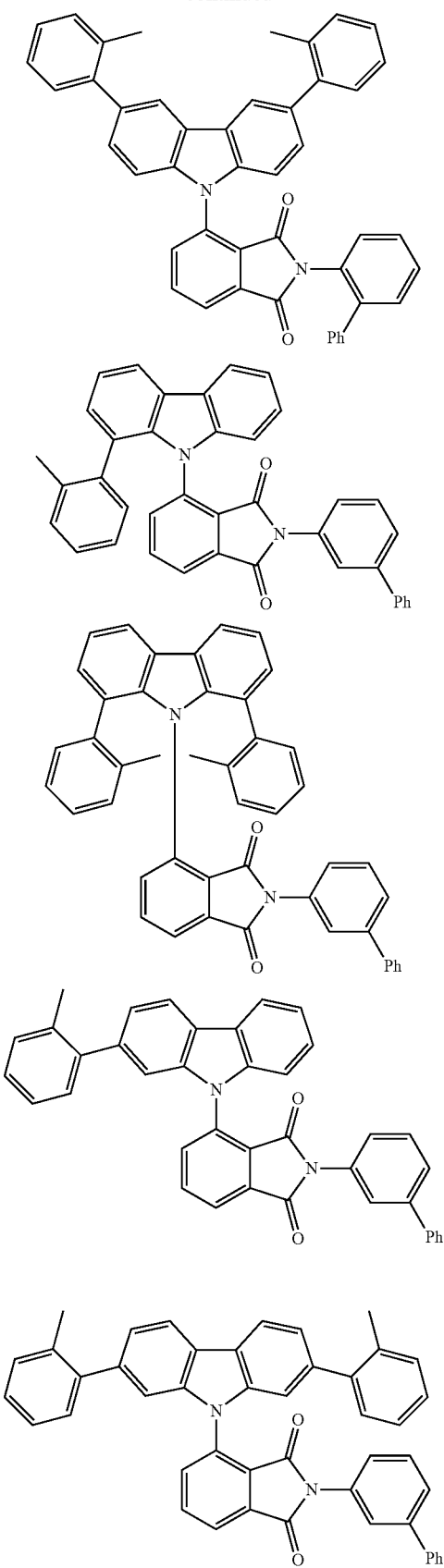

91
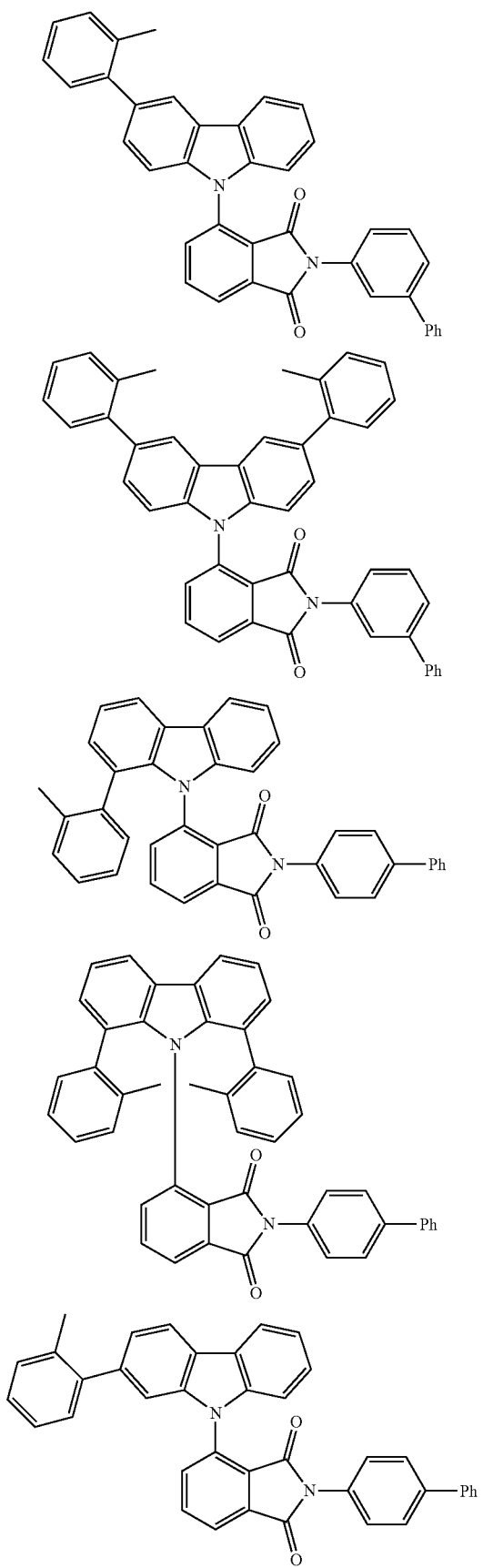
92
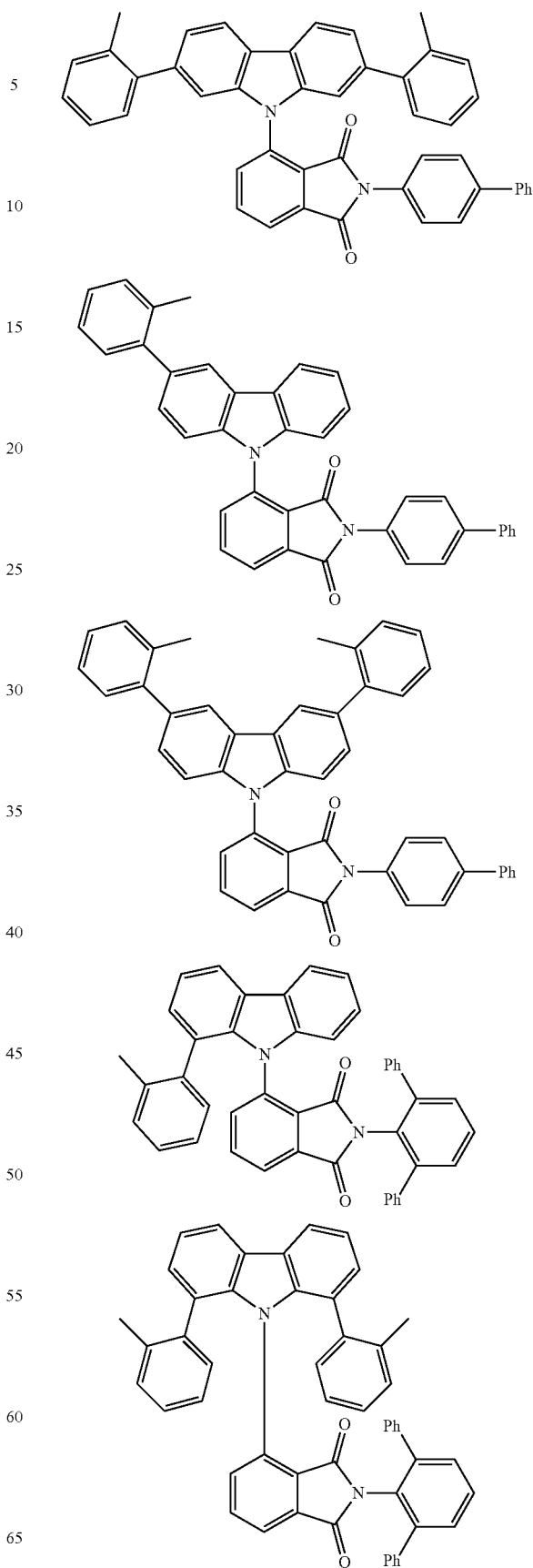

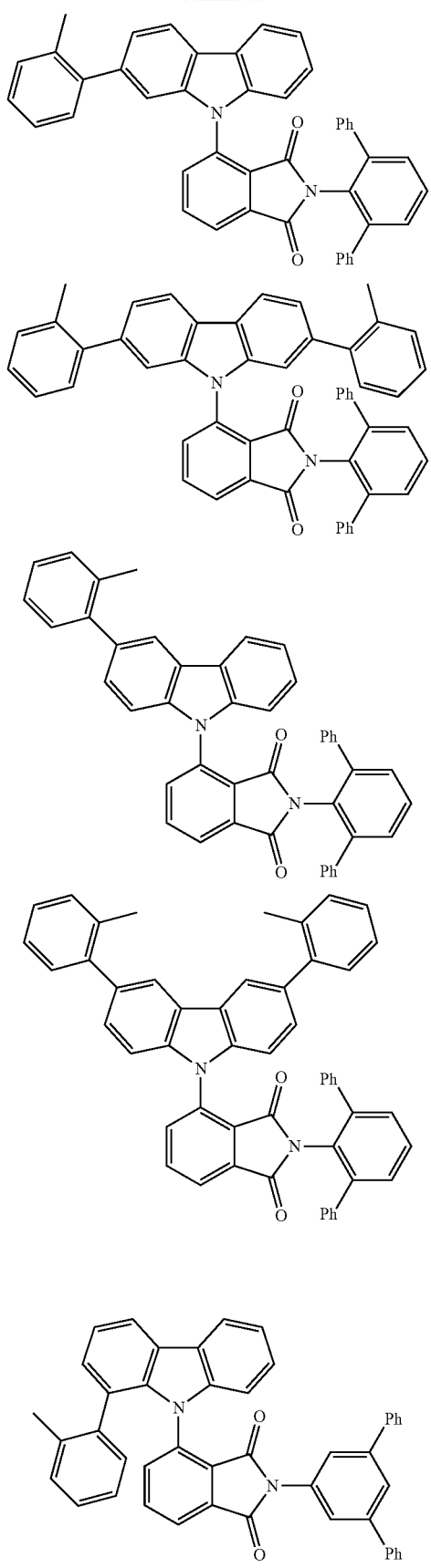
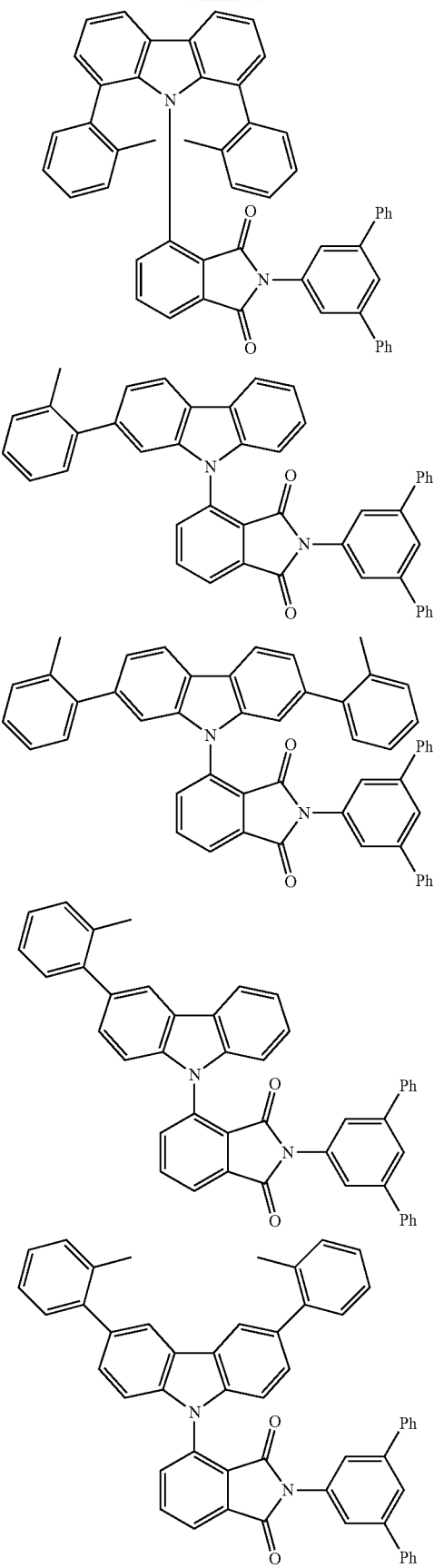

-continued
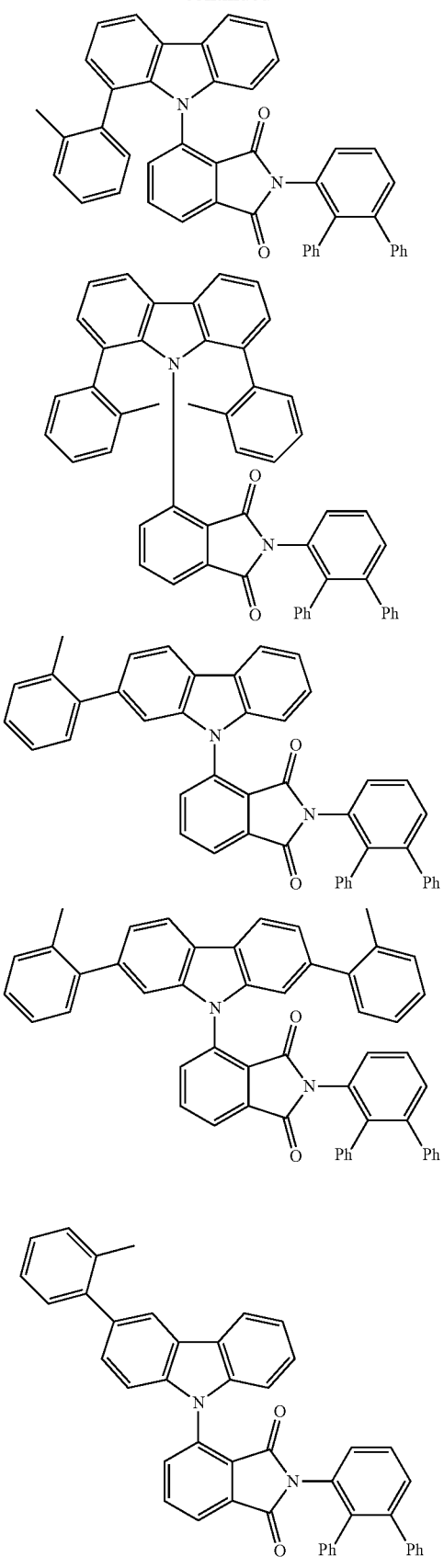
-continued
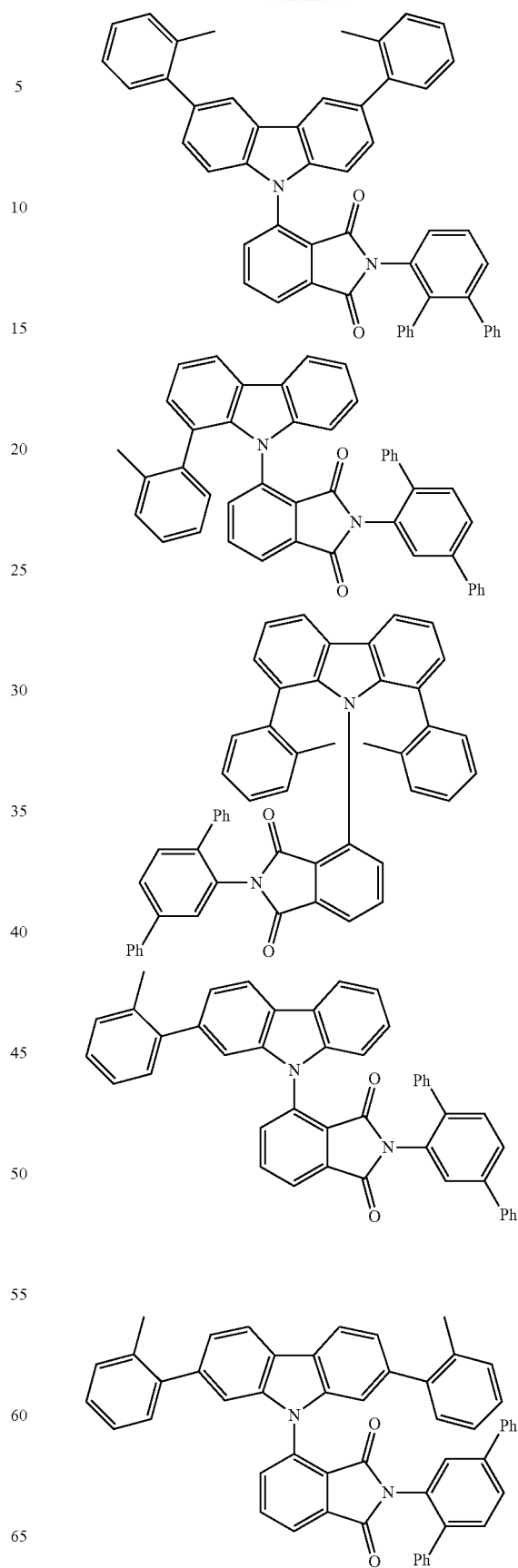

97
-continued
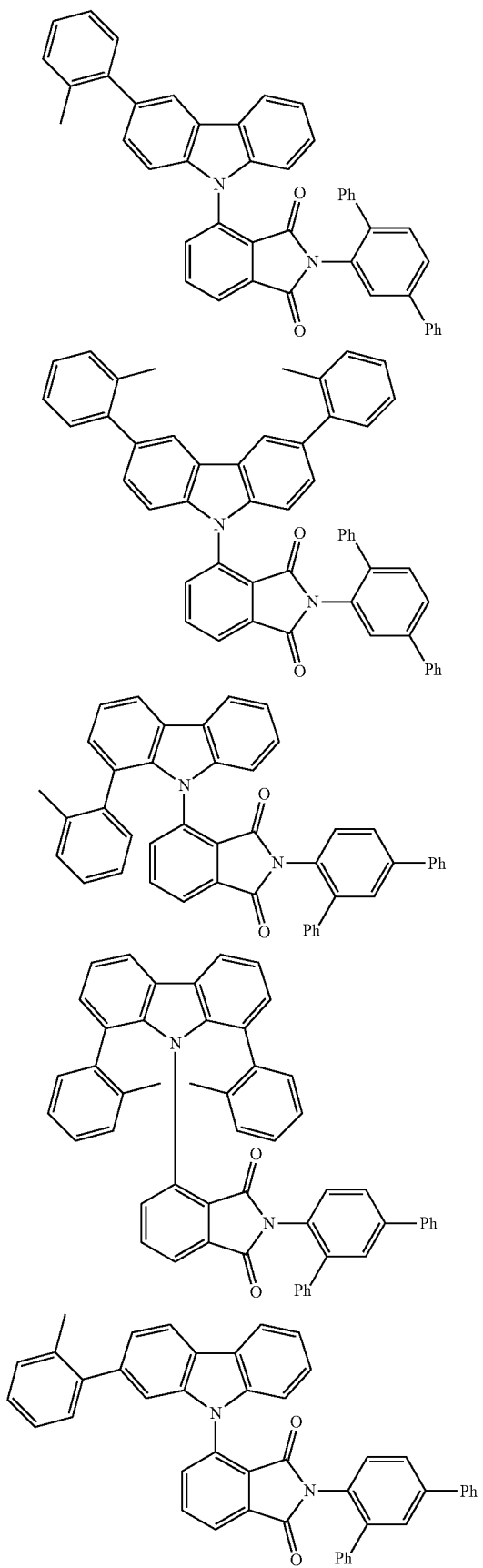
98
-continued
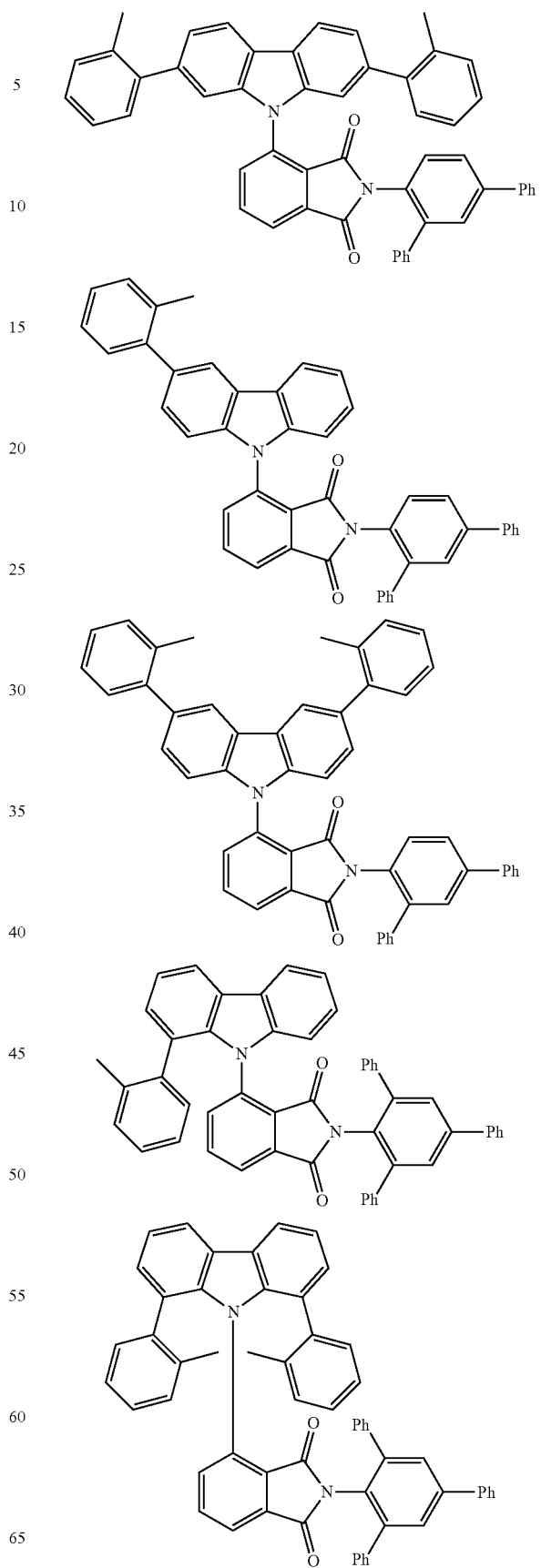

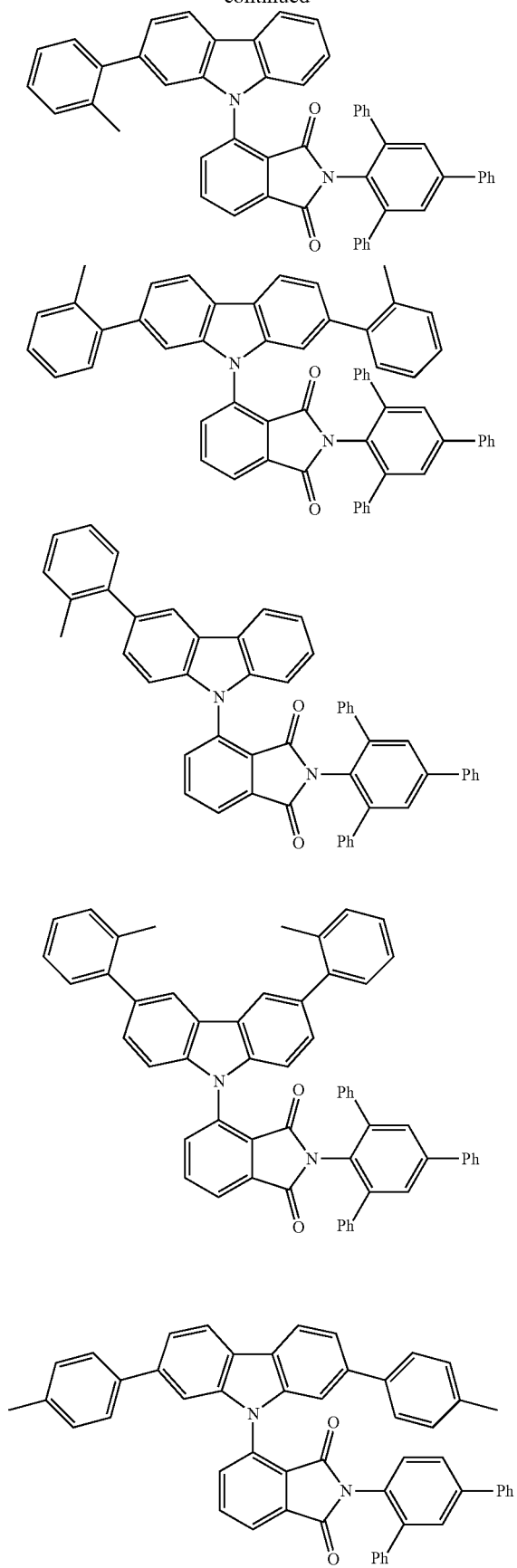

-continued
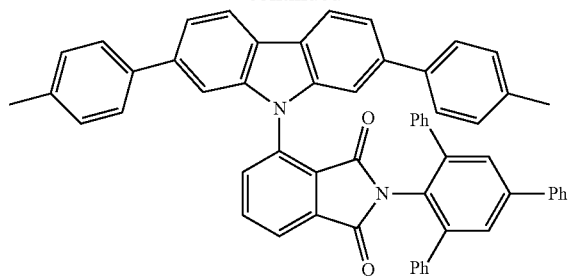
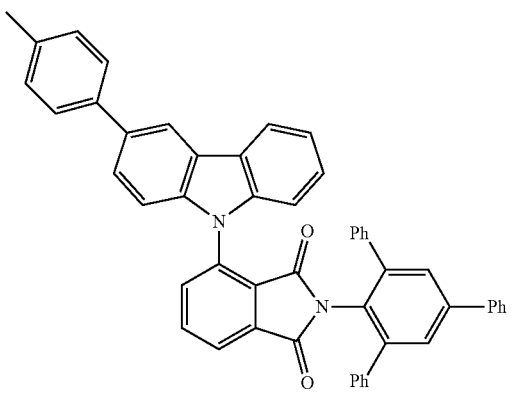
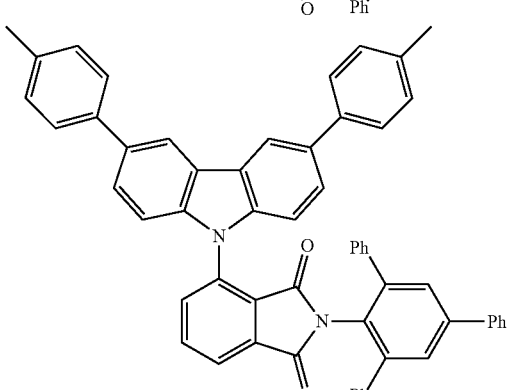
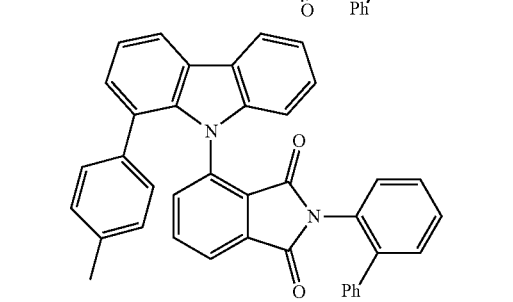
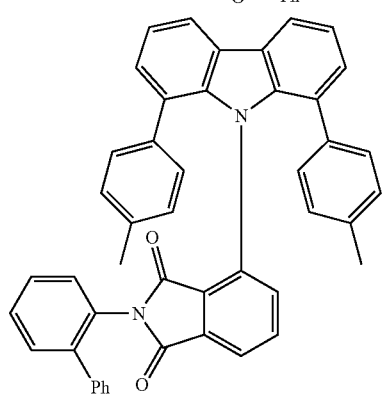
-continued
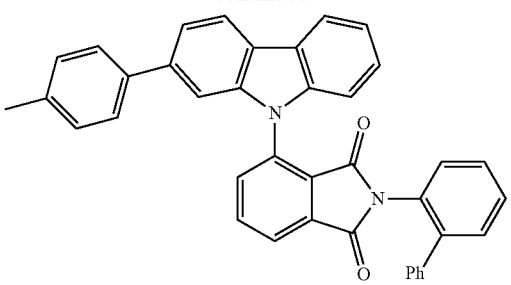
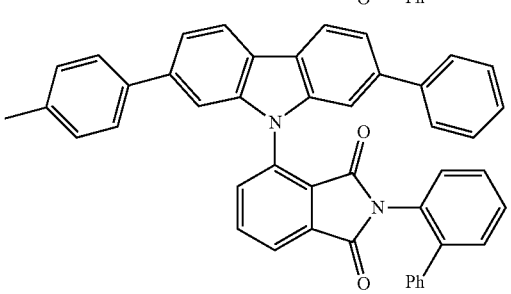
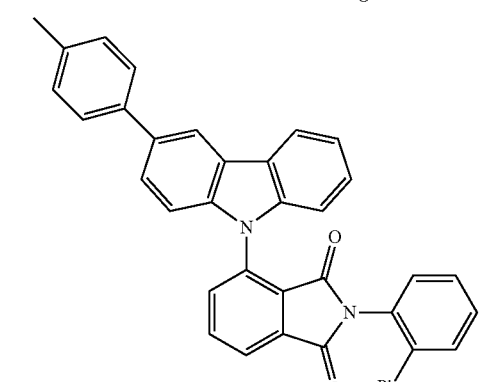
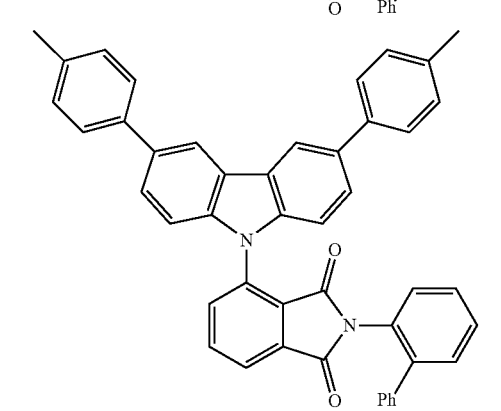
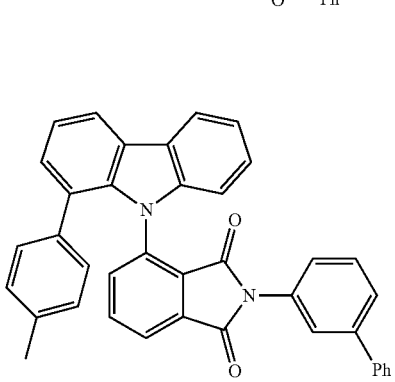

103
-continued
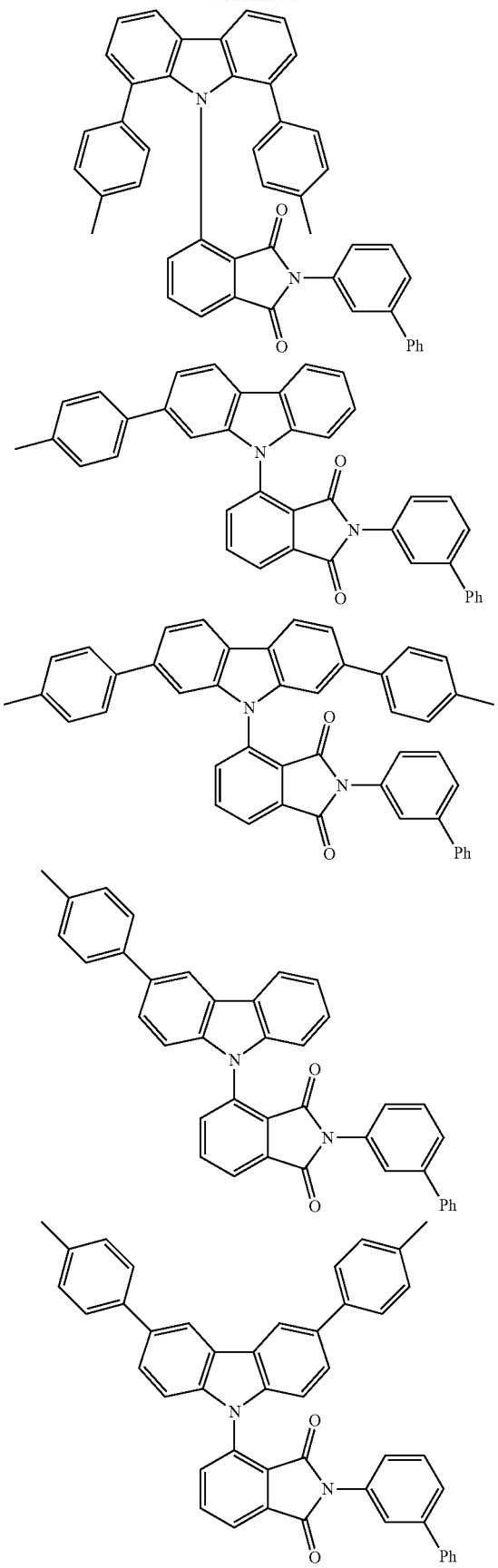
104
-continued
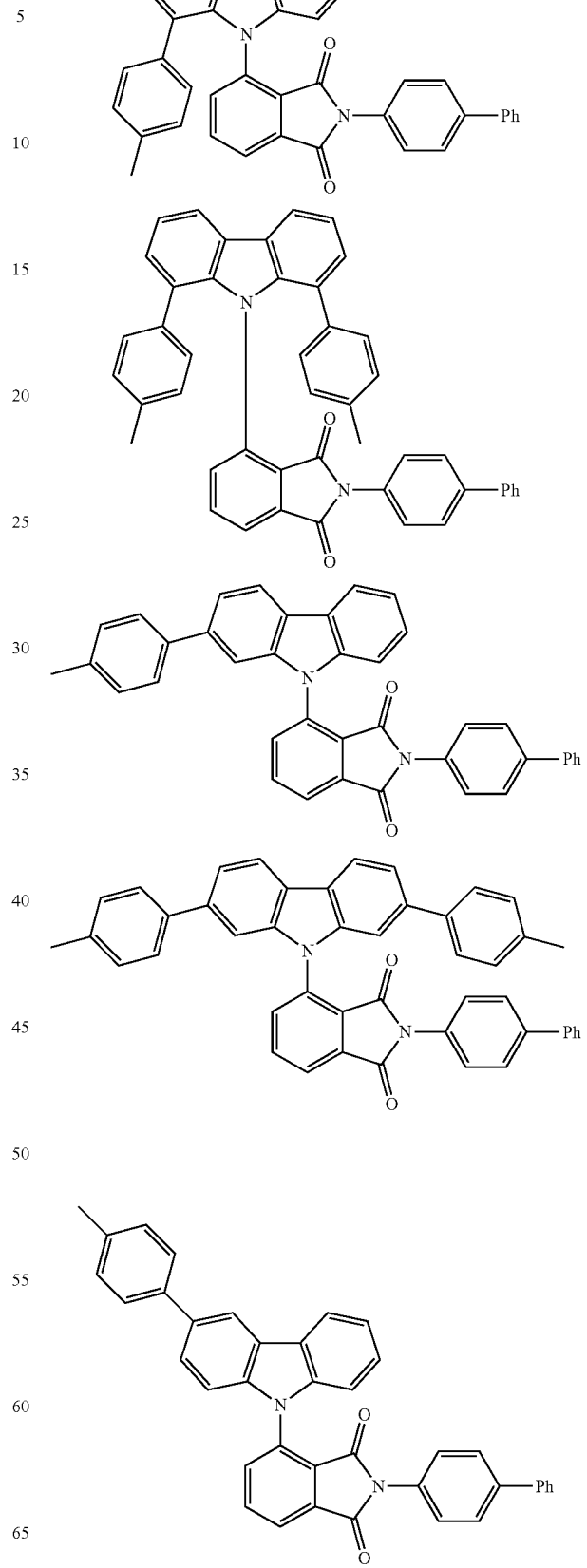

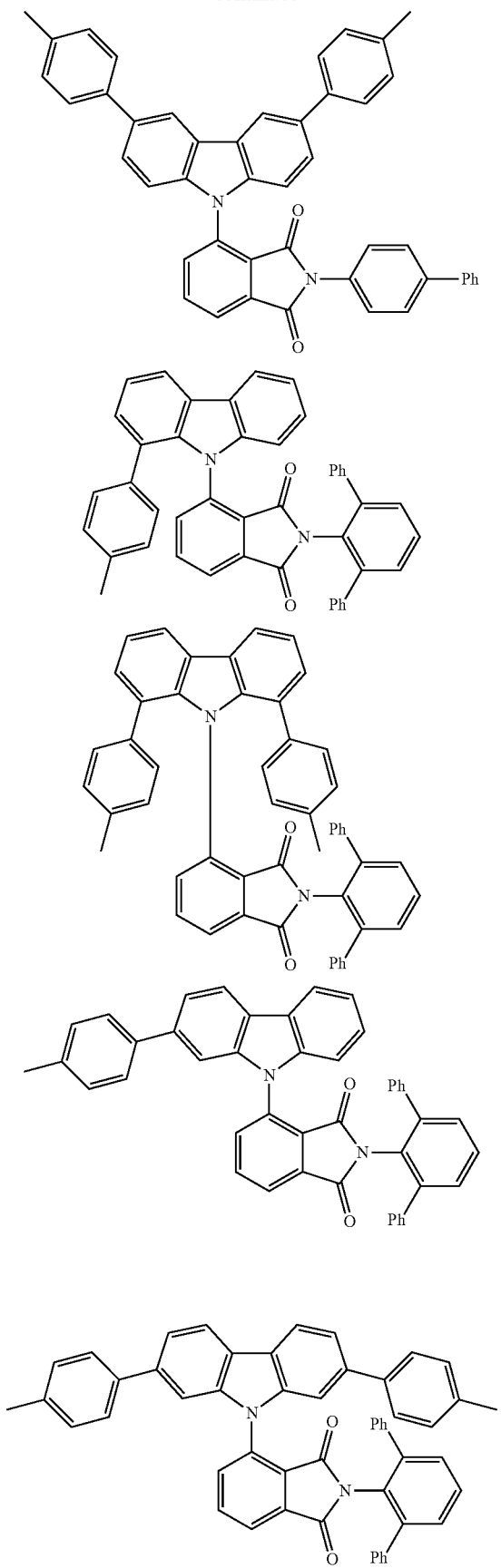
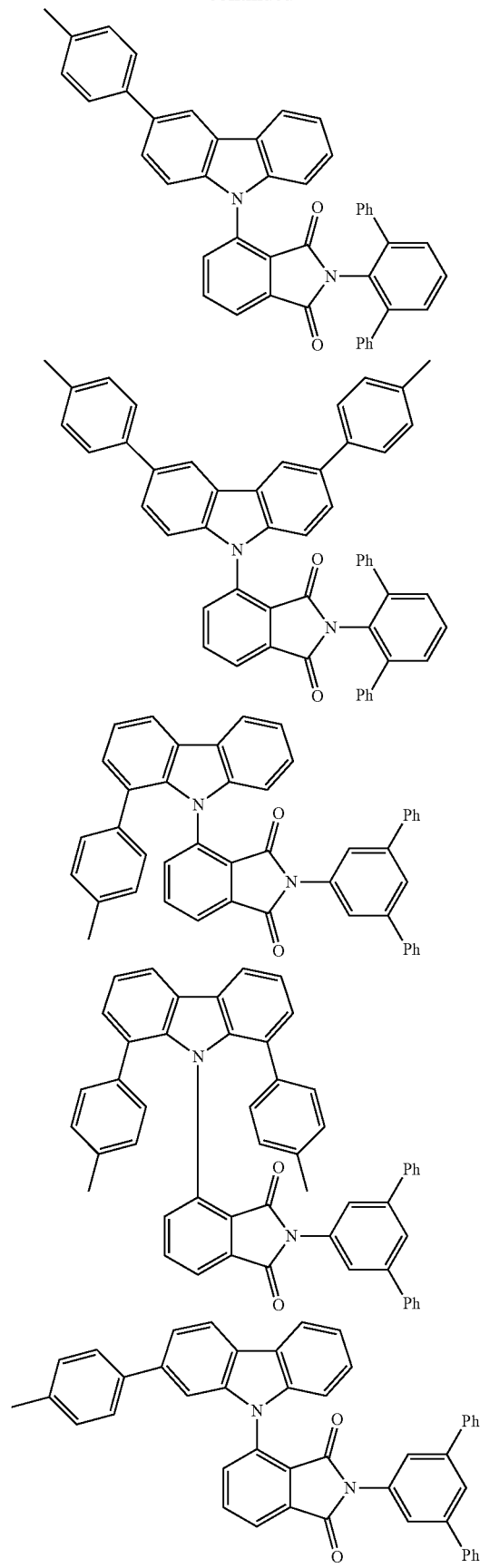

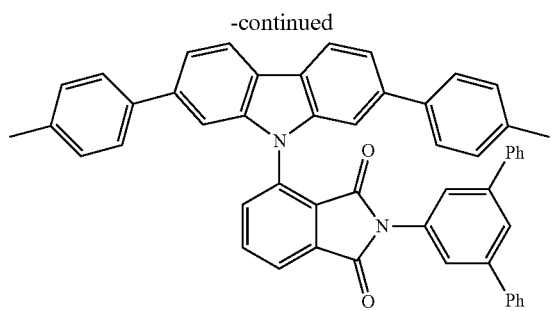
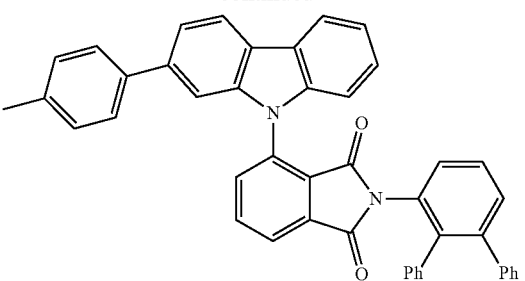
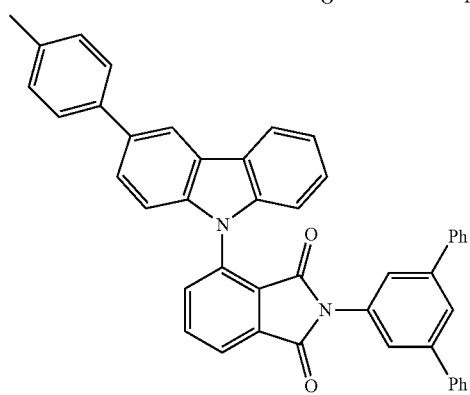
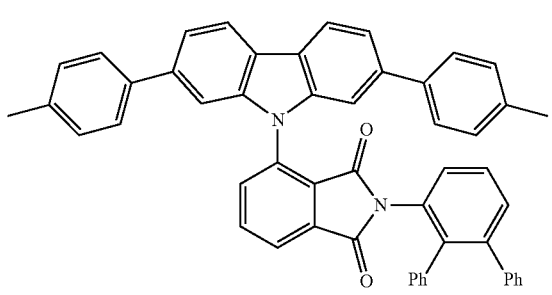
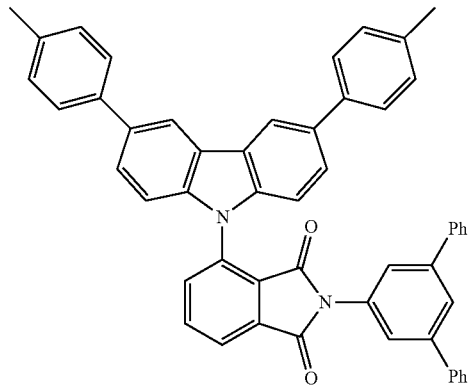
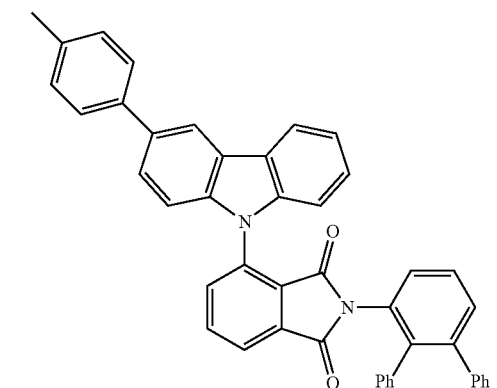
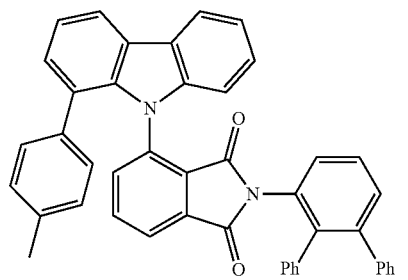
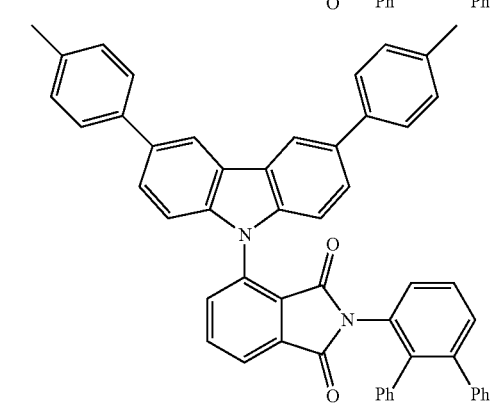
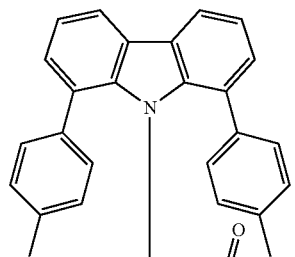
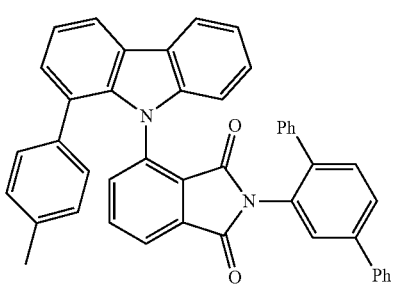

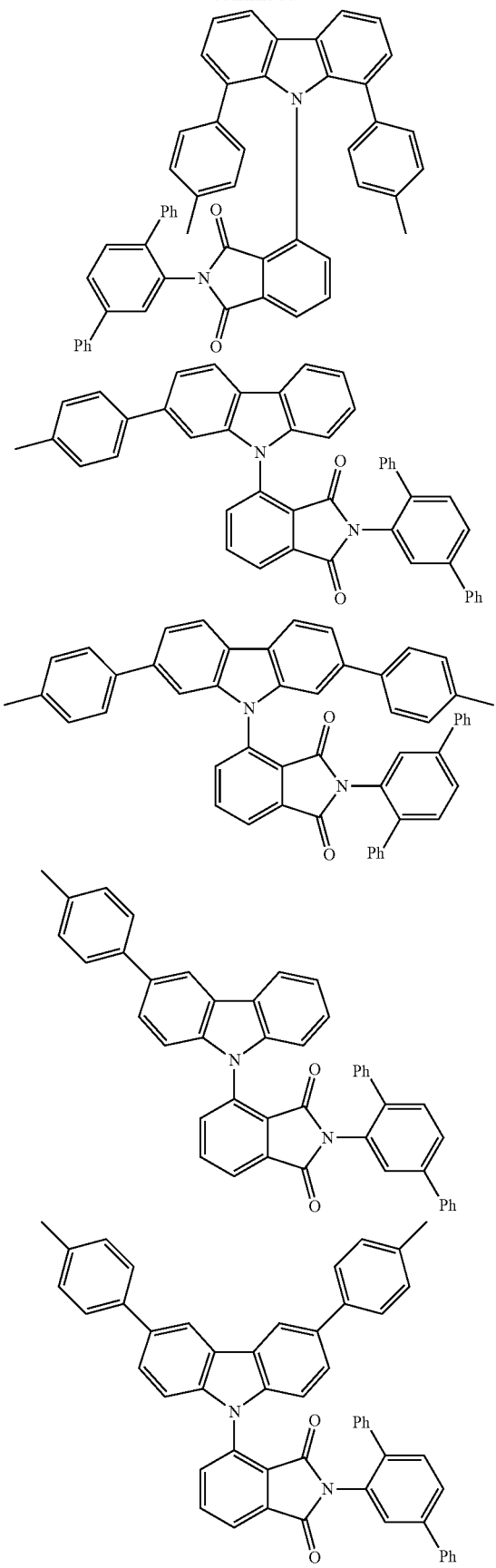
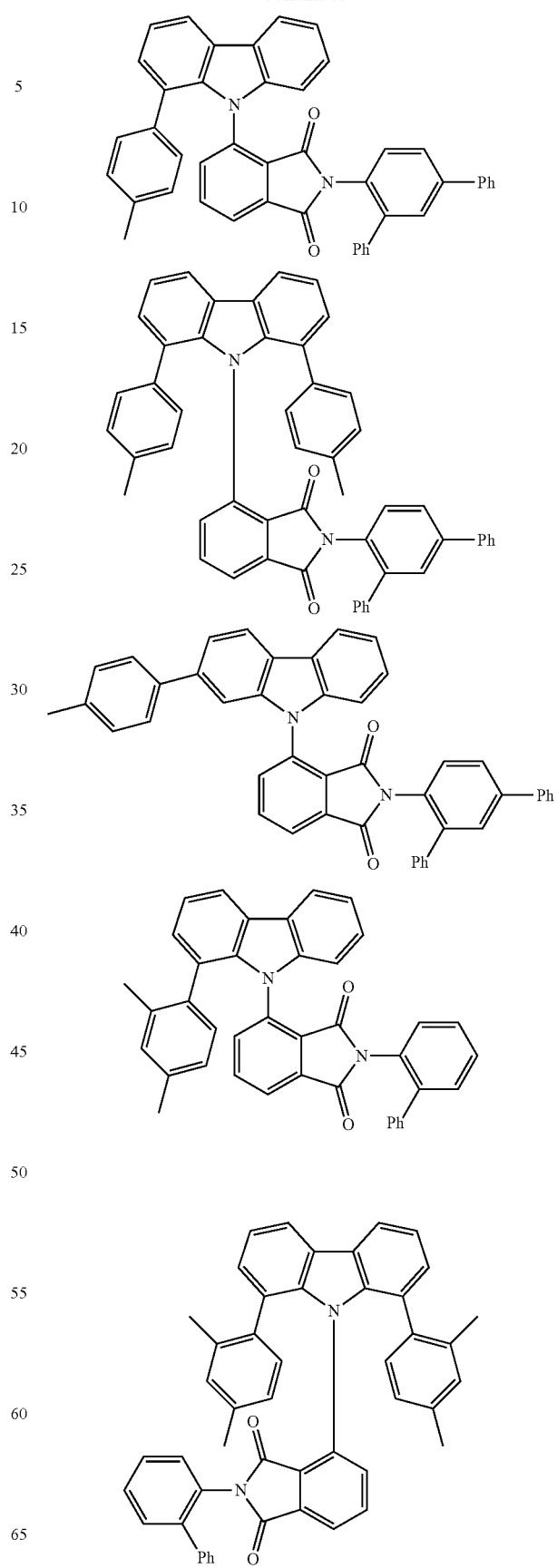

-continued
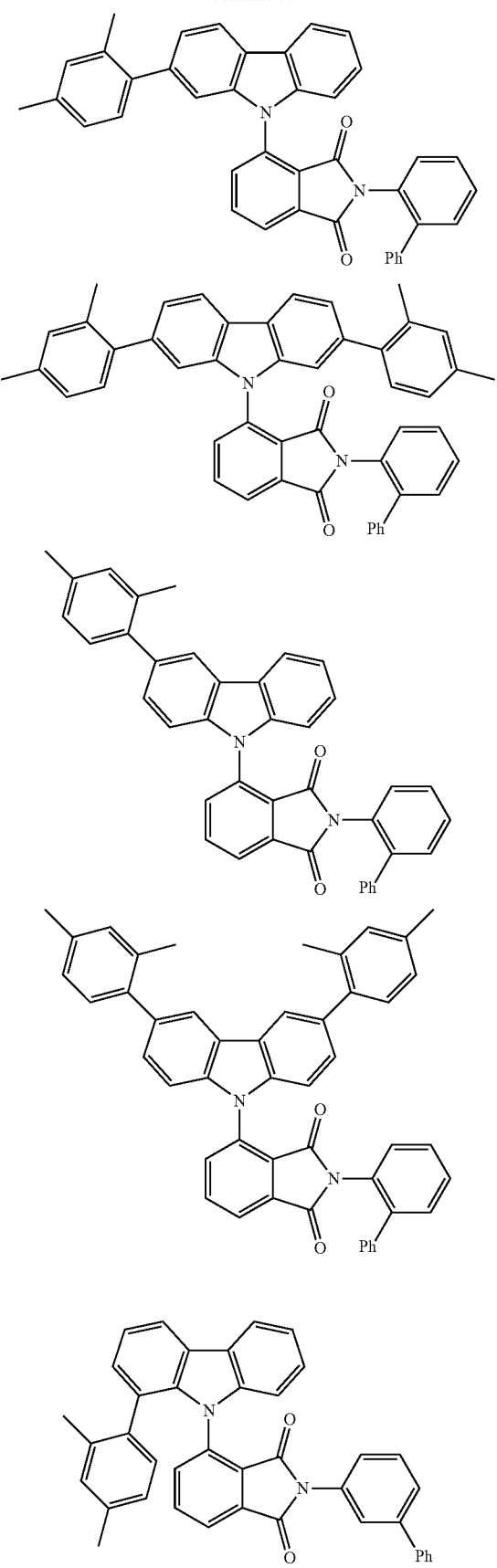
-continued
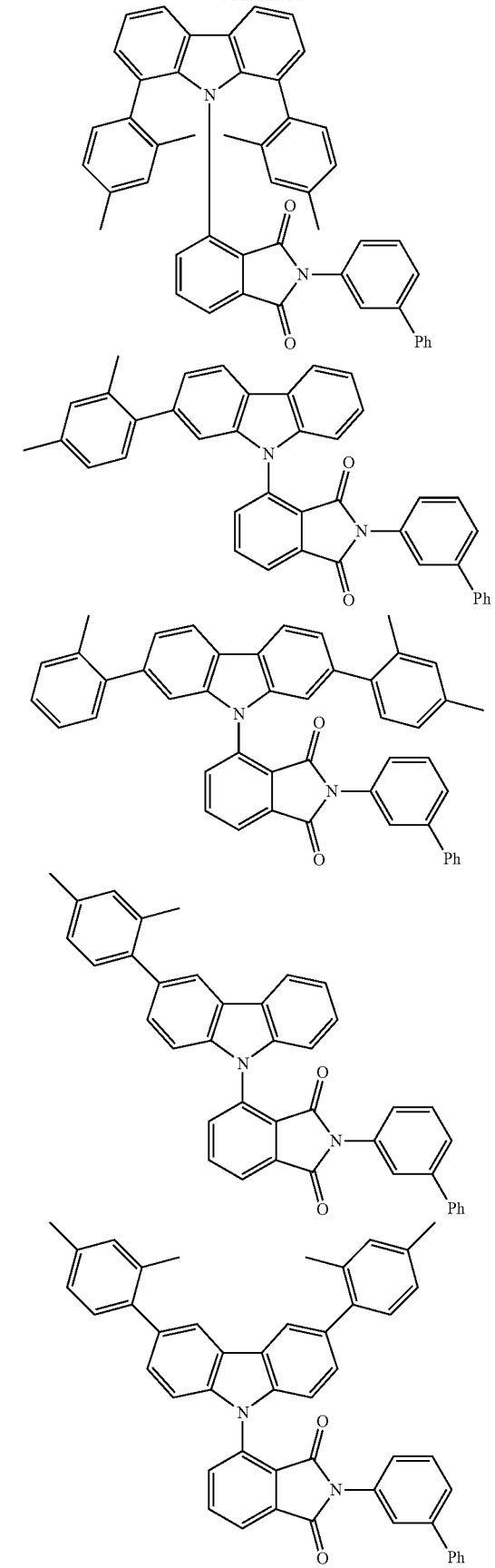

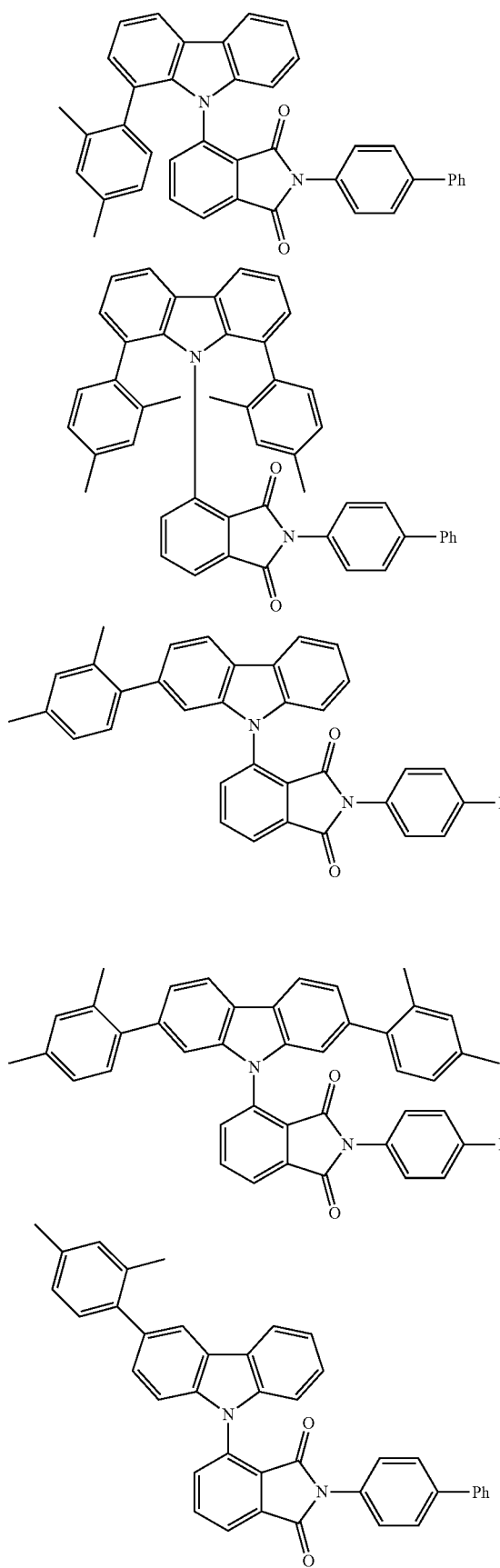

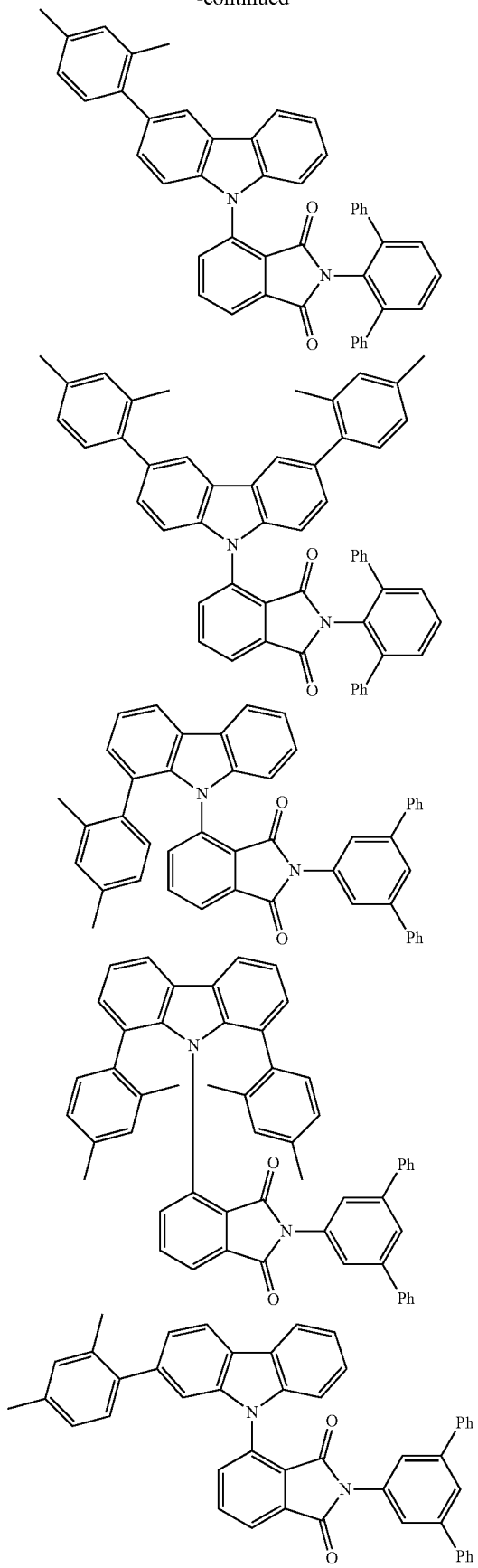
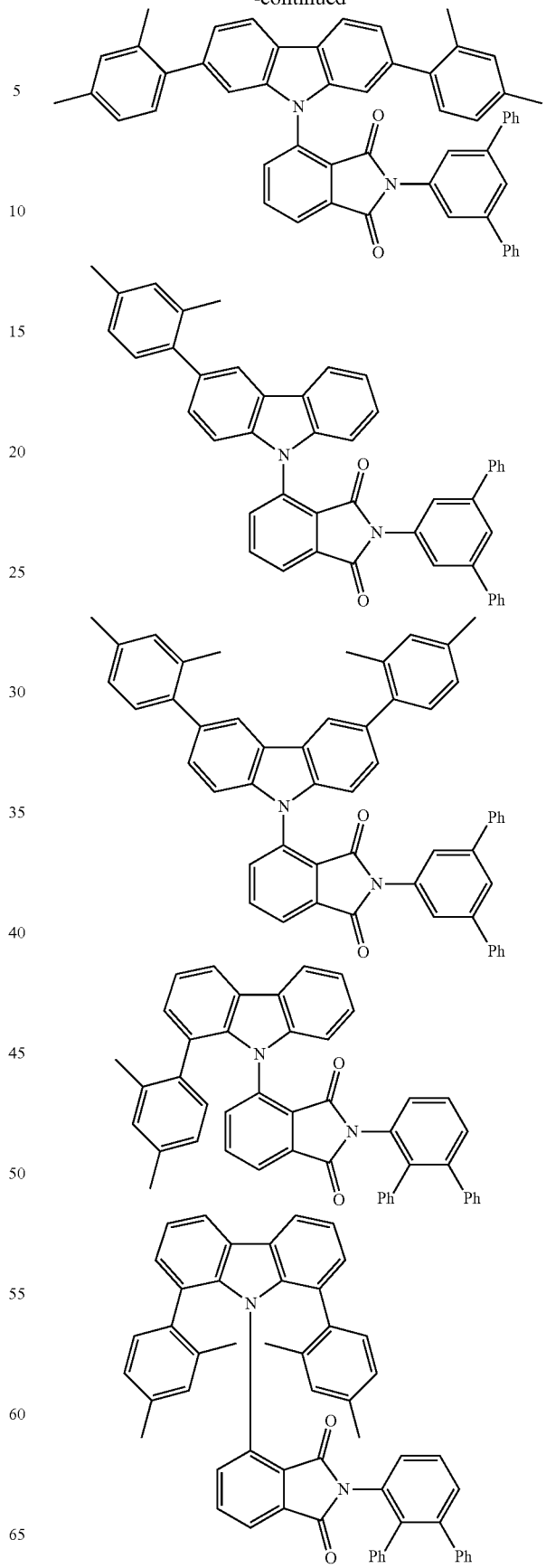

-continued
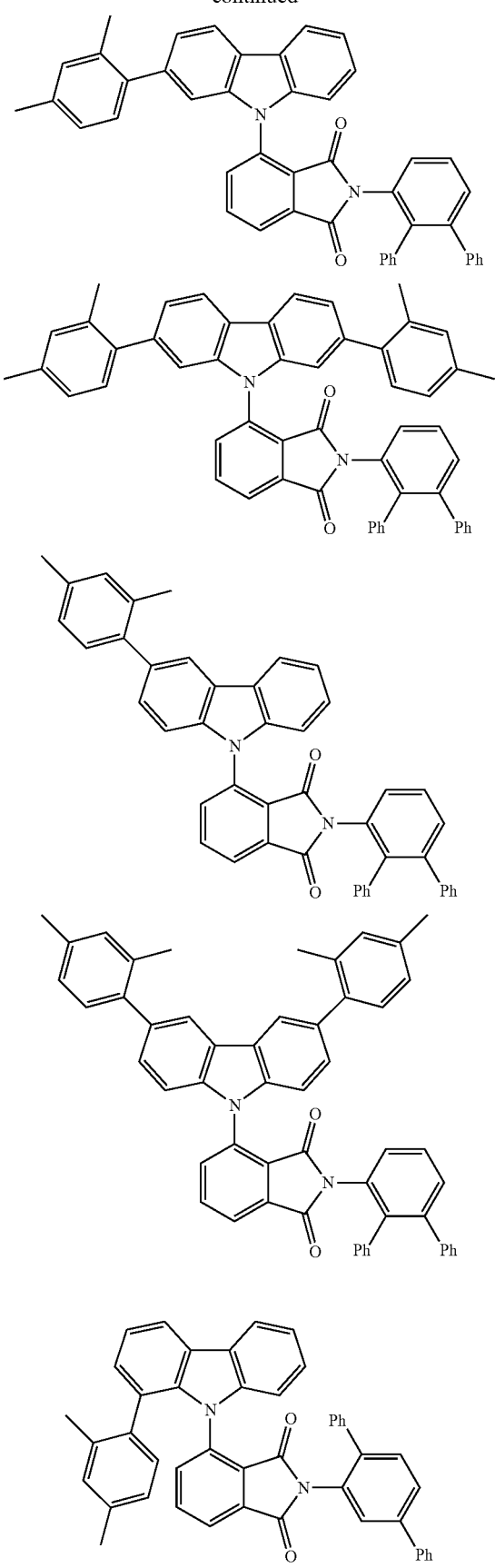
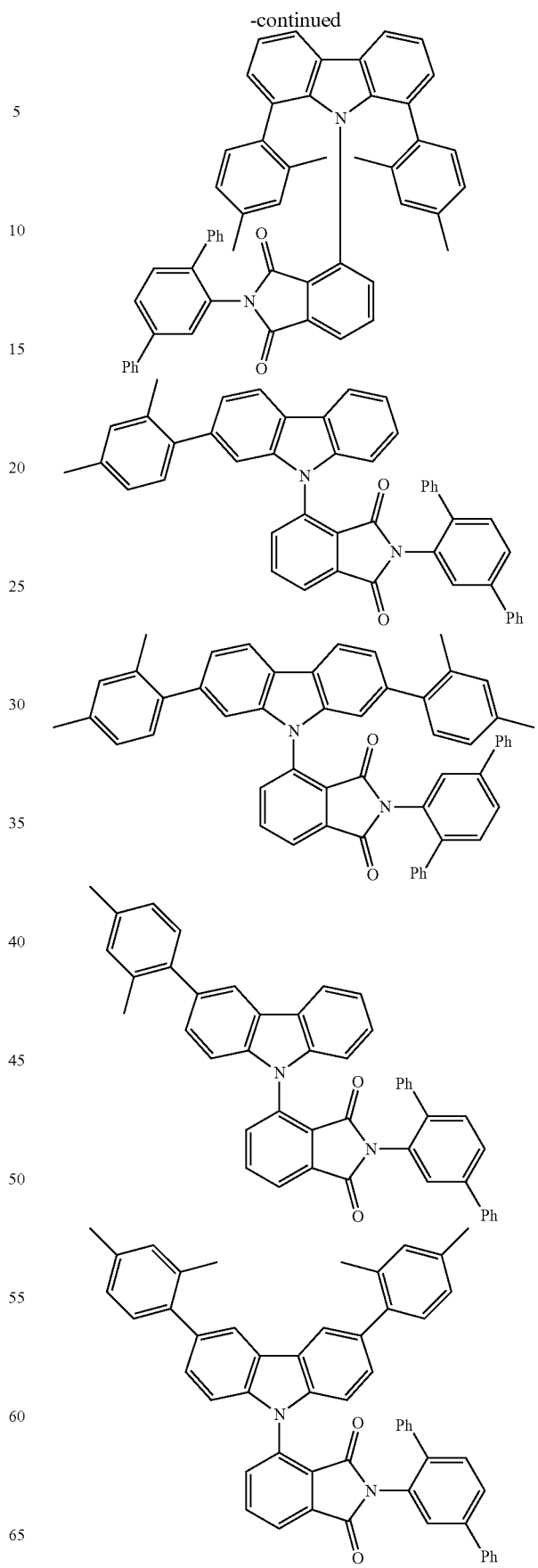

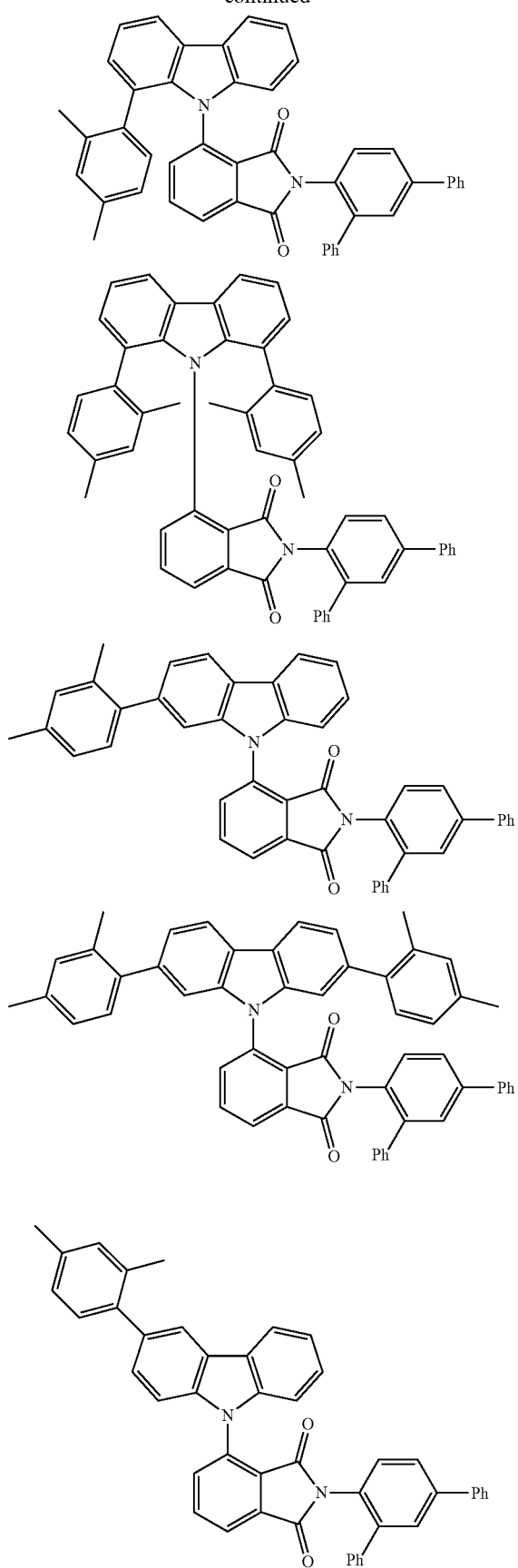

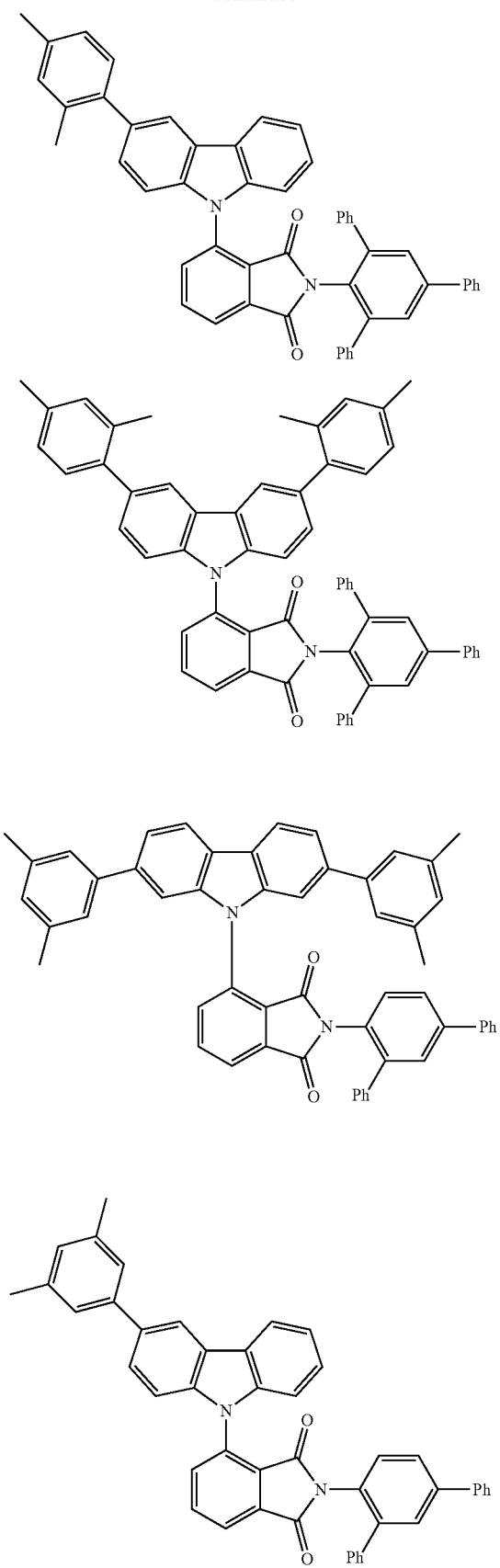
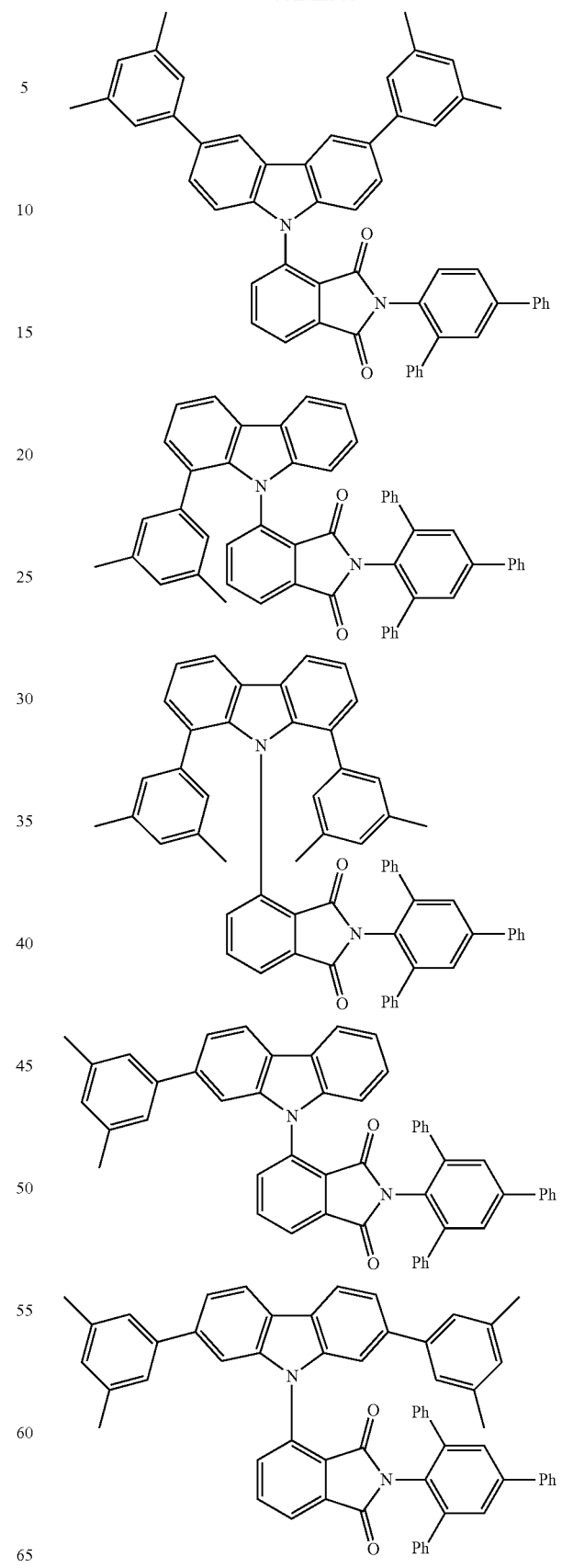

123
-continued
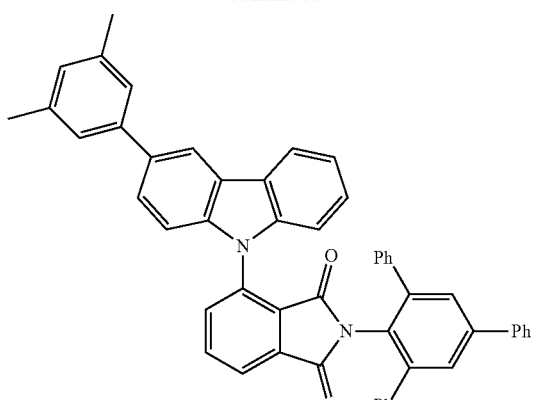
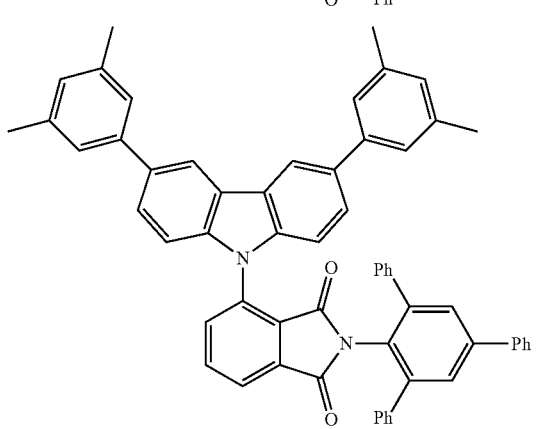
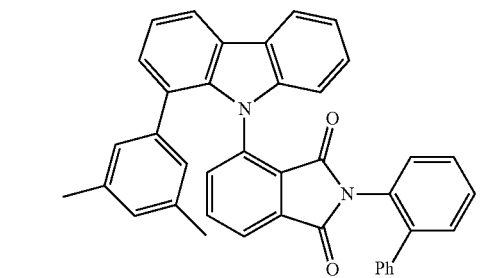
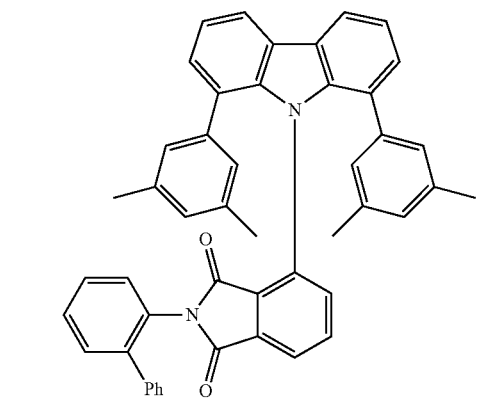
124
-continued
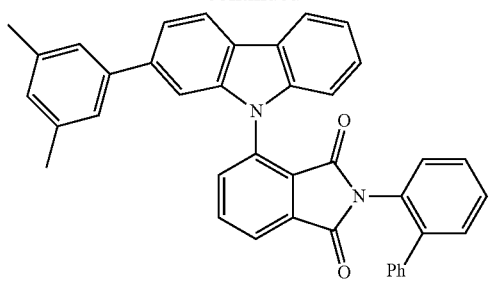
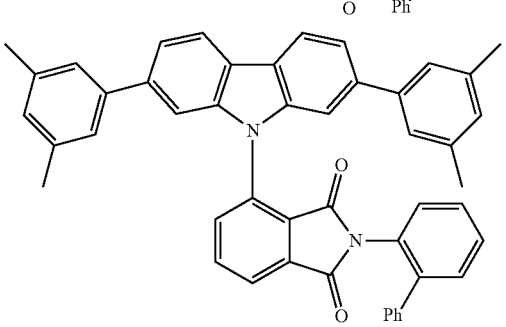
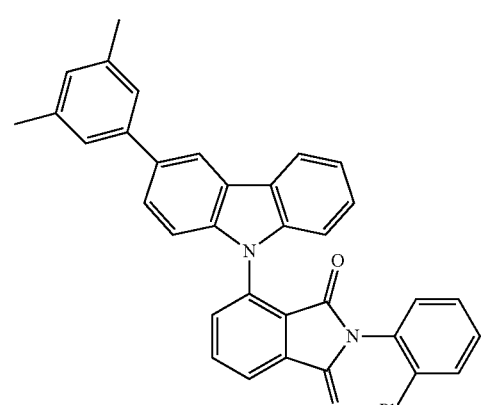
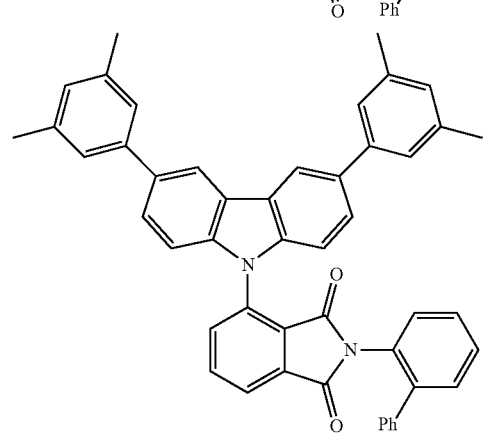
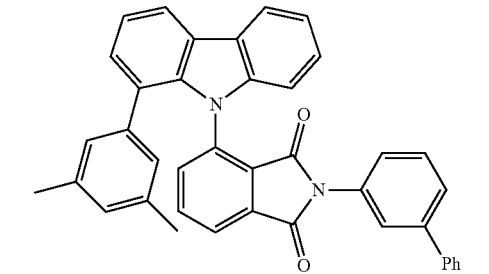

125
-continued
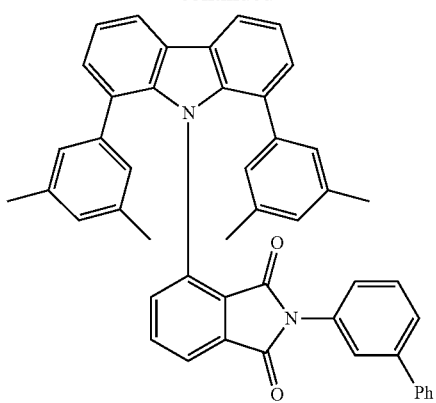
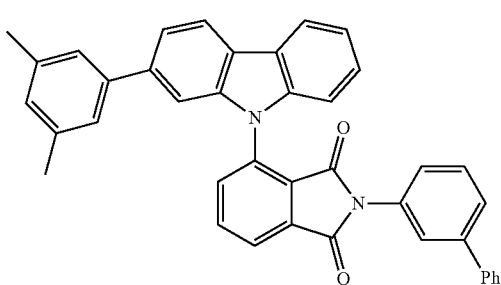
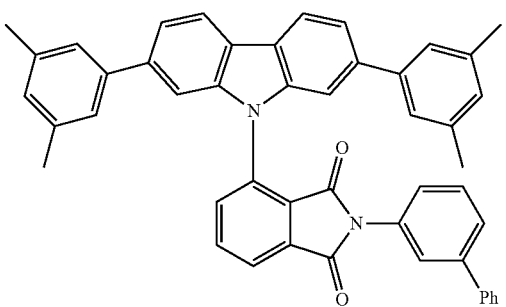
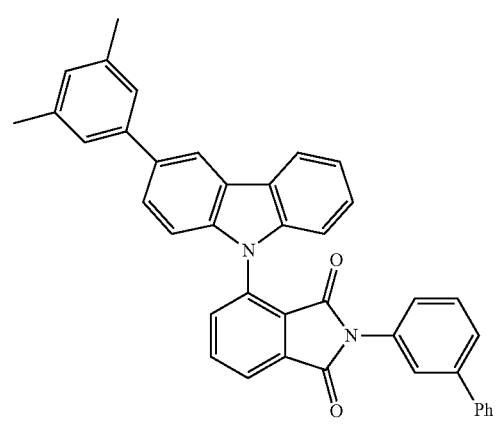
126
-continued
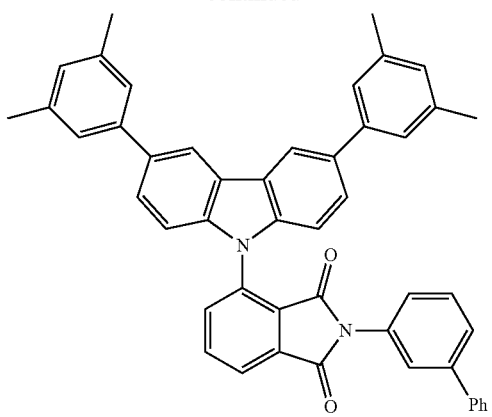
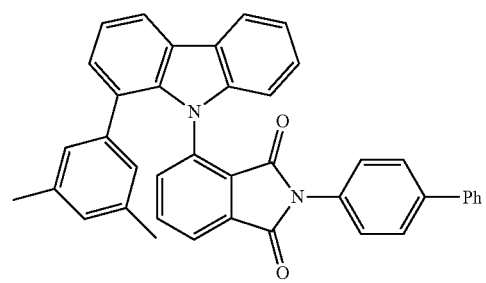
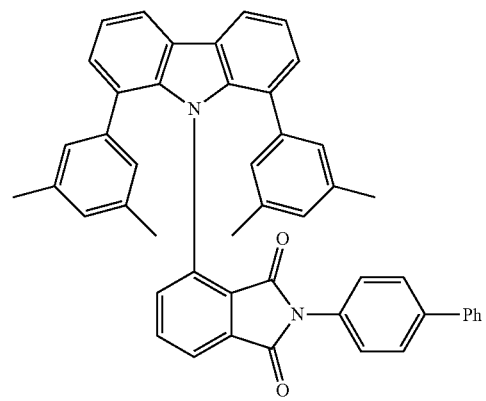
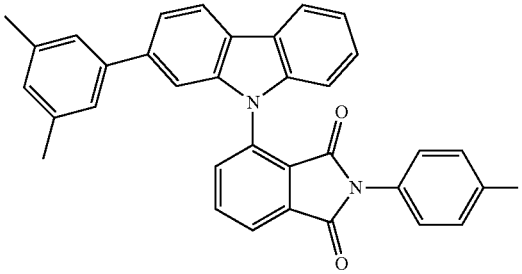
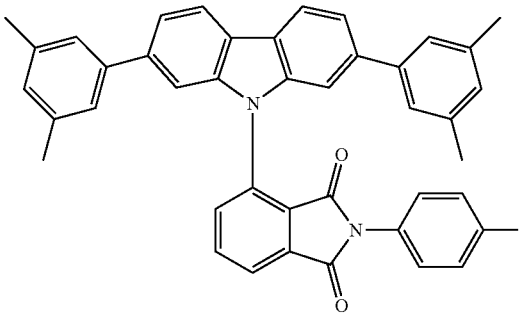

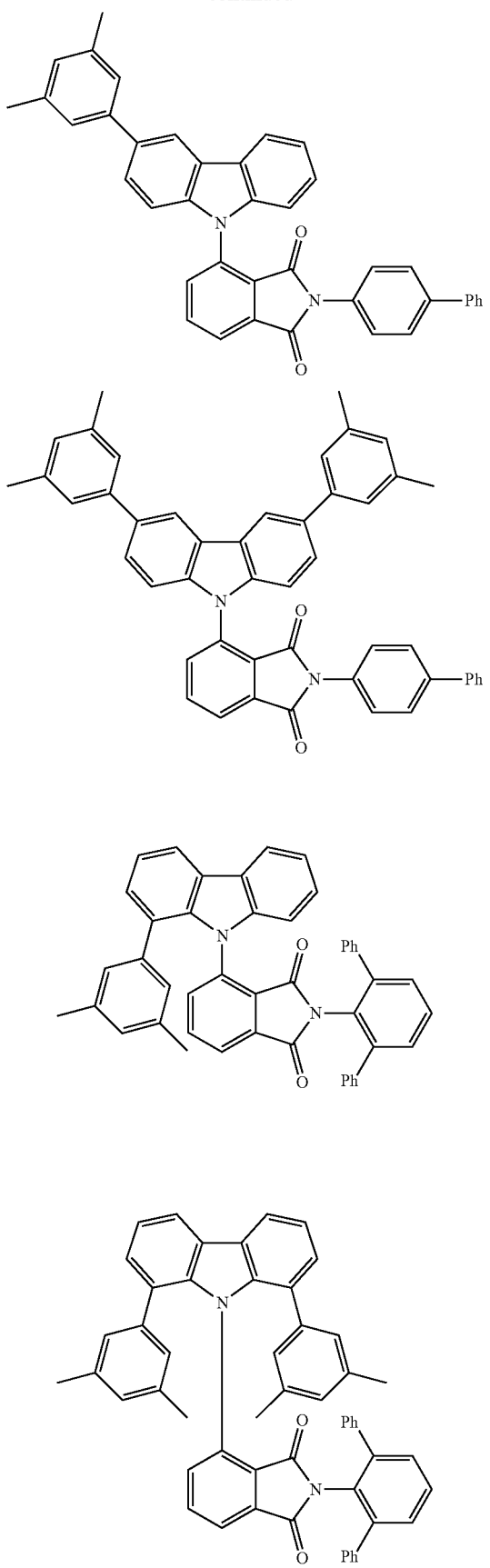
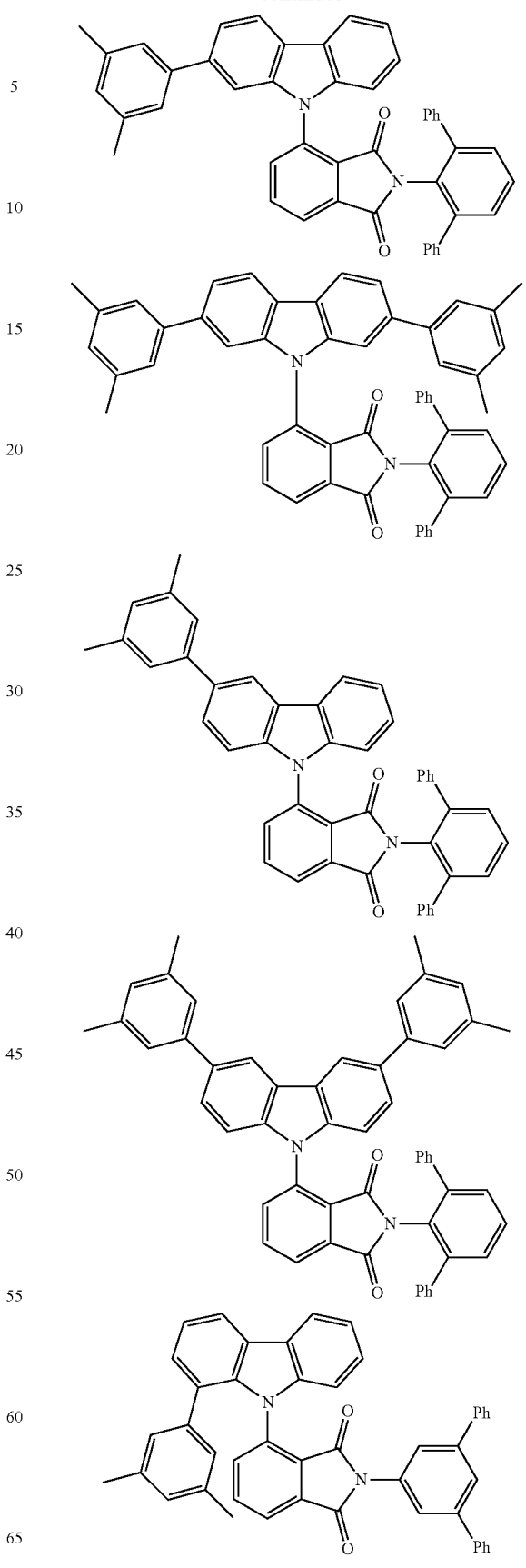

129
-continued
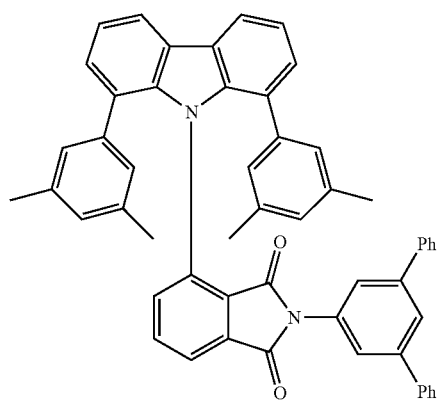
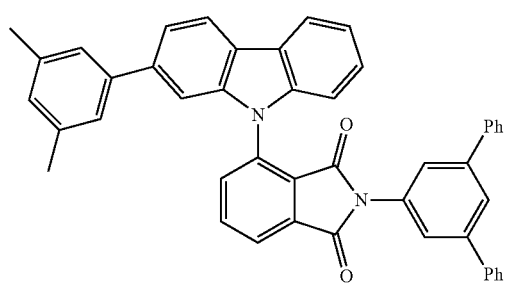
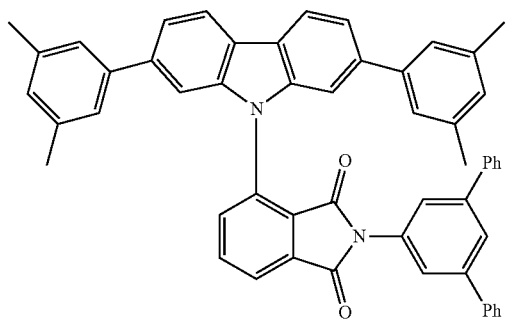
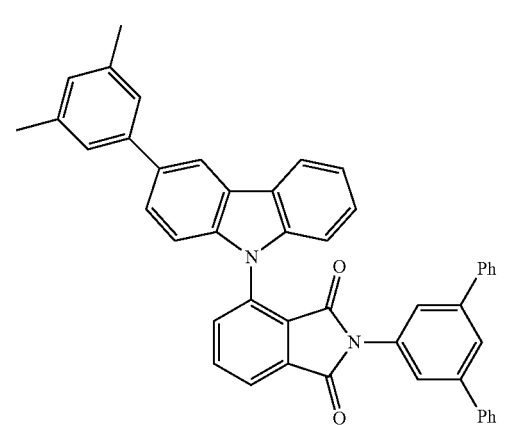
130
-continued
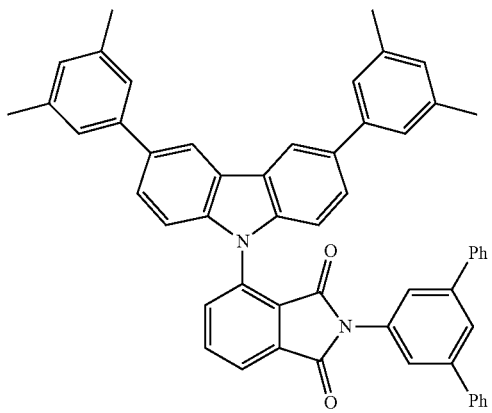
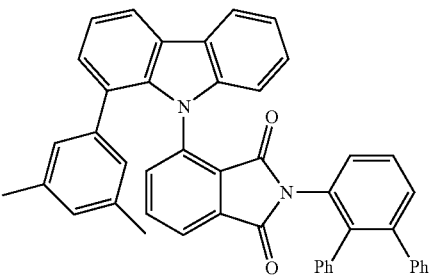
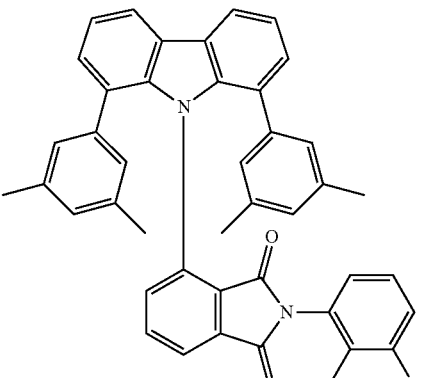
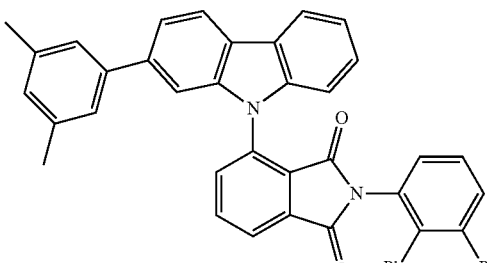
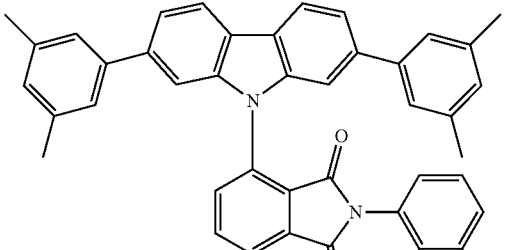

131
-continued
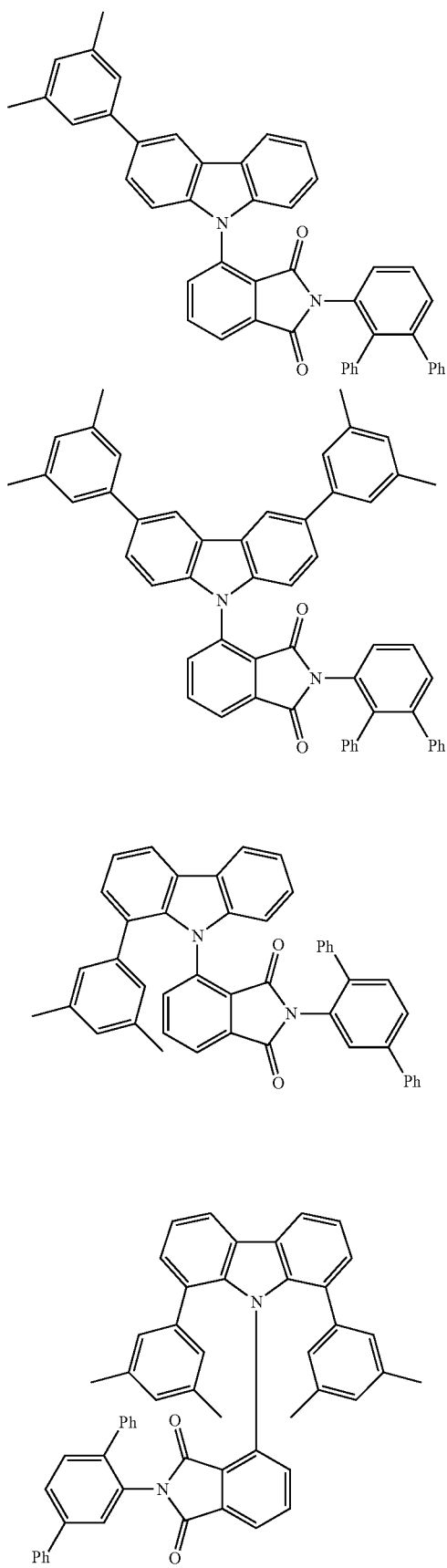
132
-continued
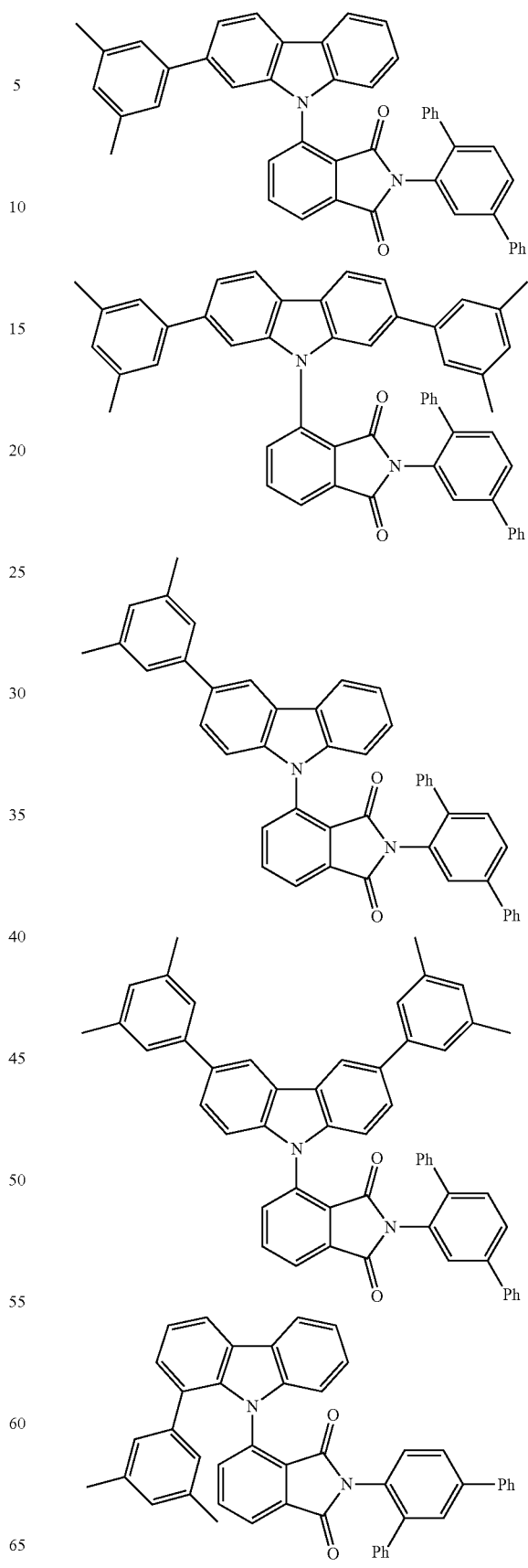

133
-continued
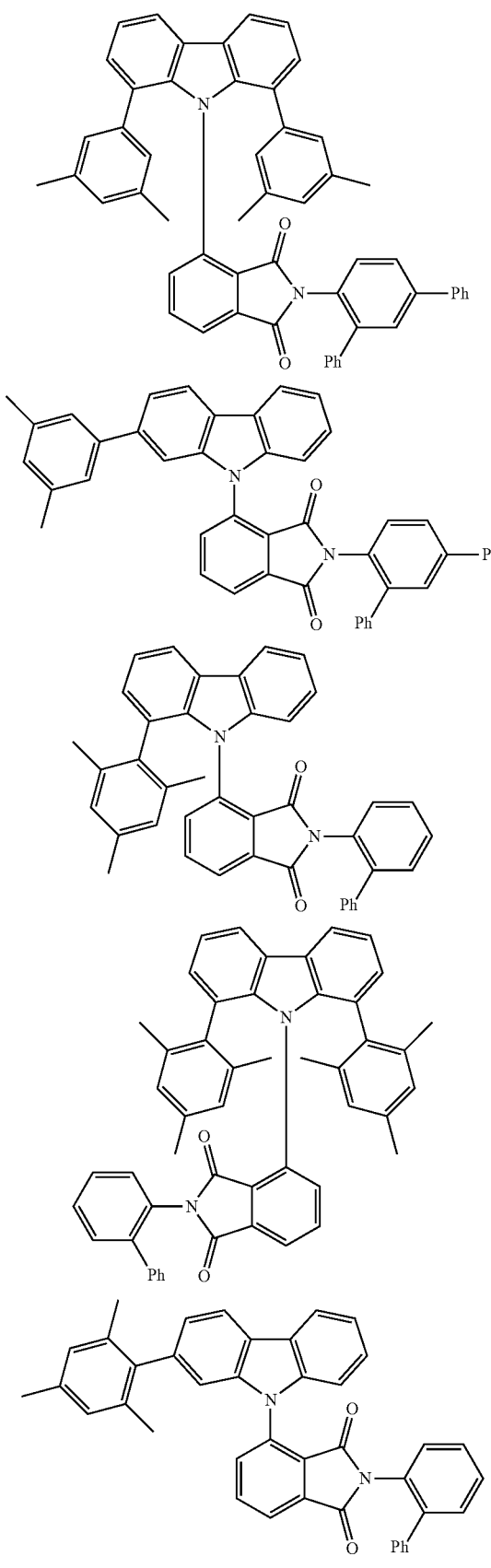
134
-continued
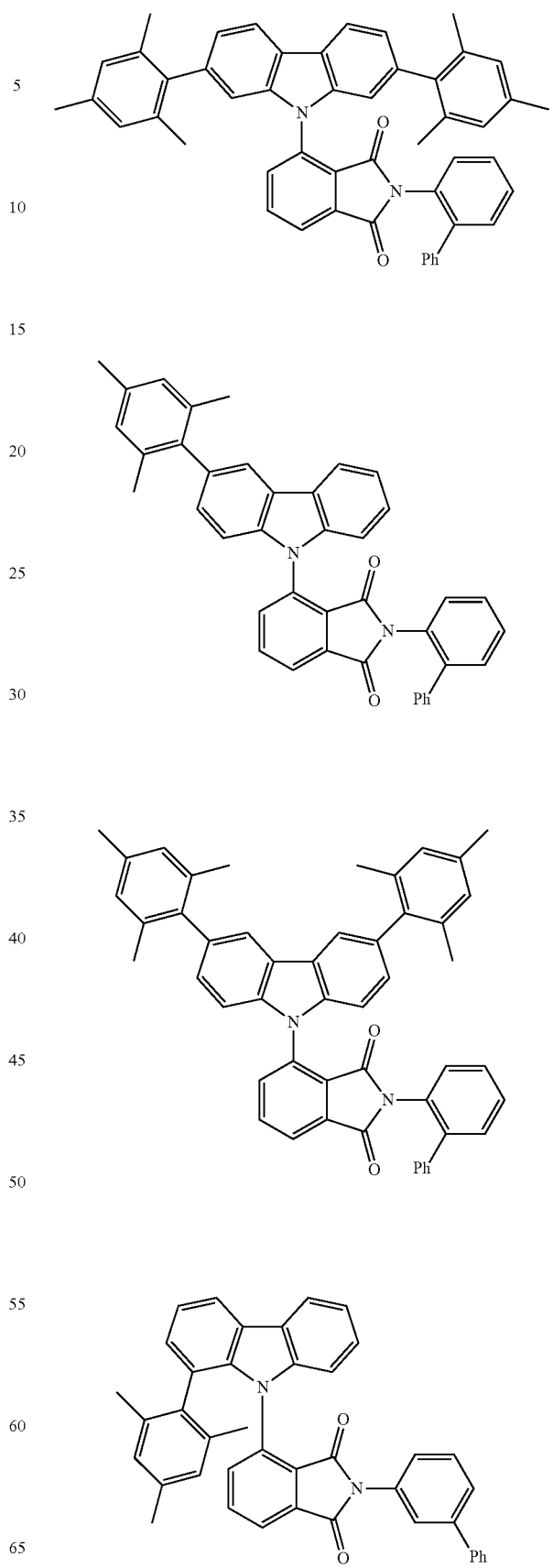

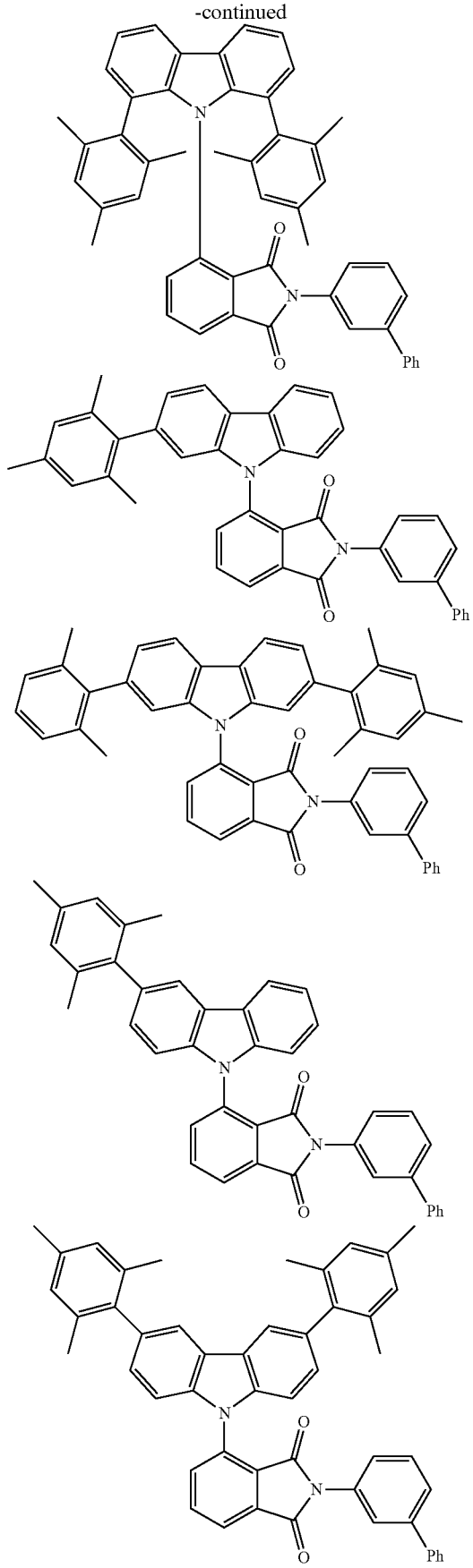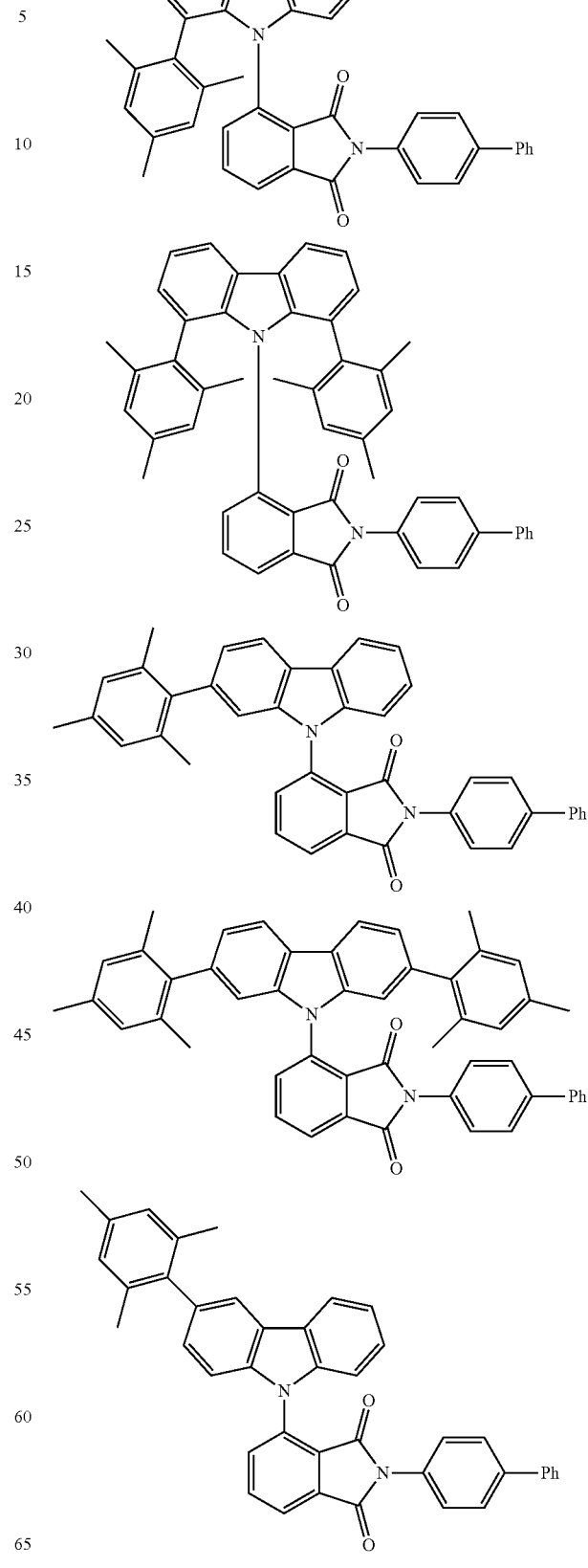

137
-continued
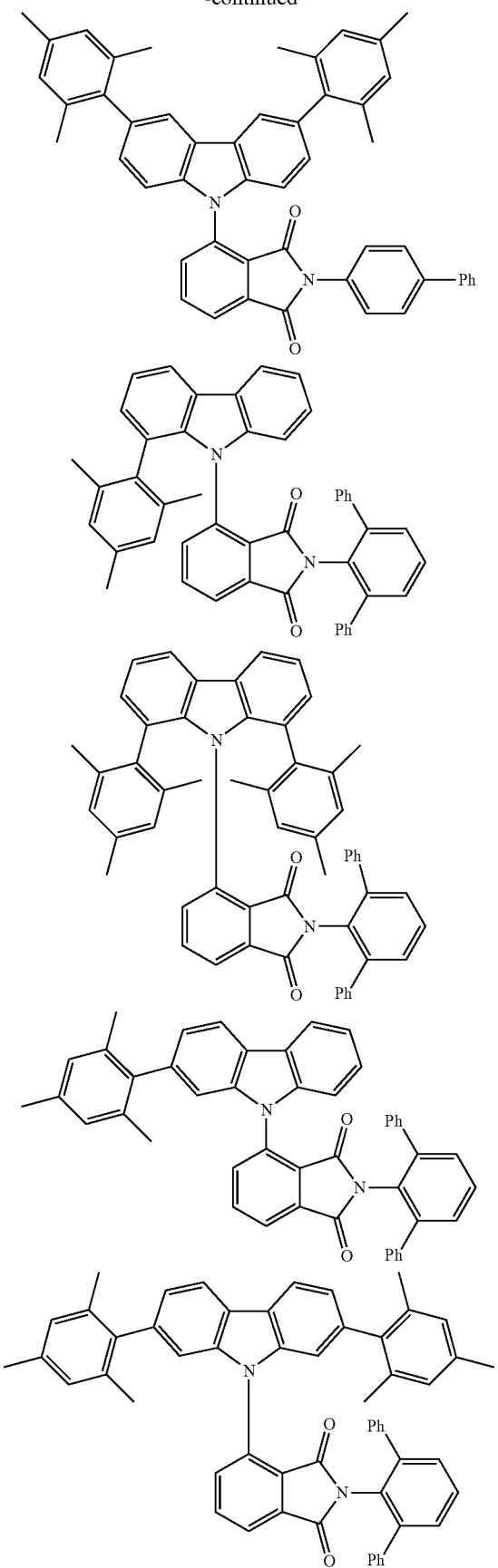
138
-continued
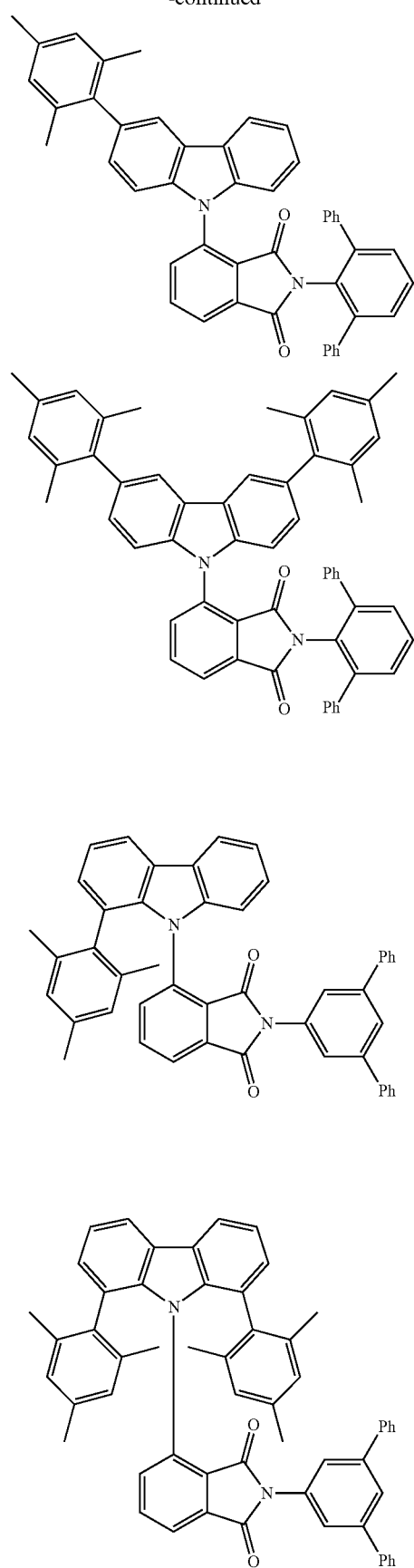

139
-continued
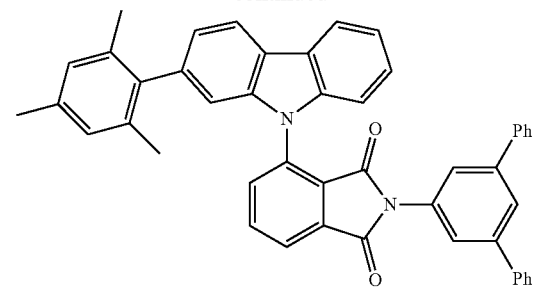
140
-continued
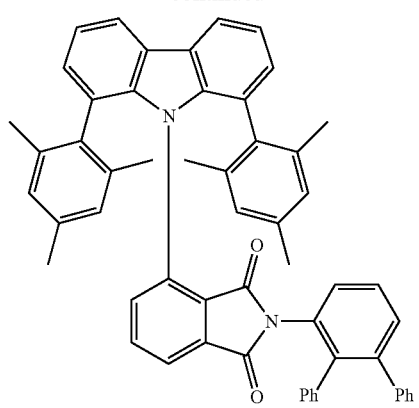
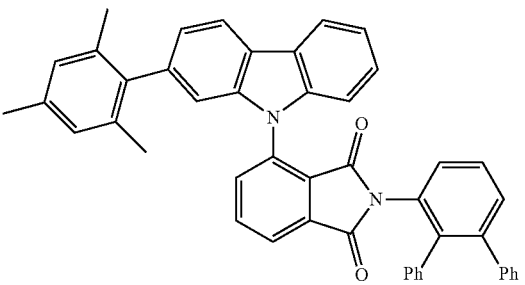
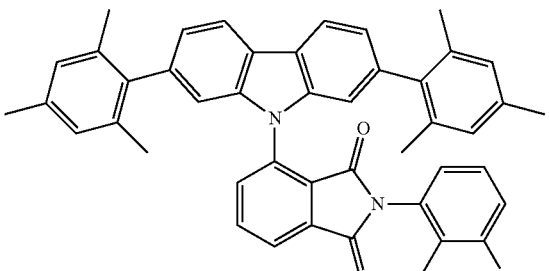
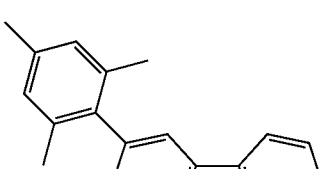
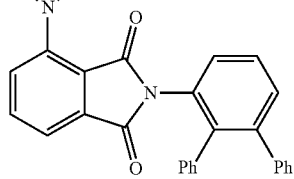

-continued
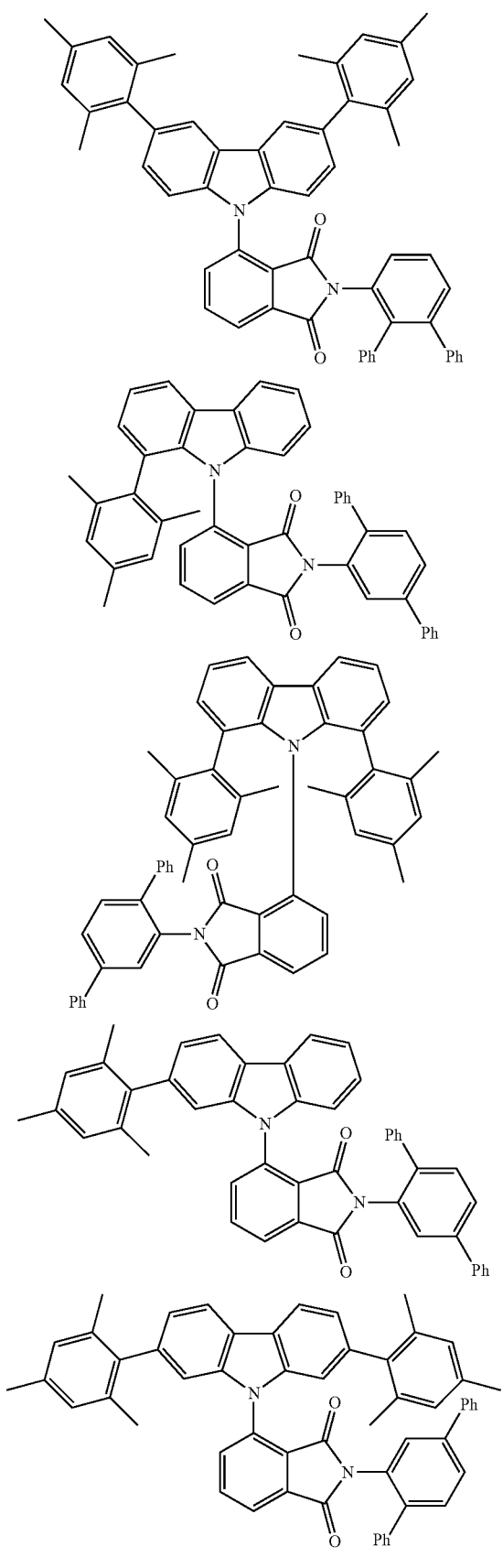
-continued
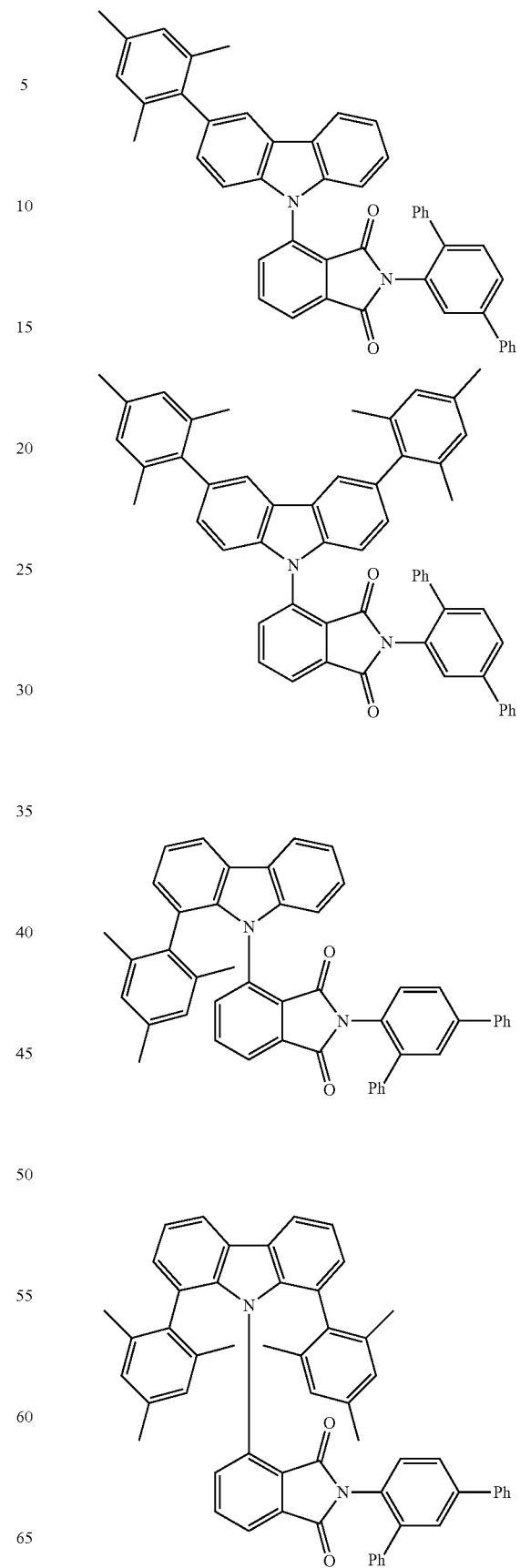

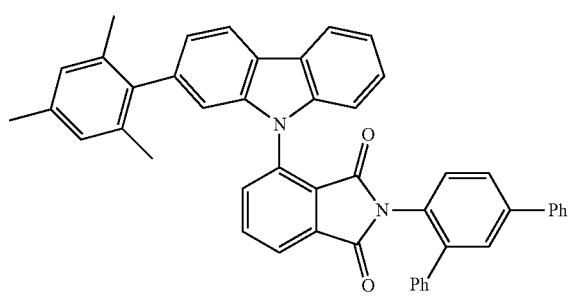
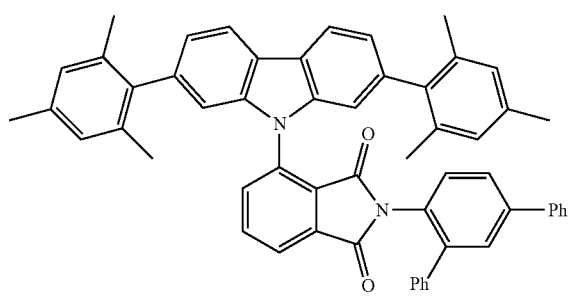
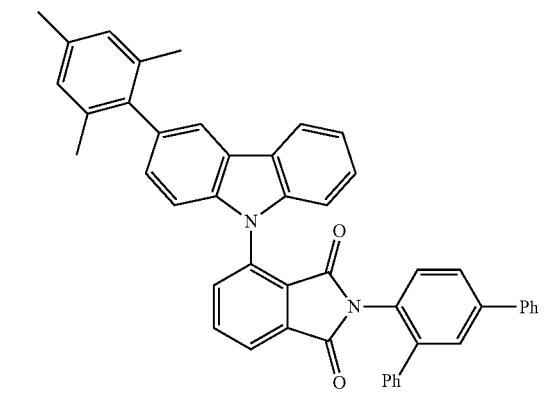
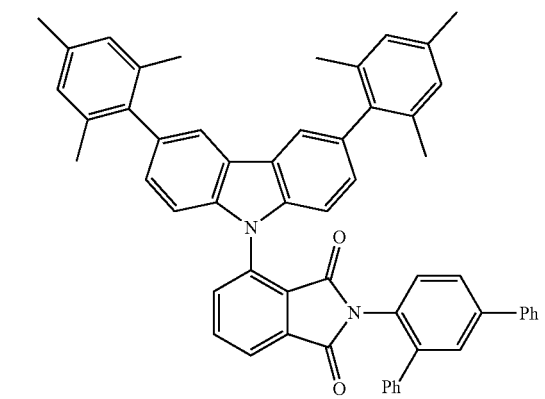
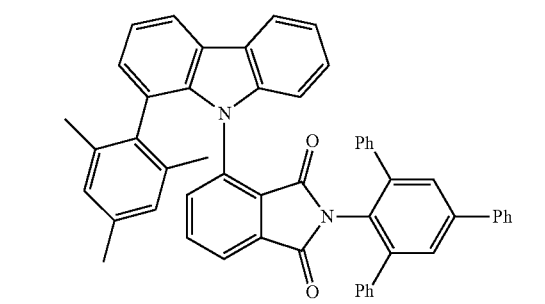
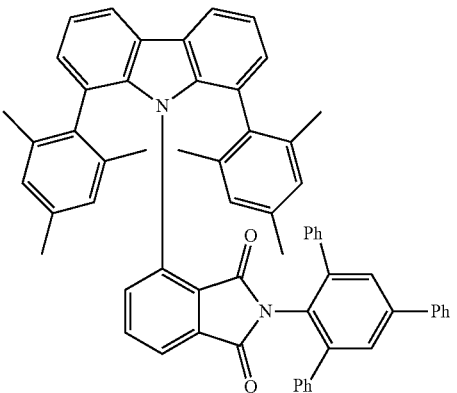
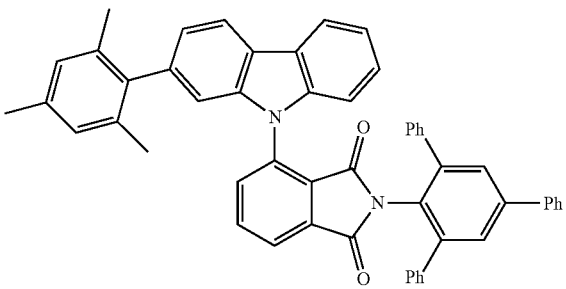
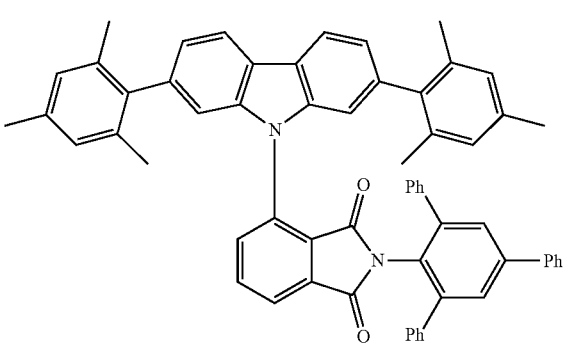
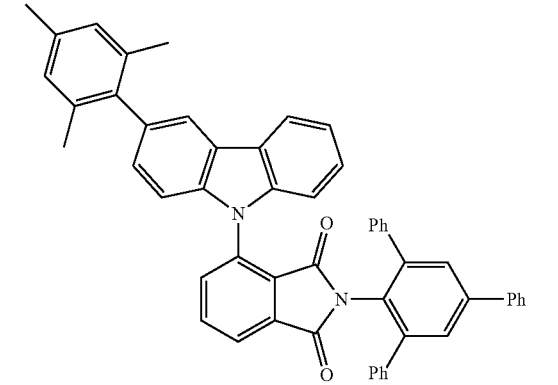

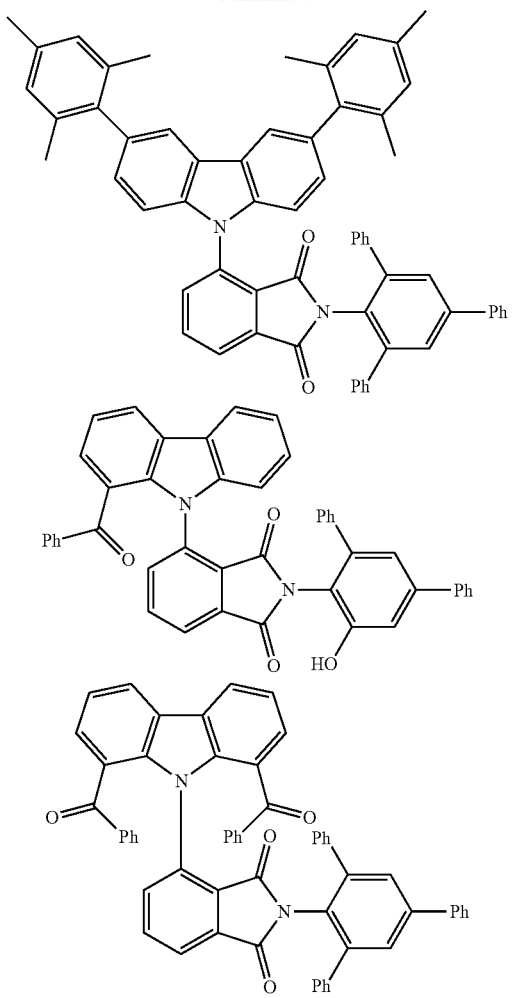
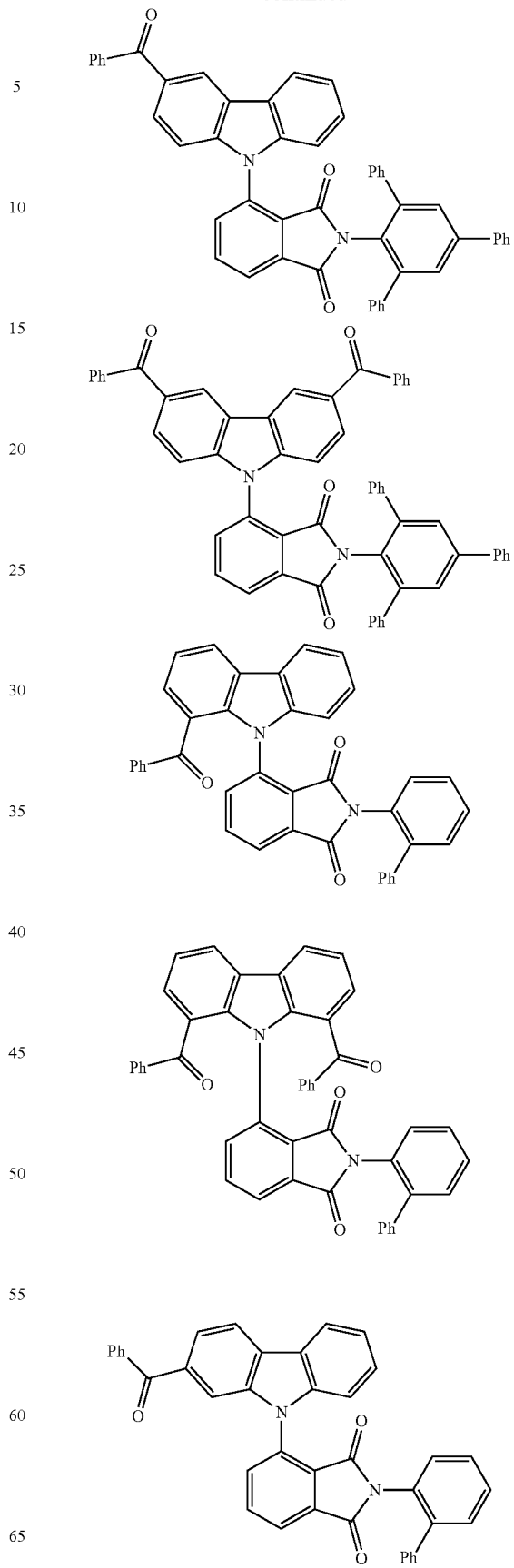

147
-continued
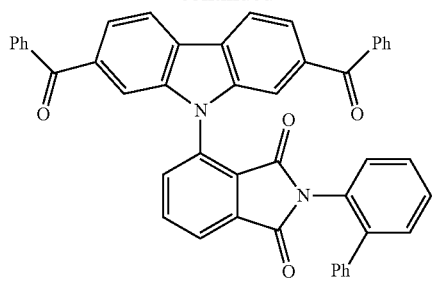
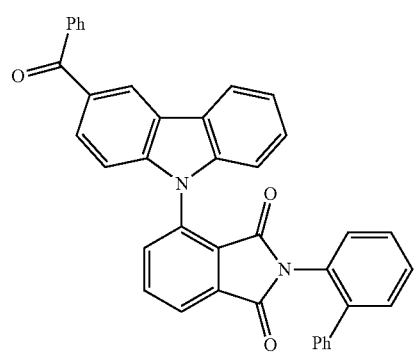
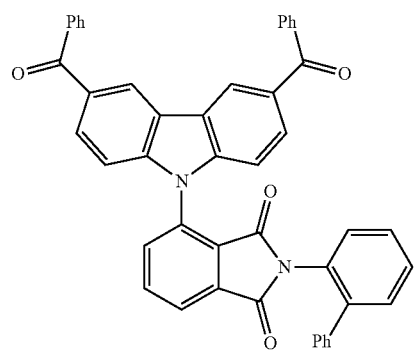
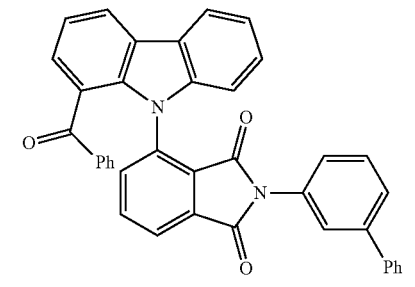
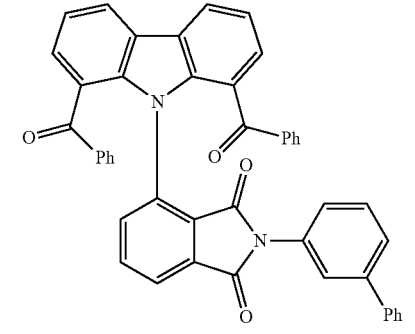
148
-continued
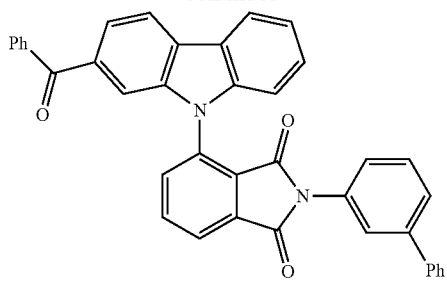
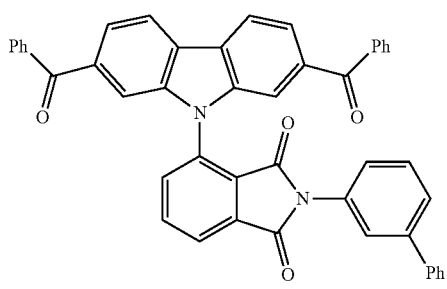
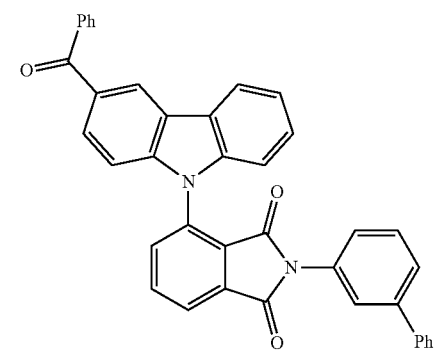
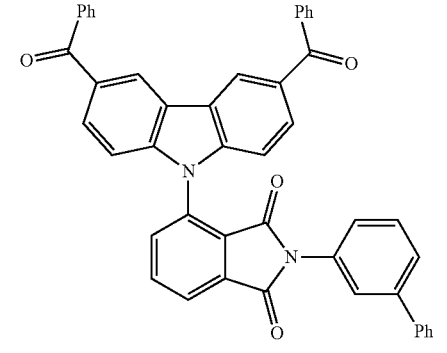
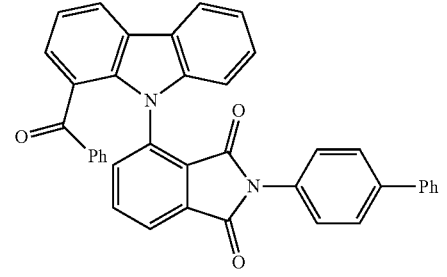

149
-continued
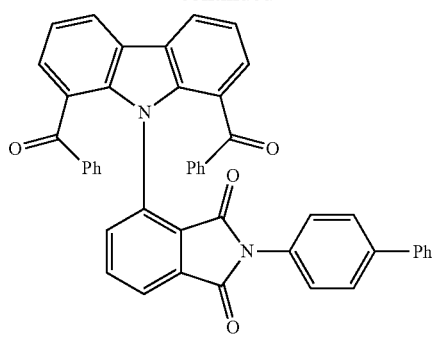
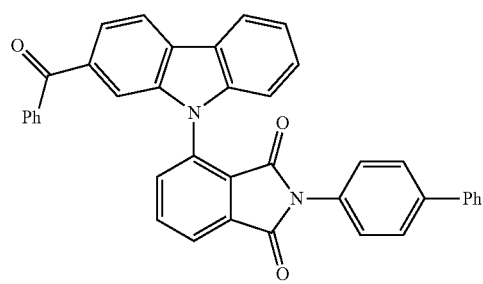
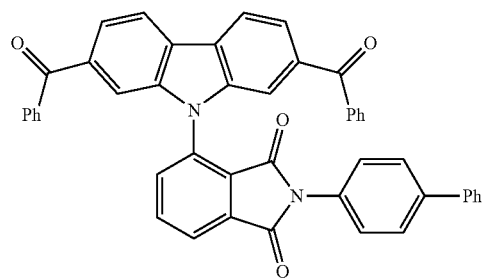
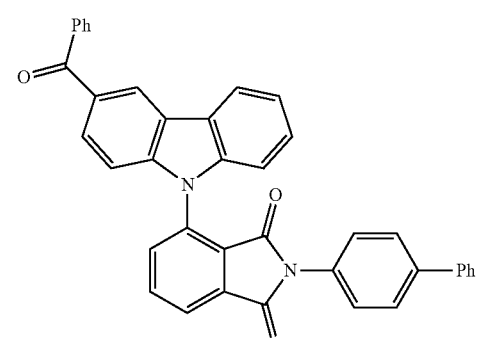
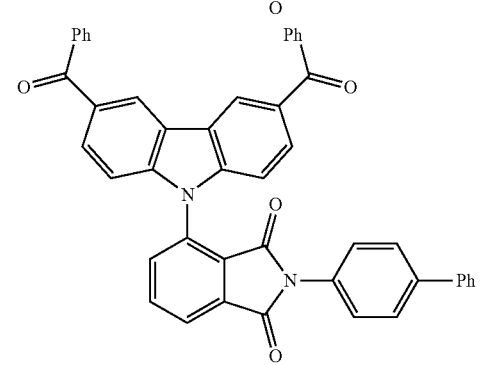
150
-continued
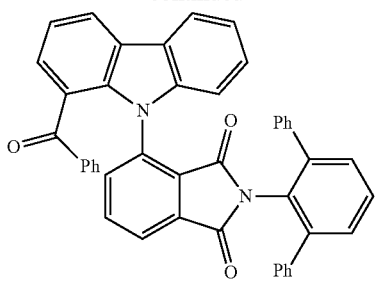
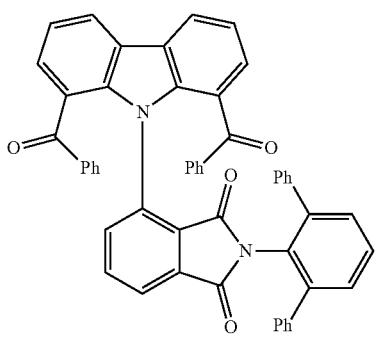
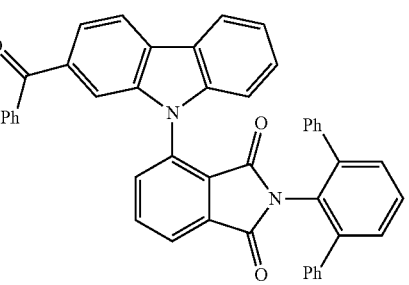
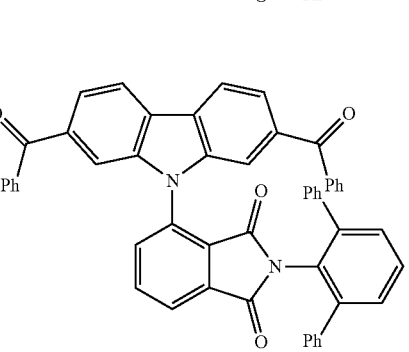
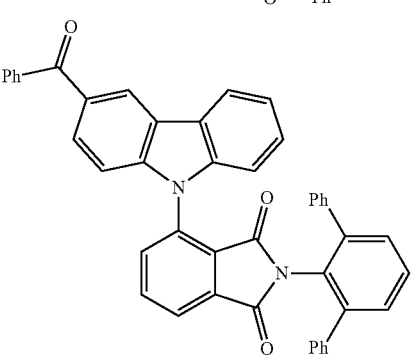

151
-continued
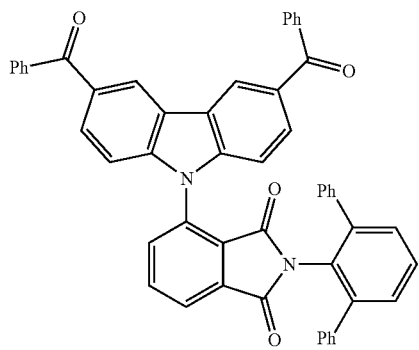
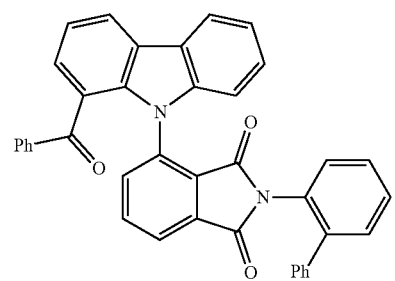
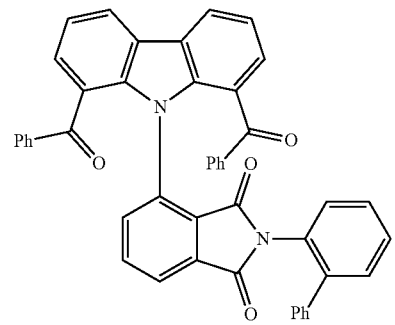
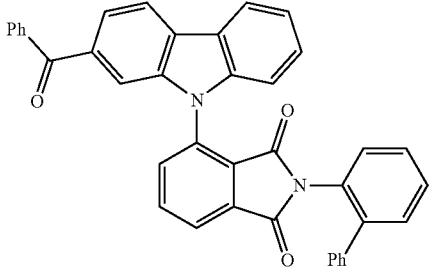
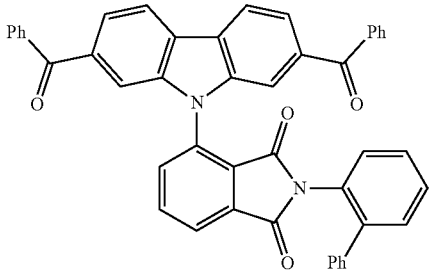
152
-continued
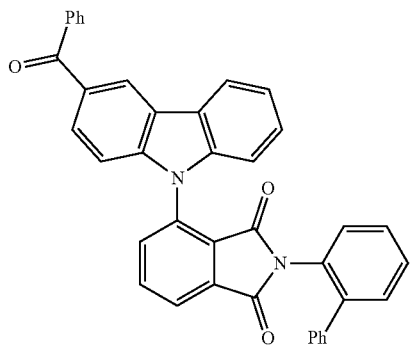
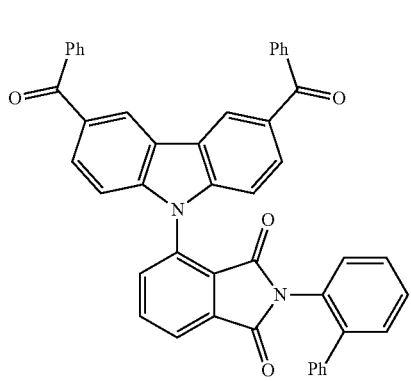
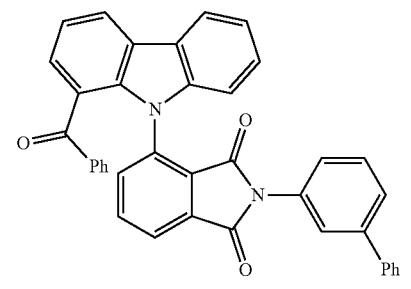
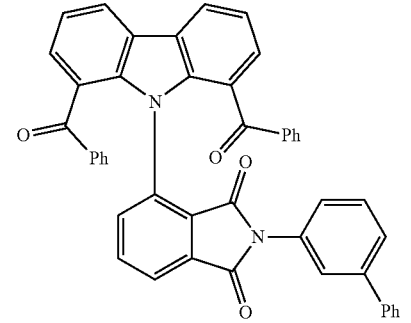
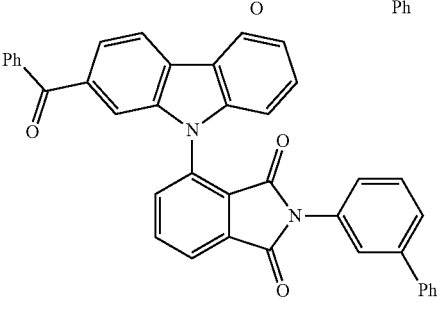

153
-continued
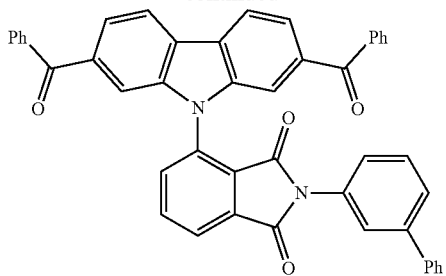
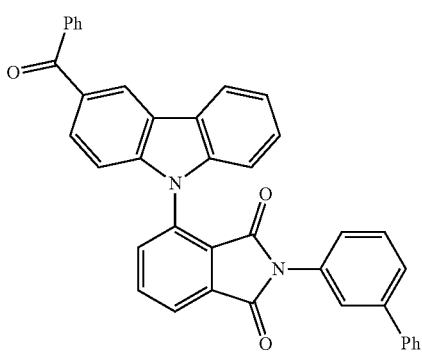
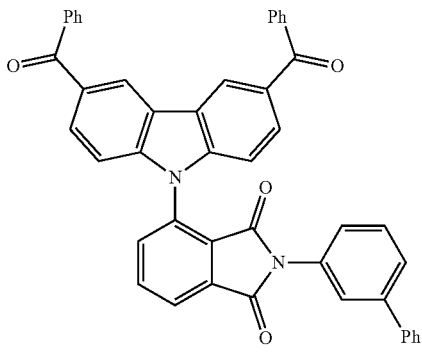
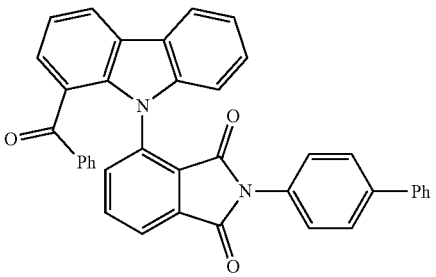
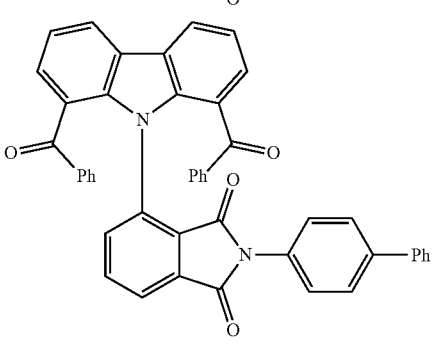
154
-continued
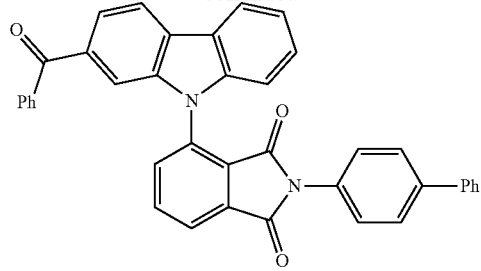
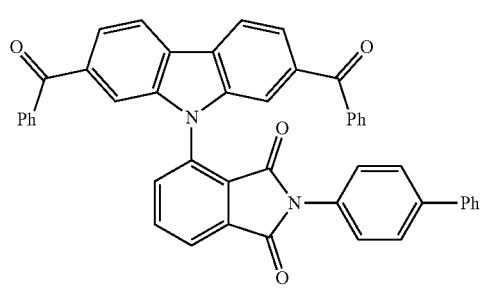
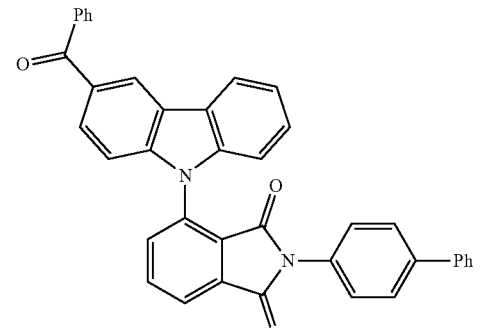
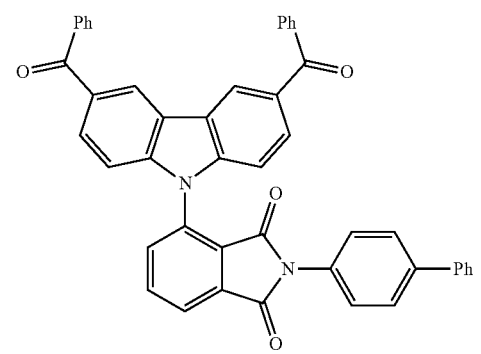
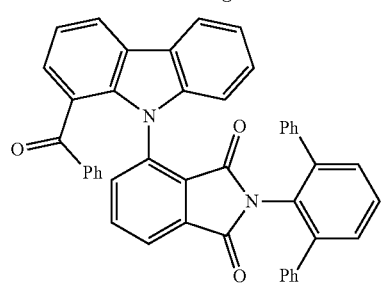

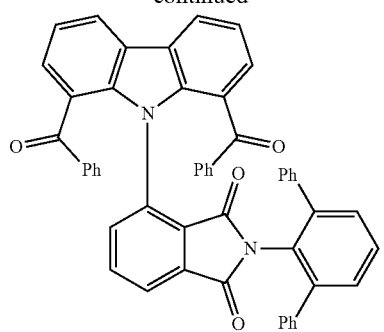
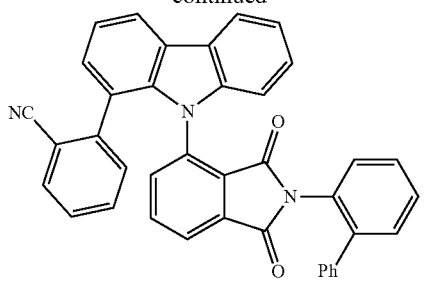
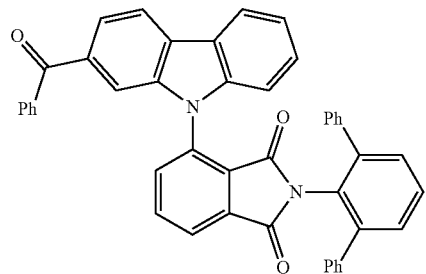
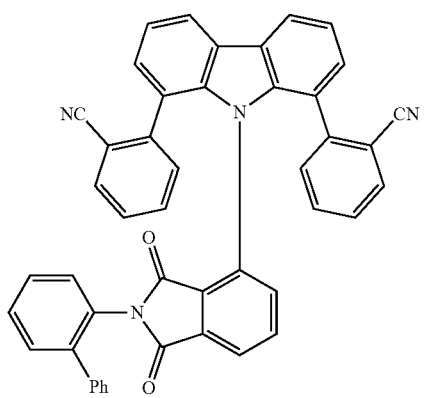
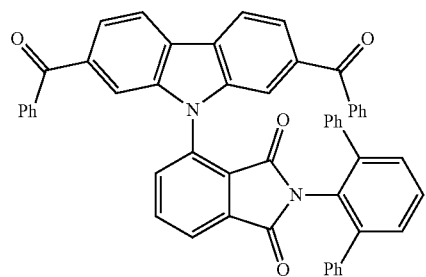
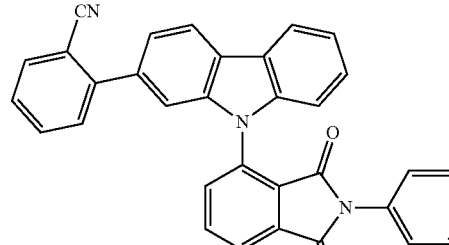
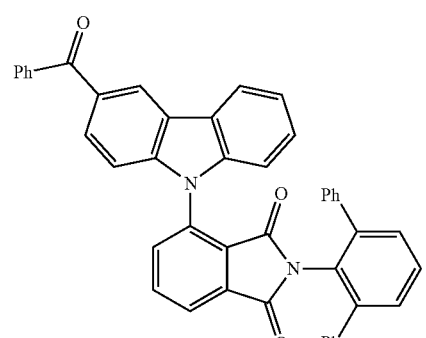
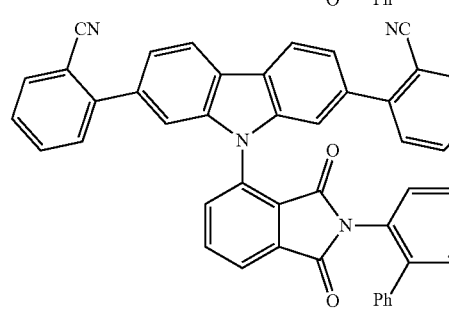
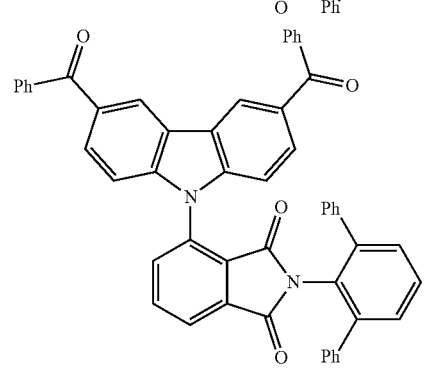
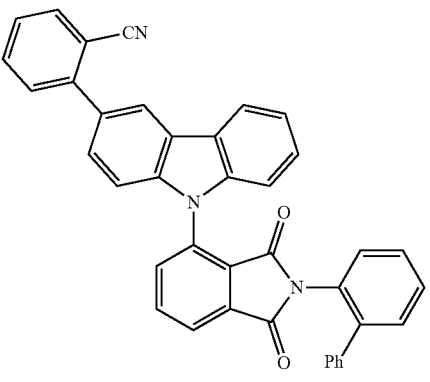

157
-continued
158
-continued
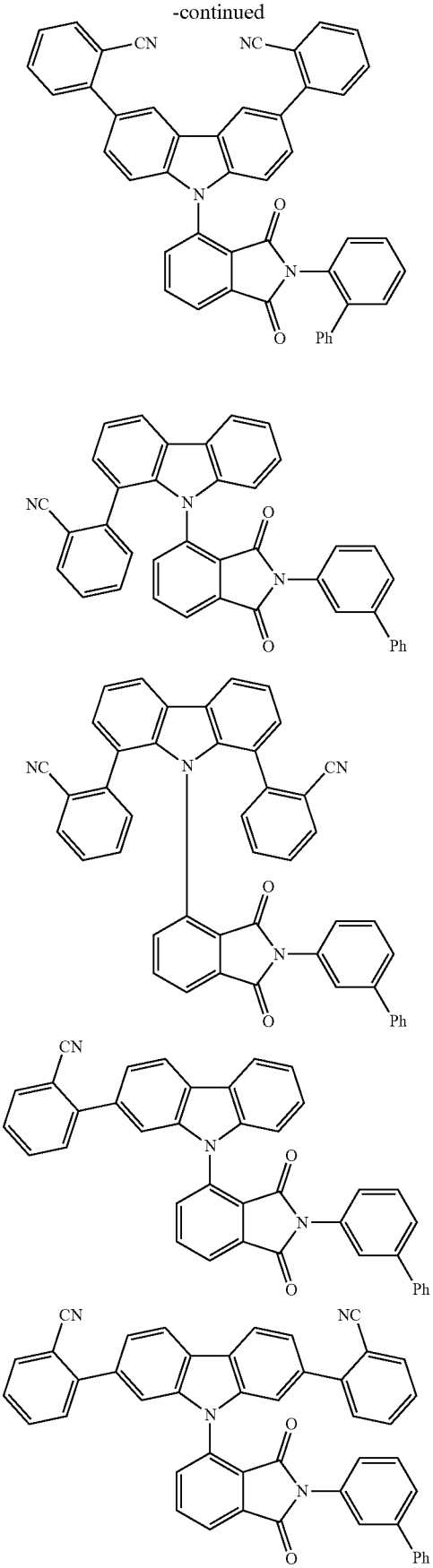
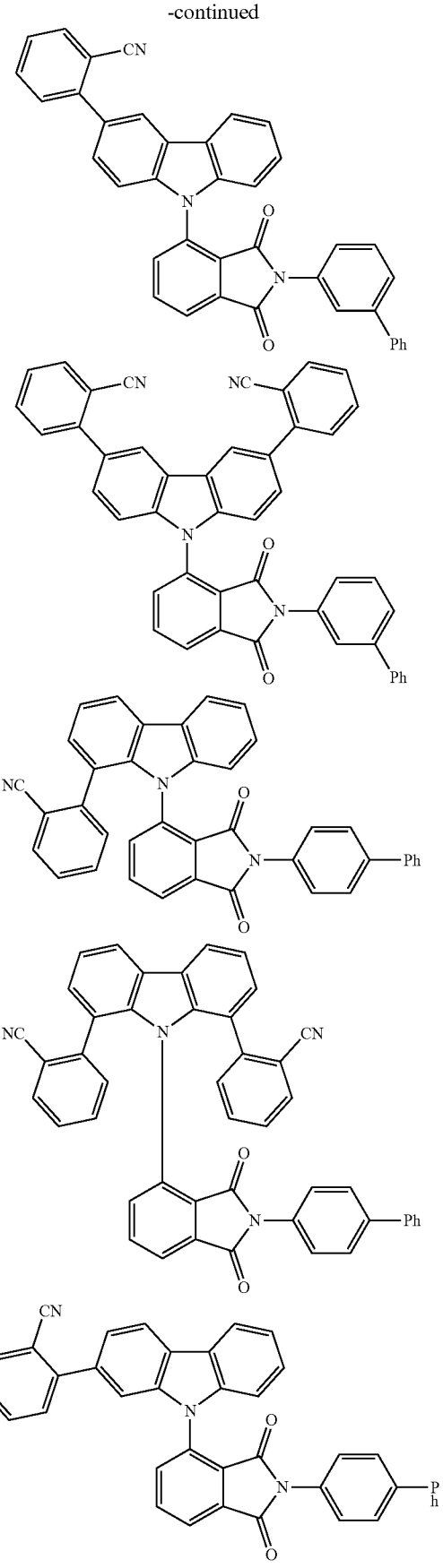

-continued
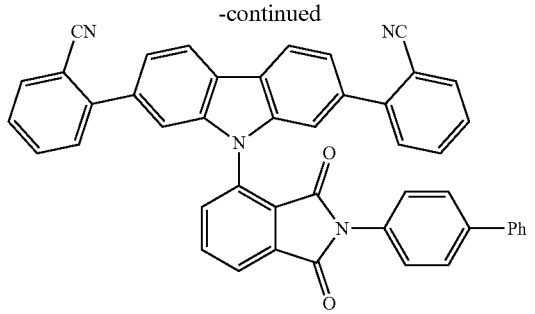
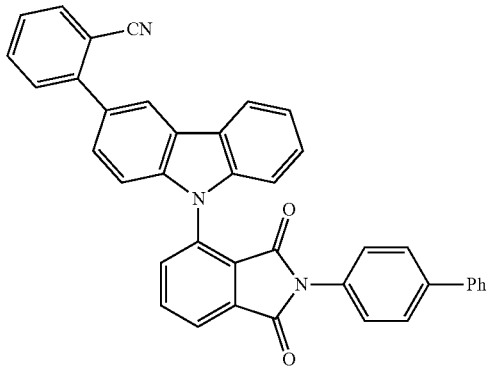
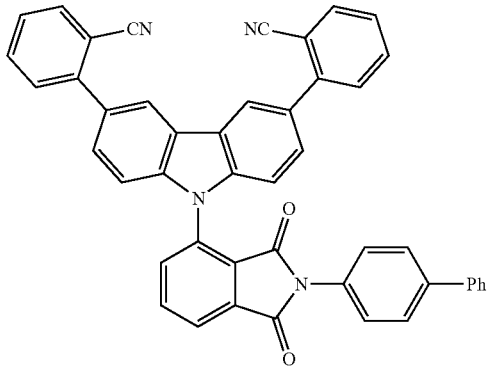
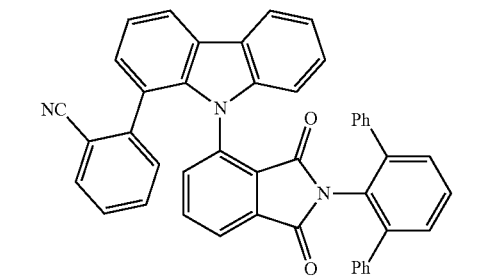
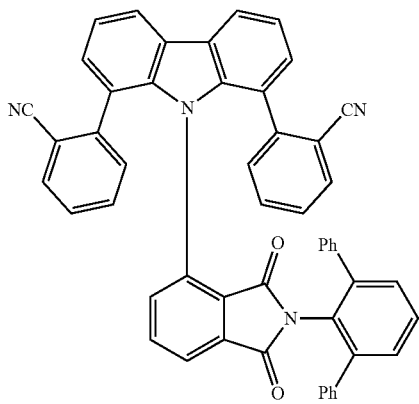
-continued
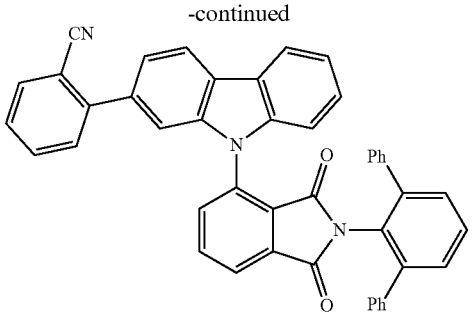
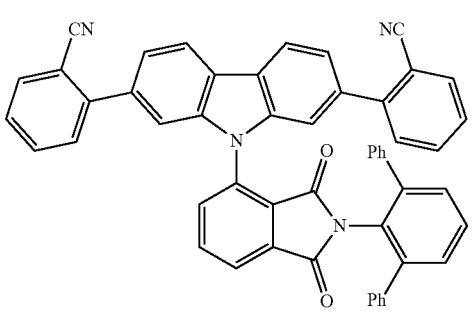
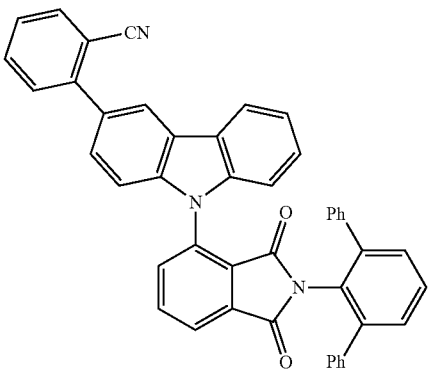
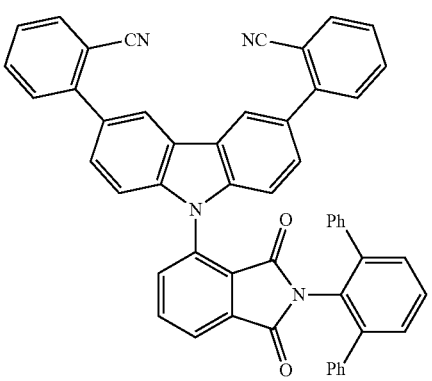
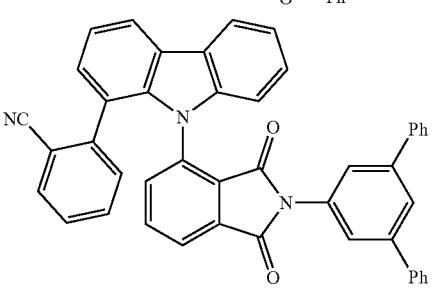

161
-continued
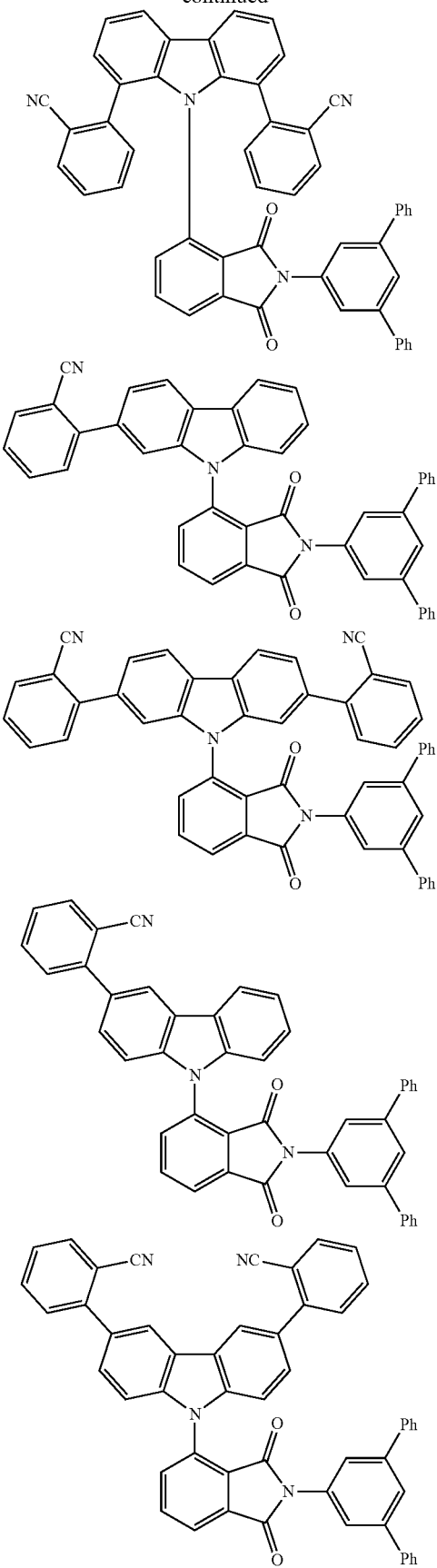
162
-continued
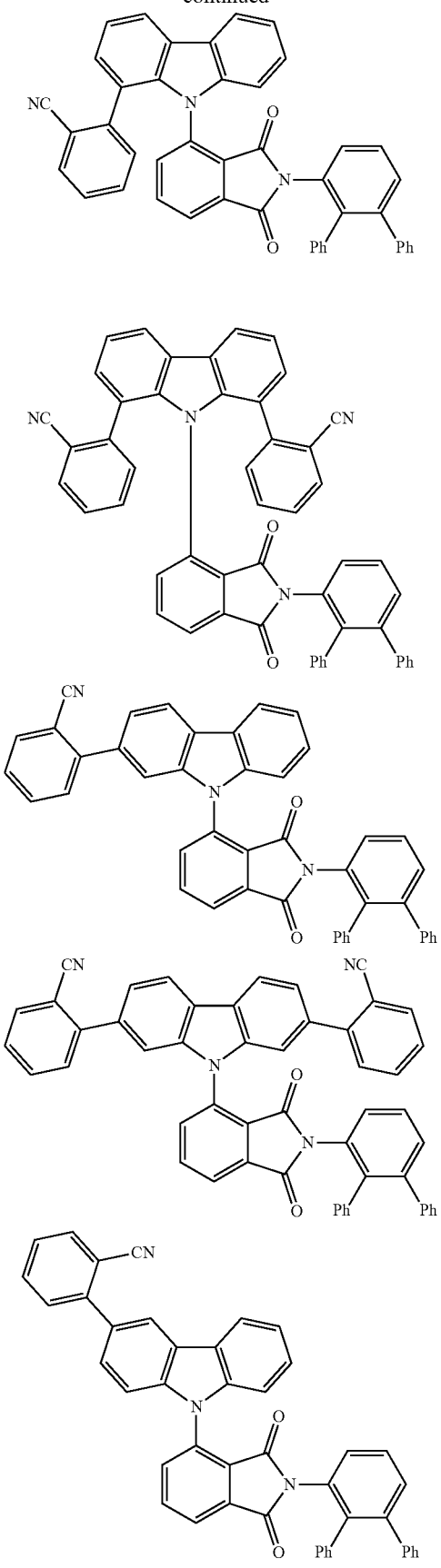

-continued
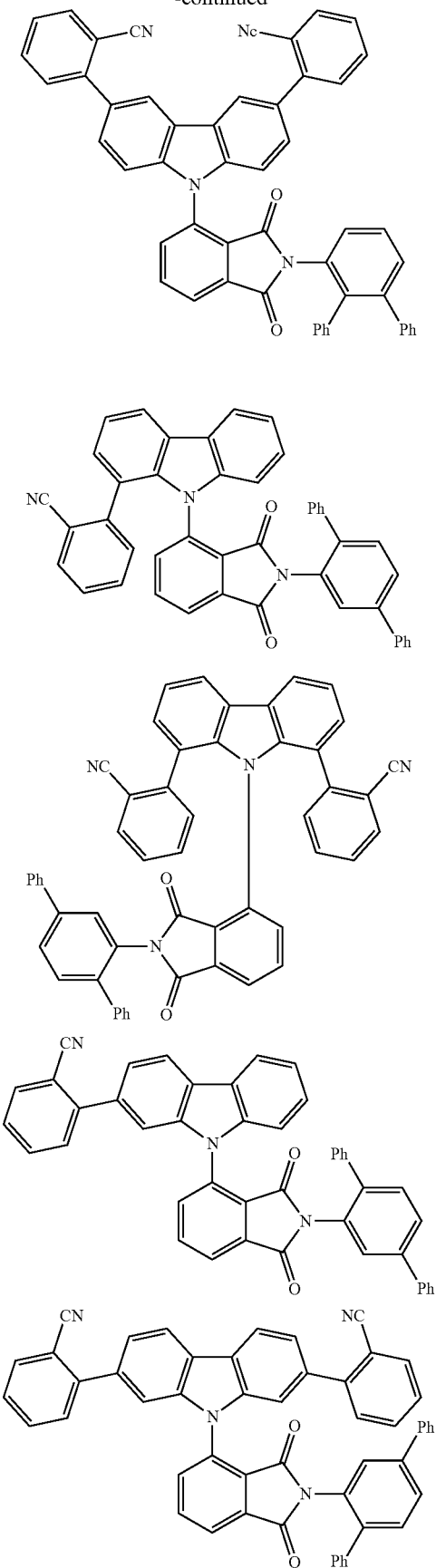
-continued
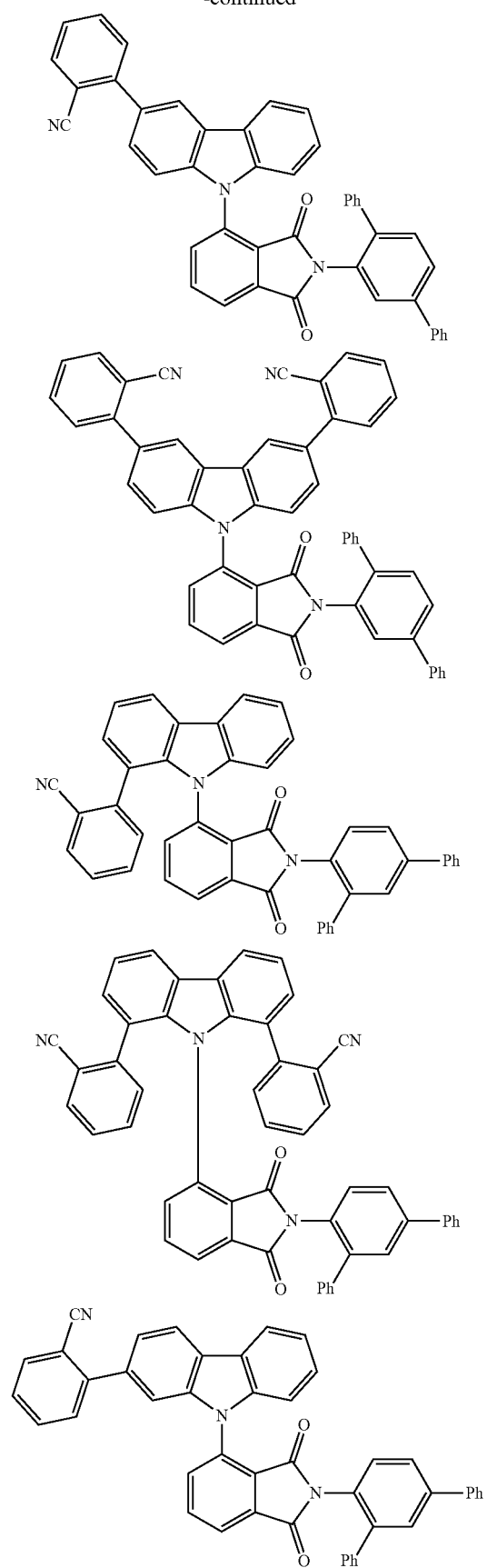

165
-continued
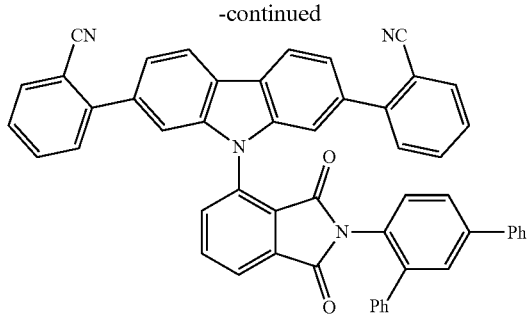
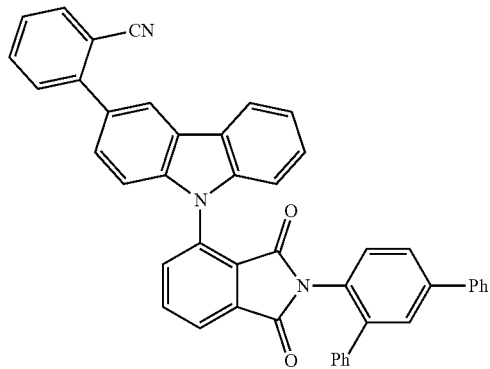
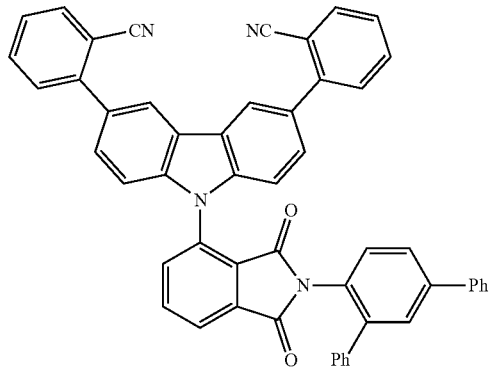
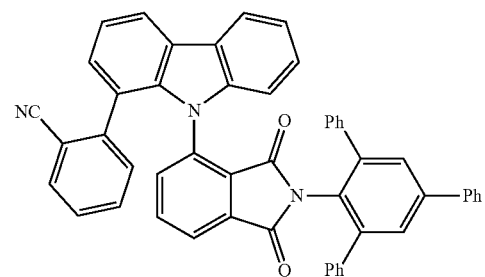
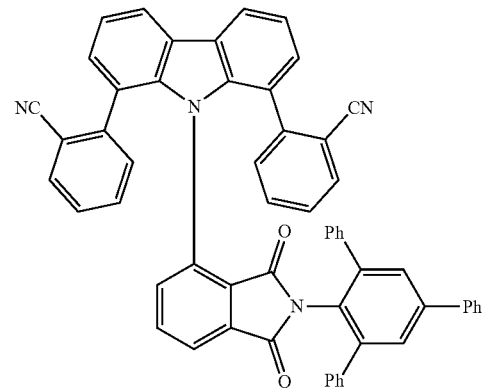
166
-continued
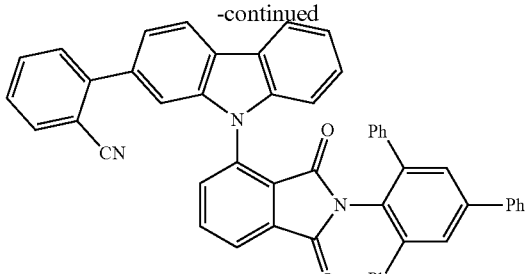
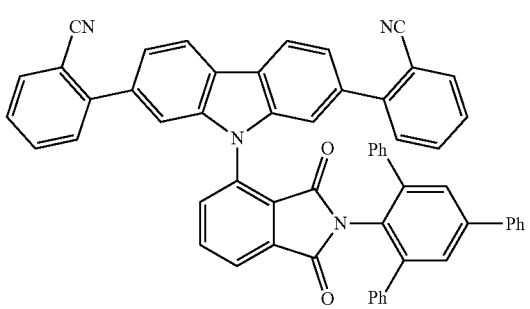
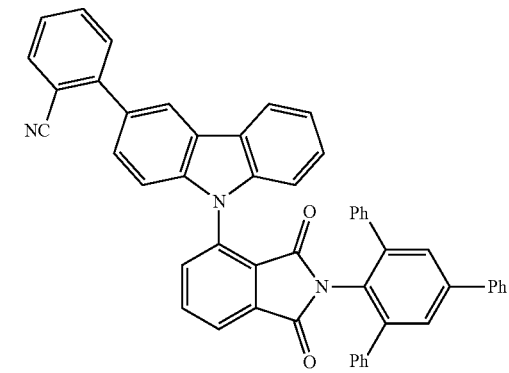
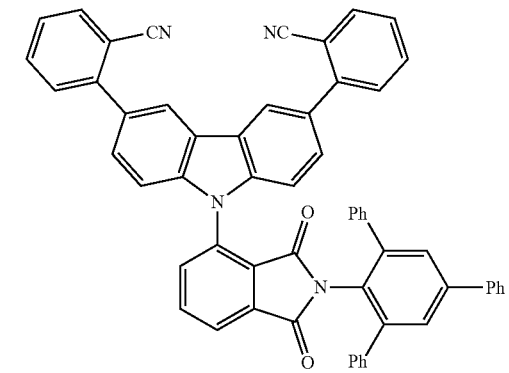
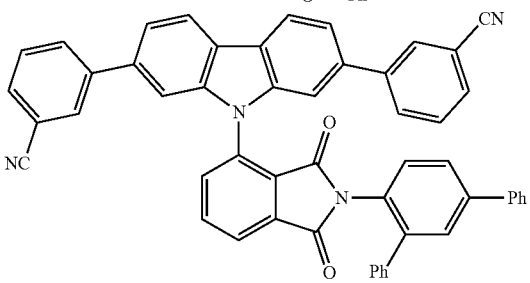

167
-continued
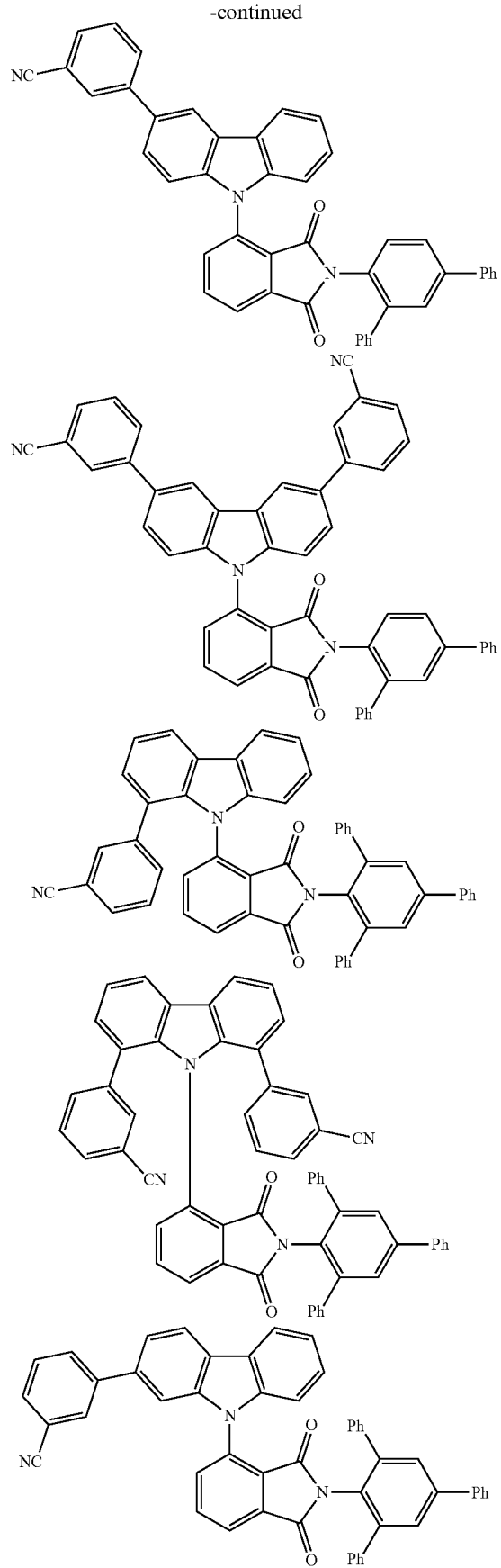
168
-continued
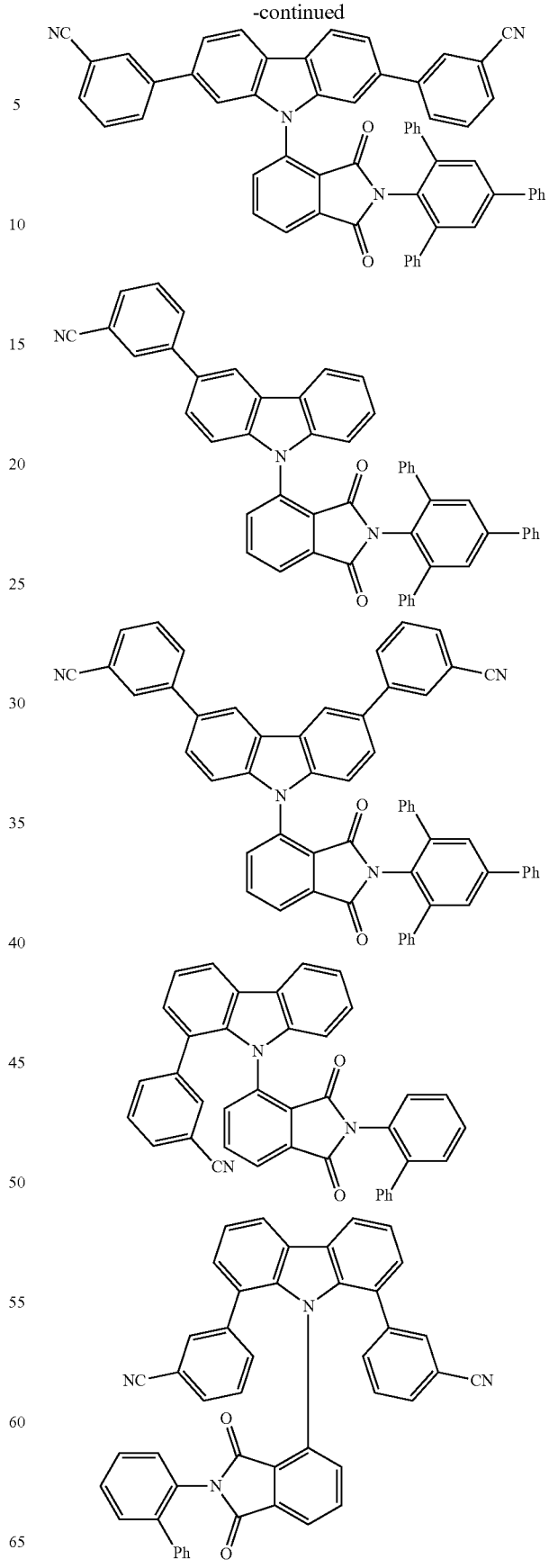

169
-continued
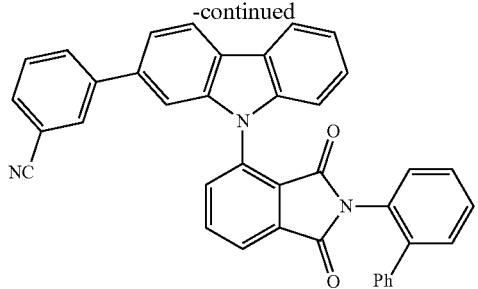
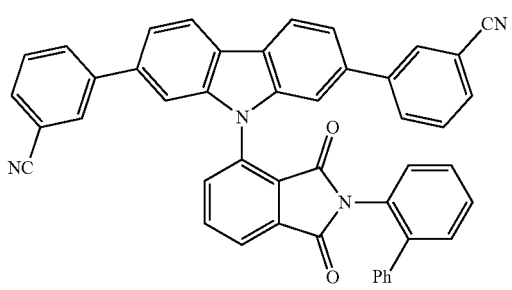
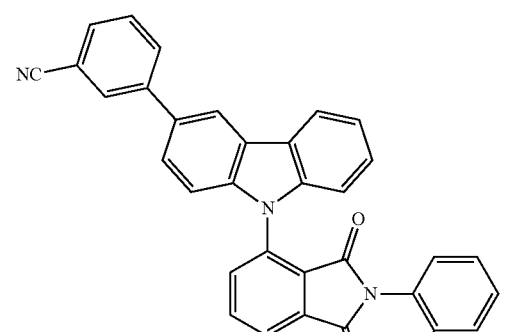
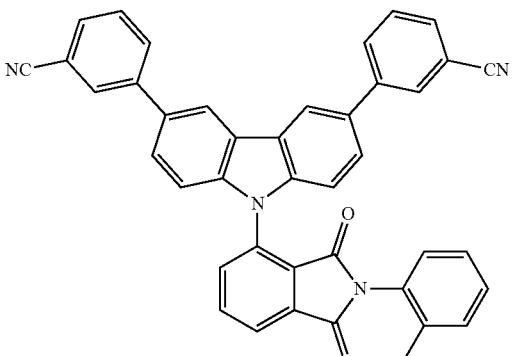
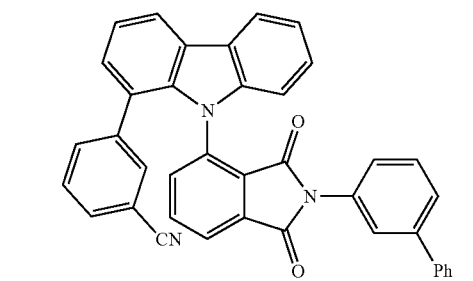
170
-continued
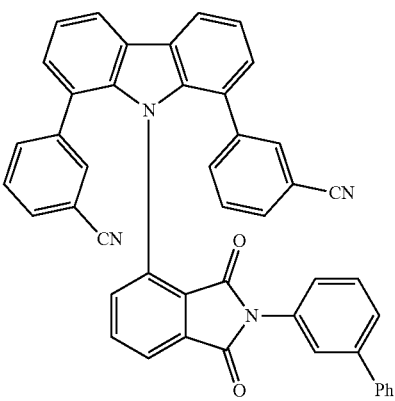
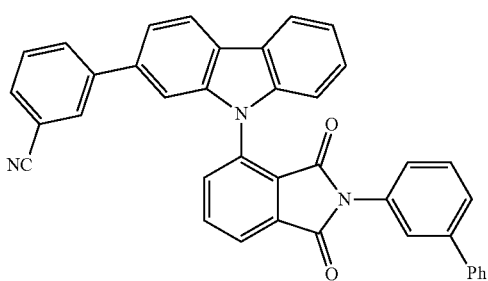
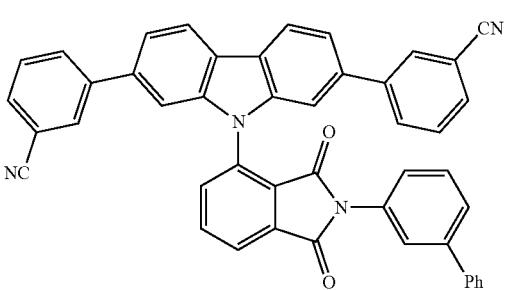
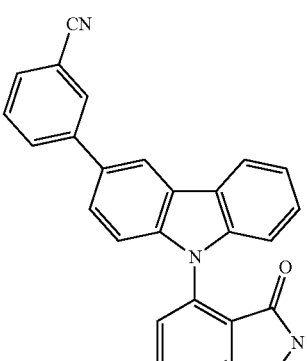
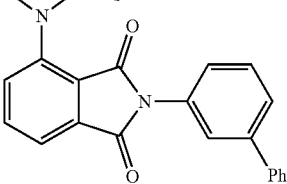

171
-continued
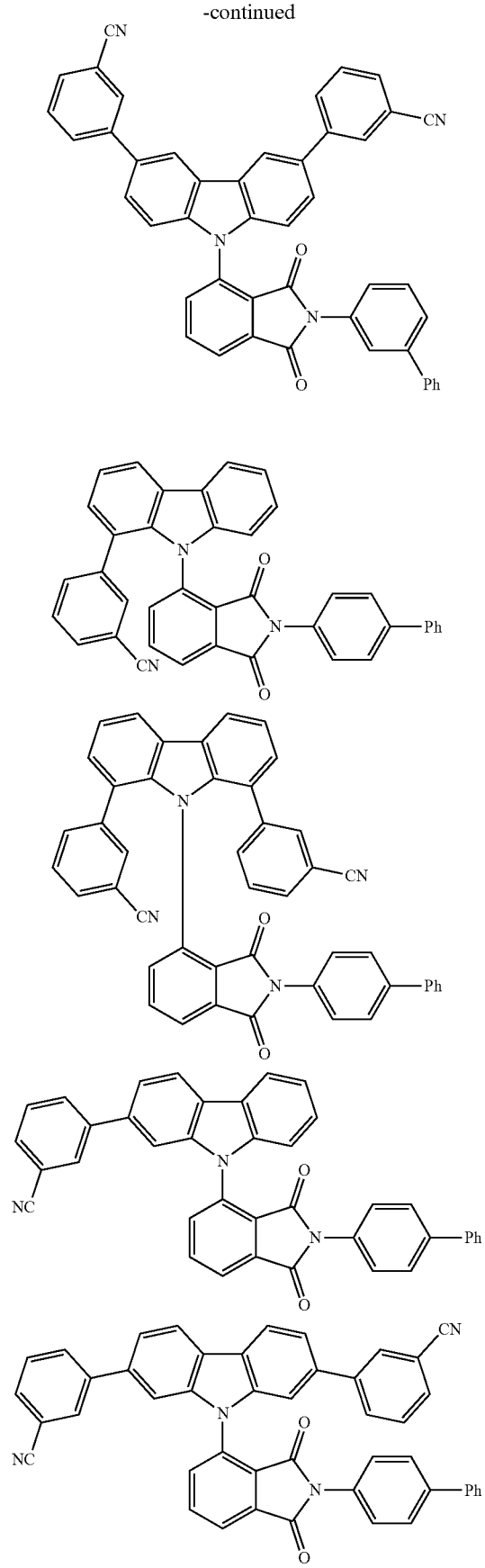
172
-continued
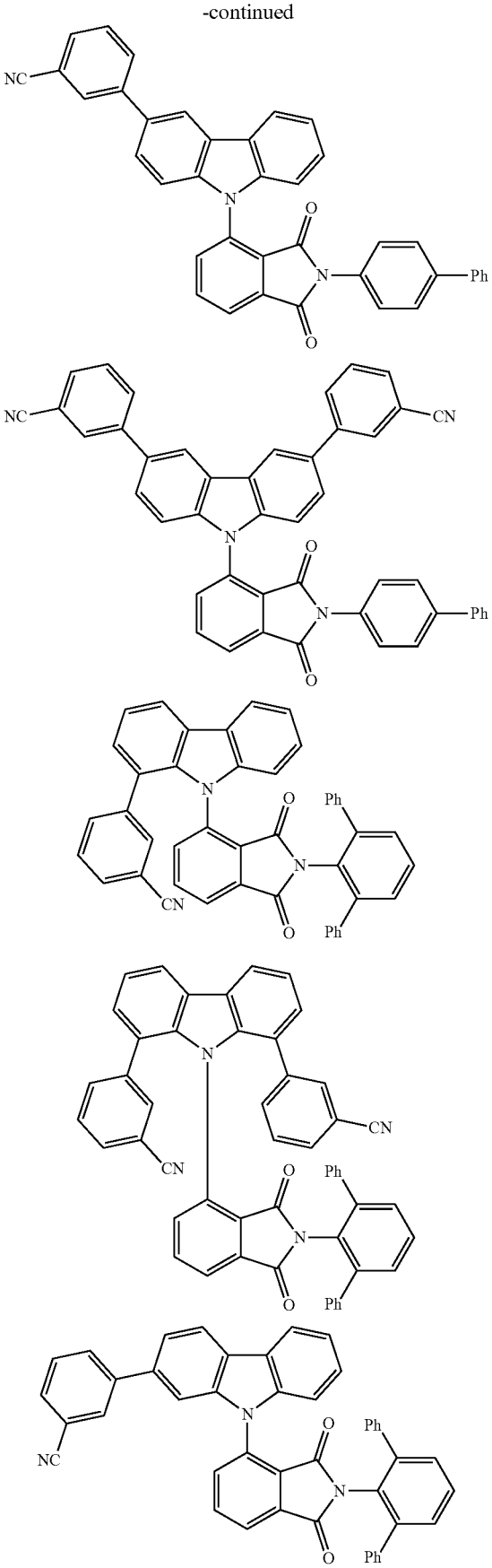

173
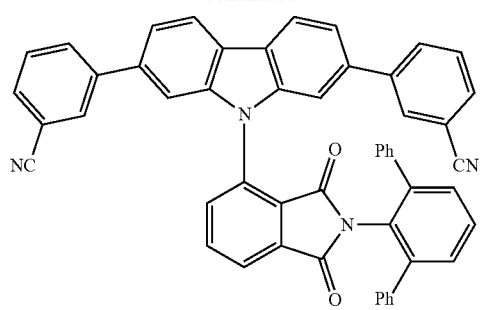
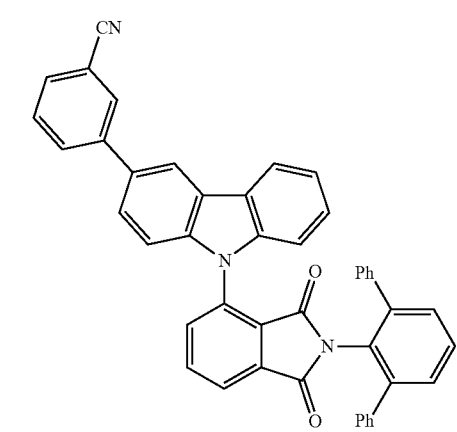
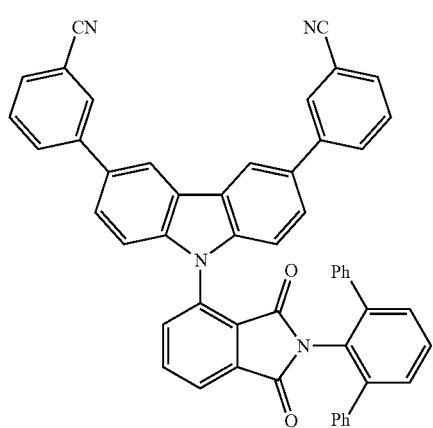
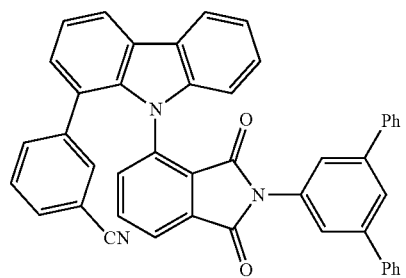
174
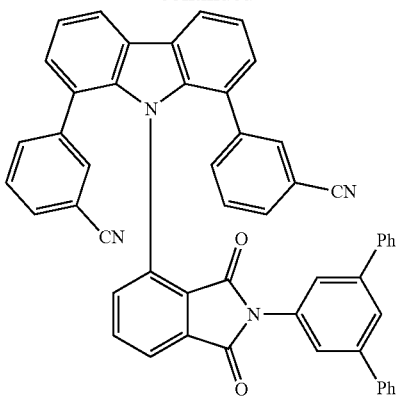
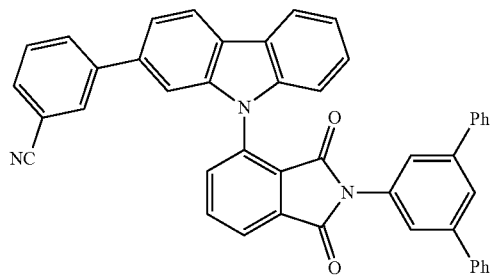
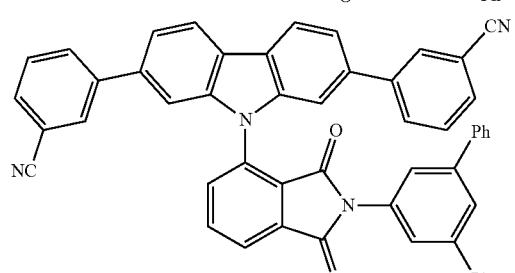
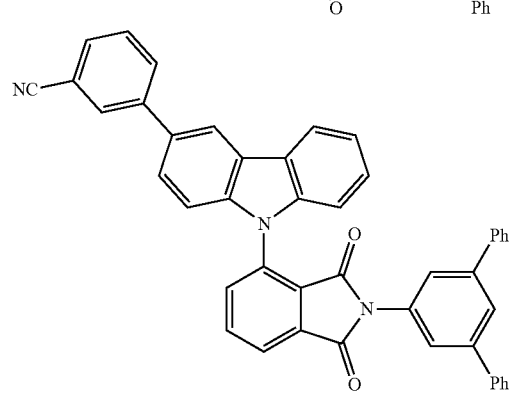
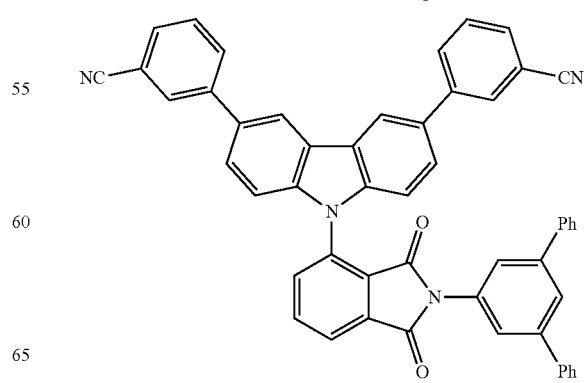

-continued
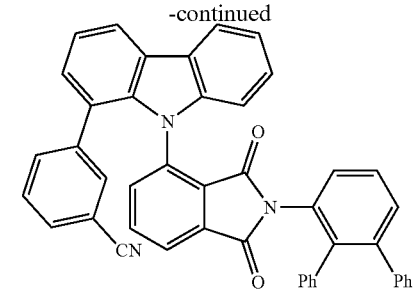
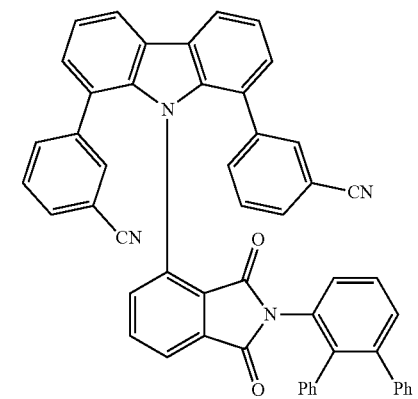
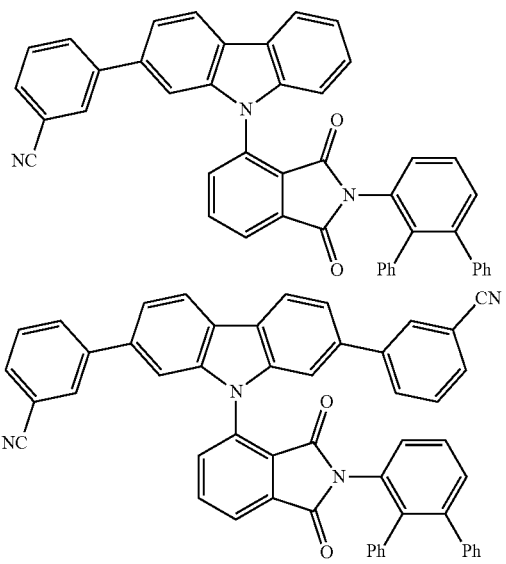
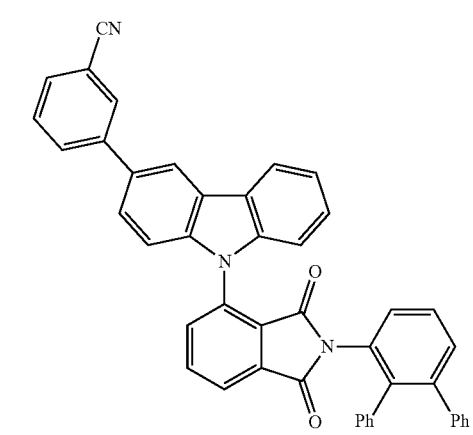
-continued
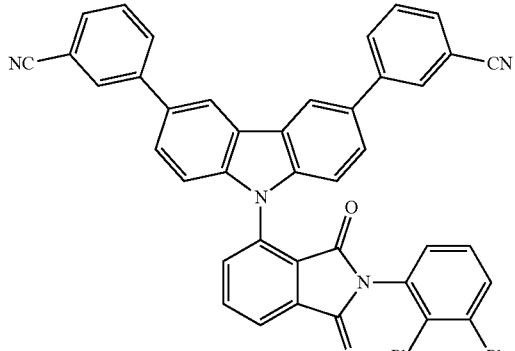
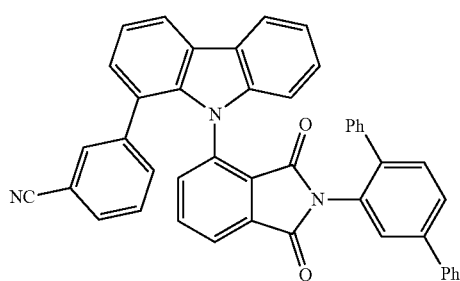
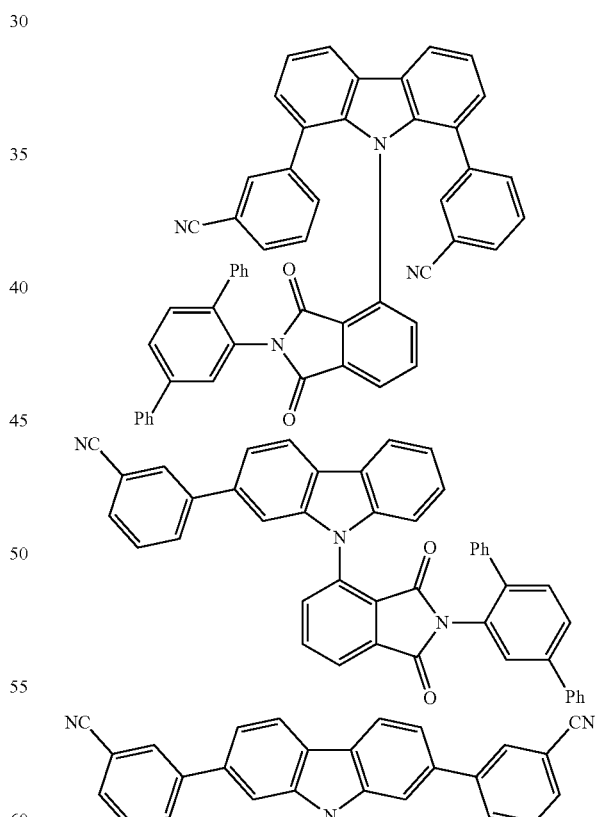

177
-continued
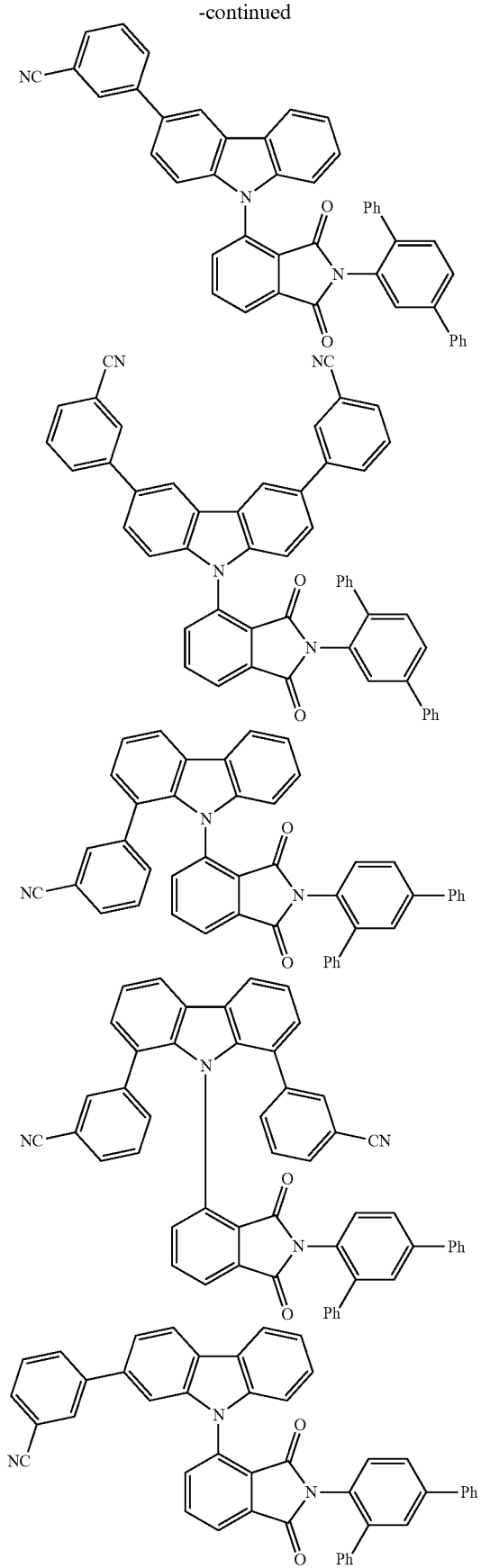
178
-continued
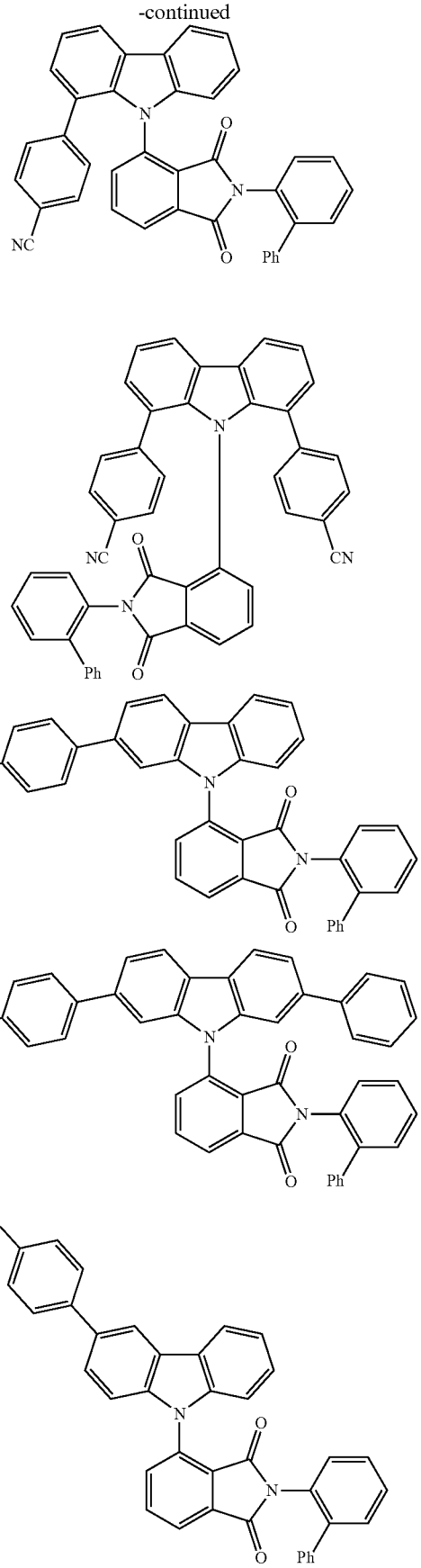

179
-continued
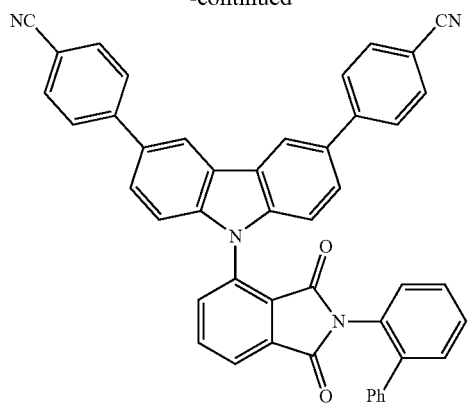
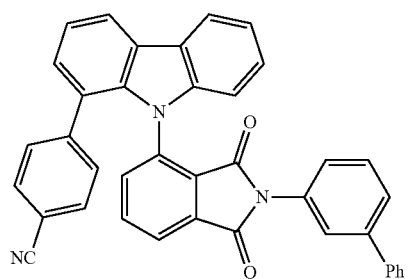
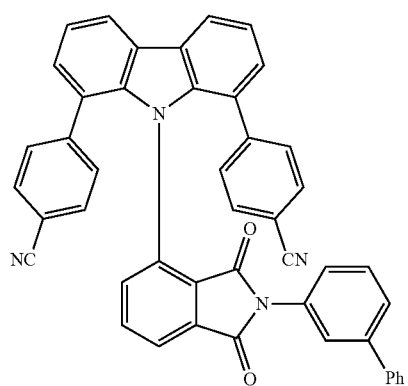
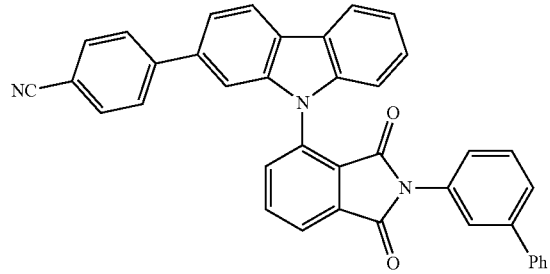
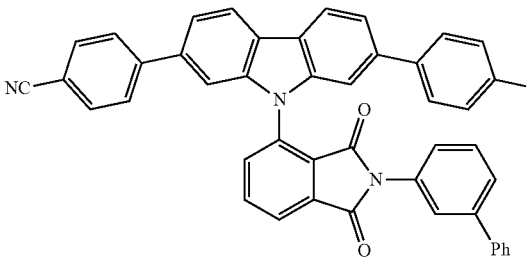
180
-continued
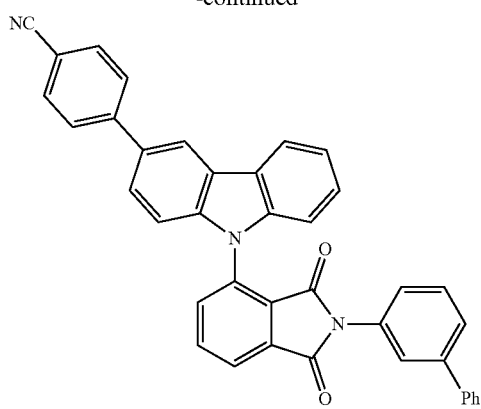
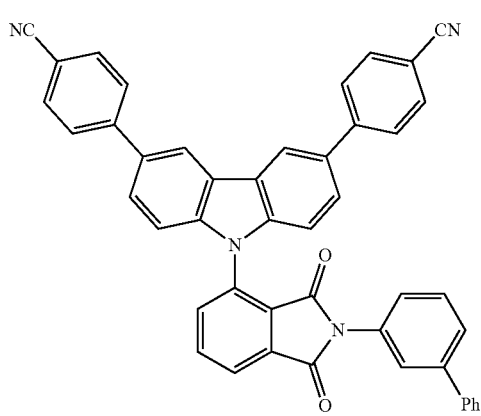
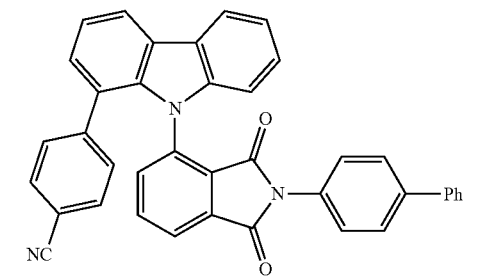
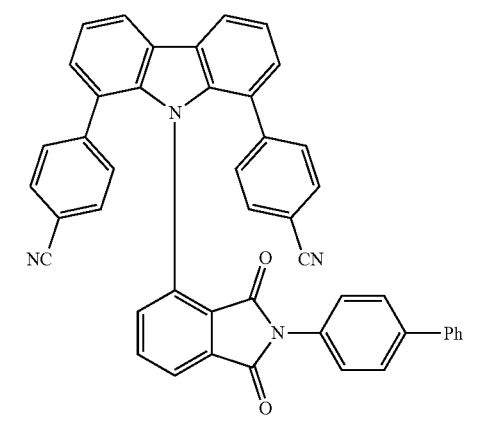

-continued
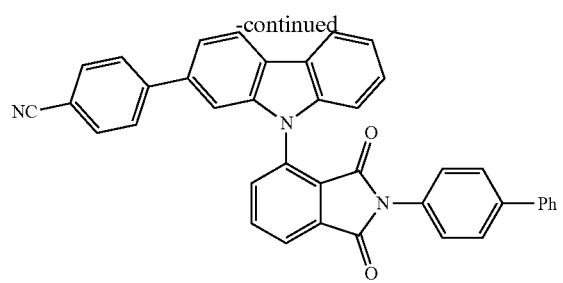
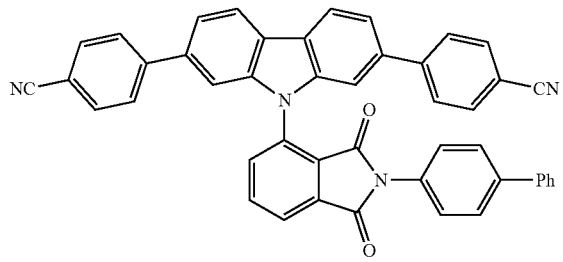
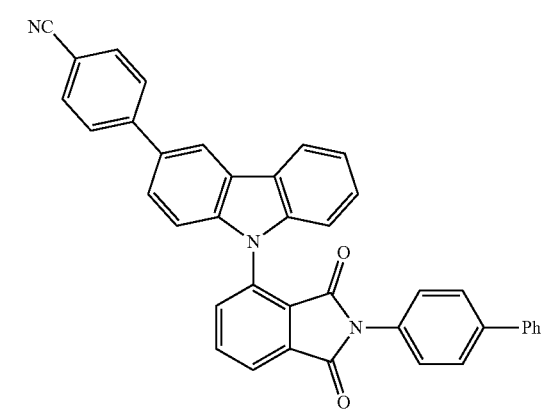
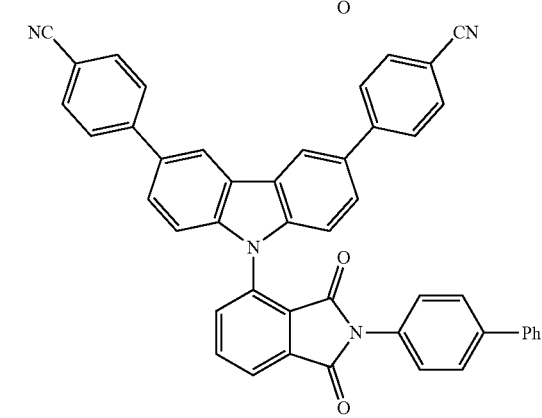
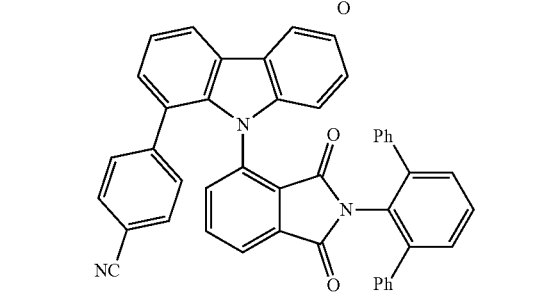
-continued
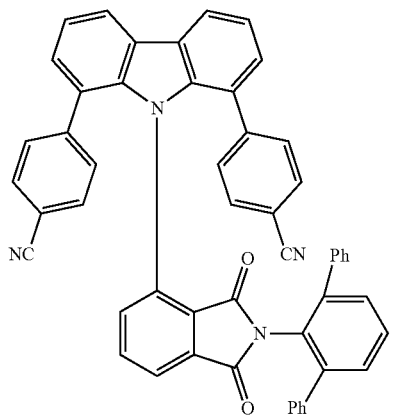
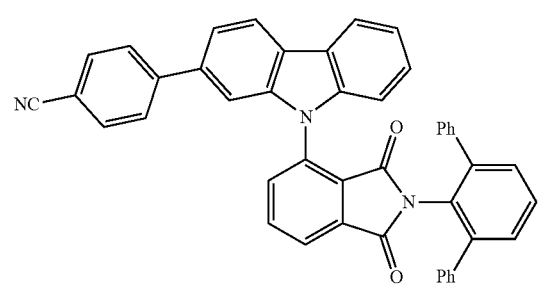
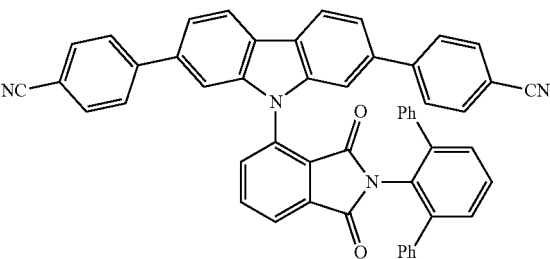
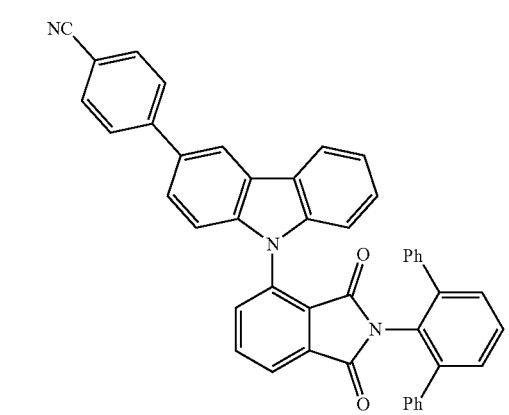

183
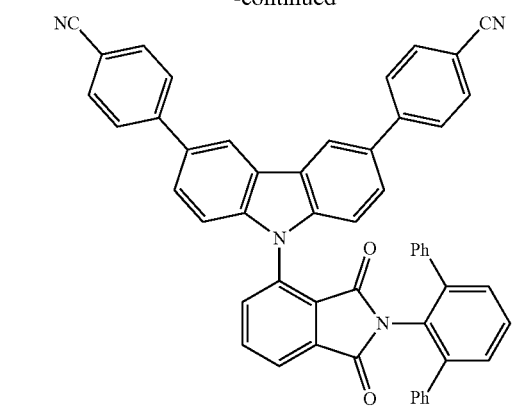
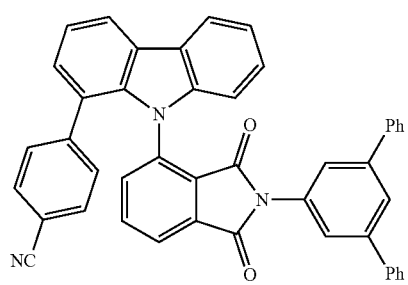
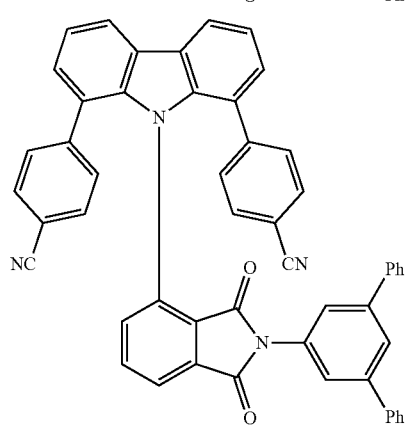
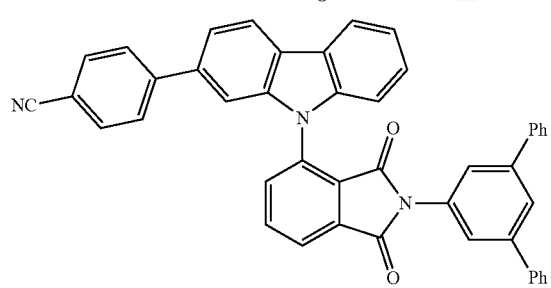
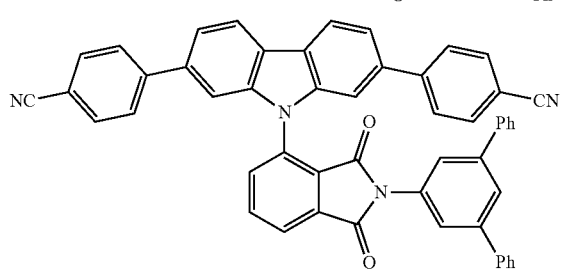
184
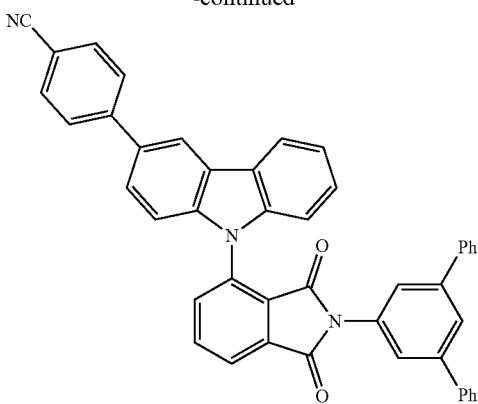
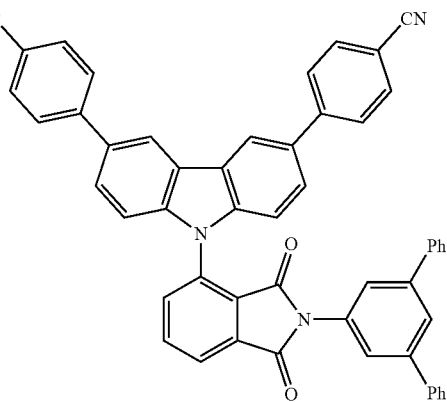
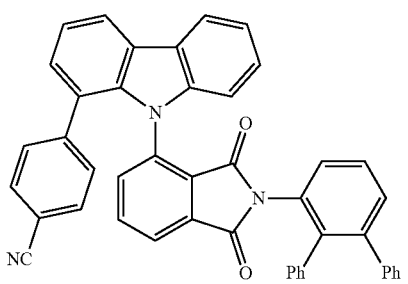
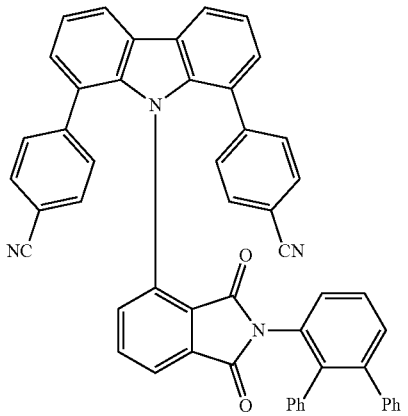

-continued
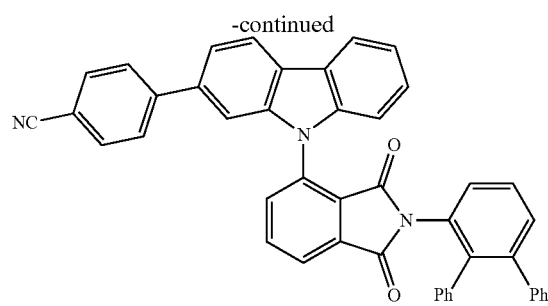
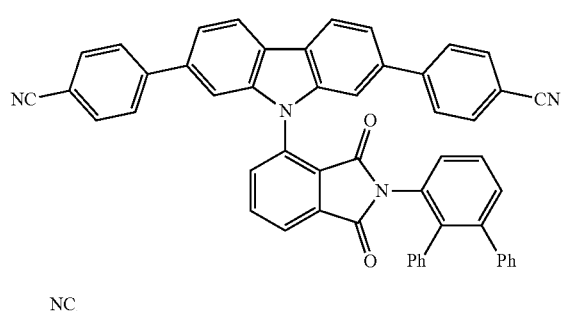
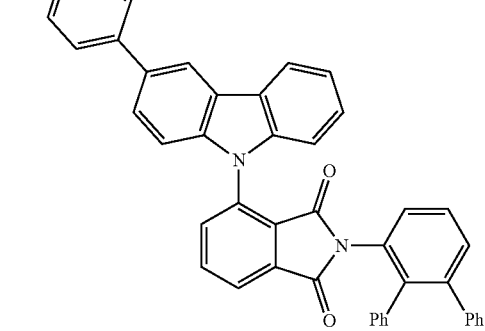
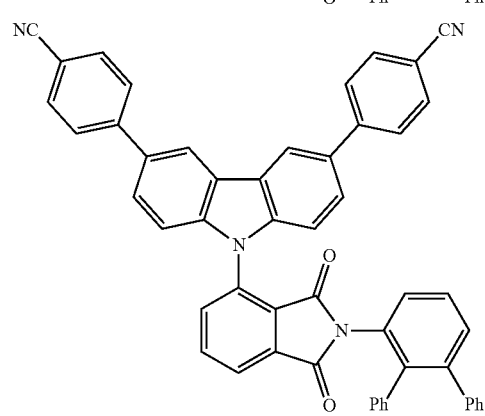
-continued
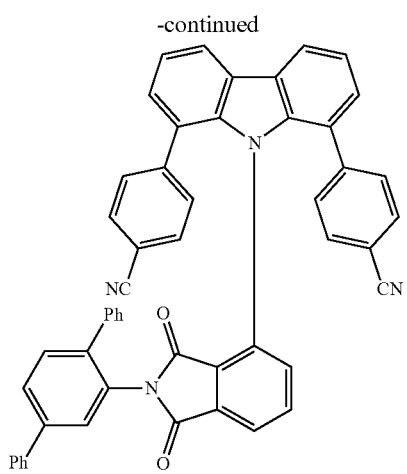
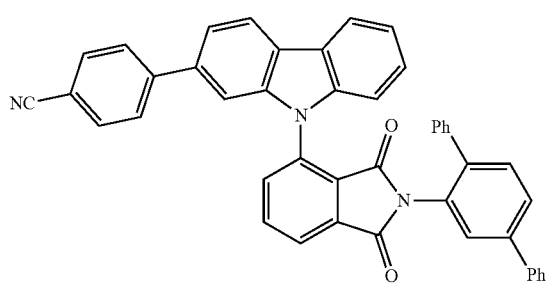
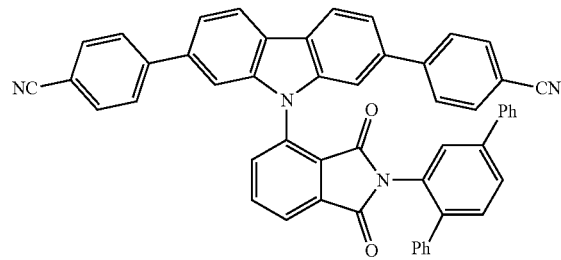
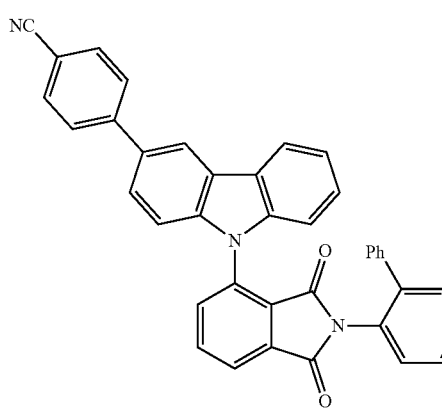

187
-continued
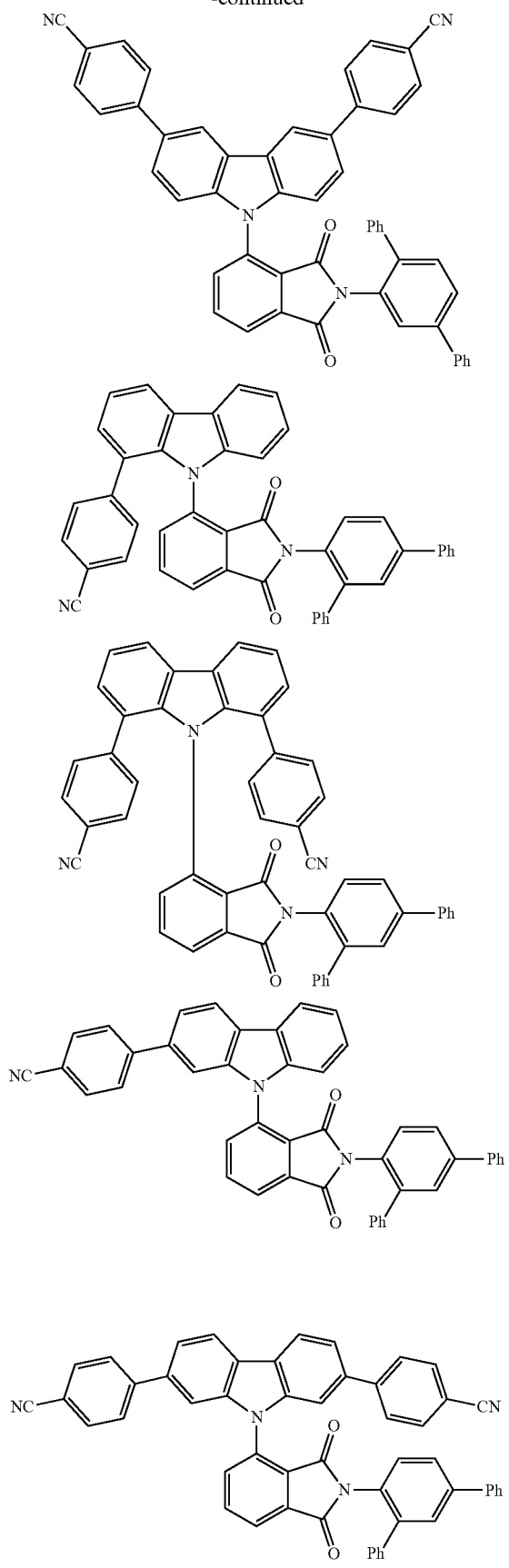
188
-continued
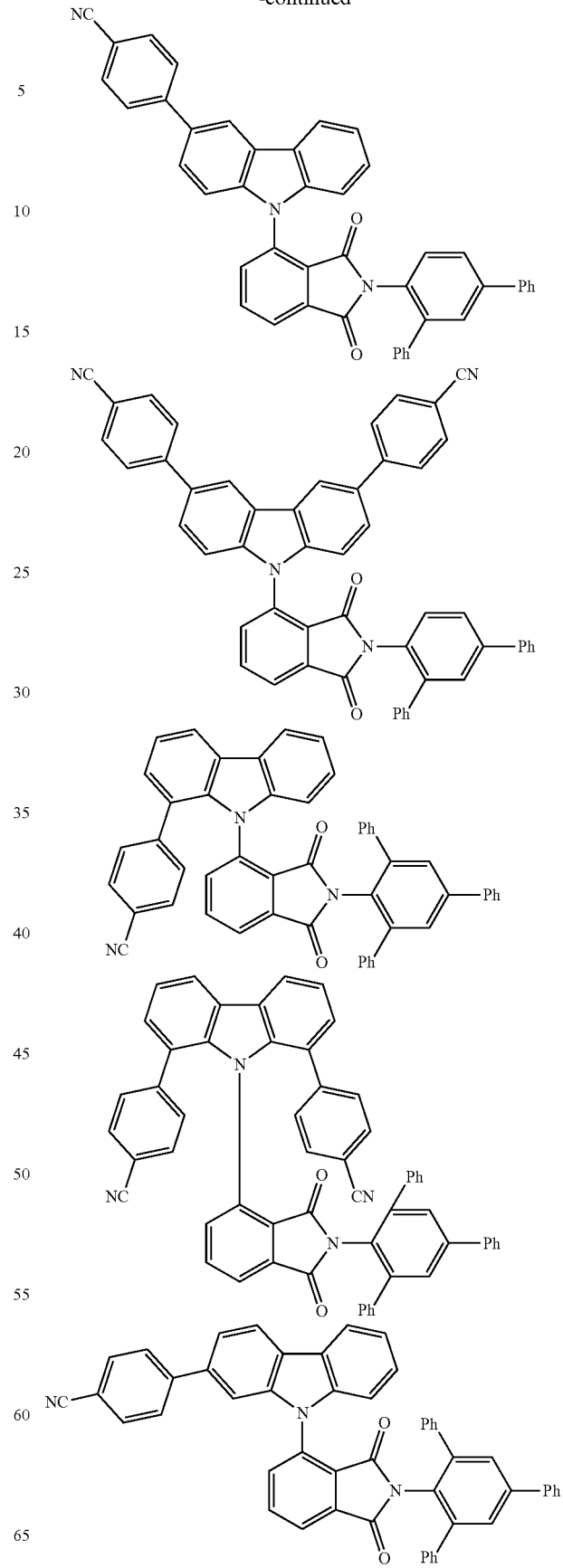

-continued
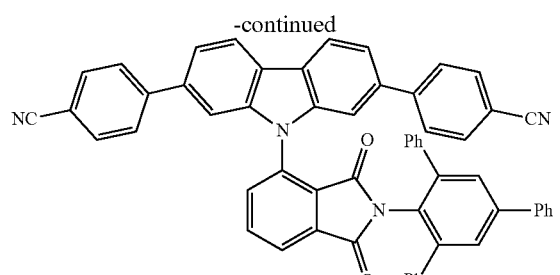
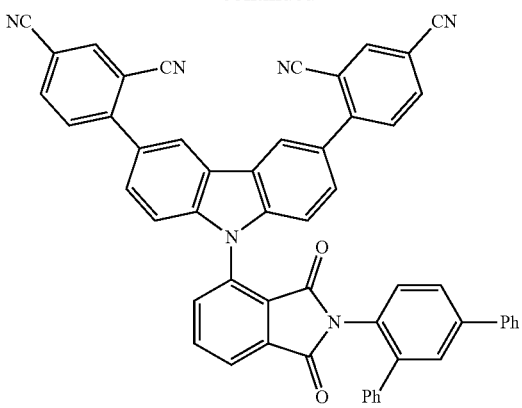
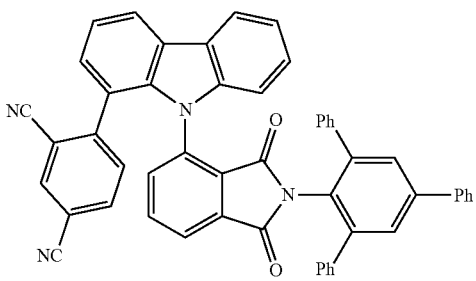
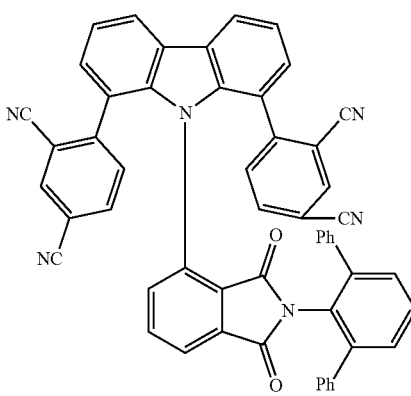
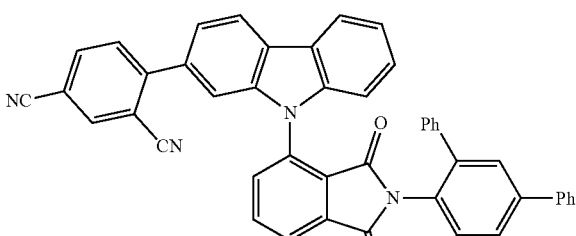
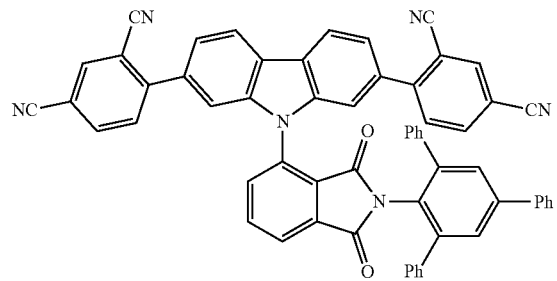

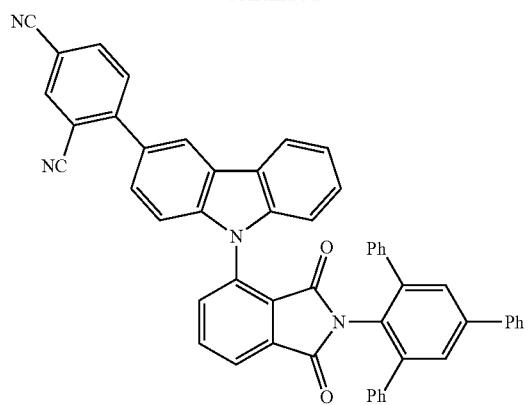
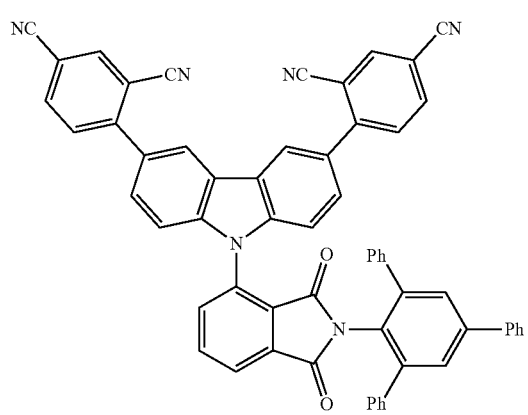
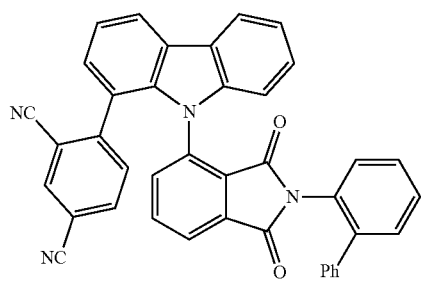
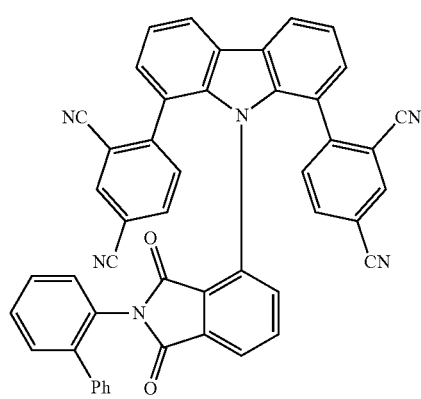
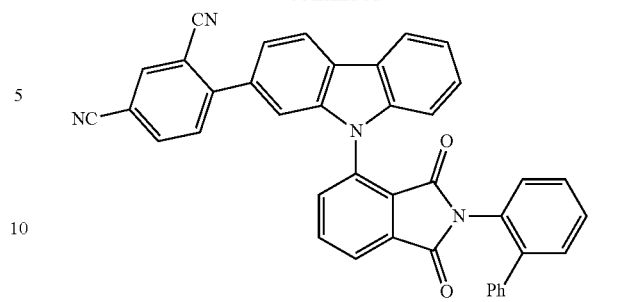
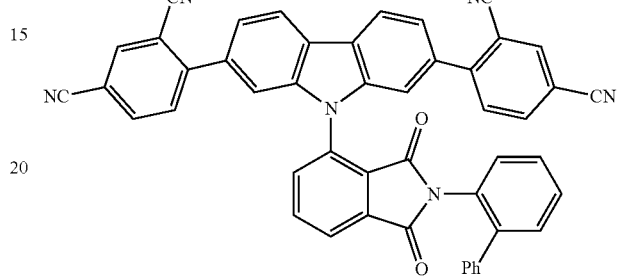
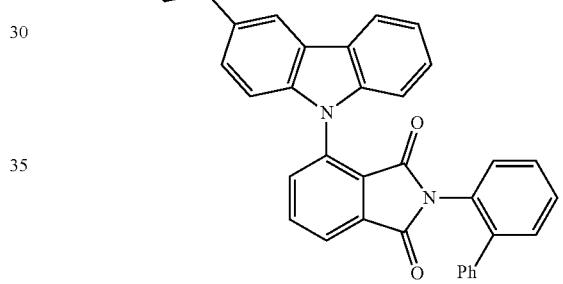

193
-continued
194
-continued
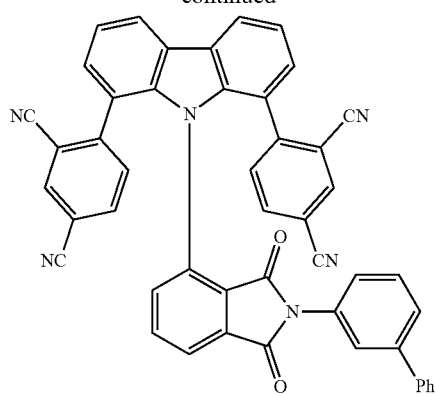
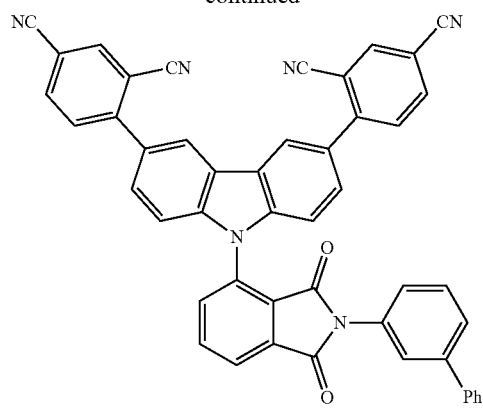
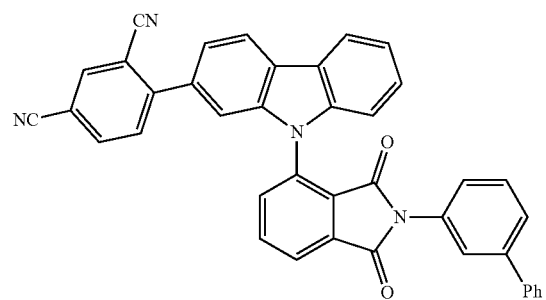
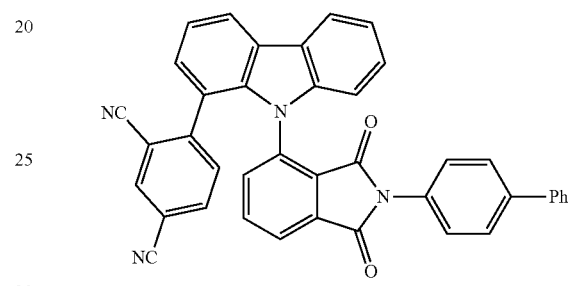
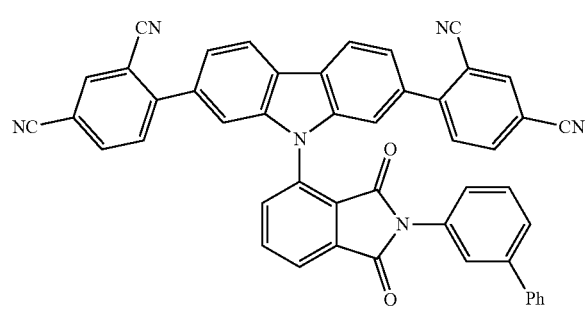
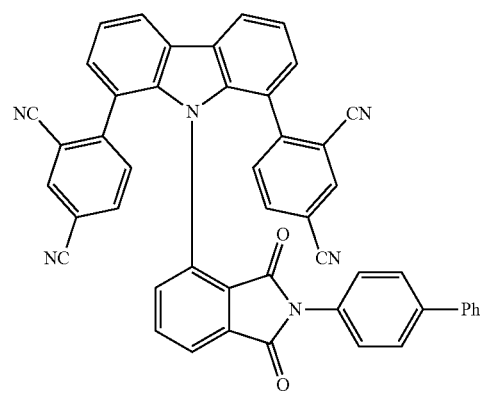
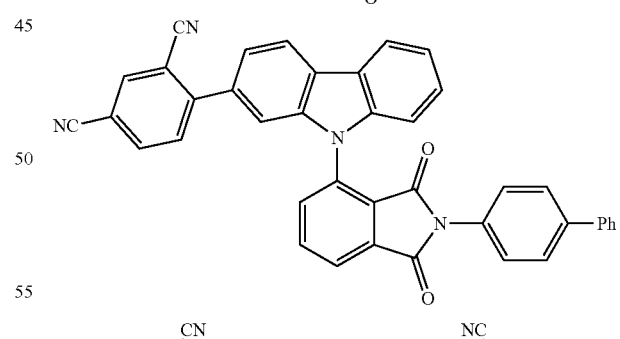
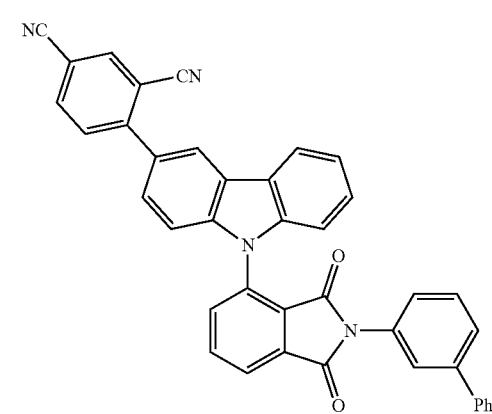
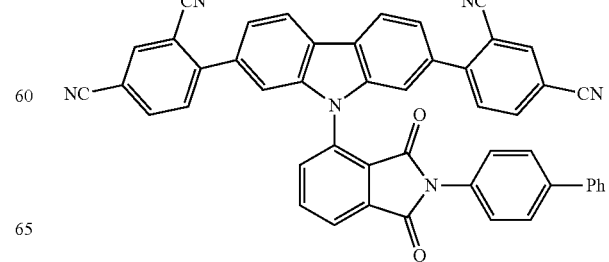

195
-continued
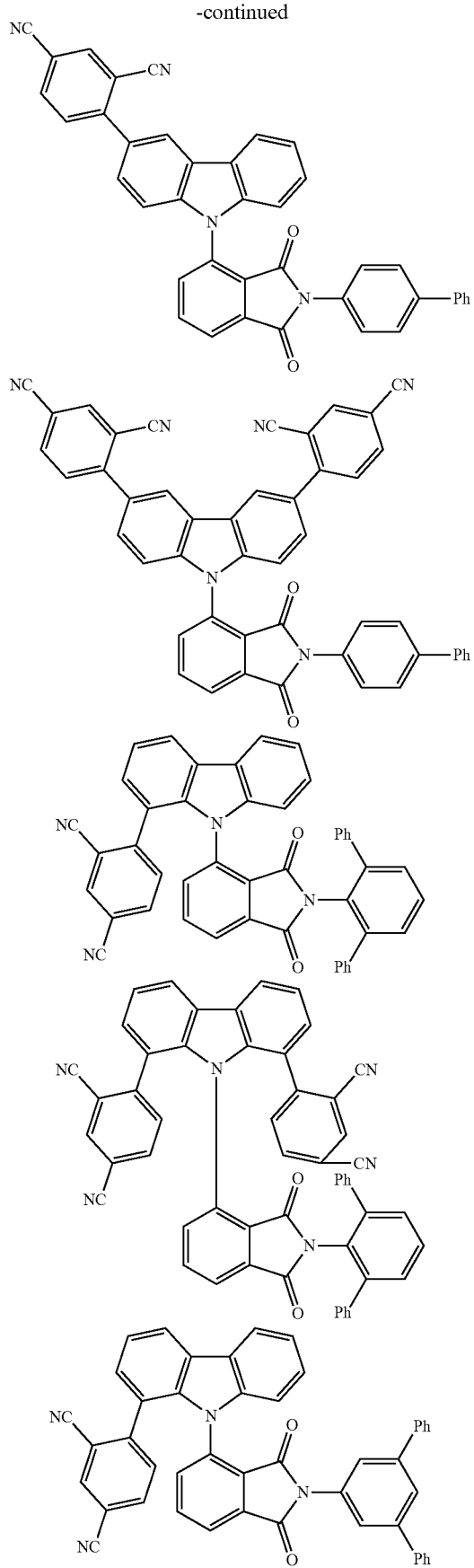
196
-continued
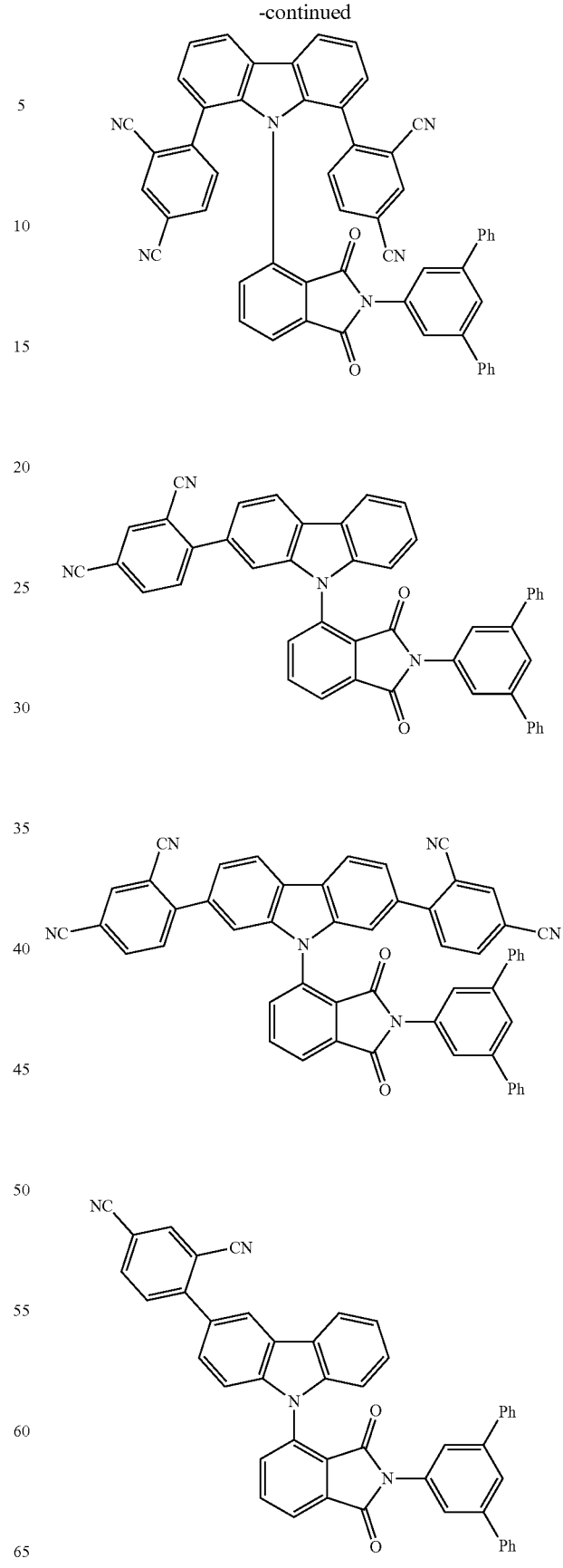

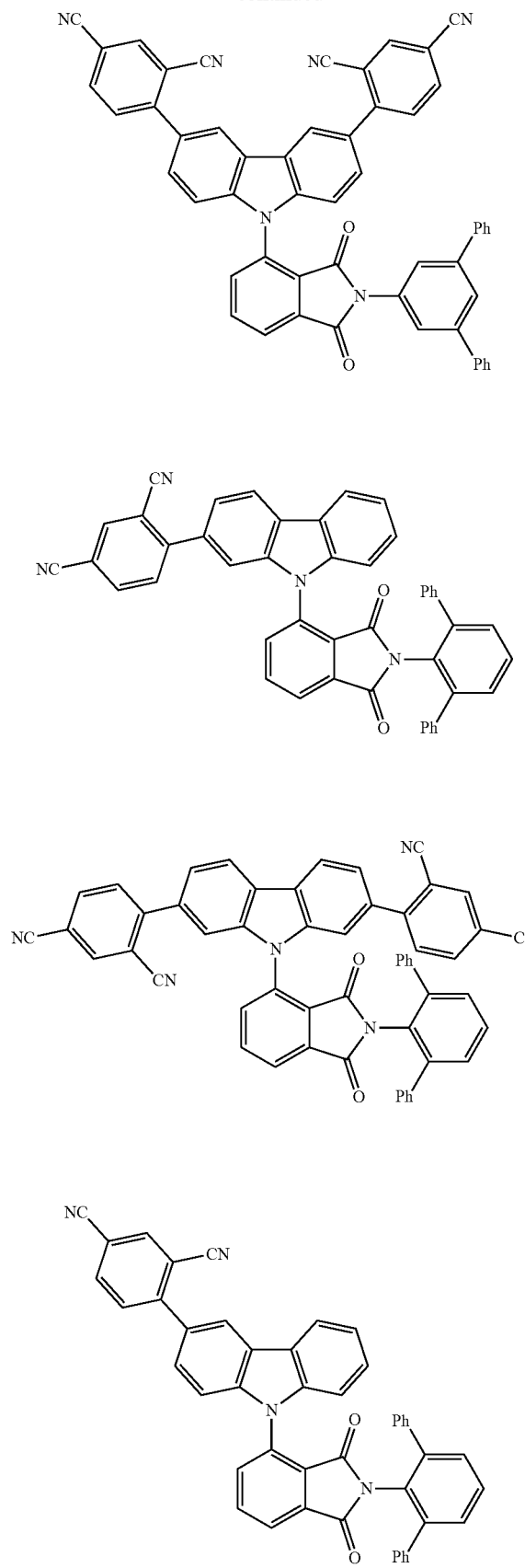
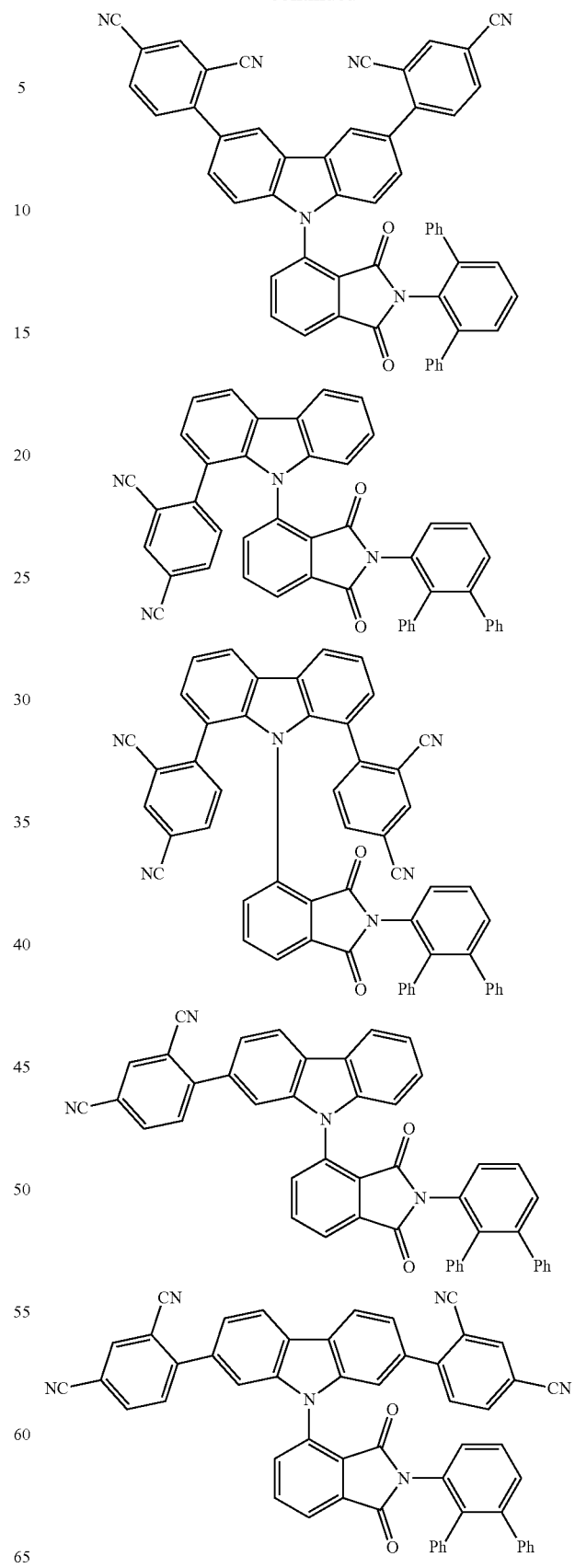

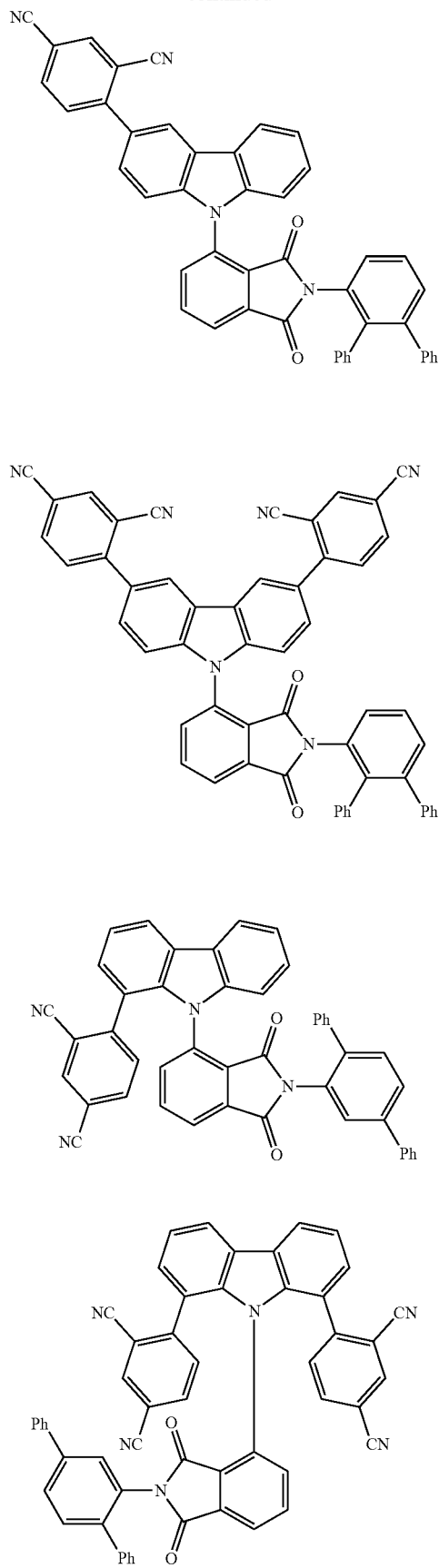

-continued
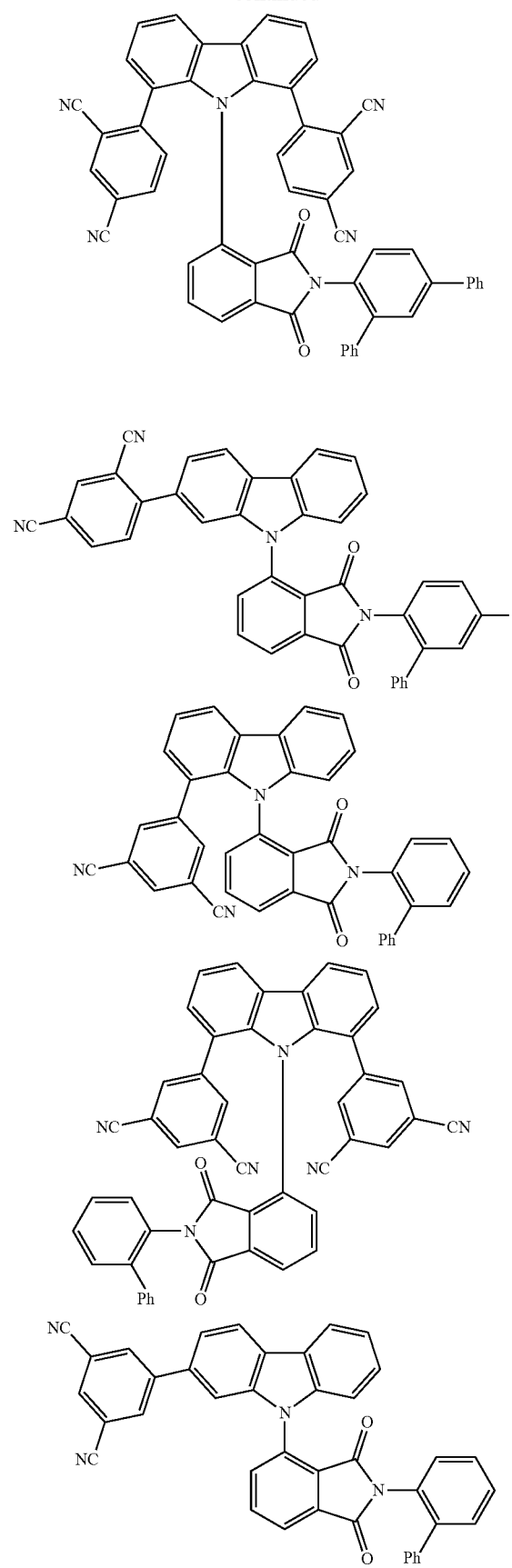 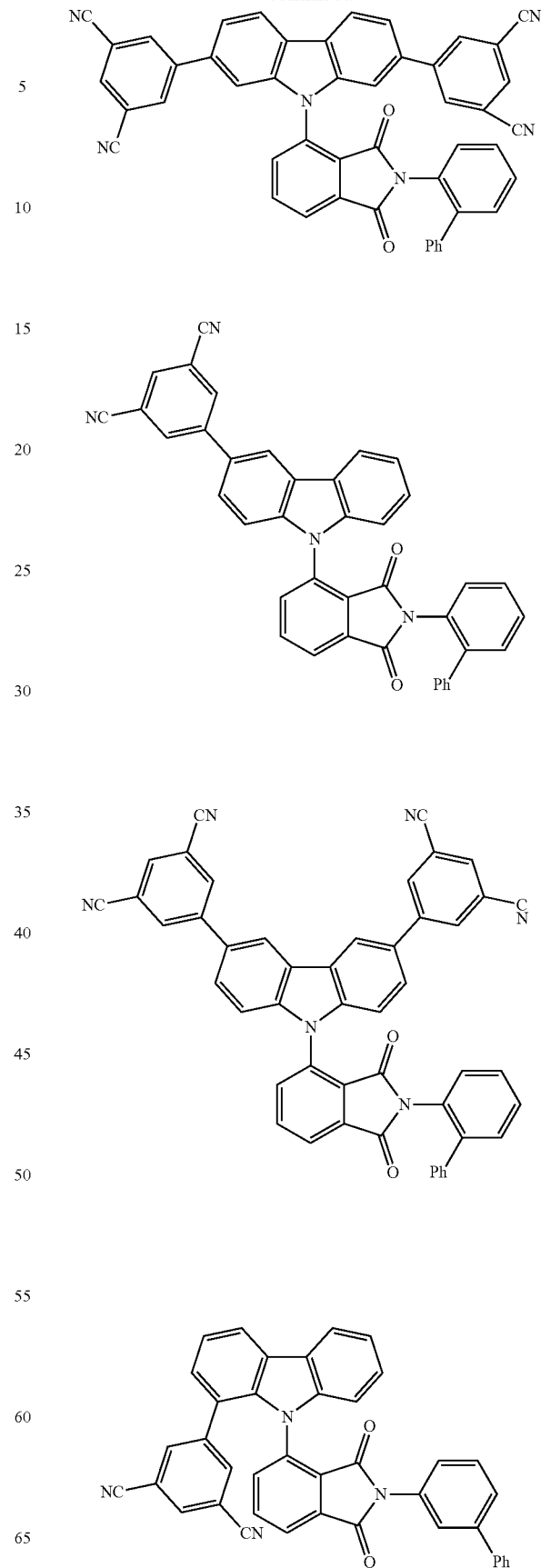

203
-continued
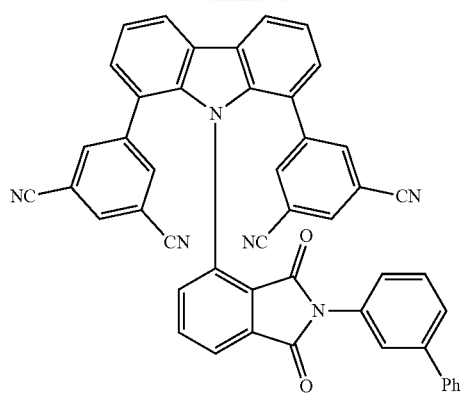
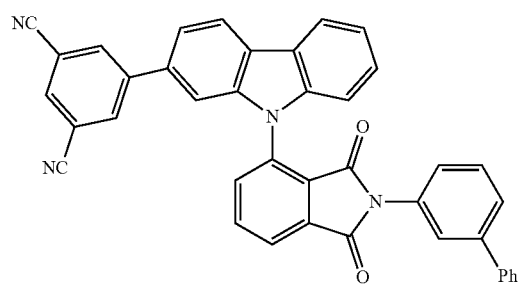
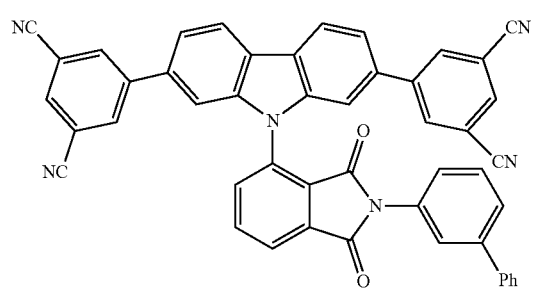
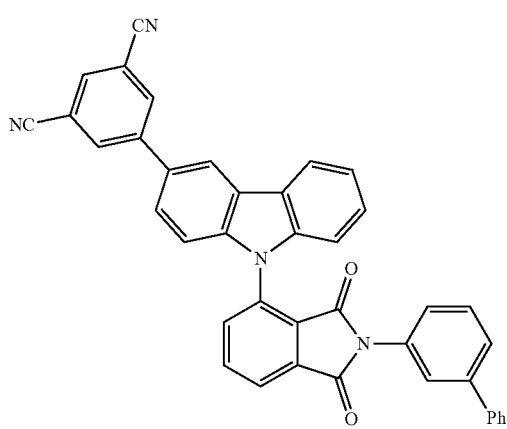
204
-continued
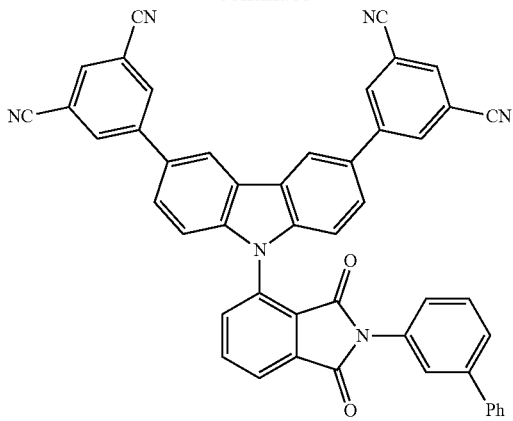
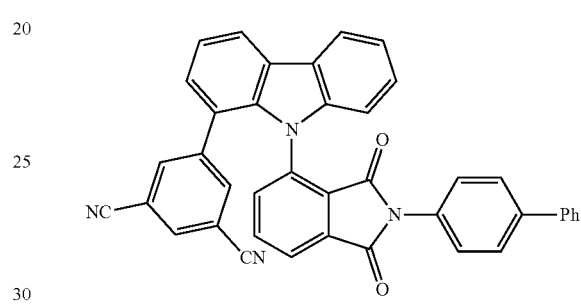
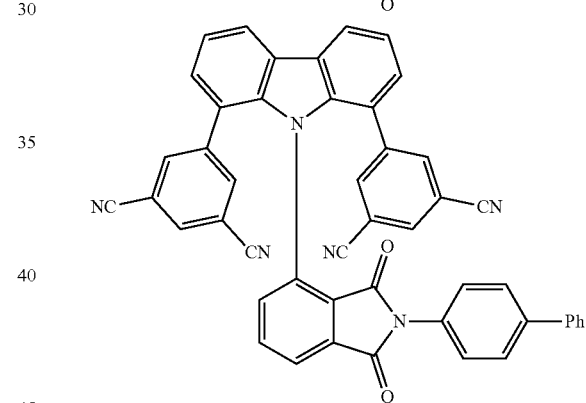
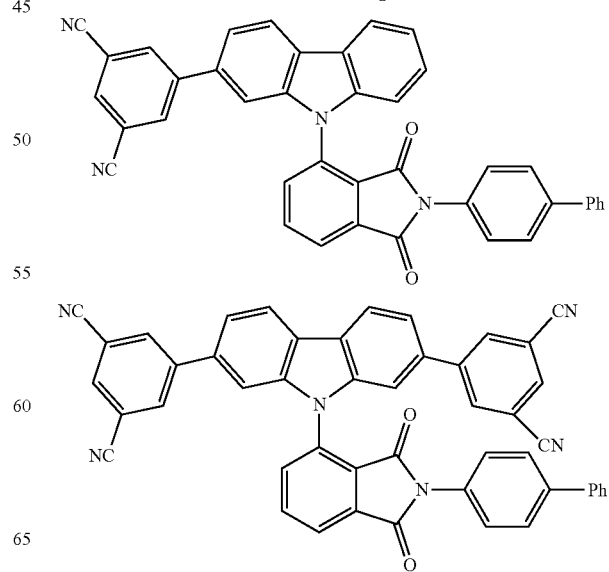

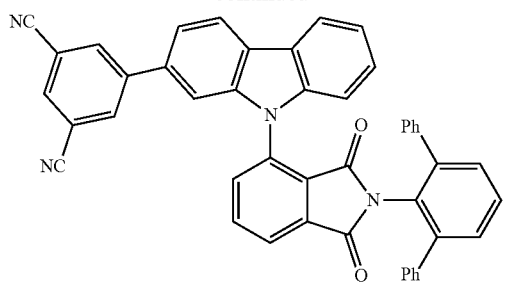
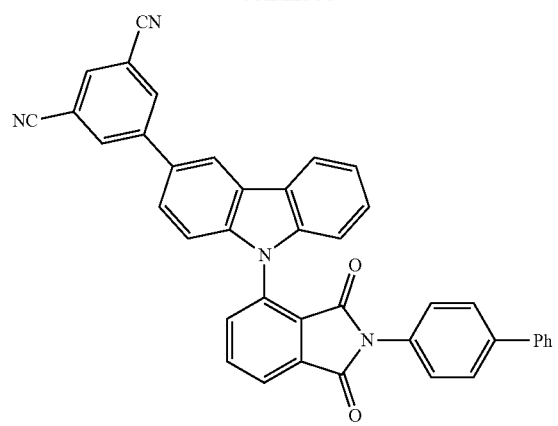
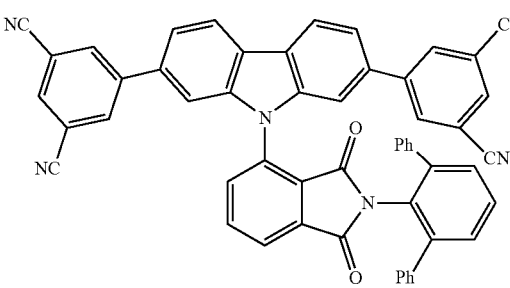
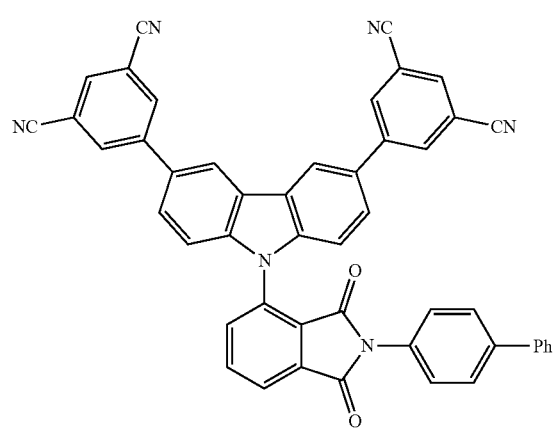
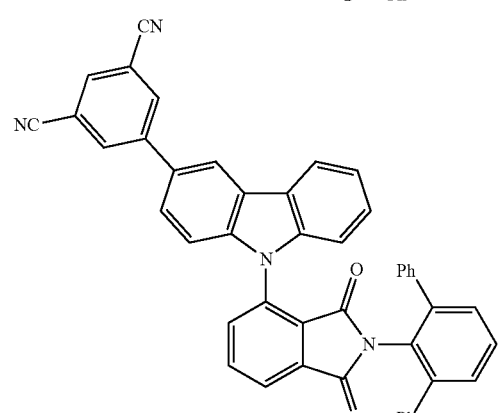
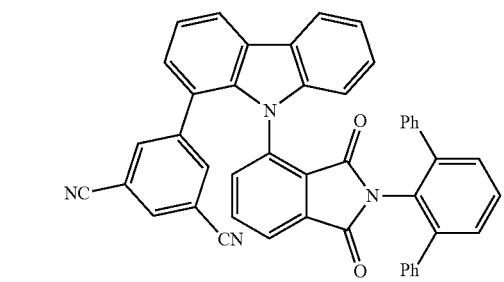
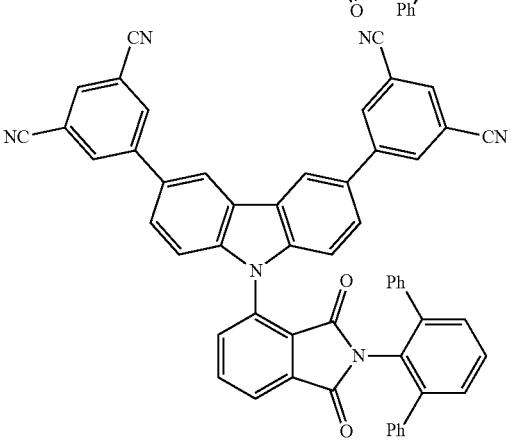
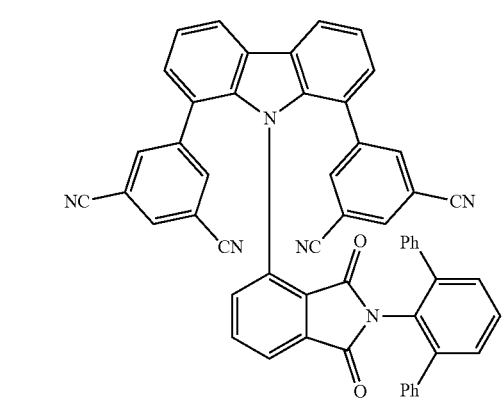
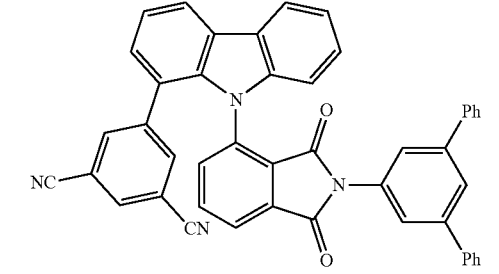

207
-continued
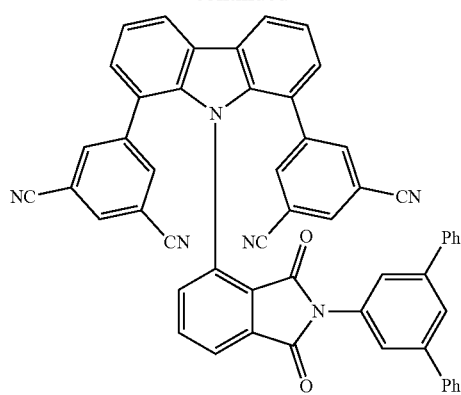
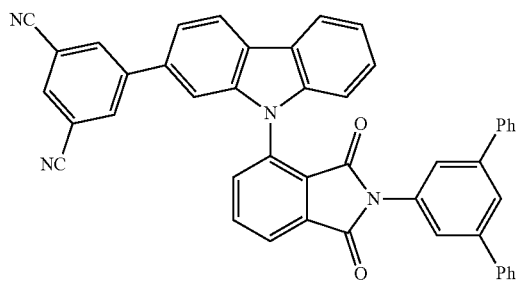
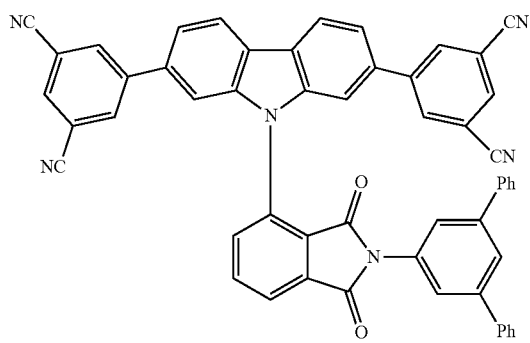
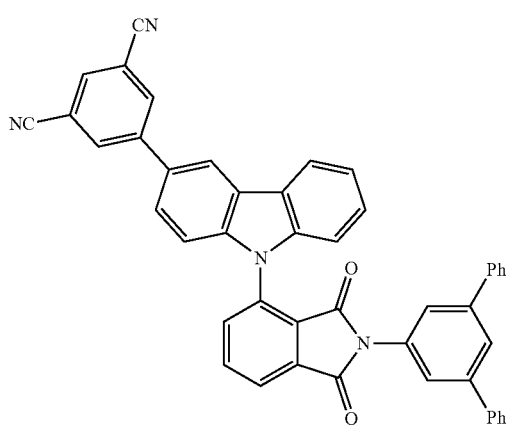
208
-continued
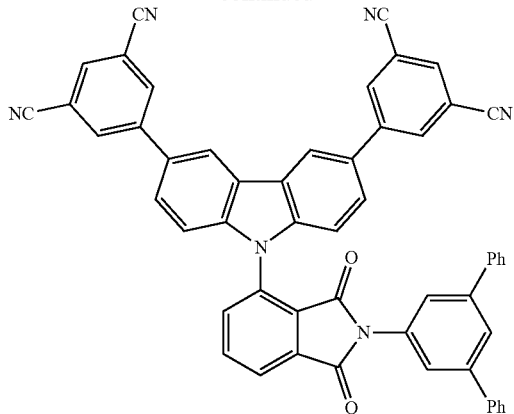
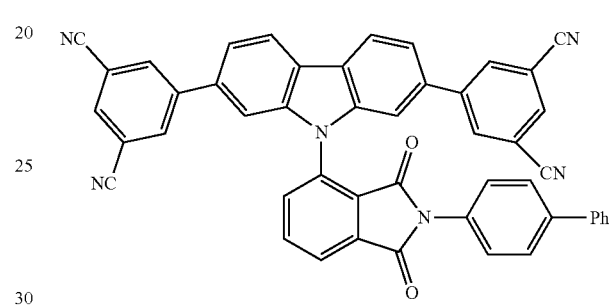
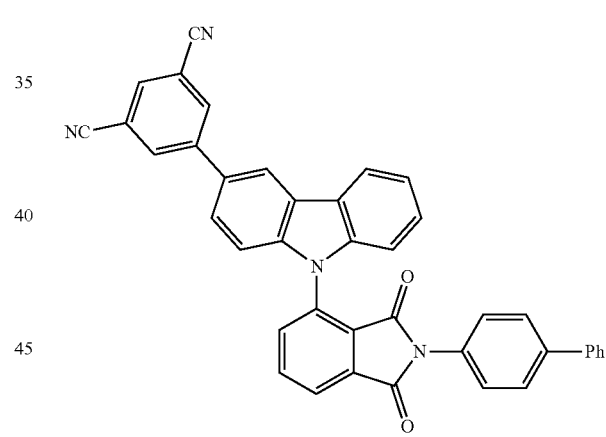
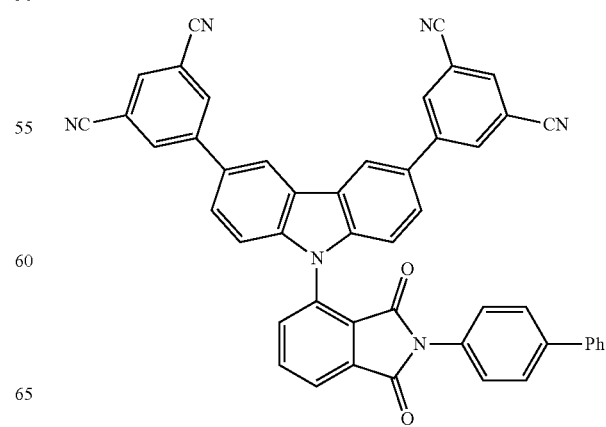

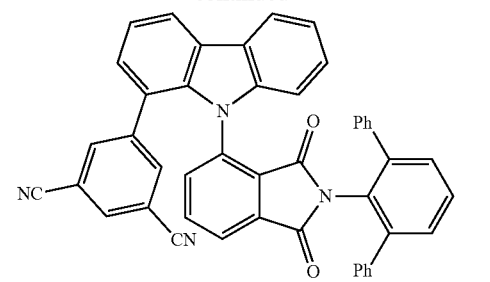
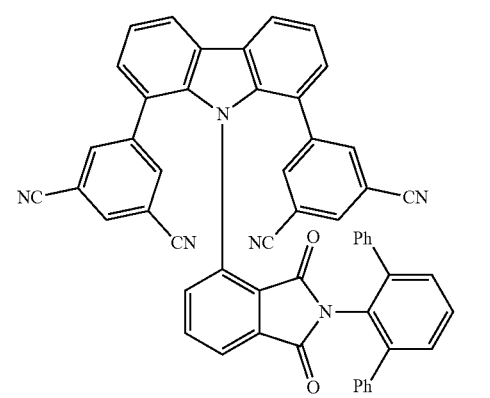
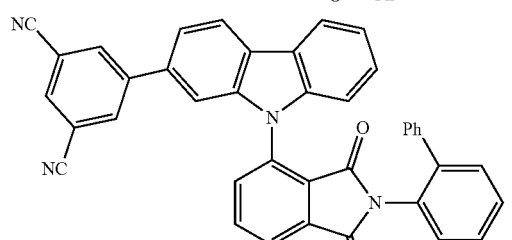
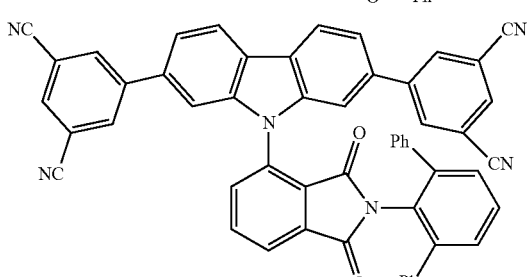
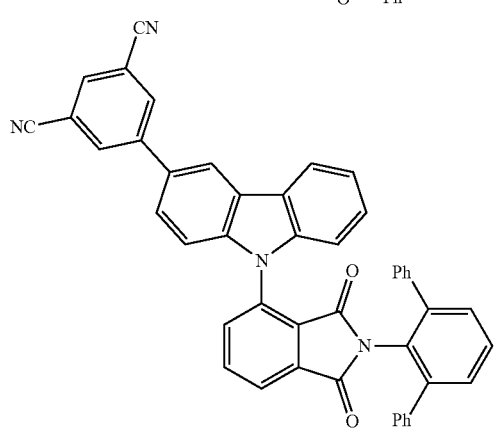
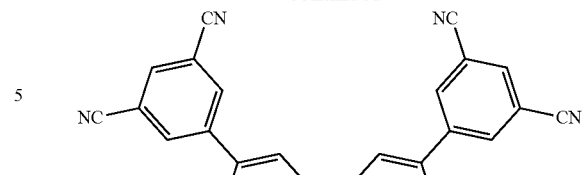
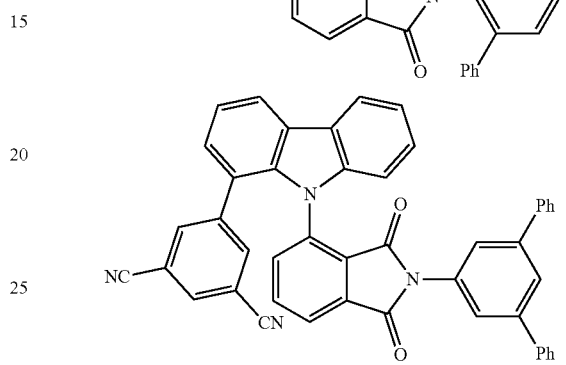
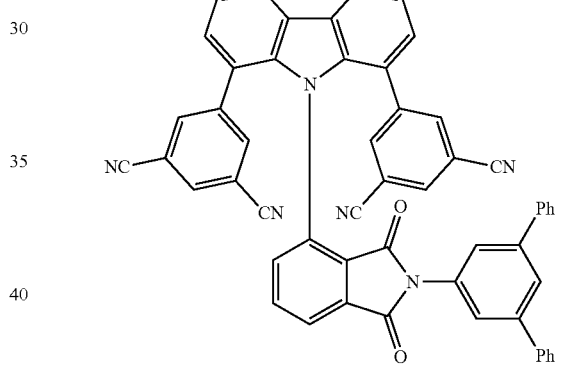
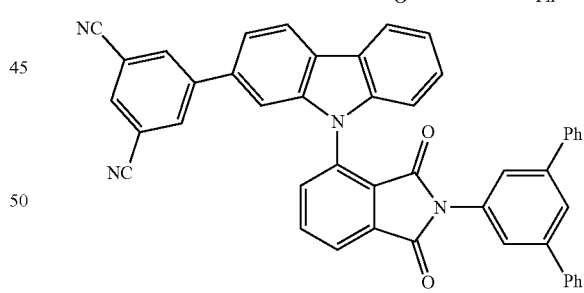
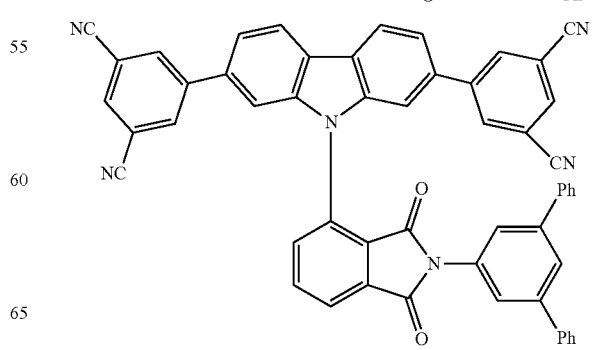

211
-continued
212
-continued
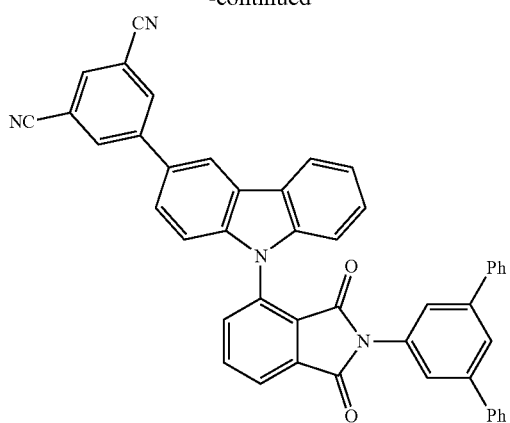
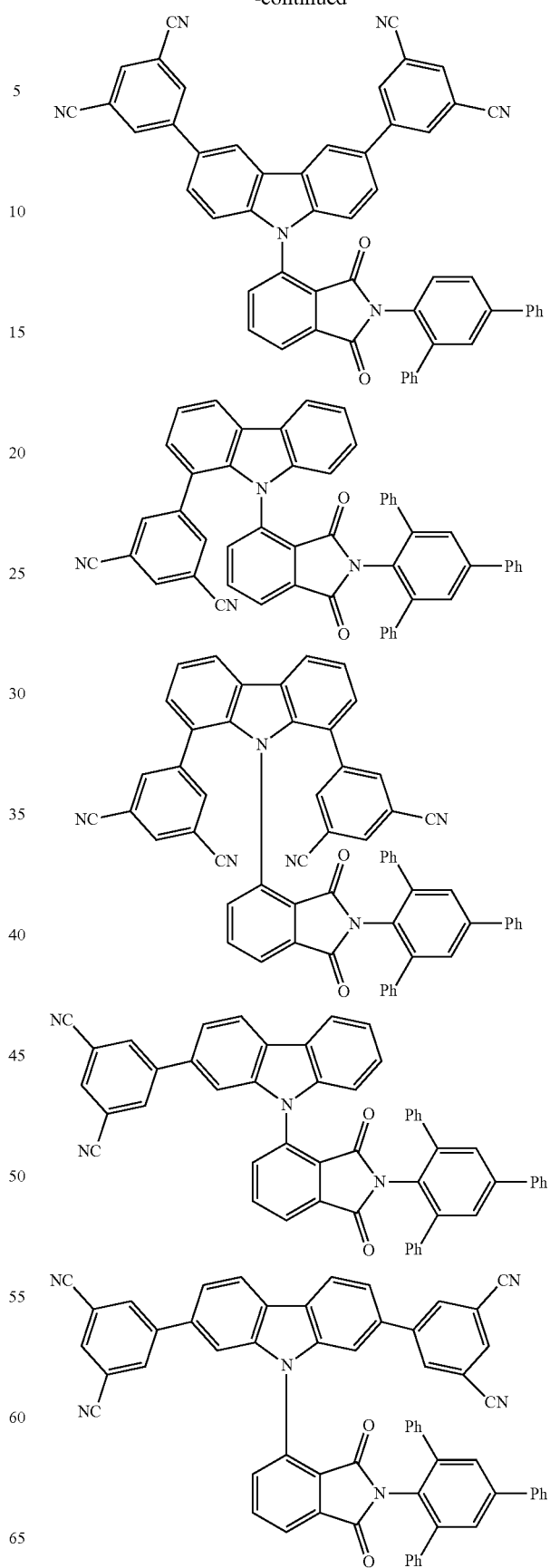

213
-continued
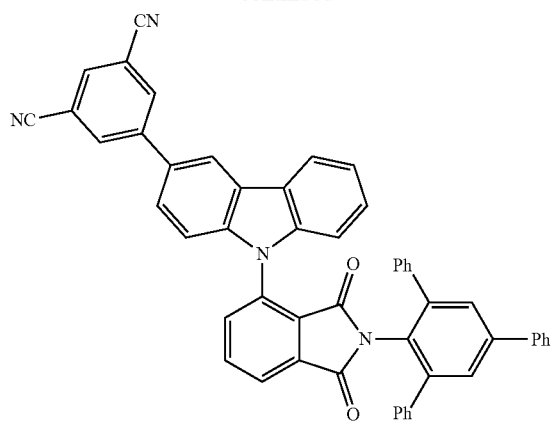
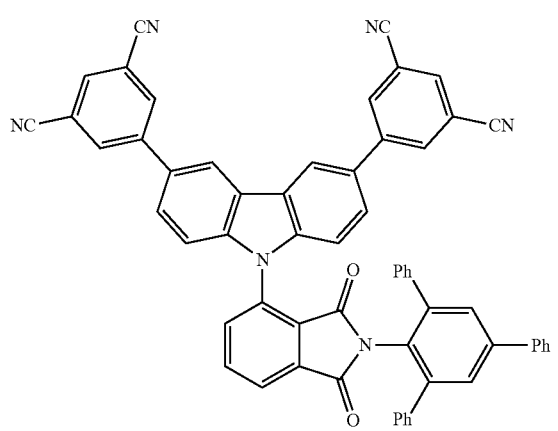
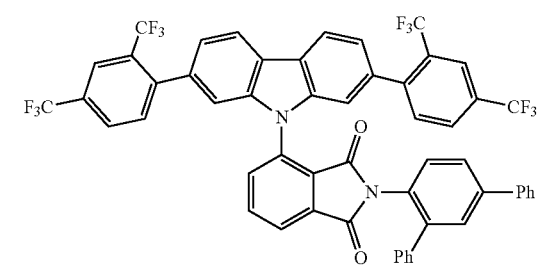
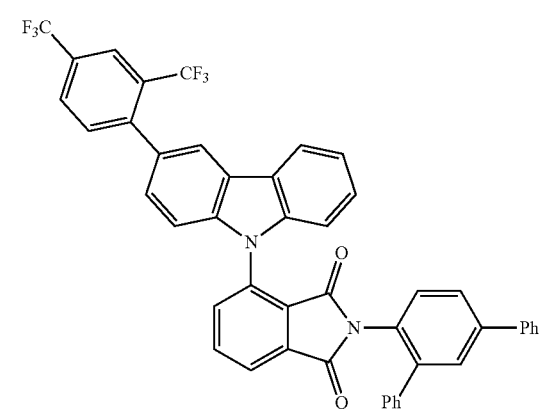
214
-continued
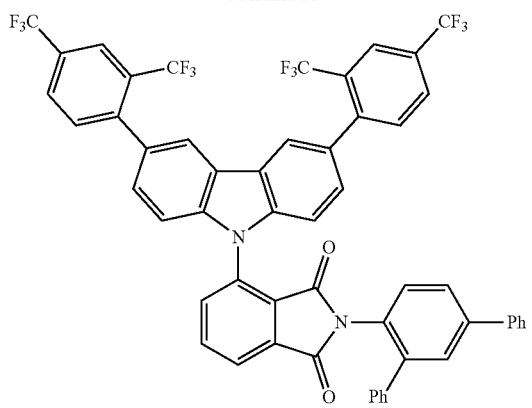
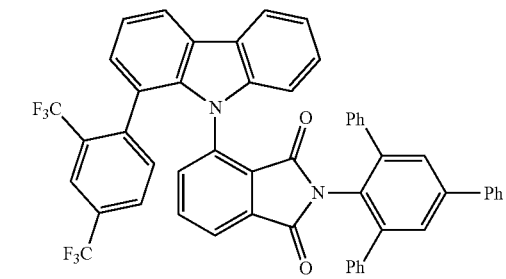
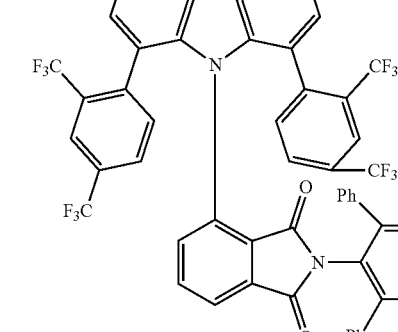
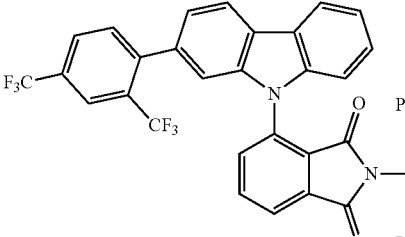
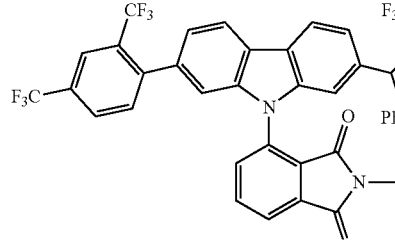

215
-continued
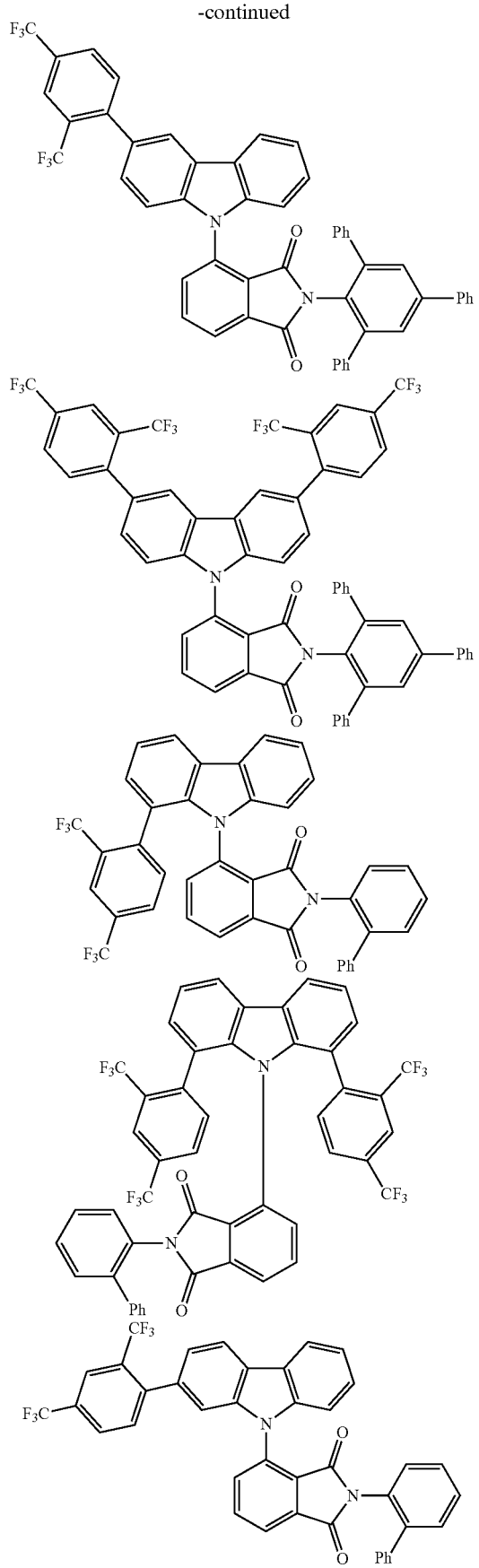
216
-continued
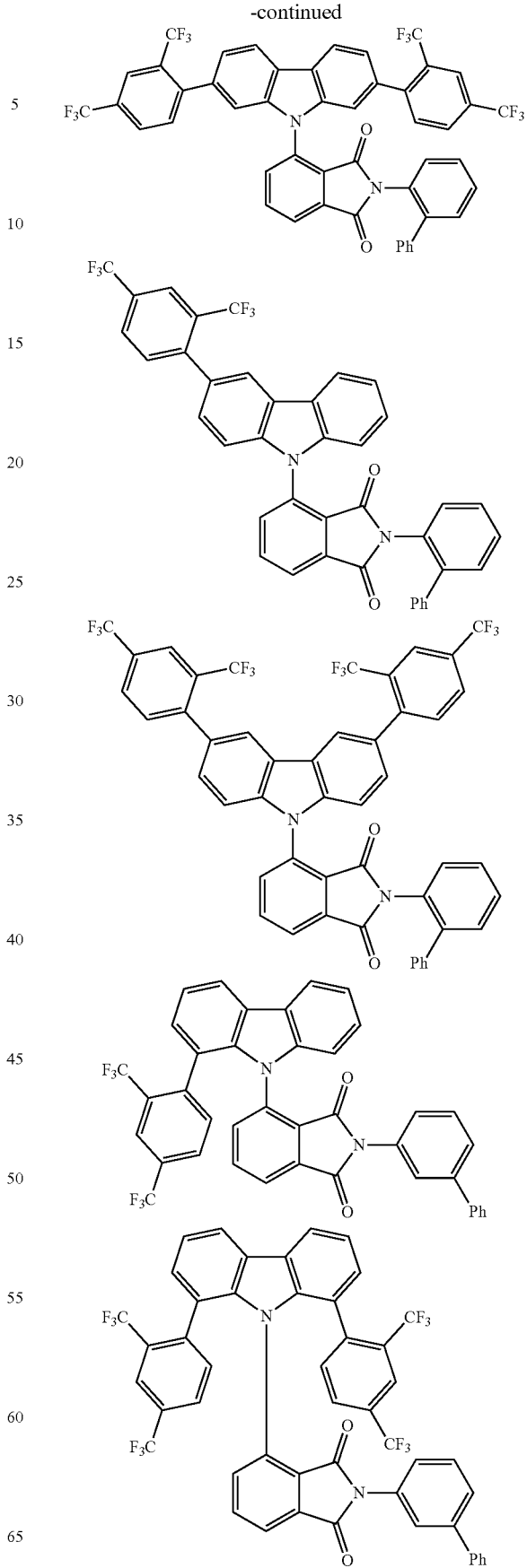

217
-continued
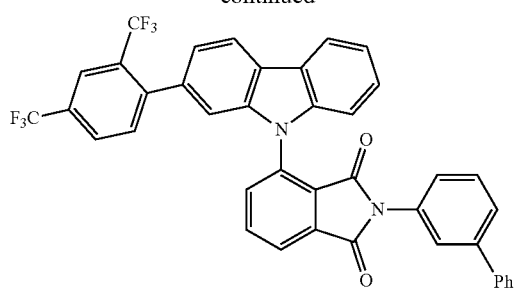
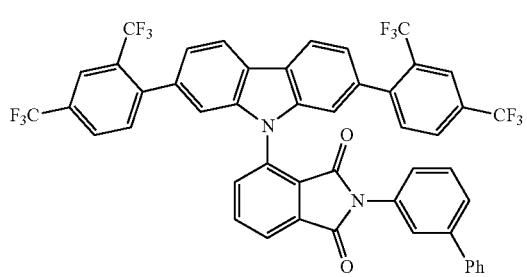
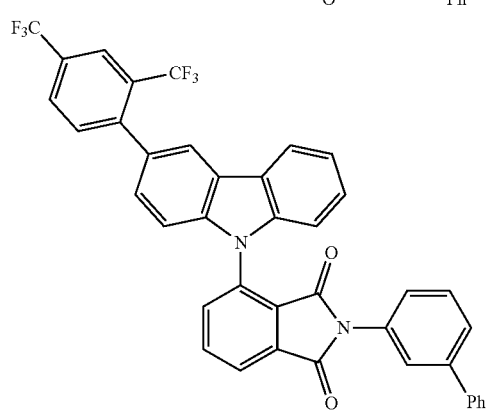
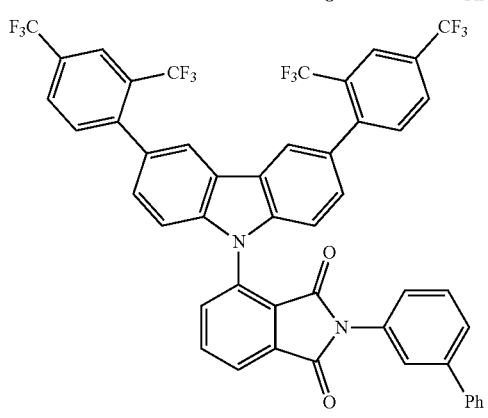
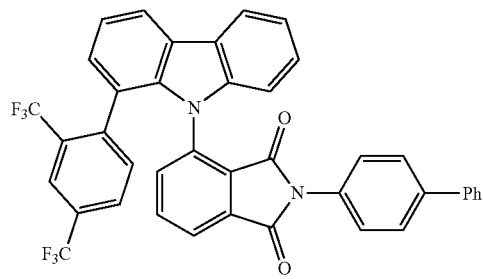
218
-continued
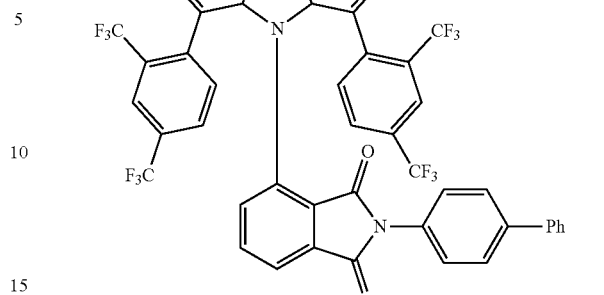
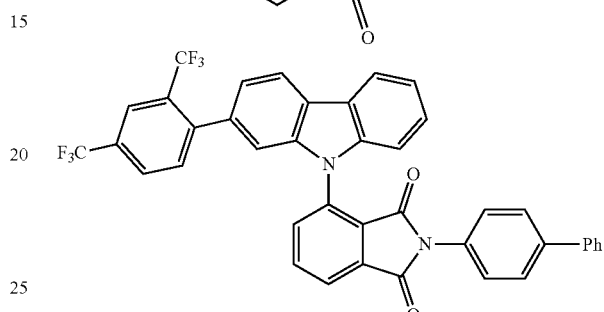
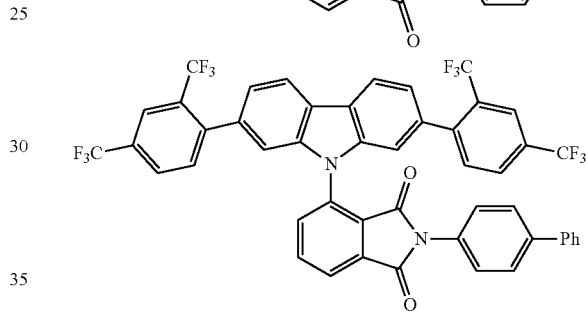
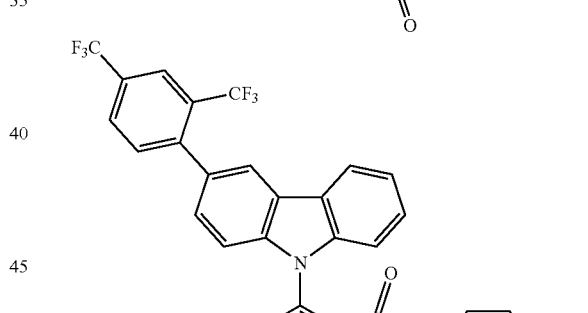
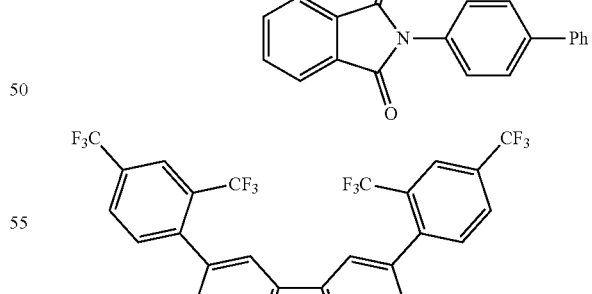
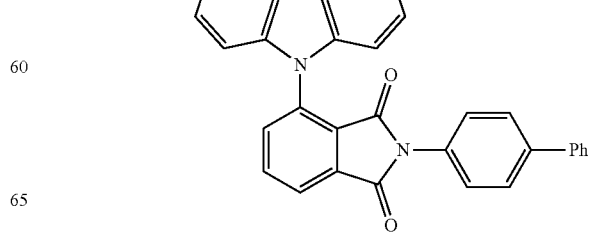

219
-continued
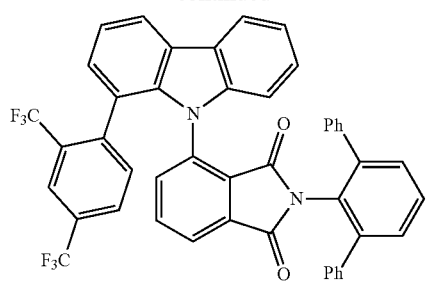
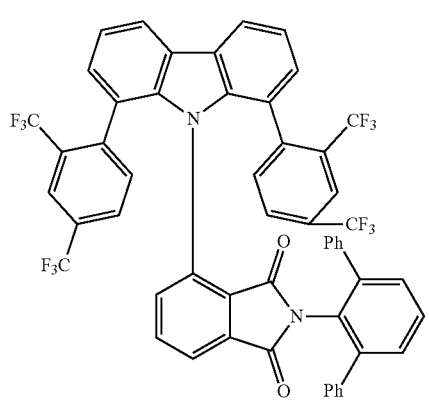
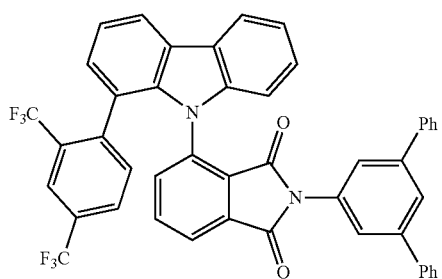
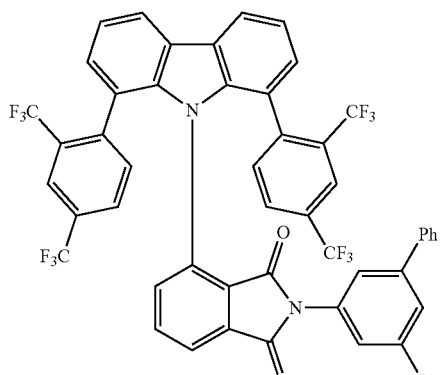
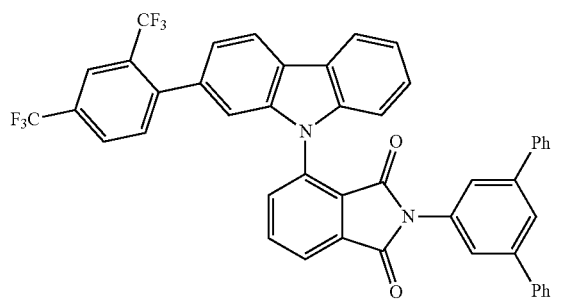
220
-continued
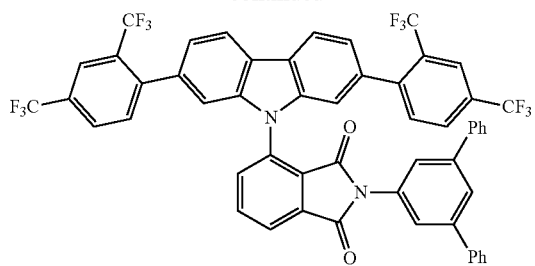
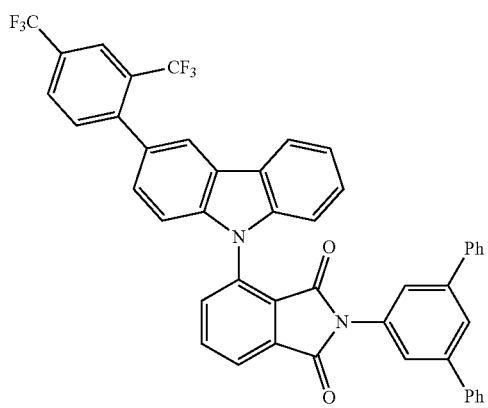
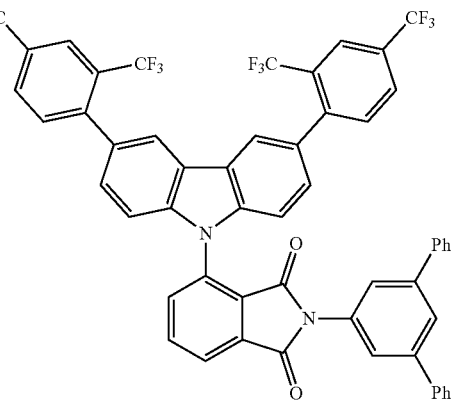
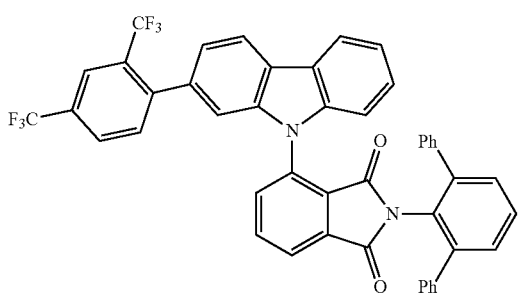
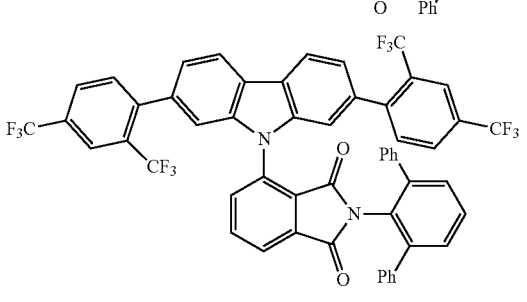

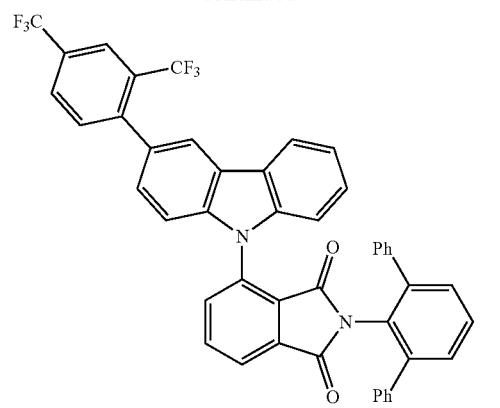
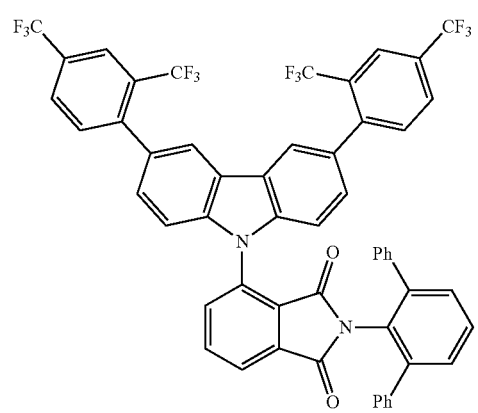
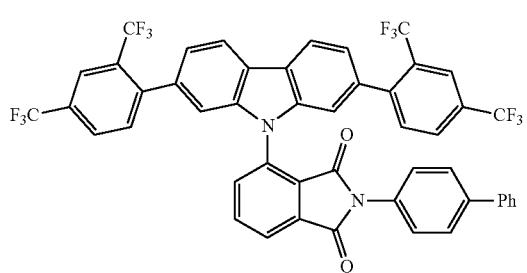
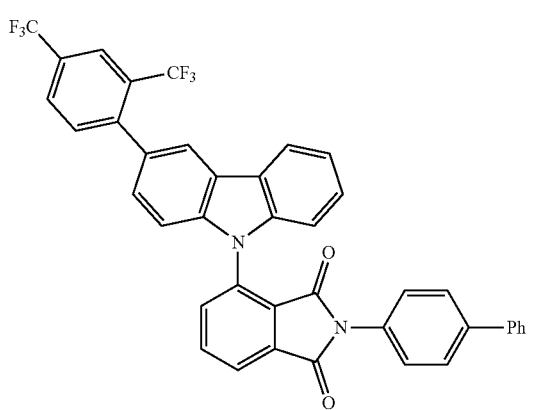
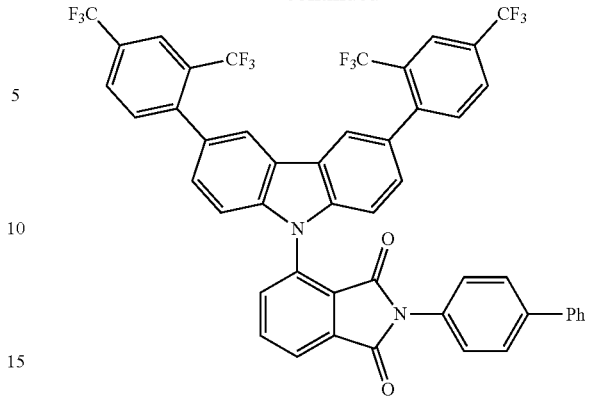
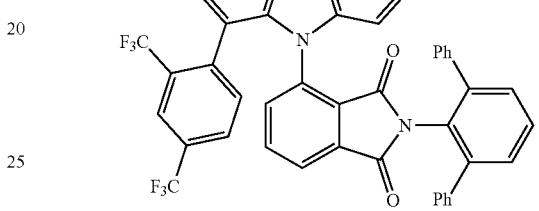
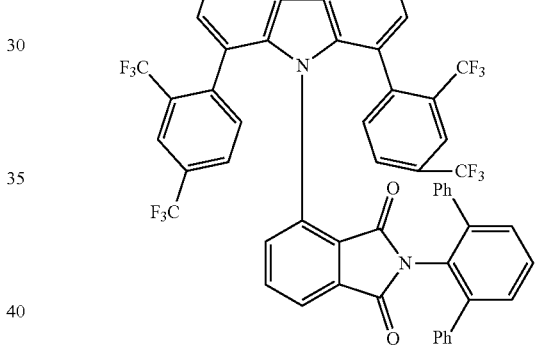
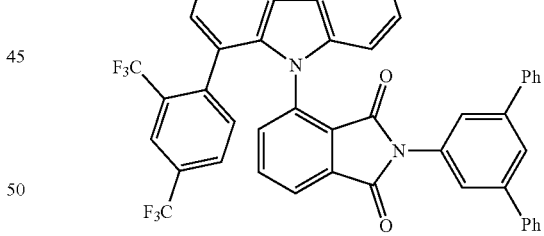
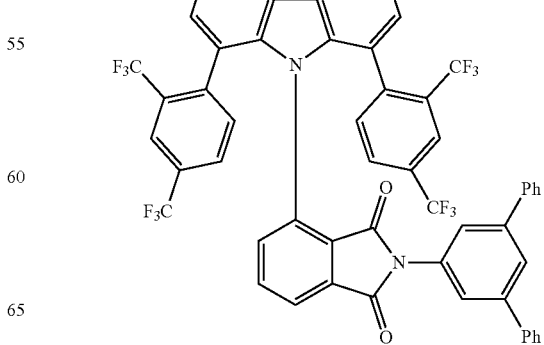

-continued
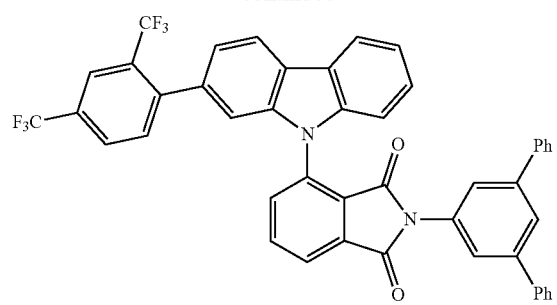
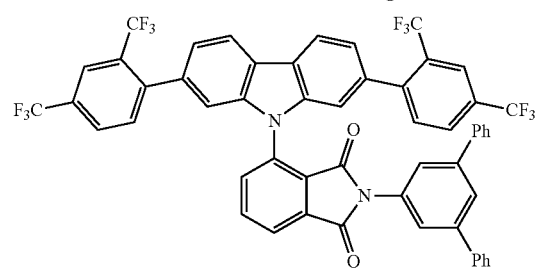
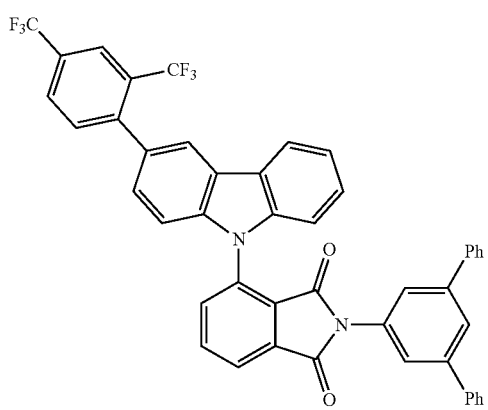
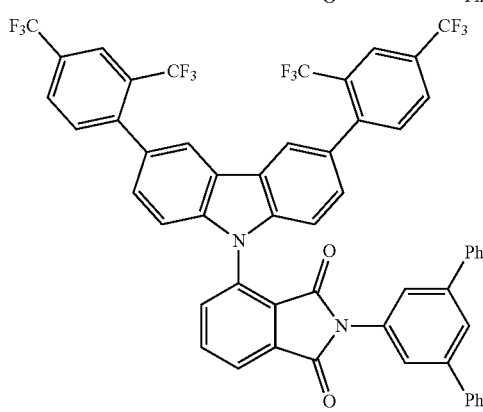
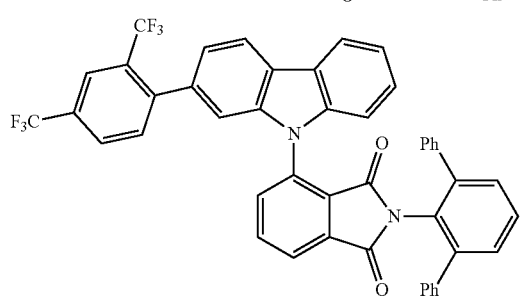
-continued
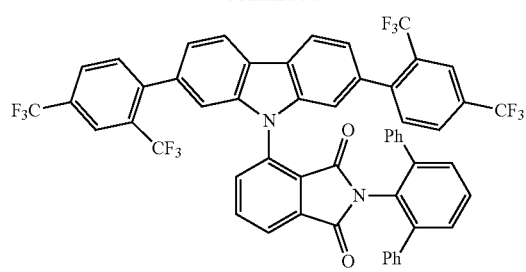
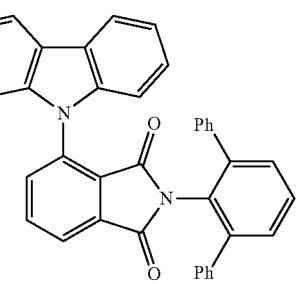
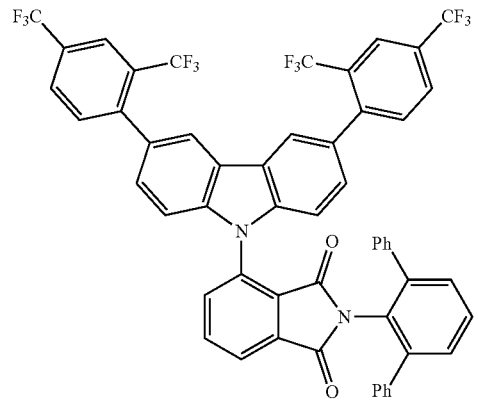
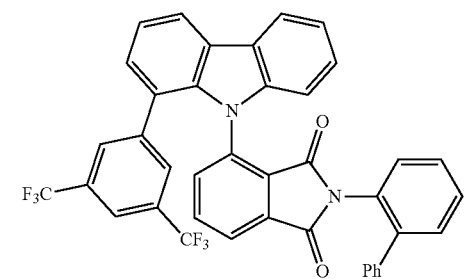

225
-continued
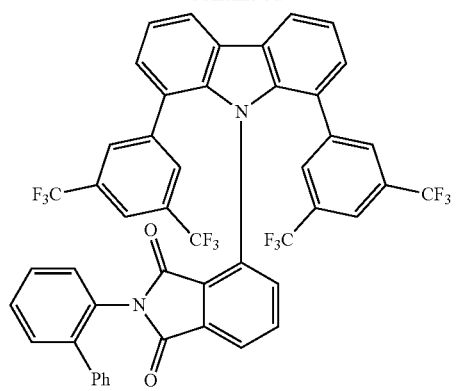
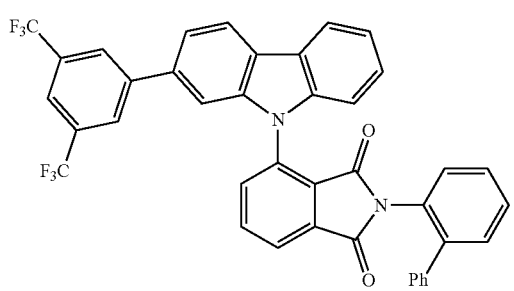
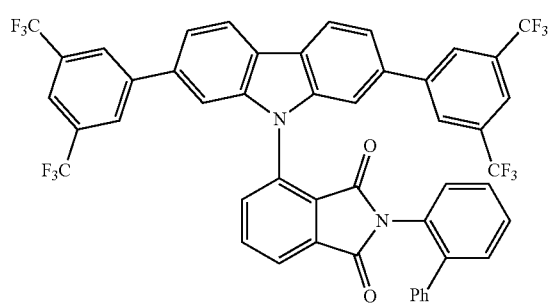
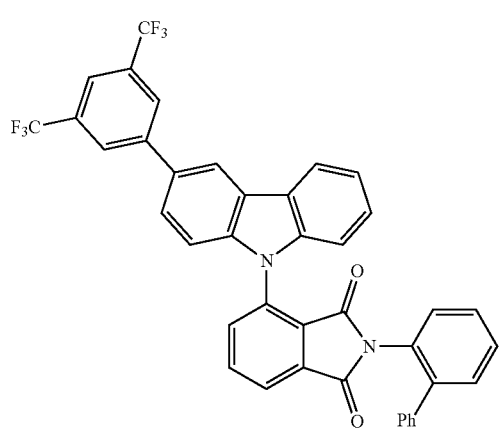
226
-continued
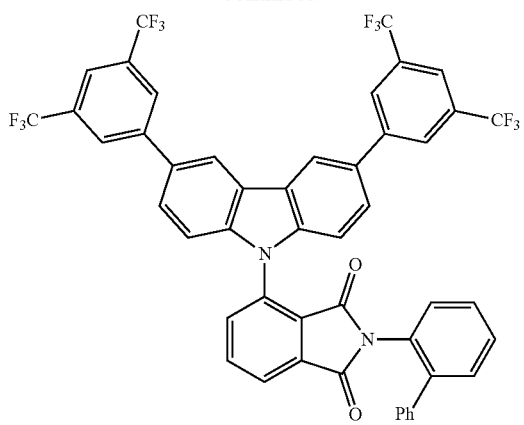
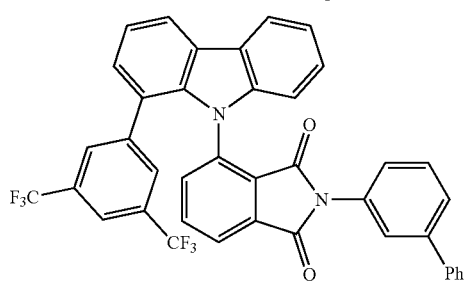
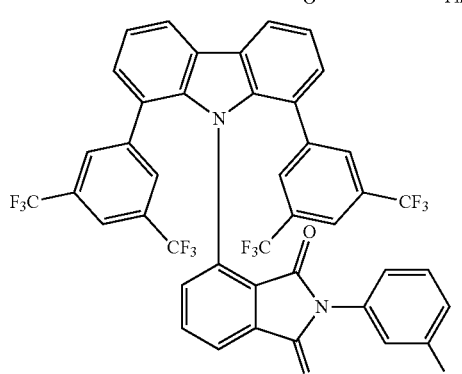
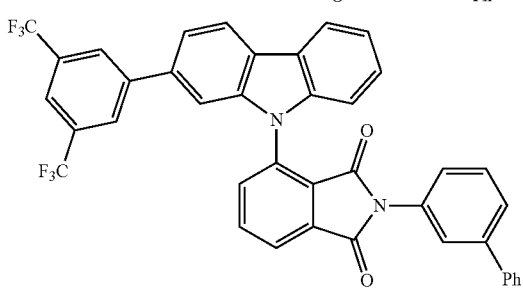
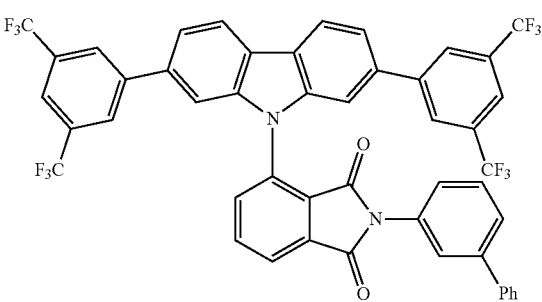

227
-continued
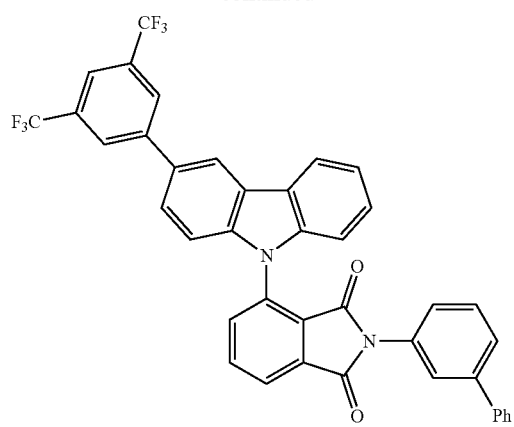
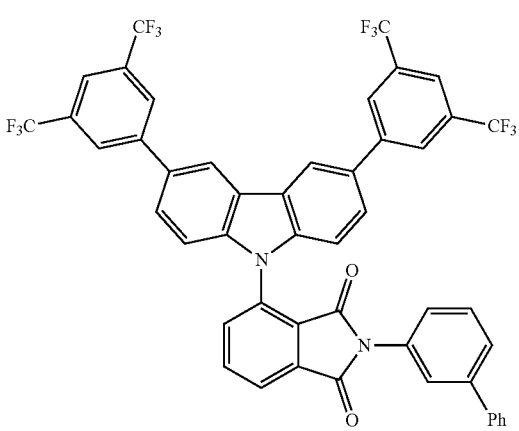
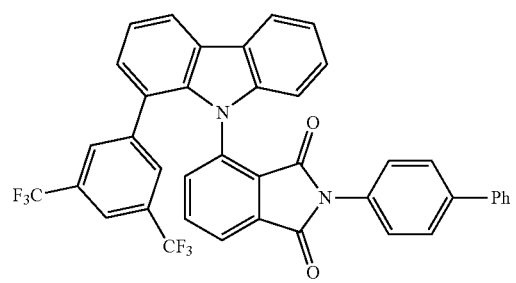
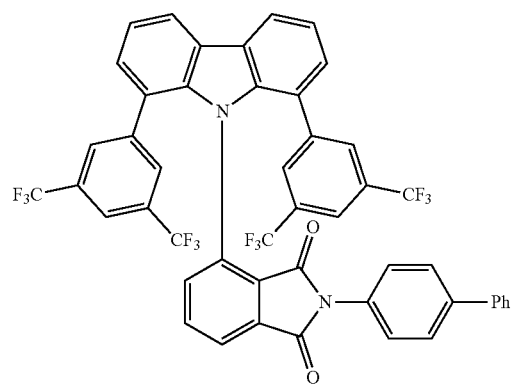
228
-continued
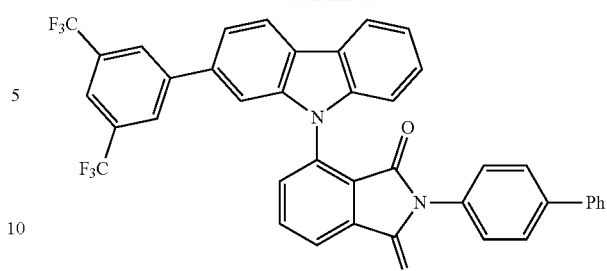
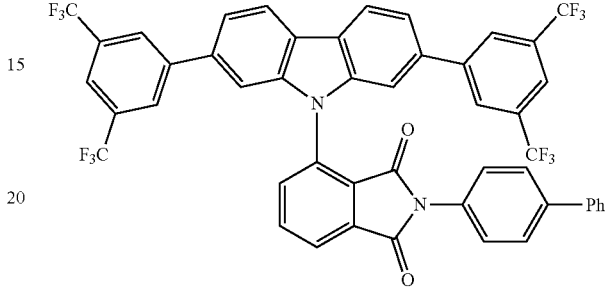
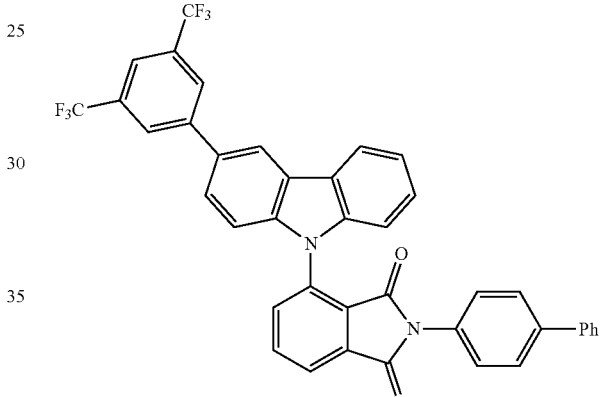
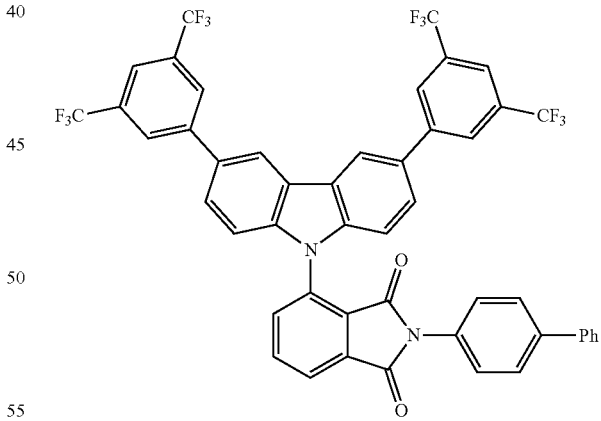
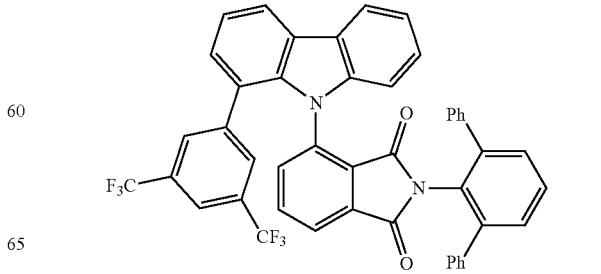

229
-continued
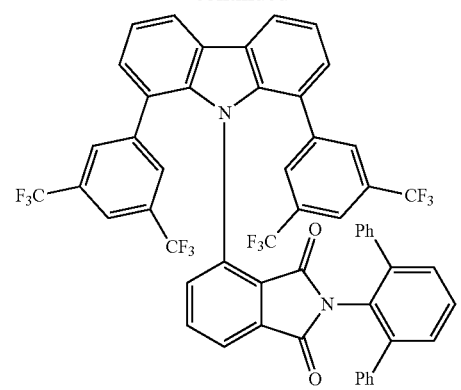
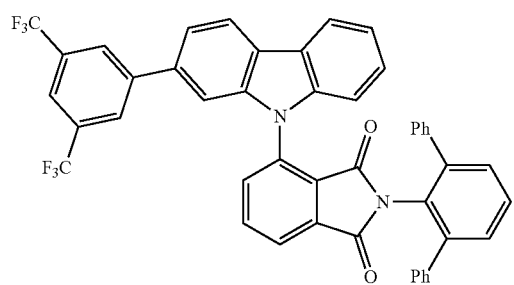
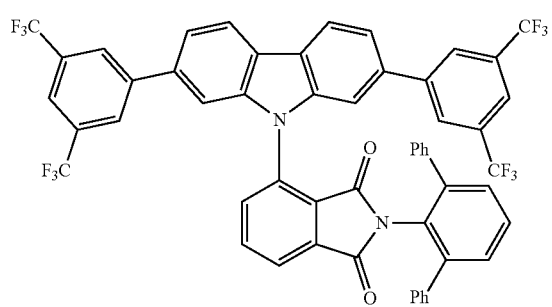
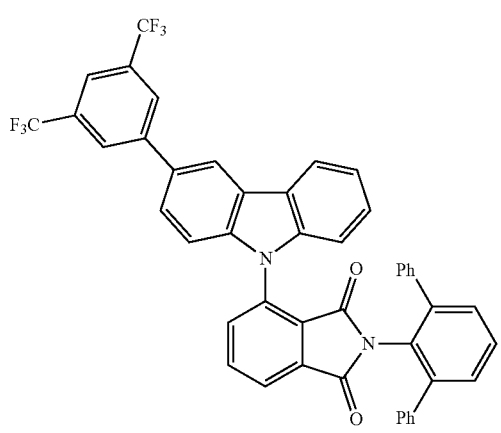
230
-continued
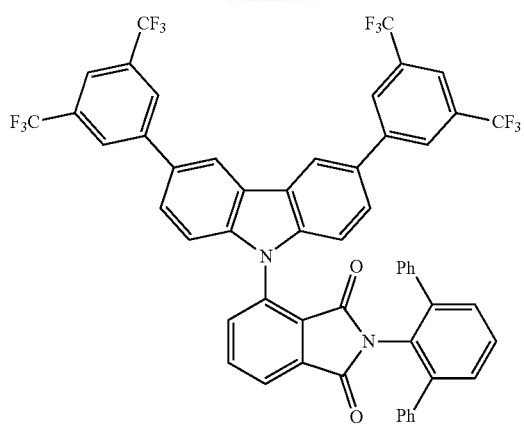
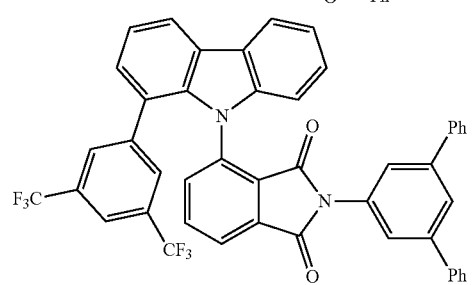
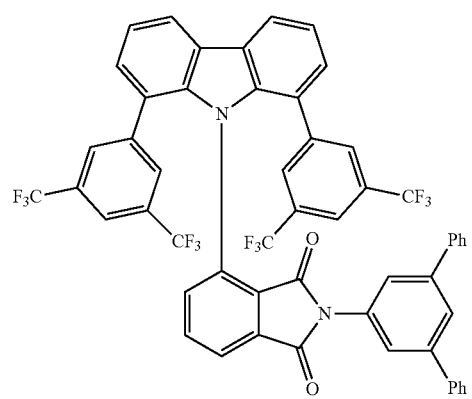
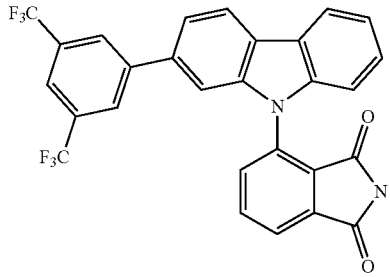
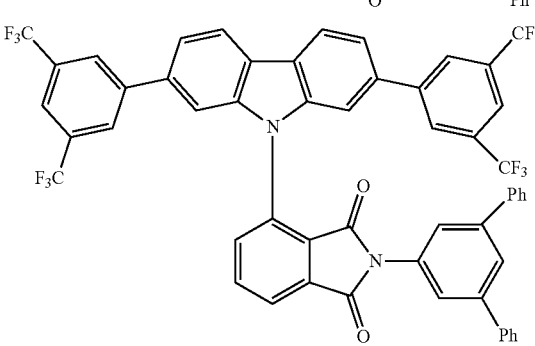

-continued
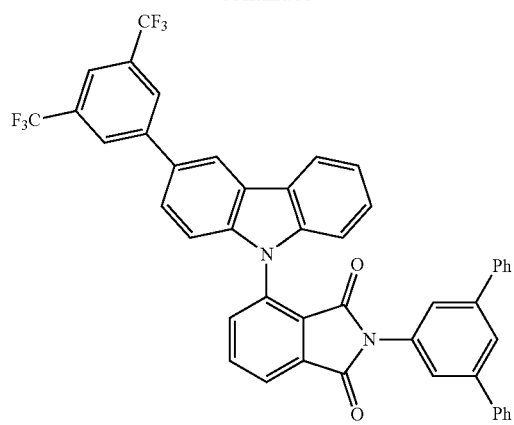
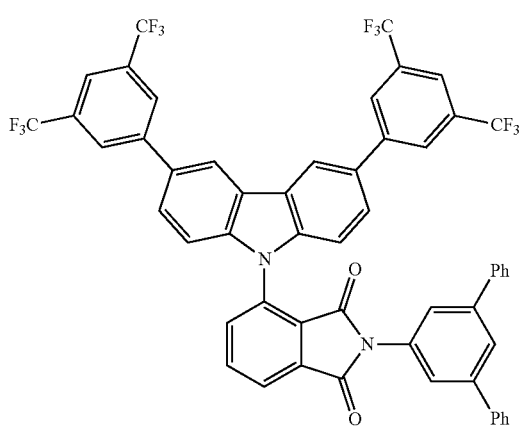
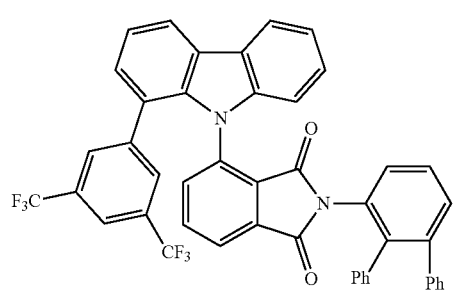
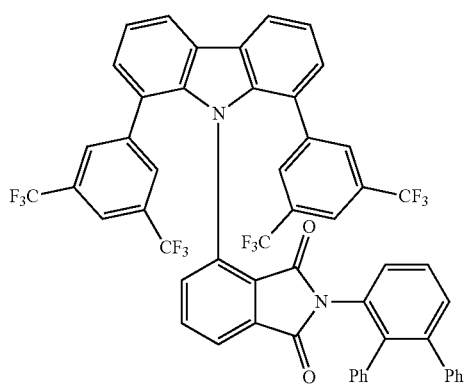
-continued
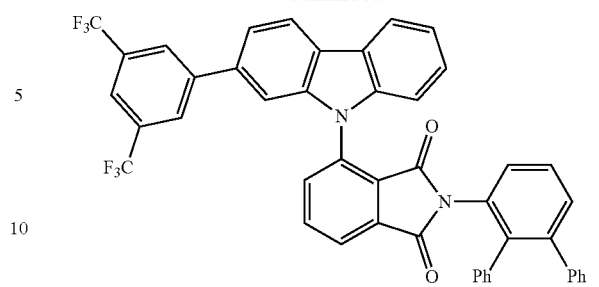
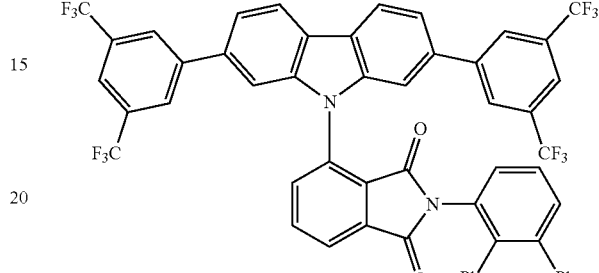
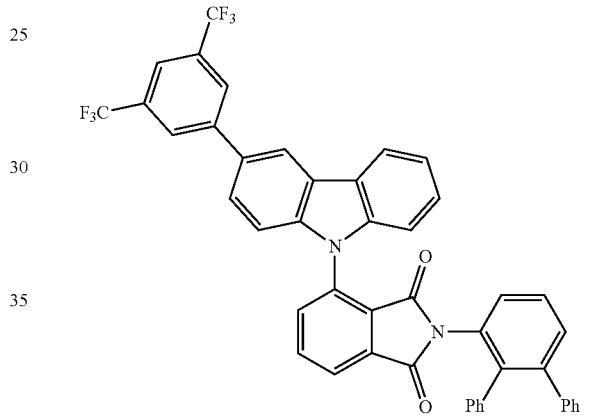

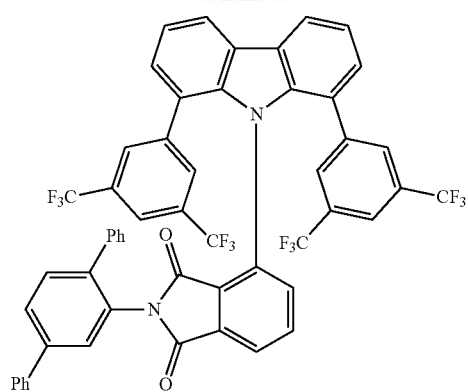
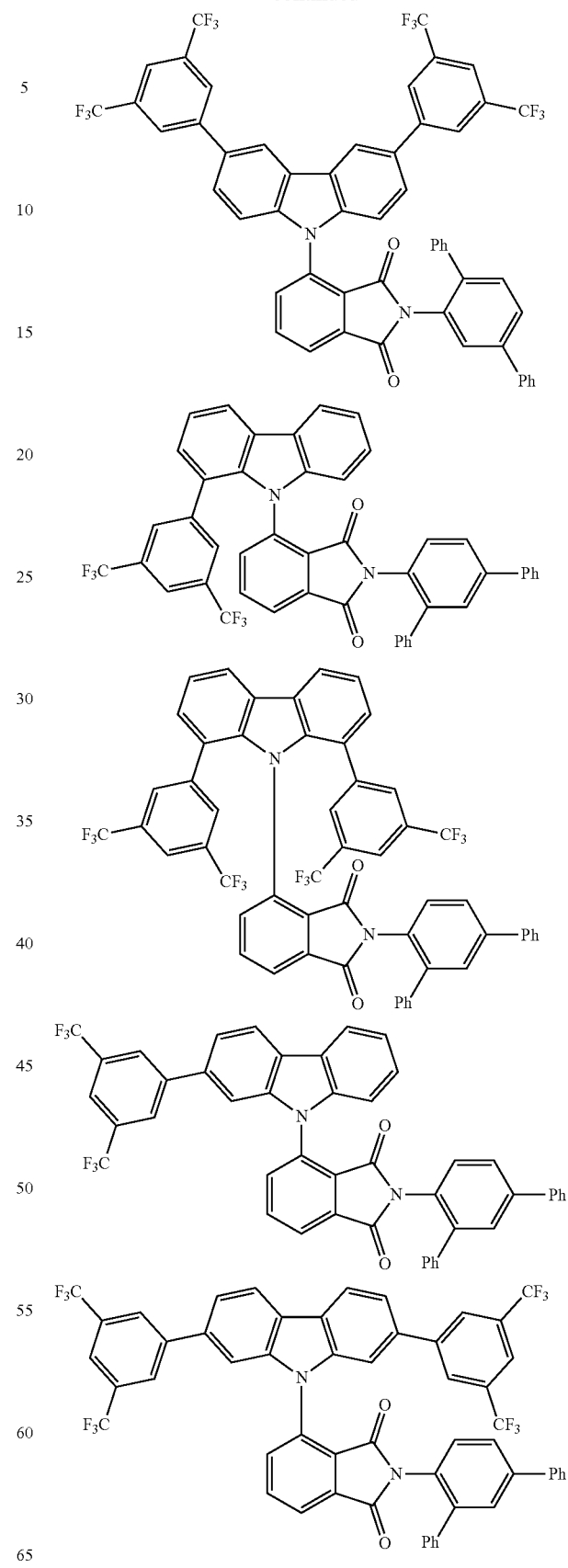

235
-continued
236
-continued
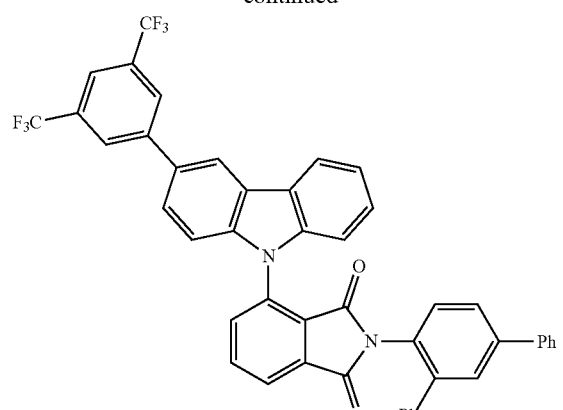
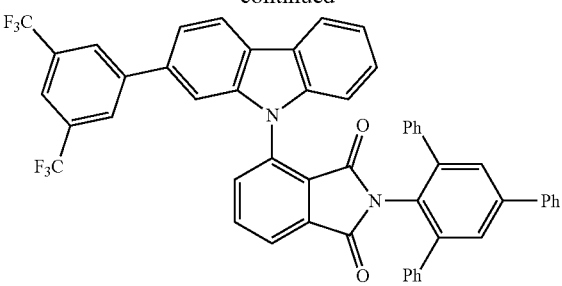
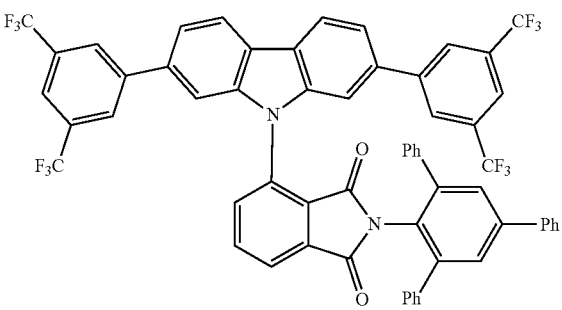
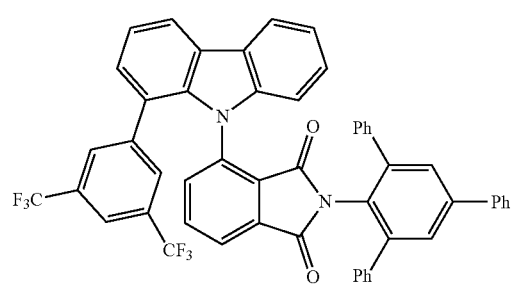
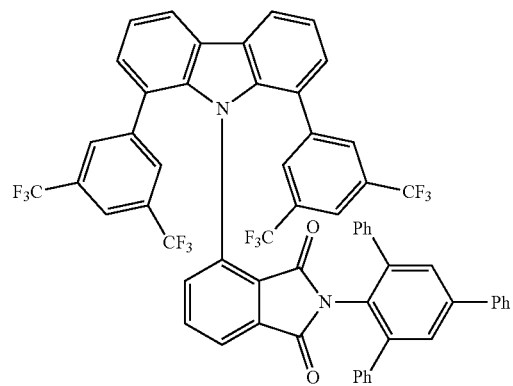
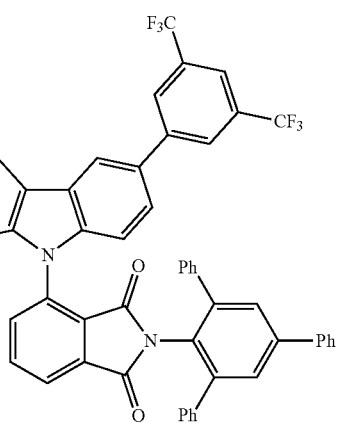

237
-continued
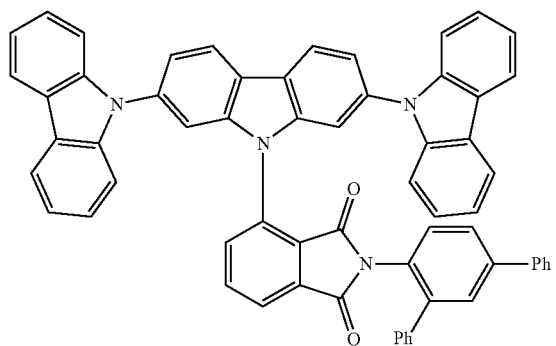
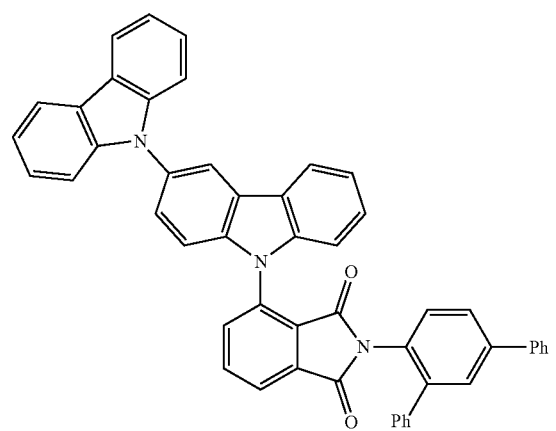
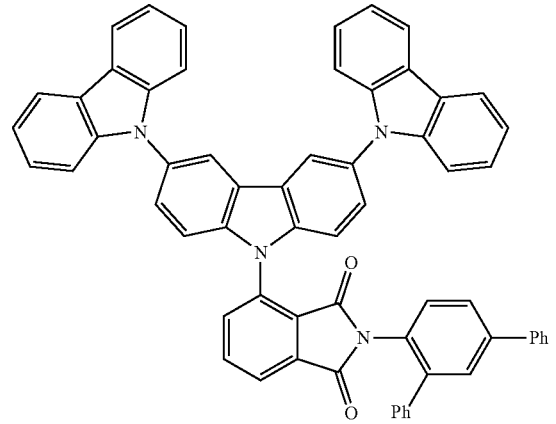
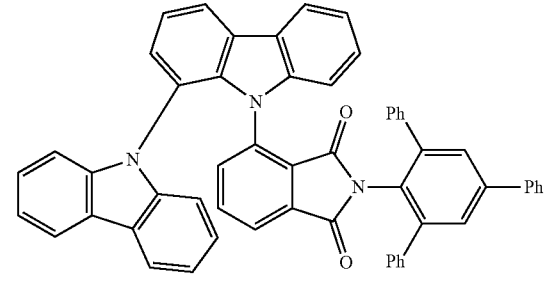
238
-continued
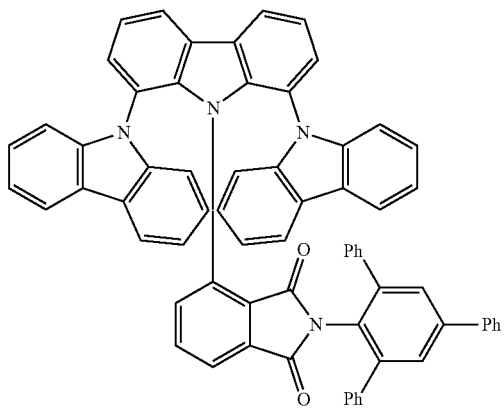
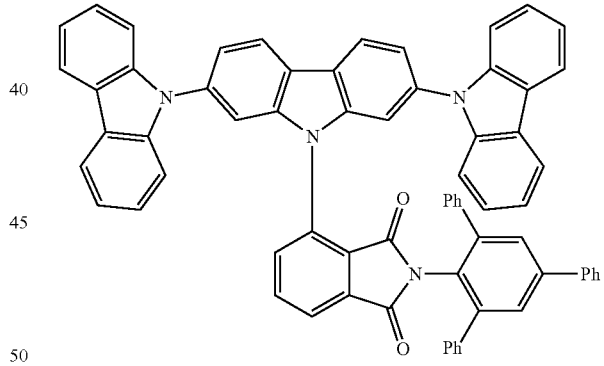
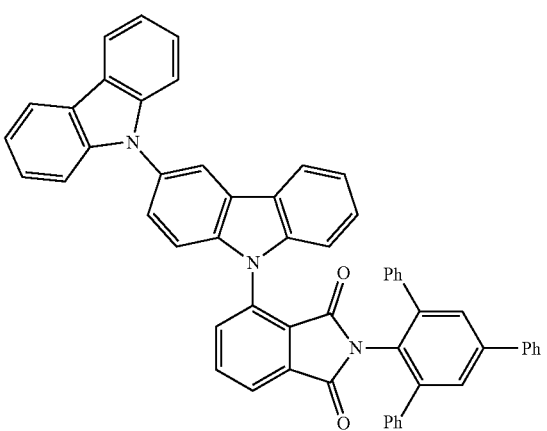

239
-continued
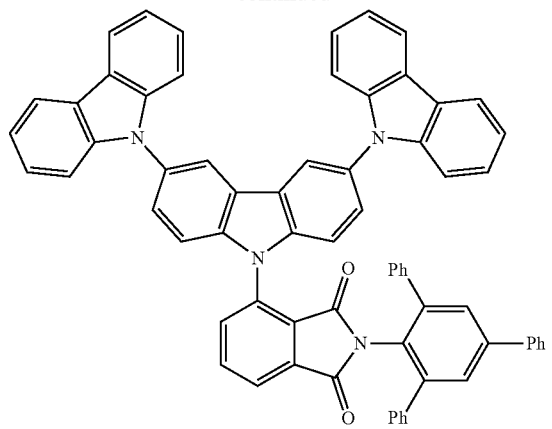
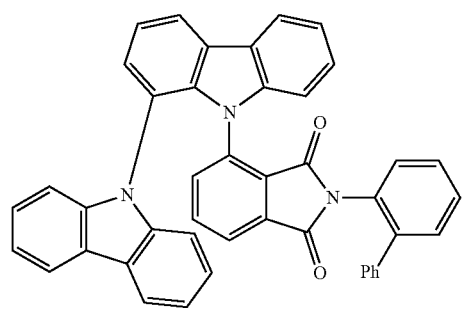
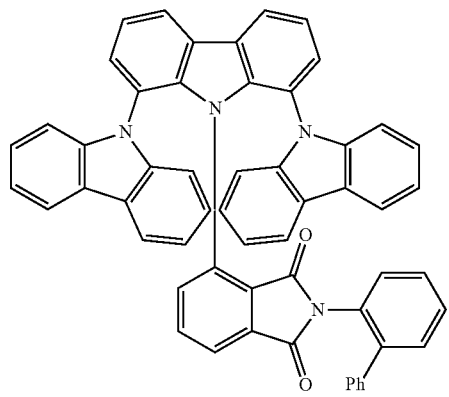
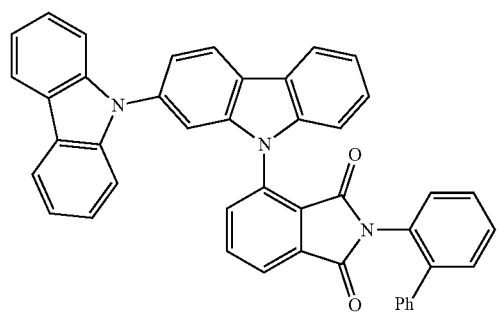
240
-continued
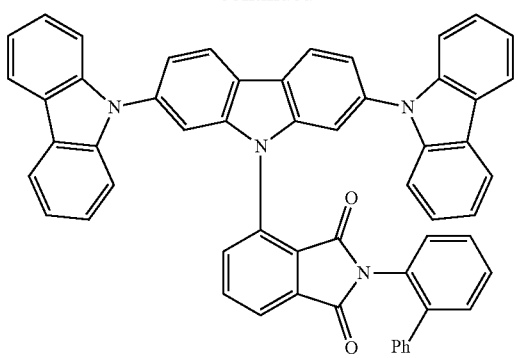
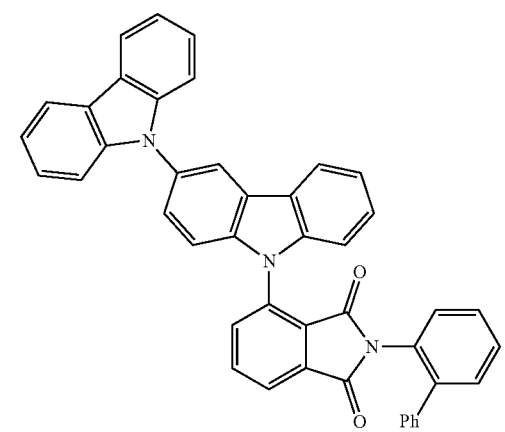
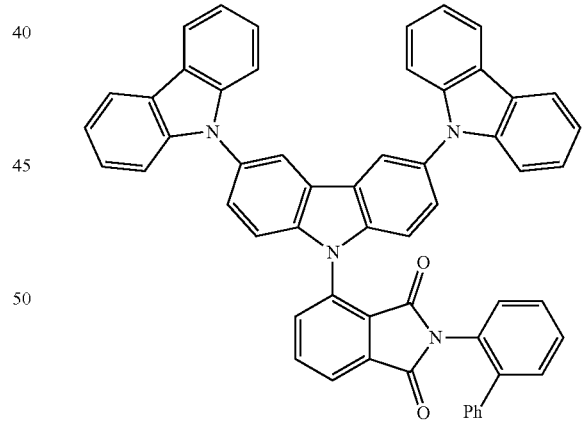
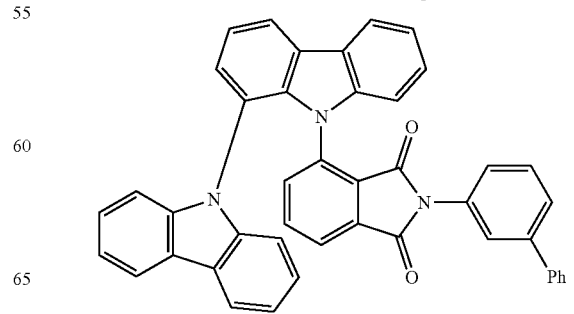

241
-continued
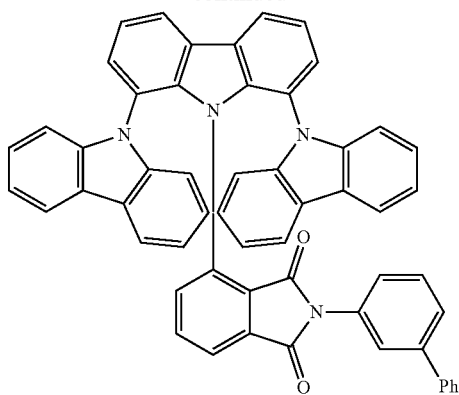
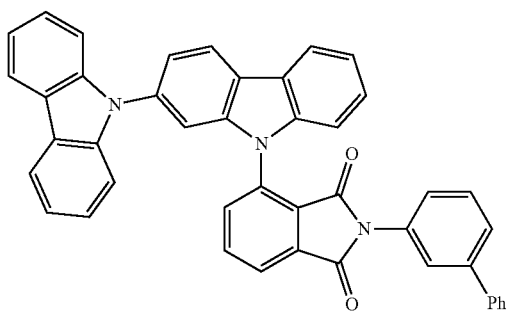
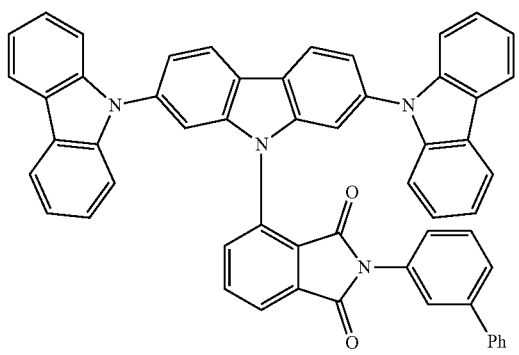
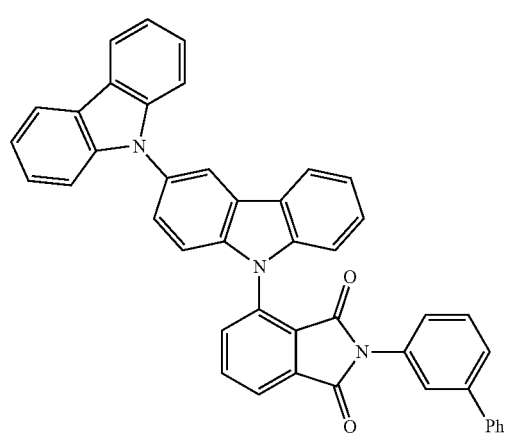
242
-continued
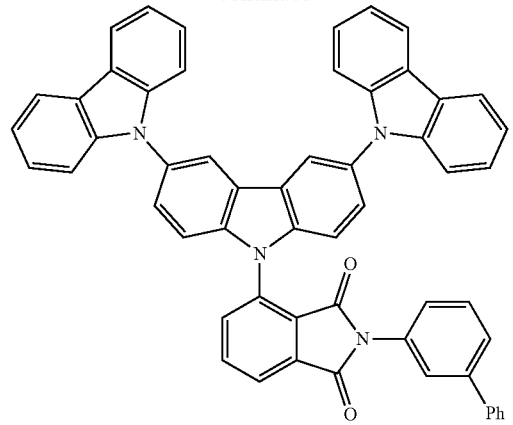
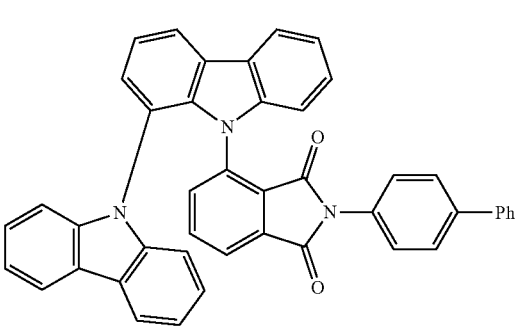
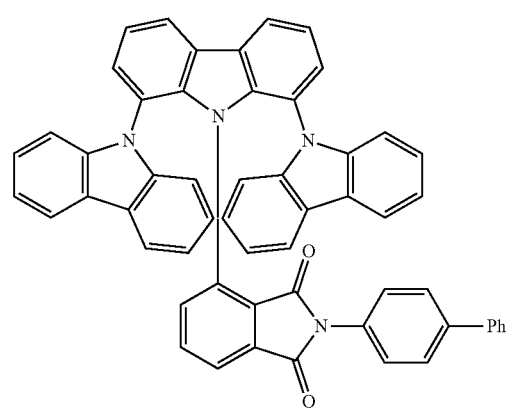
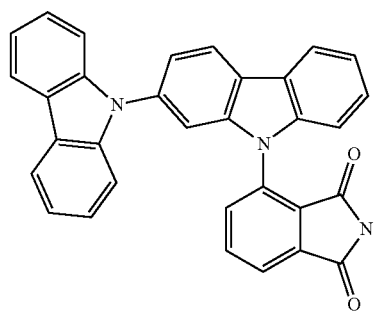

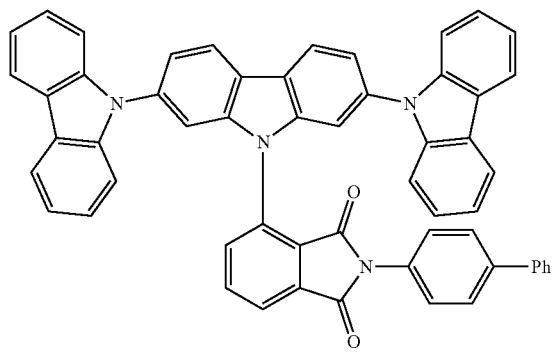
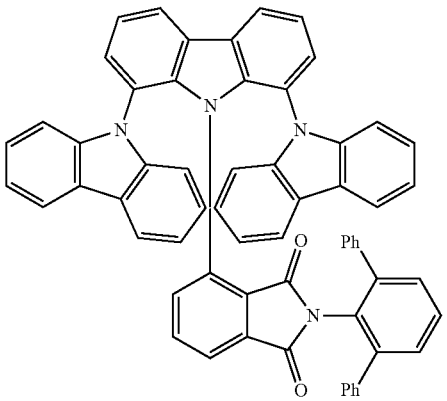
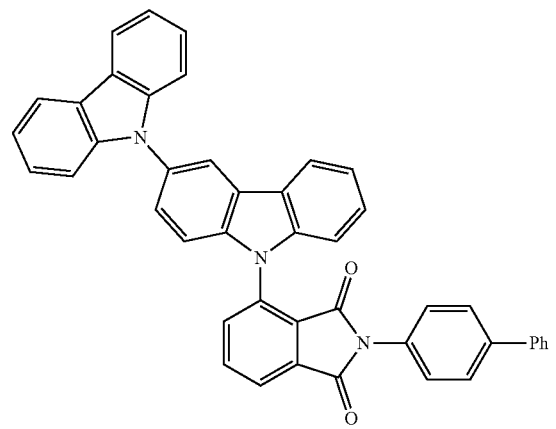
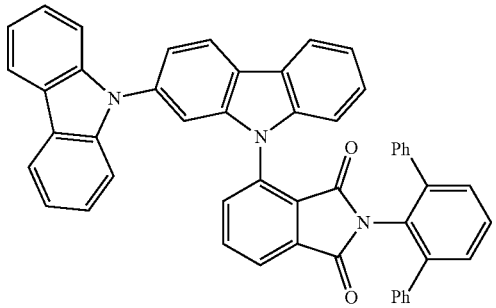
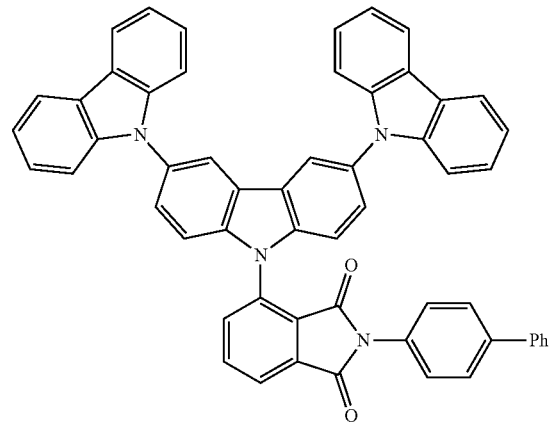
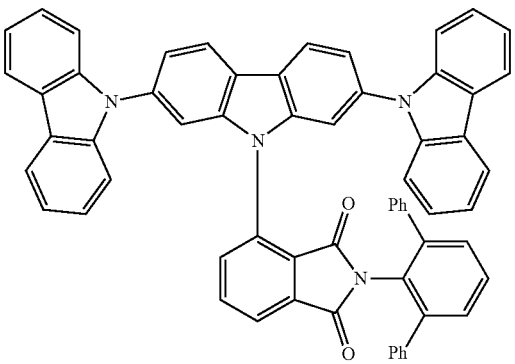
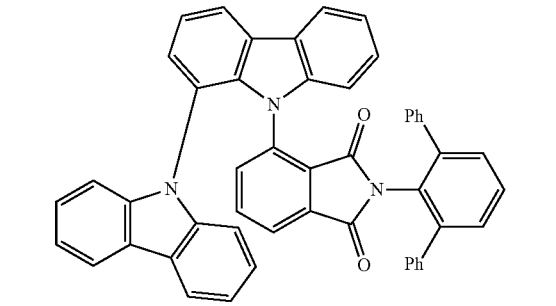
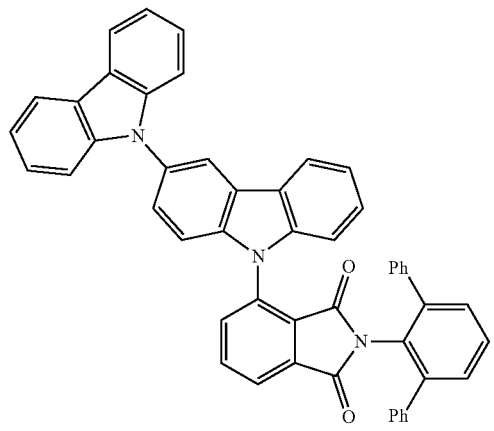

245
-continued
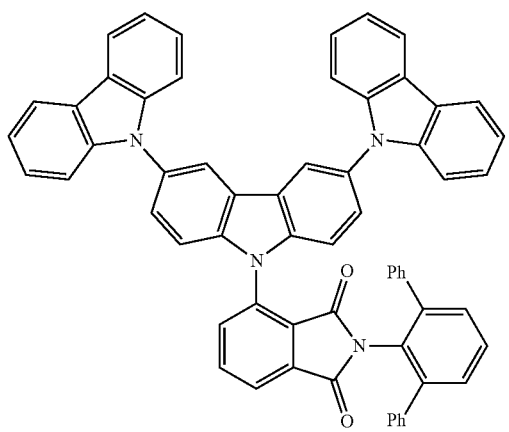
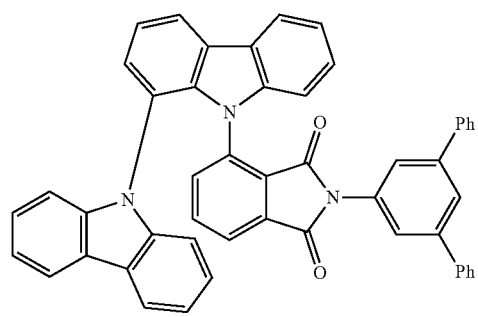
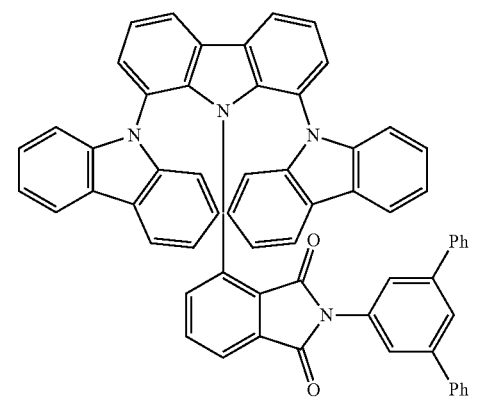
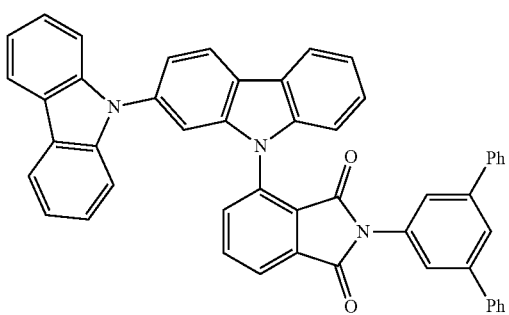
246
-continued
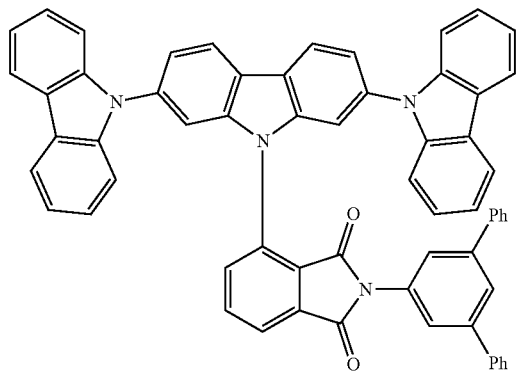
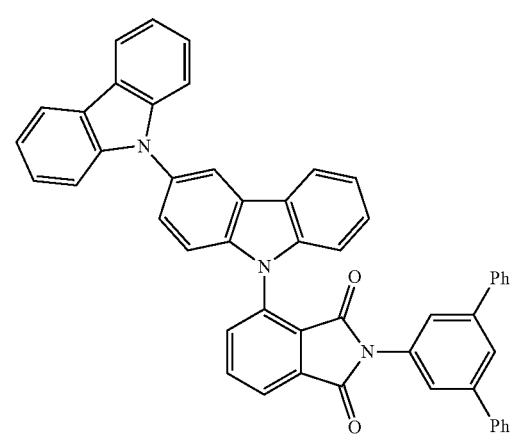
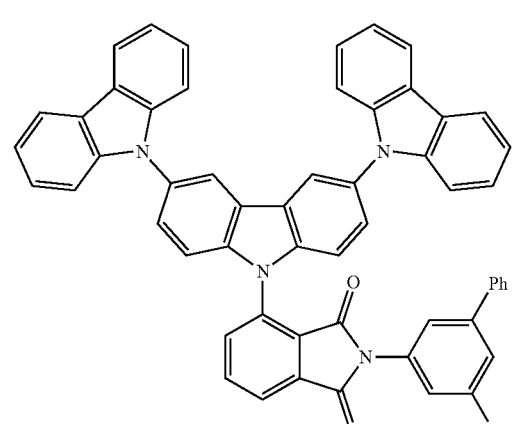
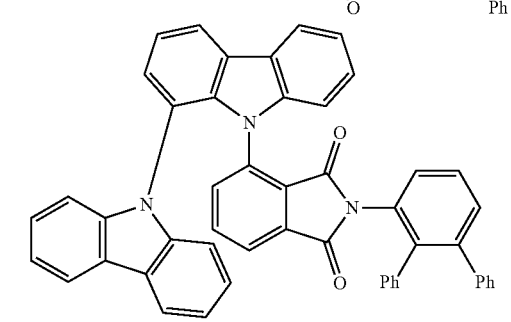

247
-continued
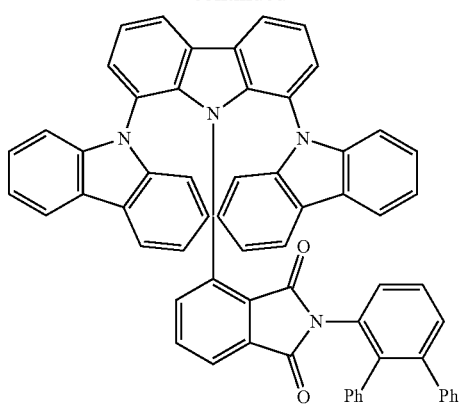
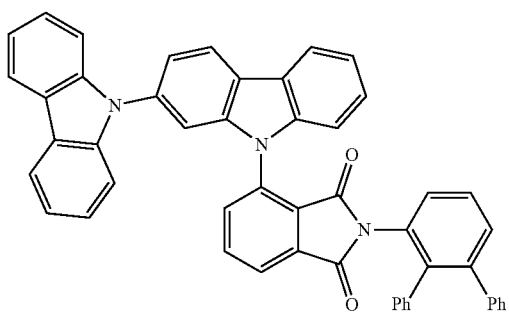
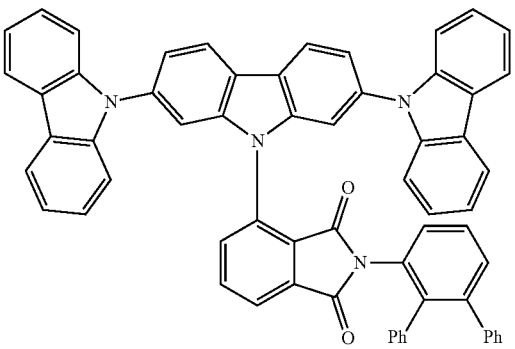
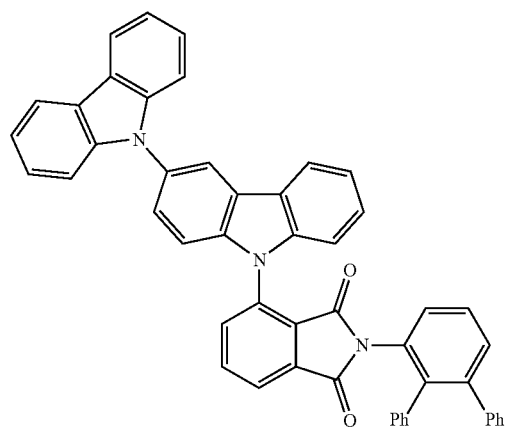
248
-continued
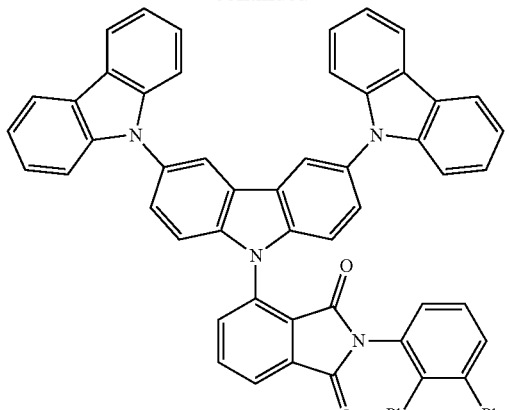
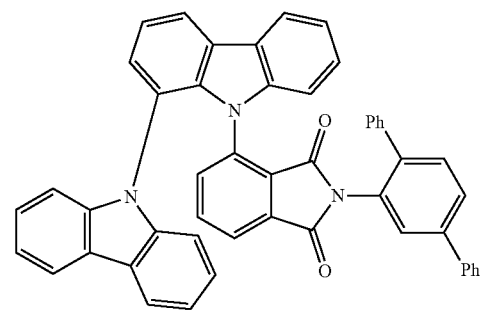
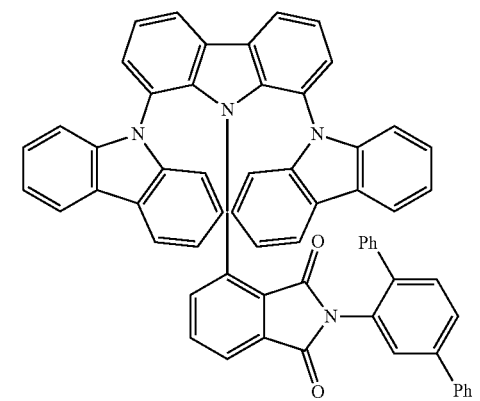
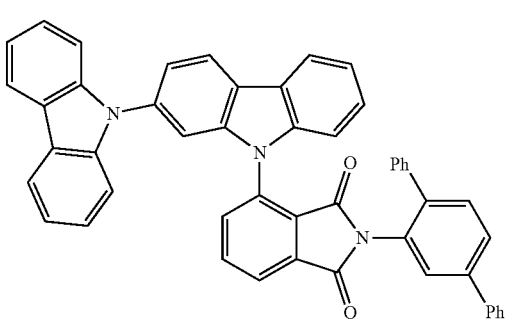

249
-continued

250
-continued

251
-continued
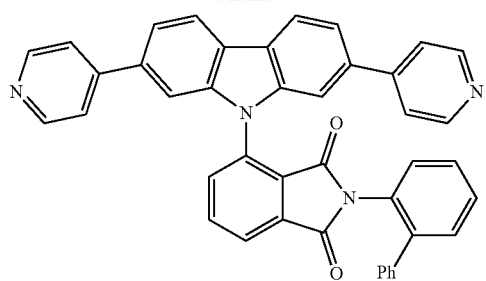
252
-continued
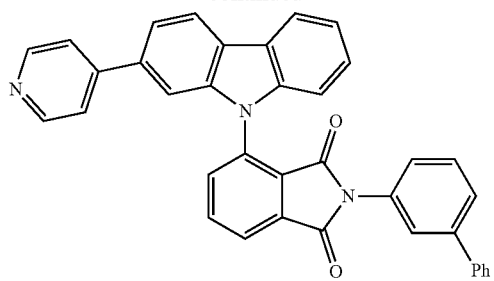
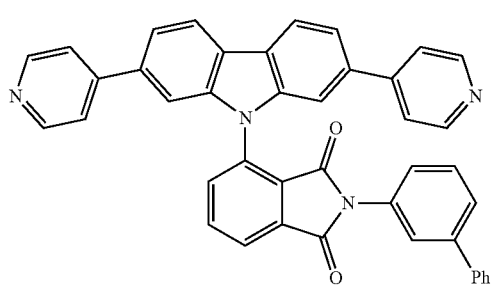
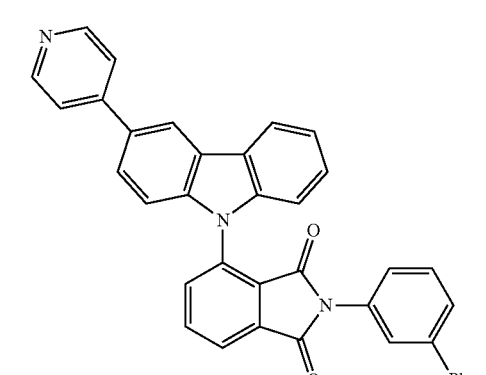
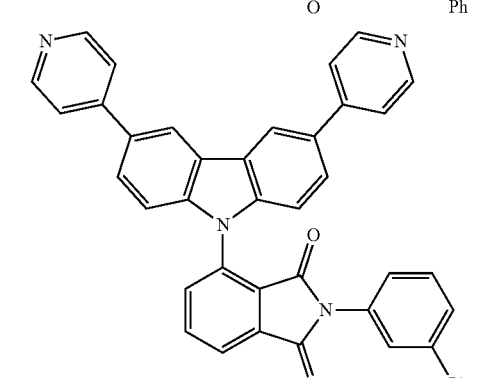
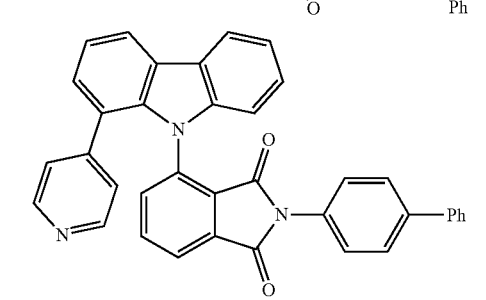

253
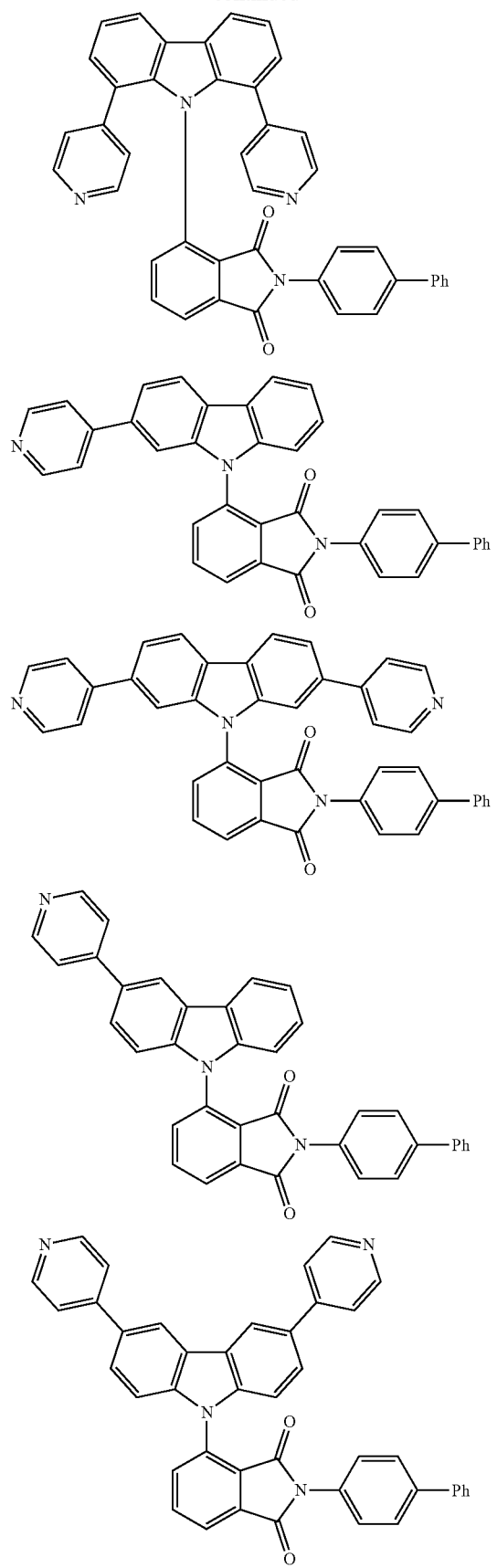
254
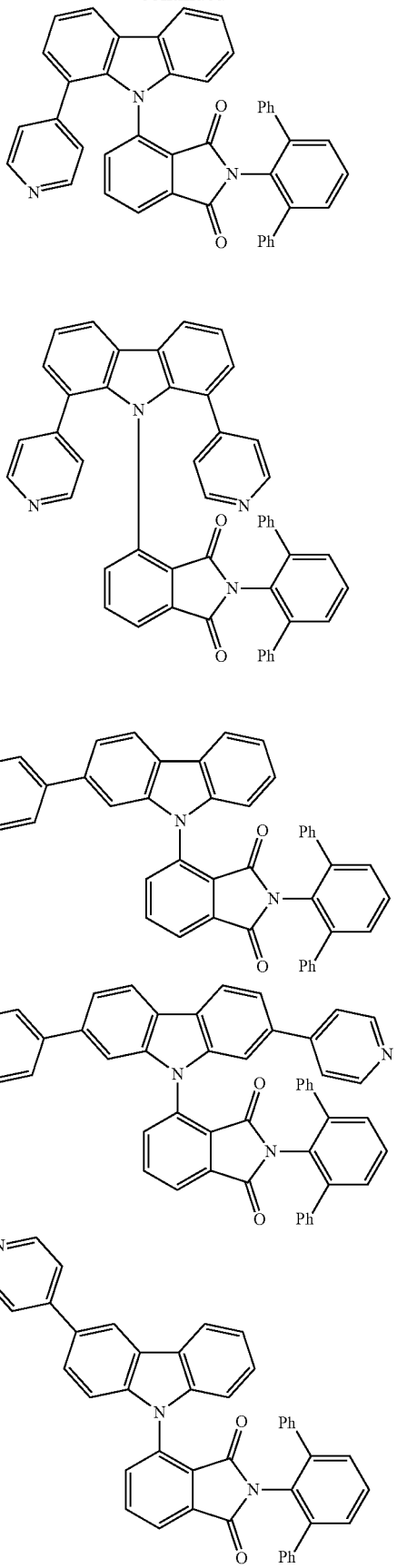

255
-continued
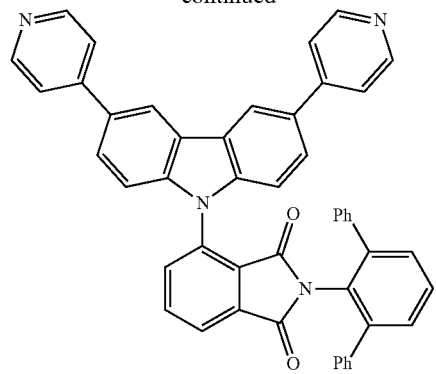
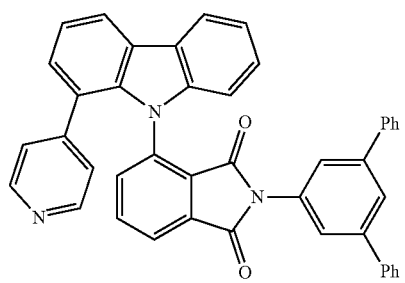
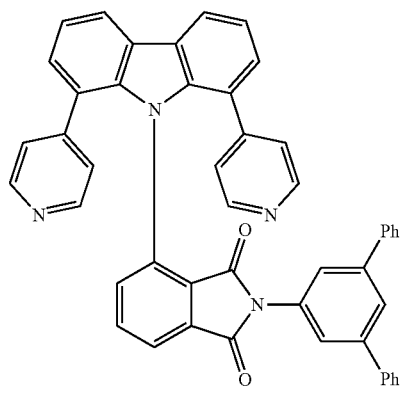
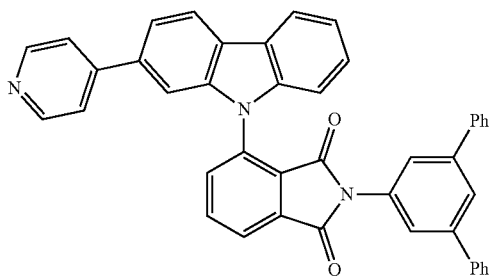
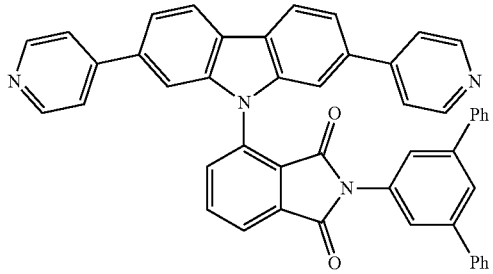
256
-continued
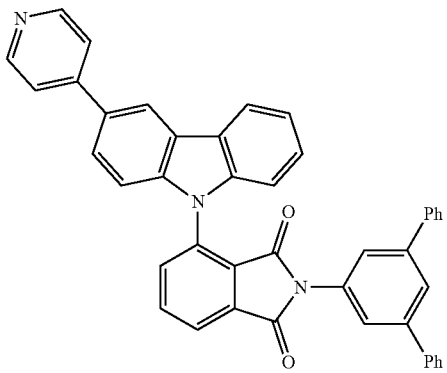
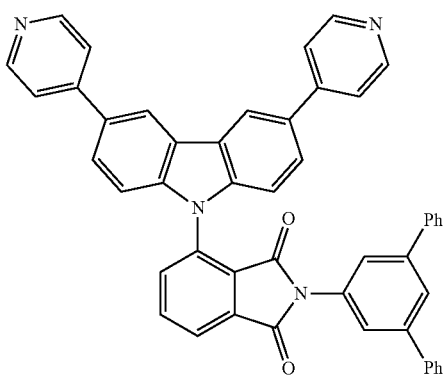
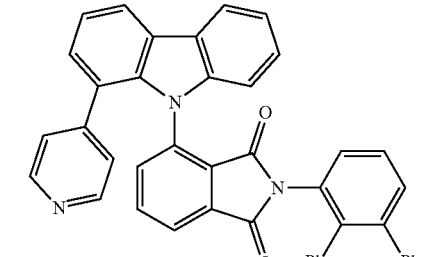
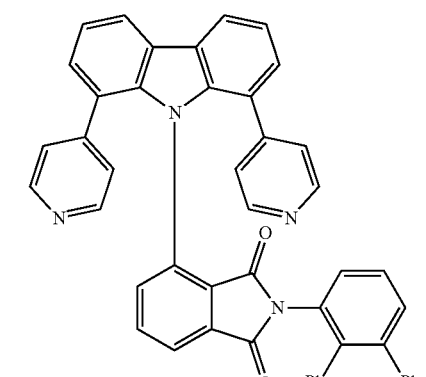
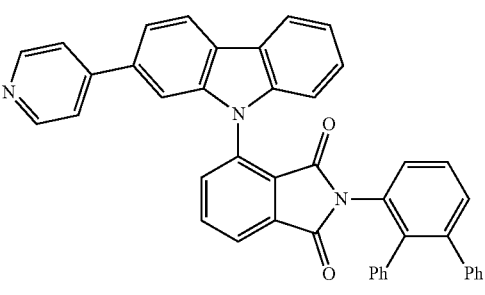

257
-continued
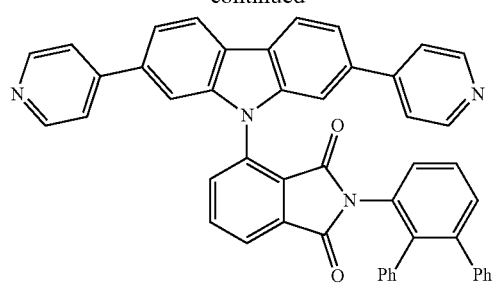
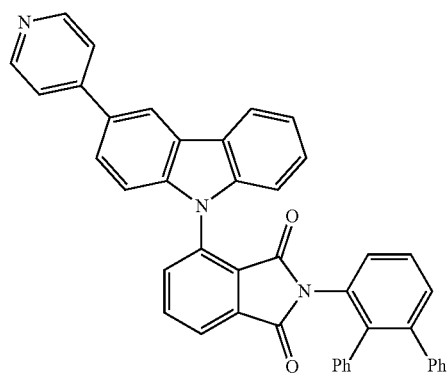
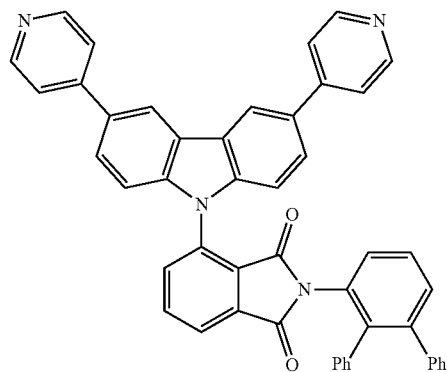
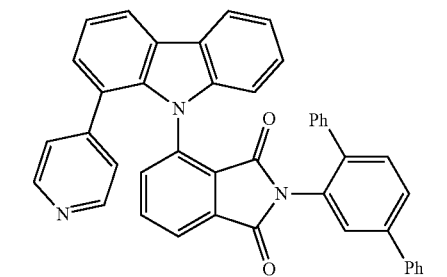
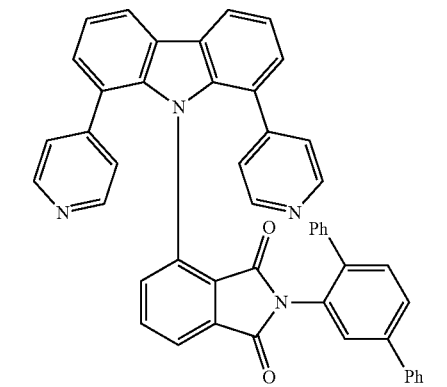
258
-continued
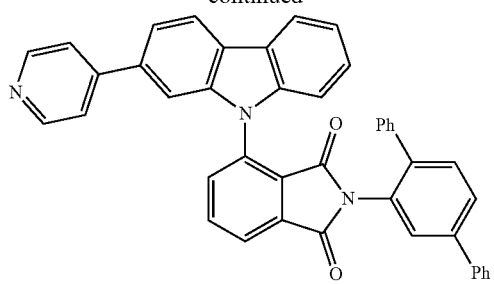
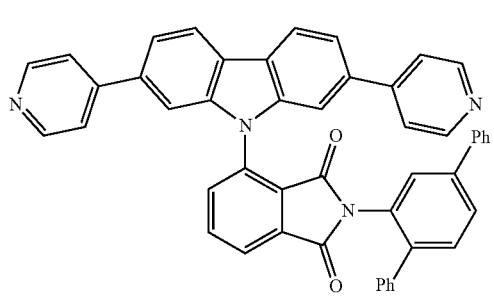
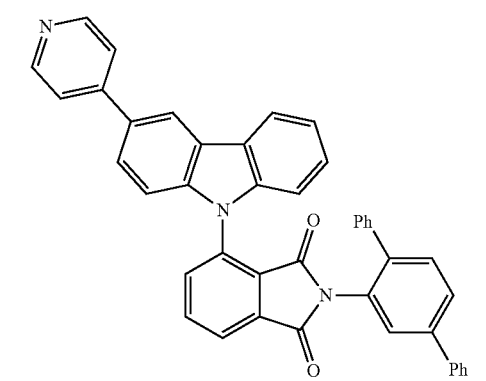
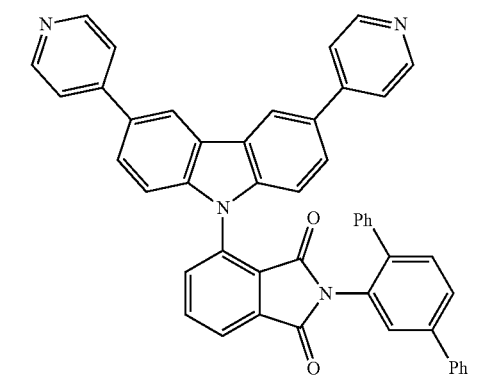
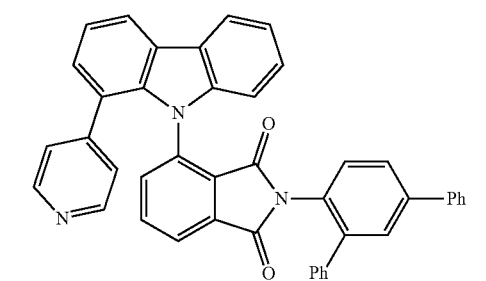

-continued
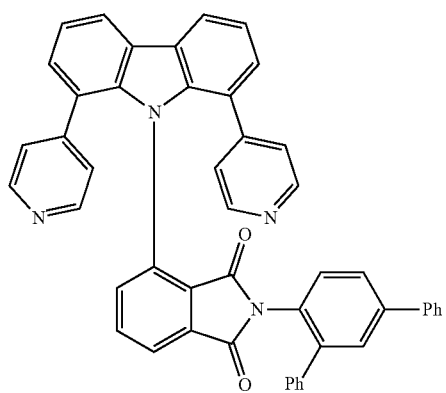
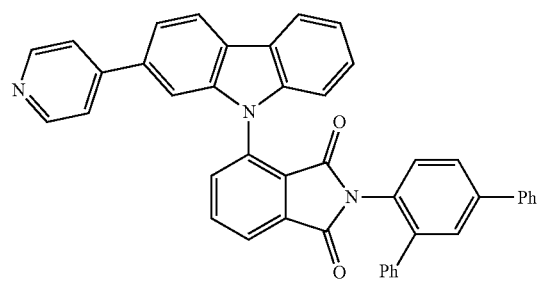
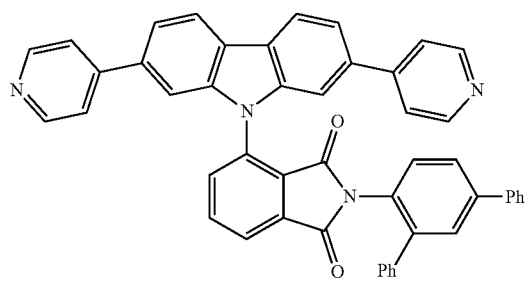
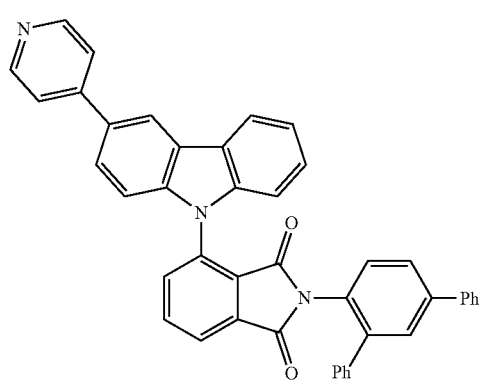
-continued
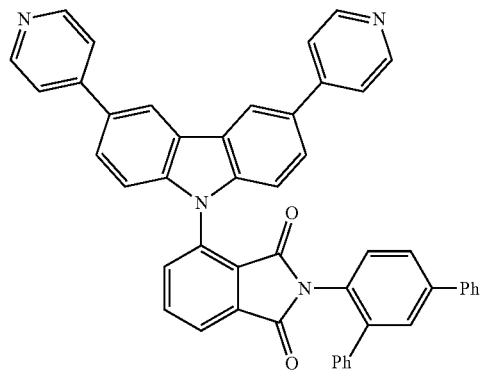
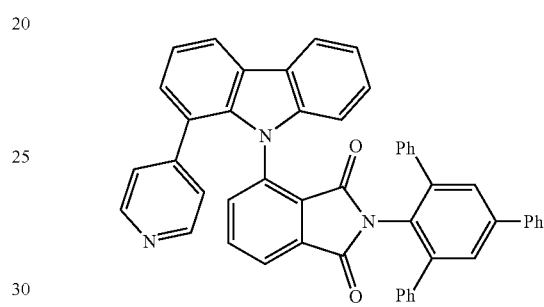
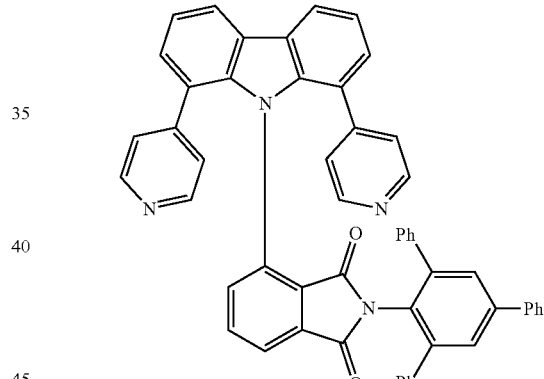
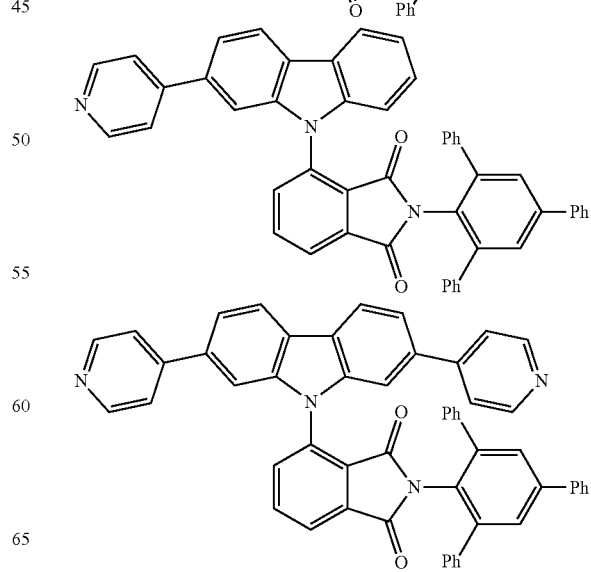

261
-continued
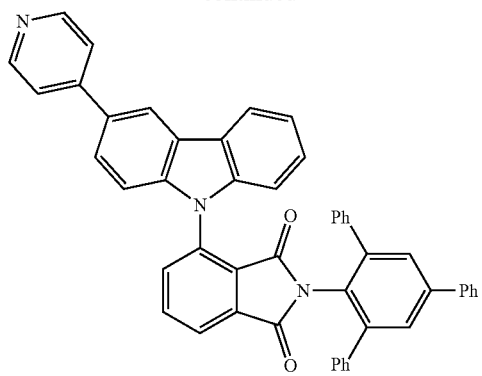
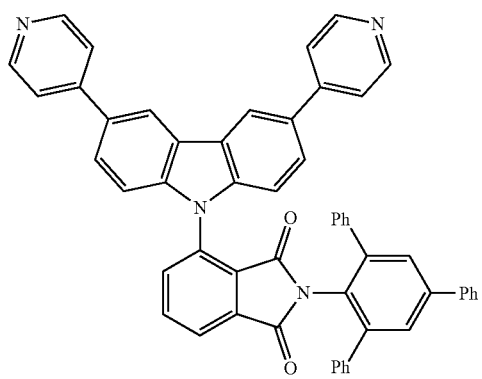
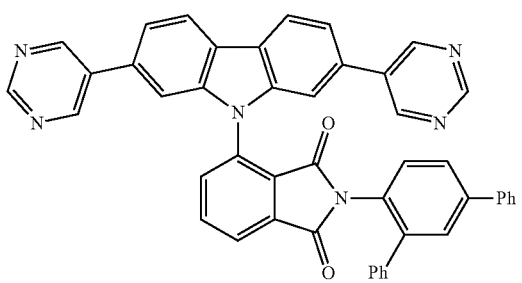
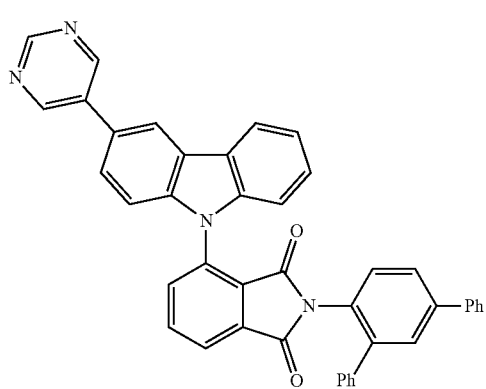
262
-continued
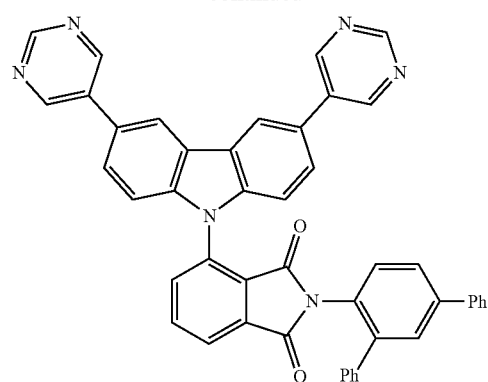
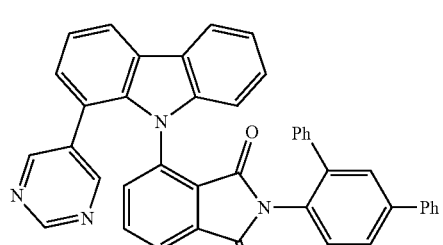
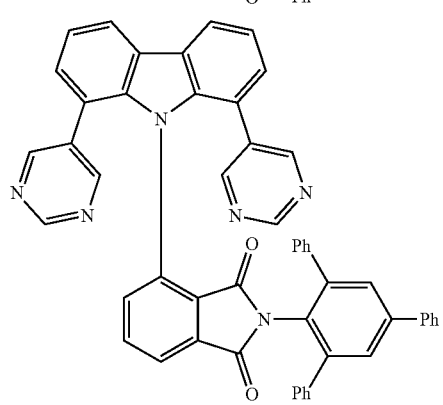
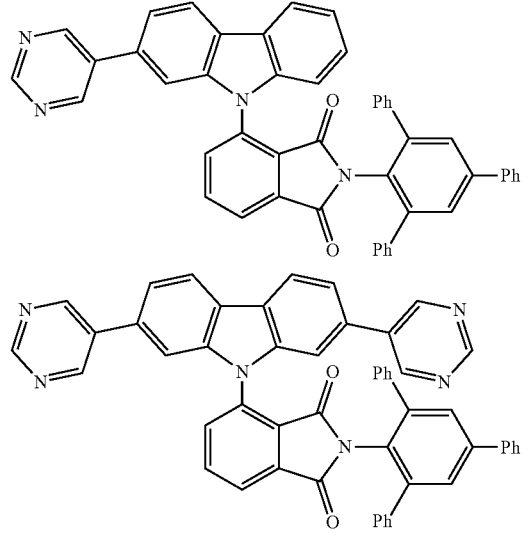

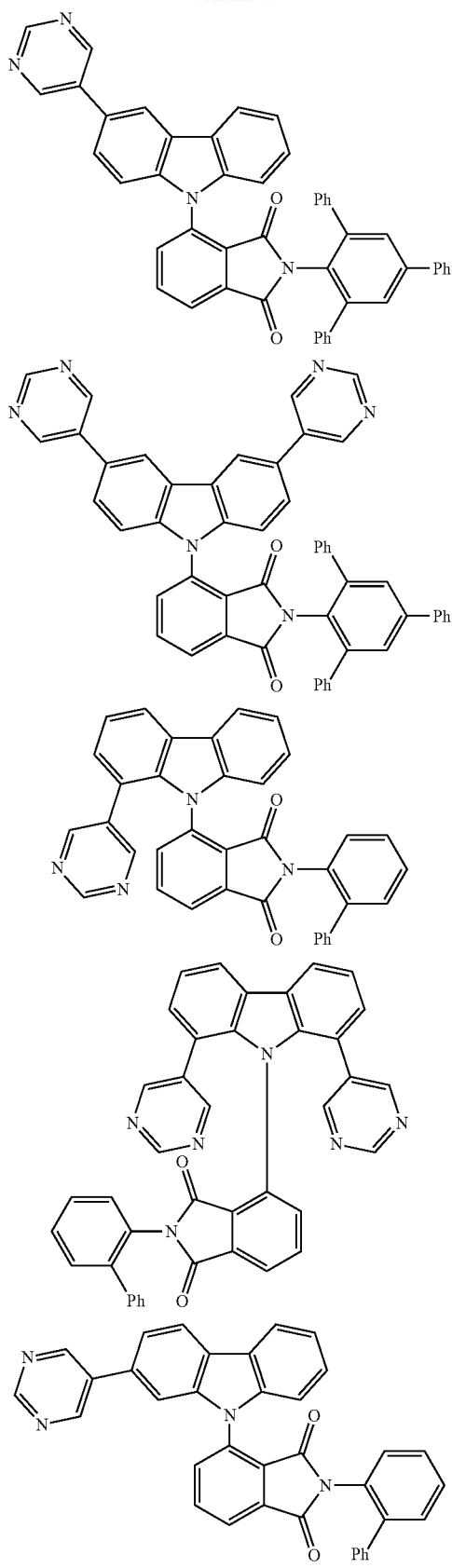
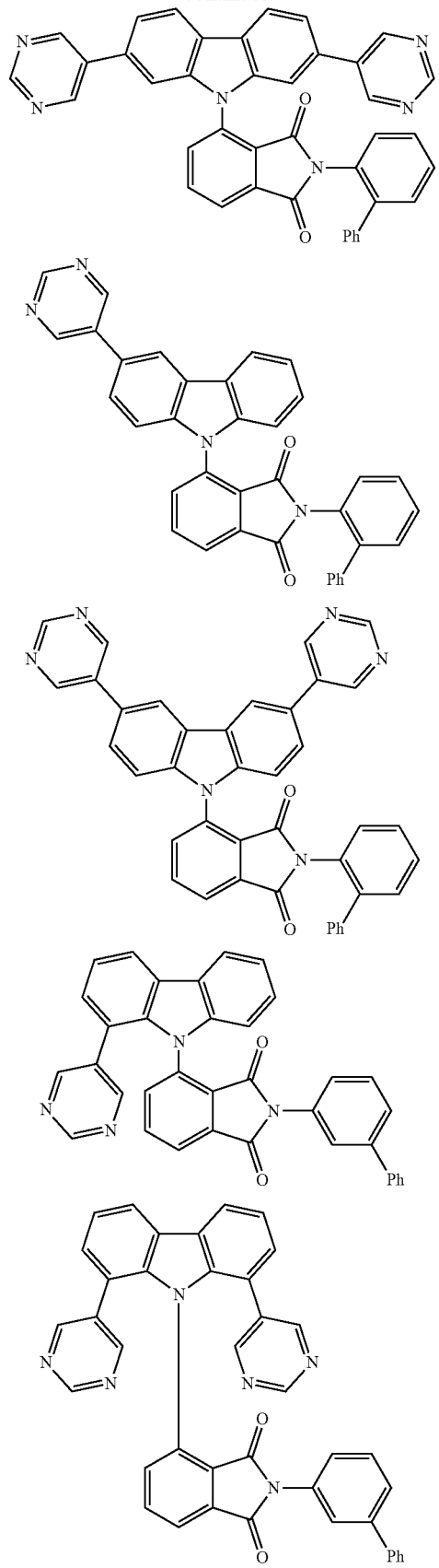

-continued
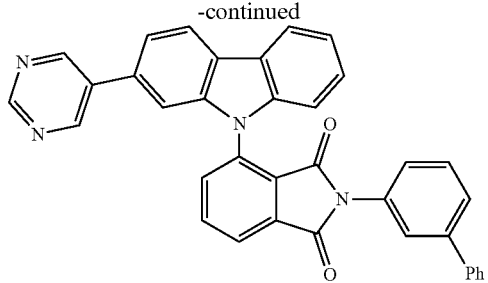
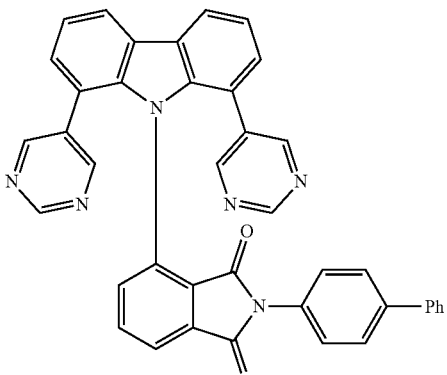
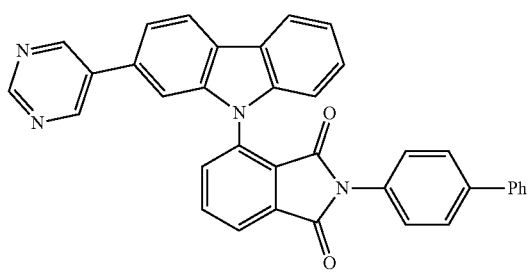
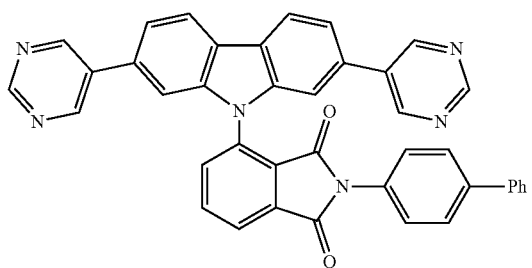
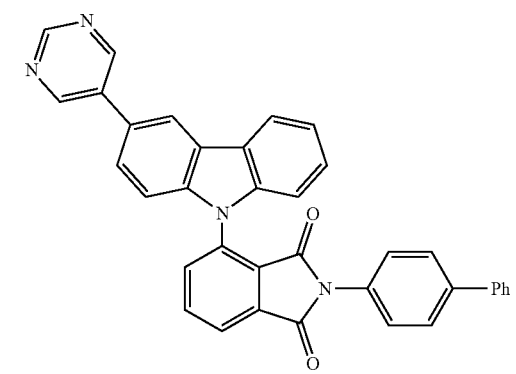
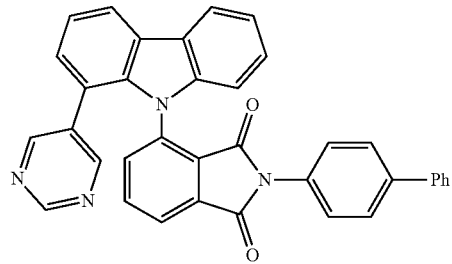
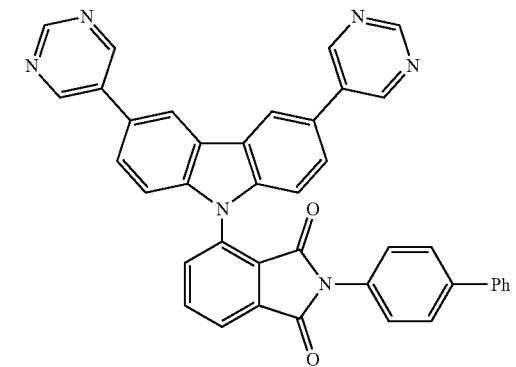

267
-continued
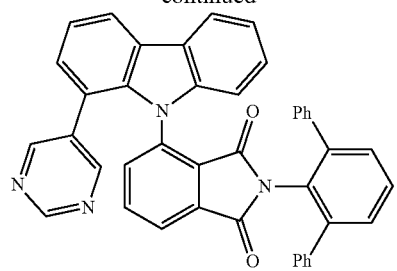
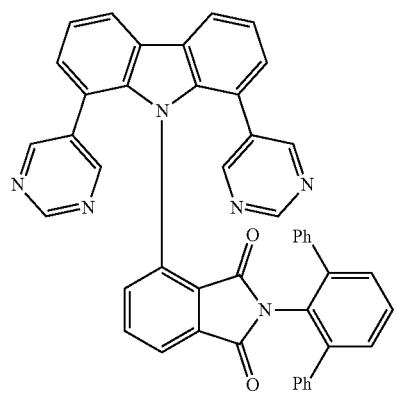
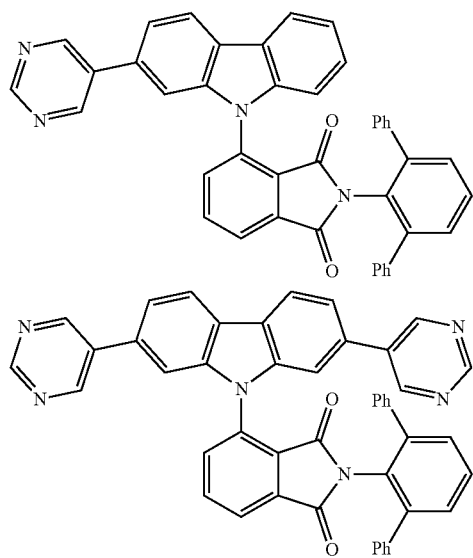
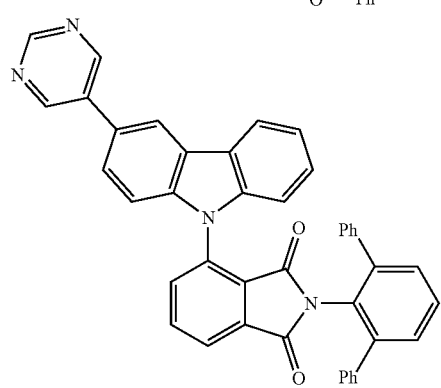
268
-continued
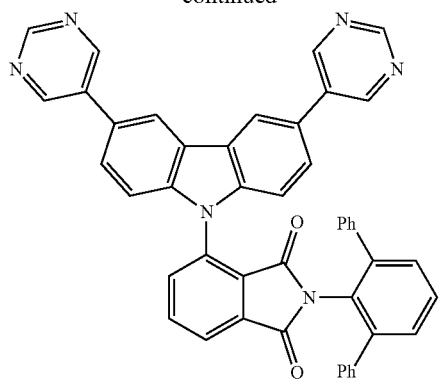
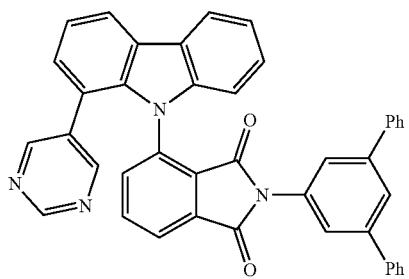
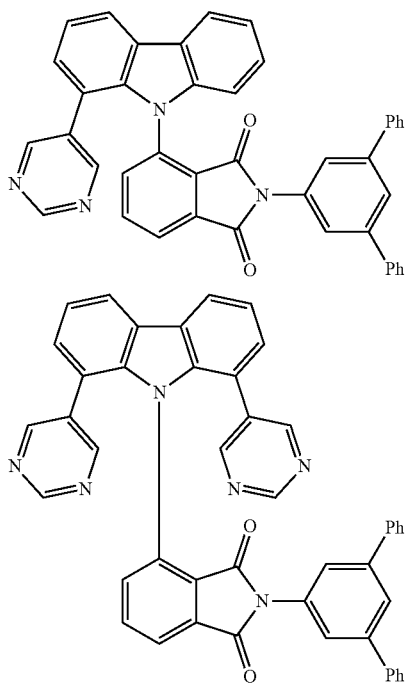
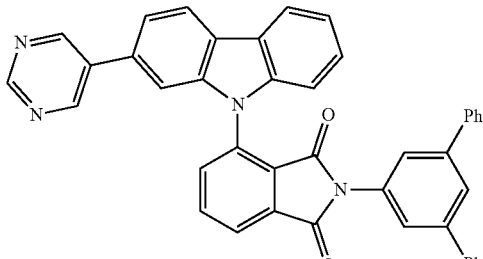
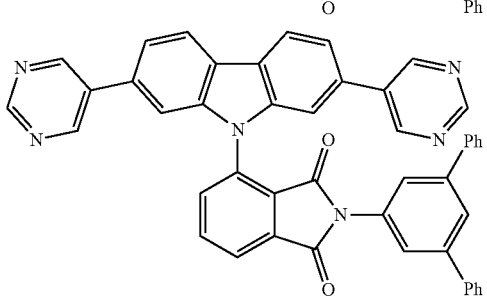

269
-continued
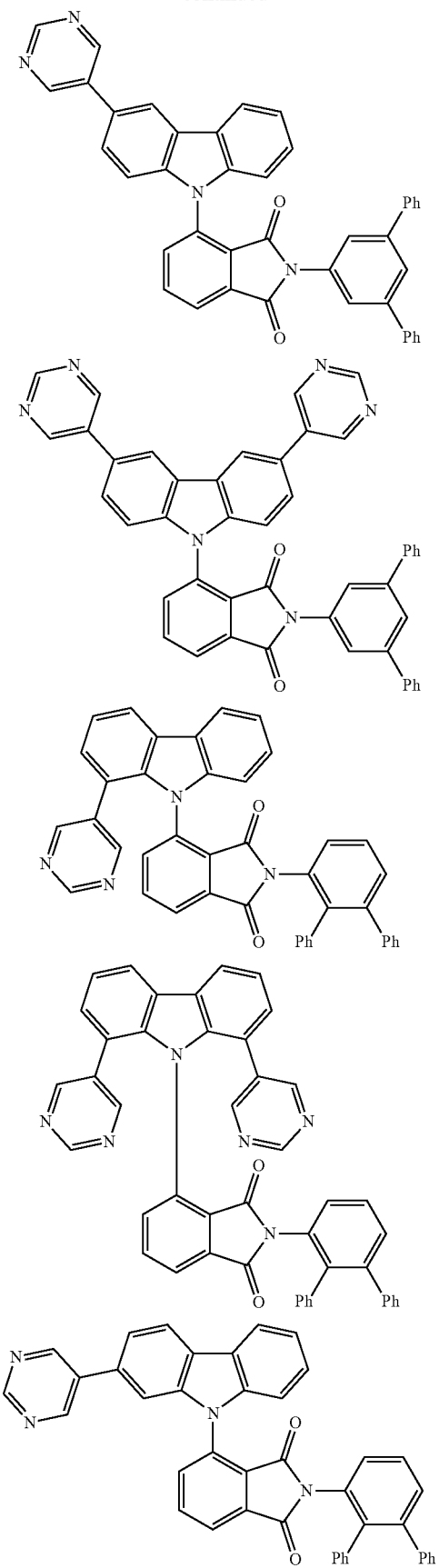
270
-continued
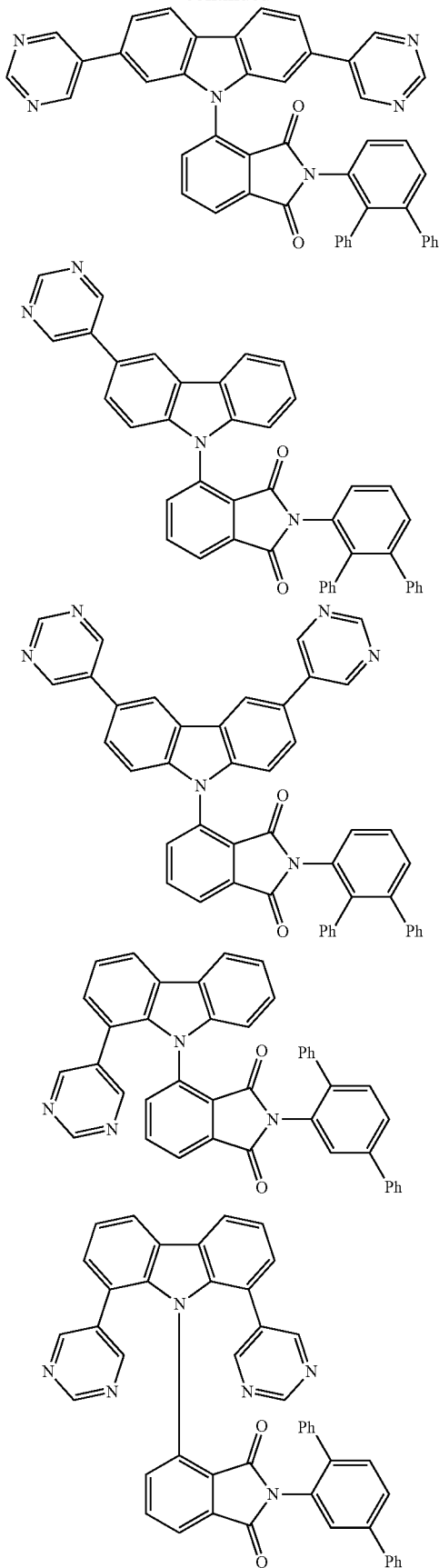

271
-continued
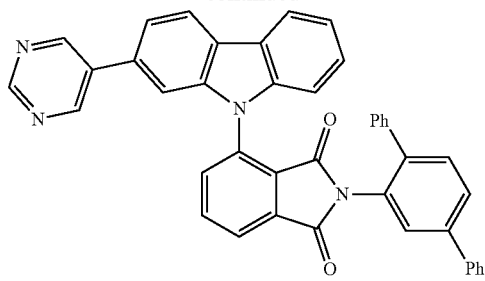
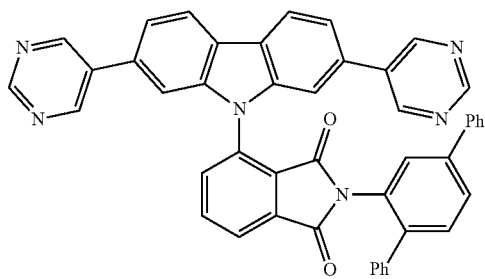
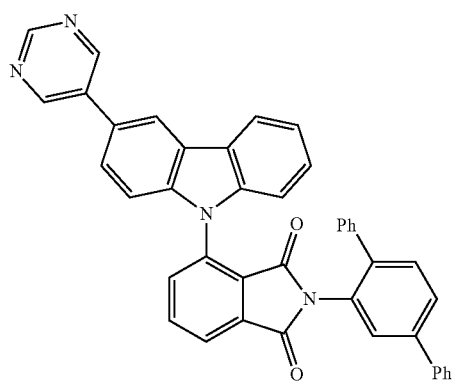
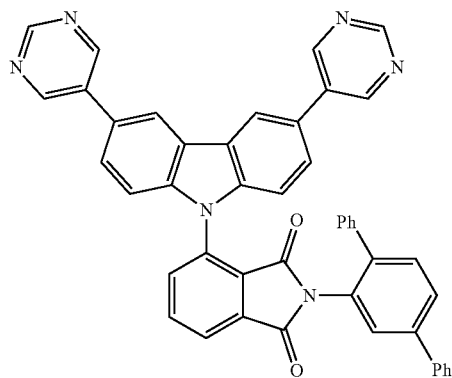
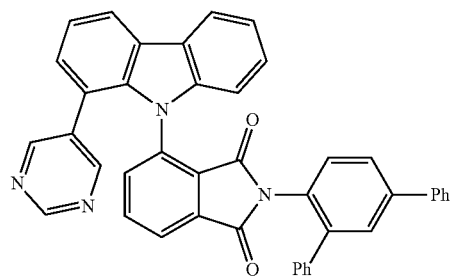
272
-continued
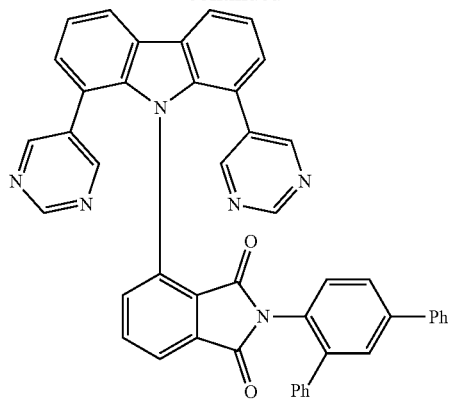
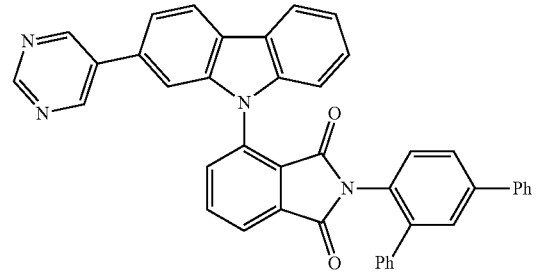
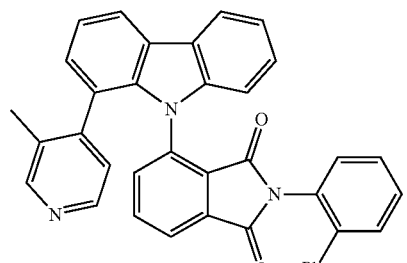
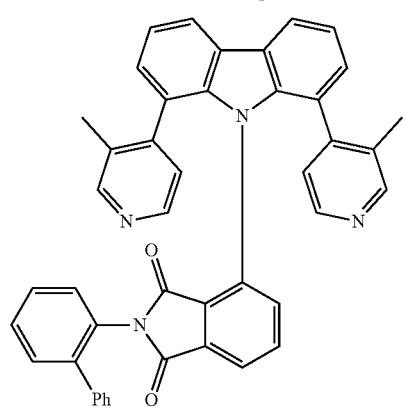
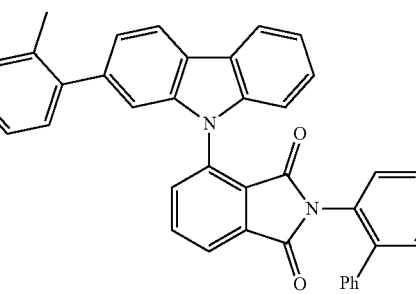

273
-continued
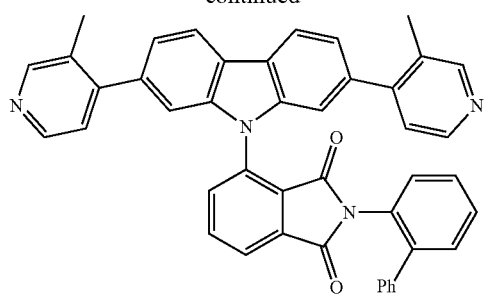
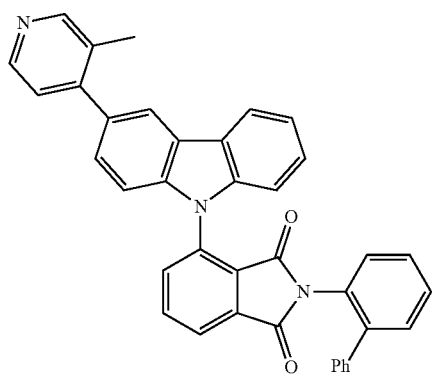
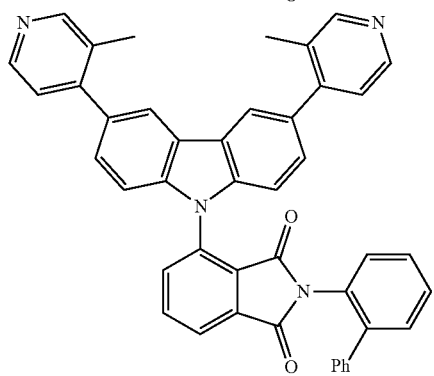
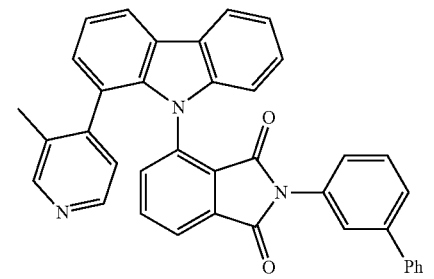
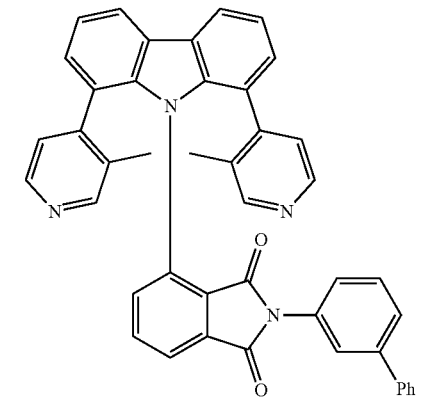
274
-continued
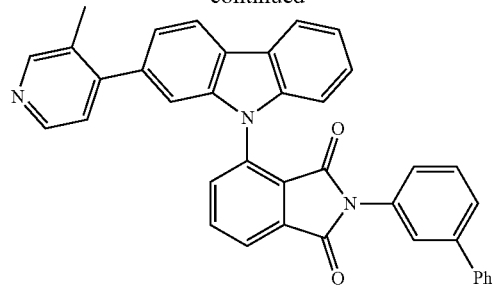
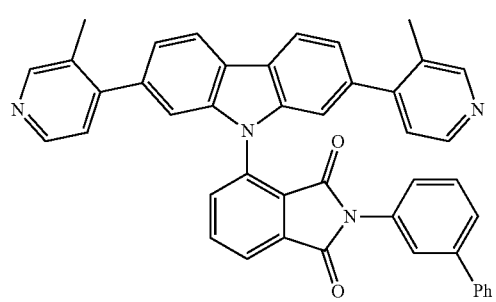
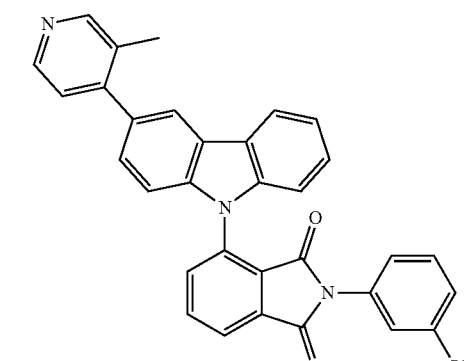
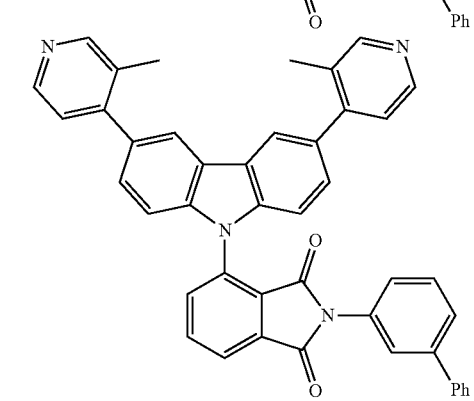
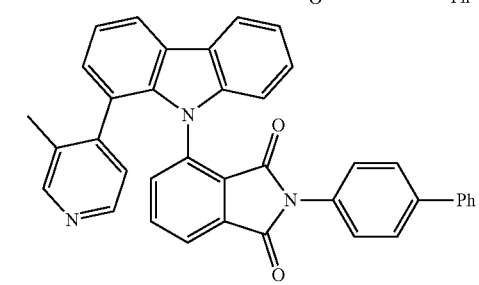

275
-continued
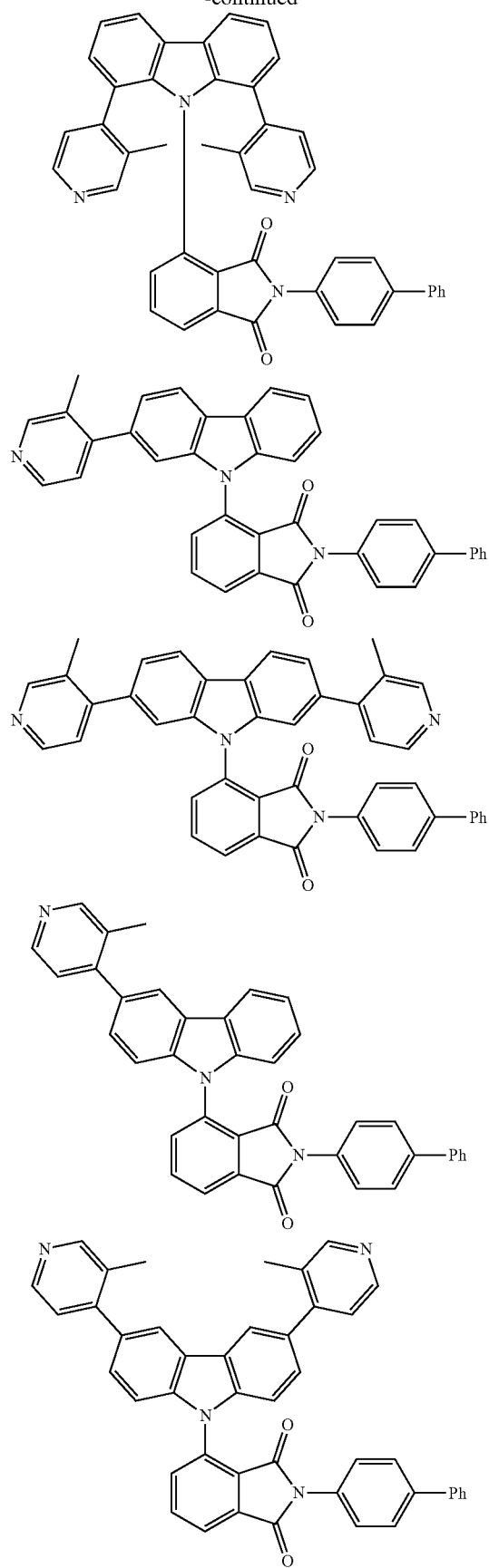
276
-continued
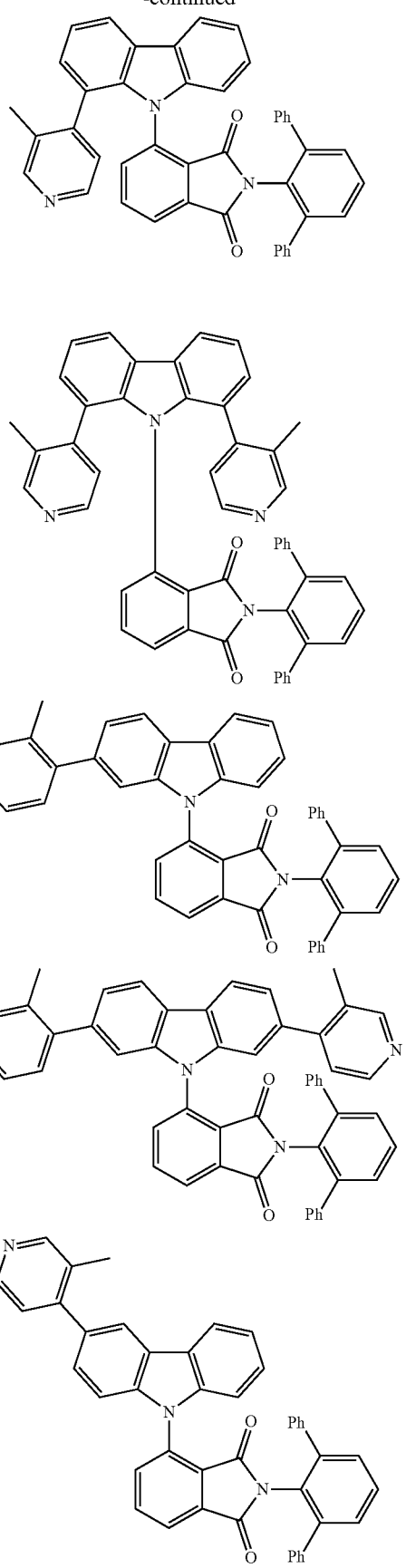

277
-continued
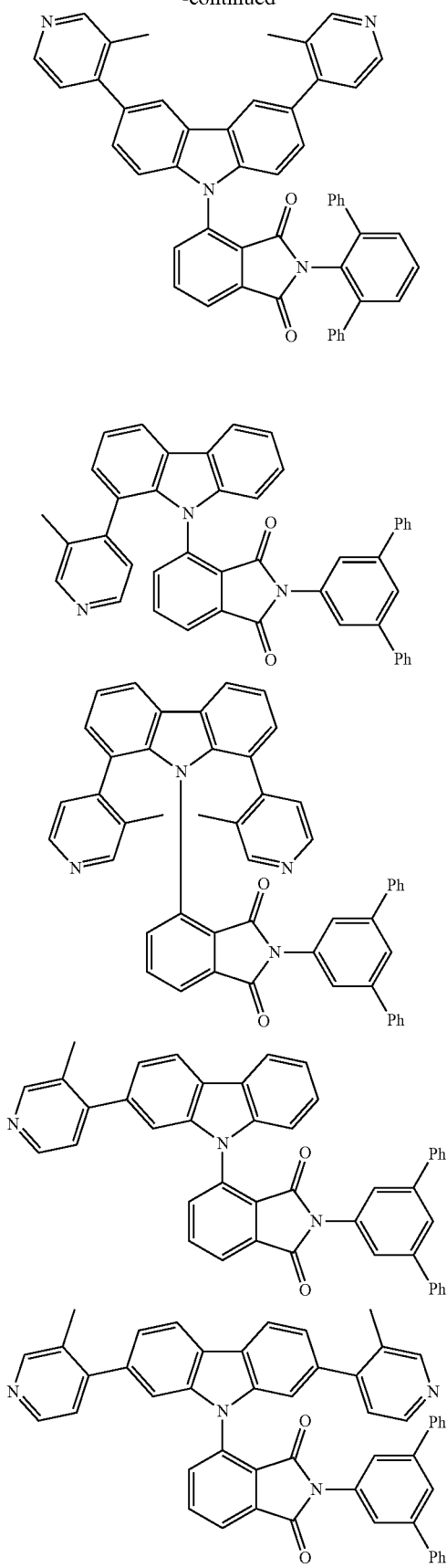
278
-continued
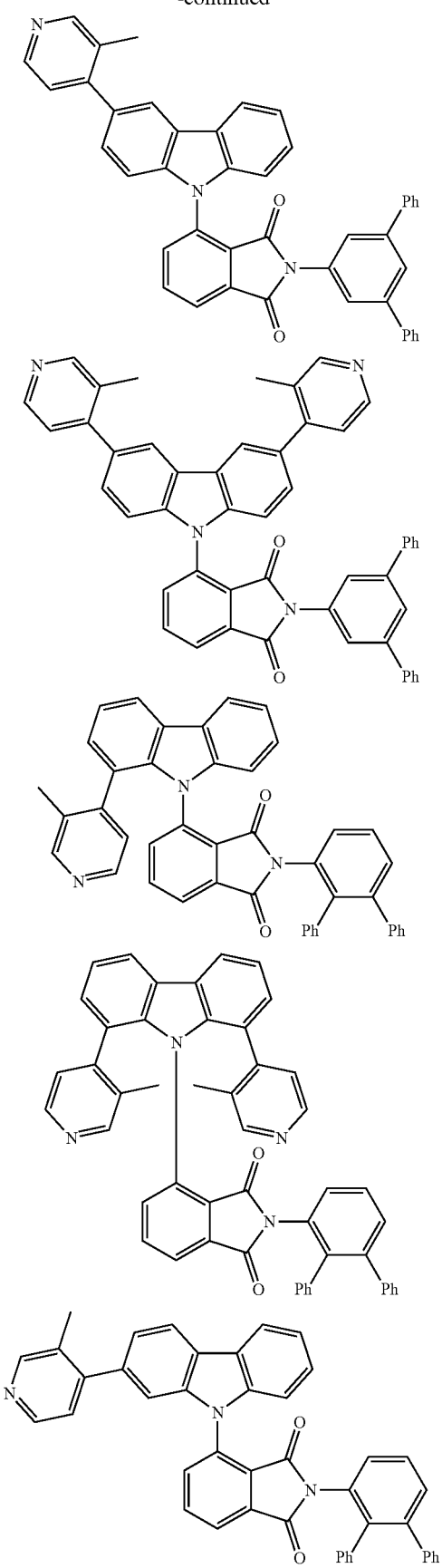

-continued
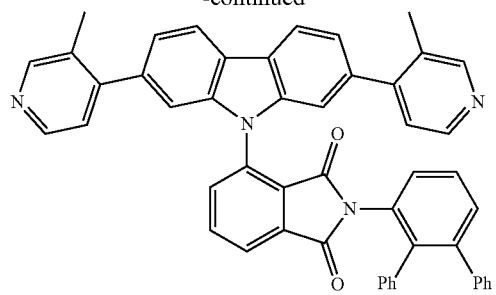
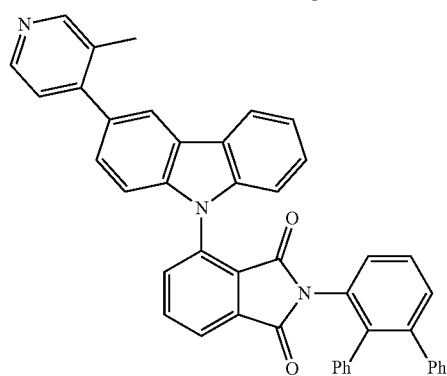
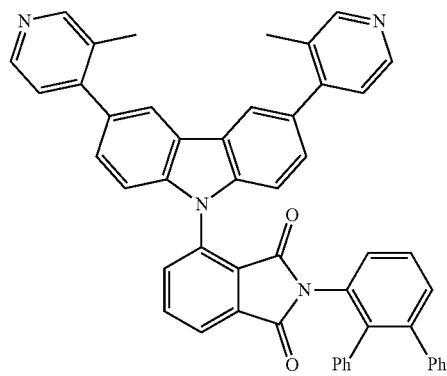
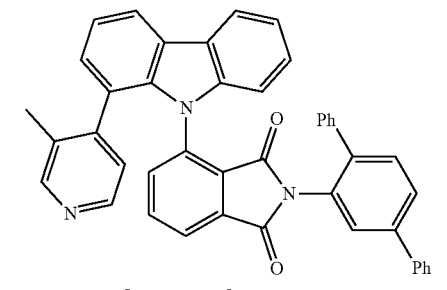
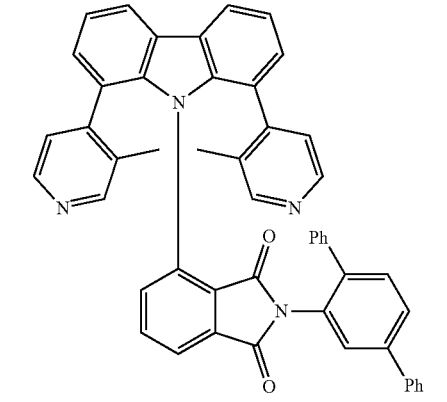
-continued
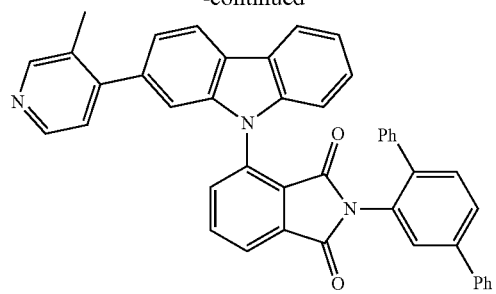
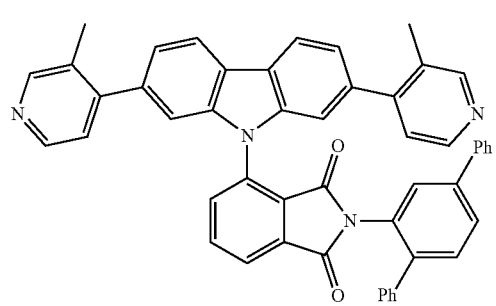
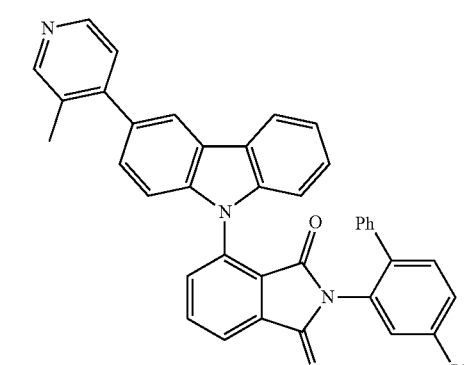
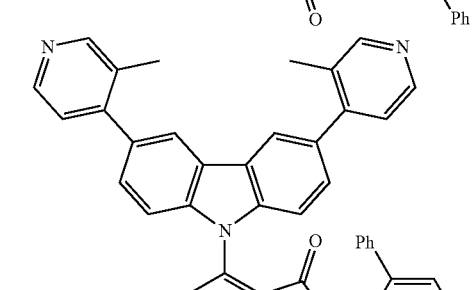
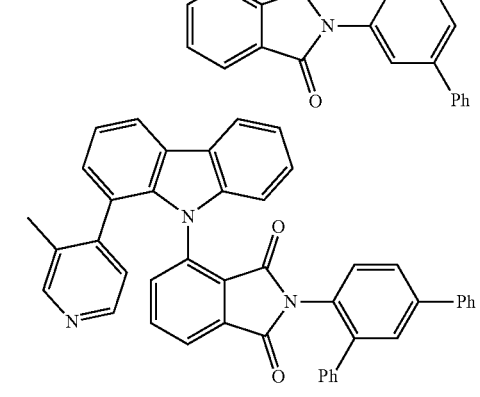

-continued
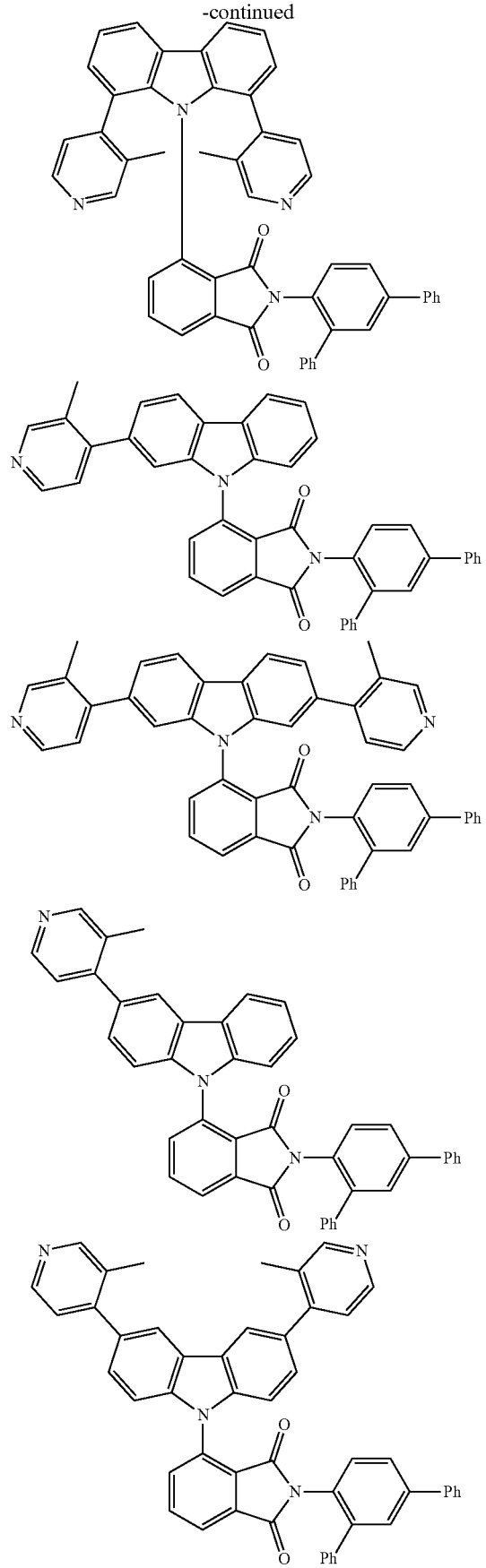
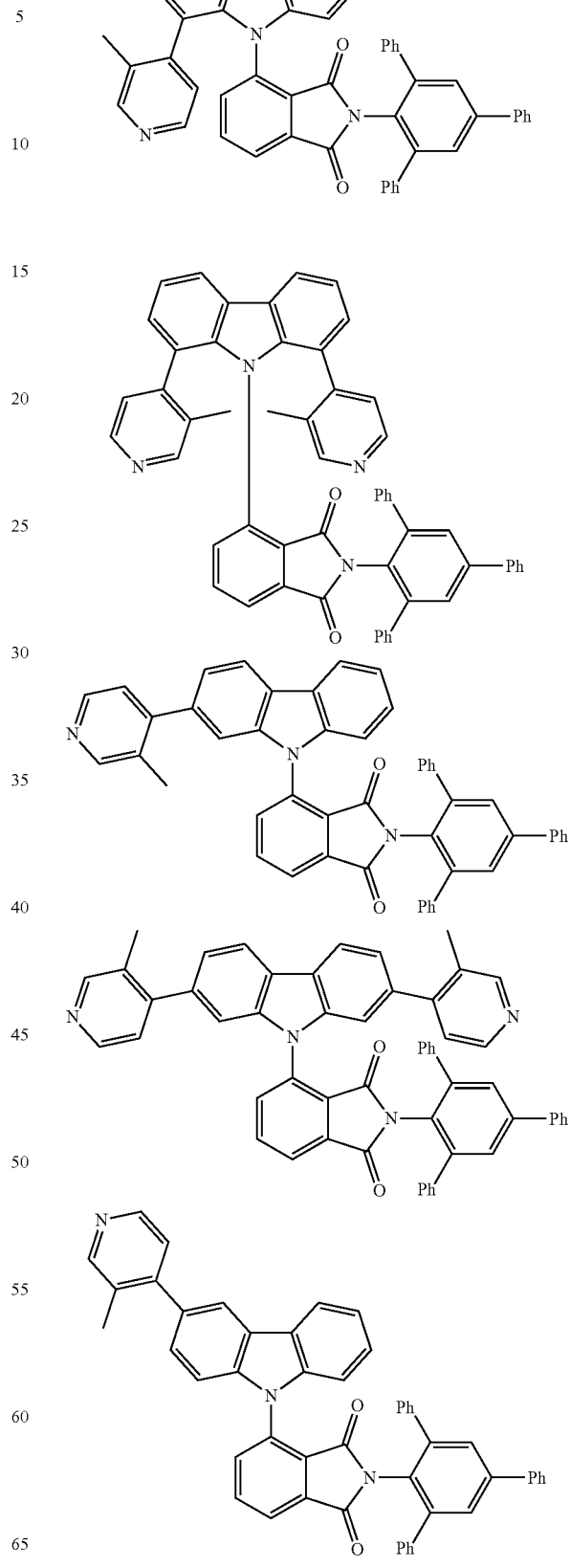

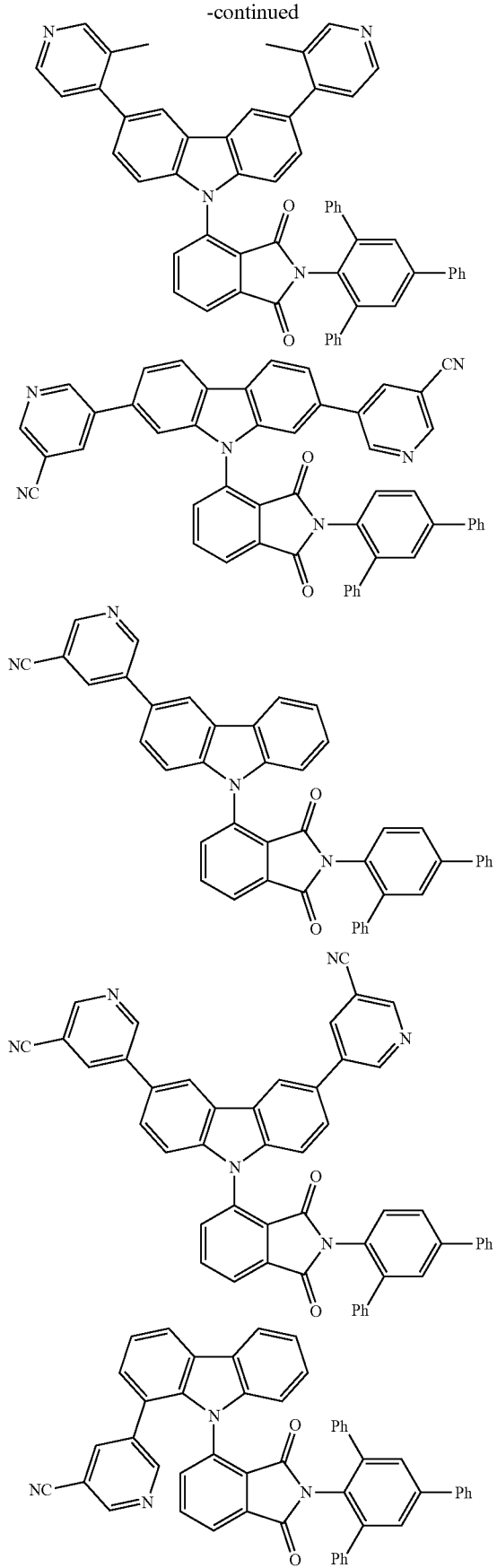
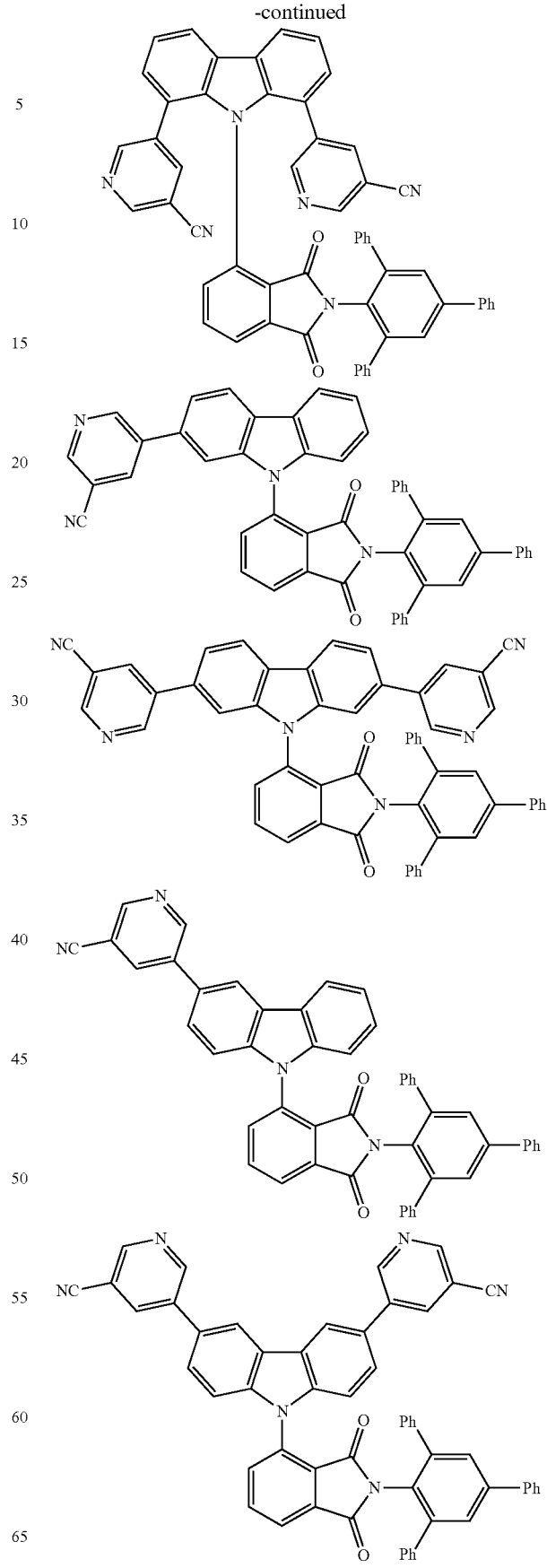

285
-continued
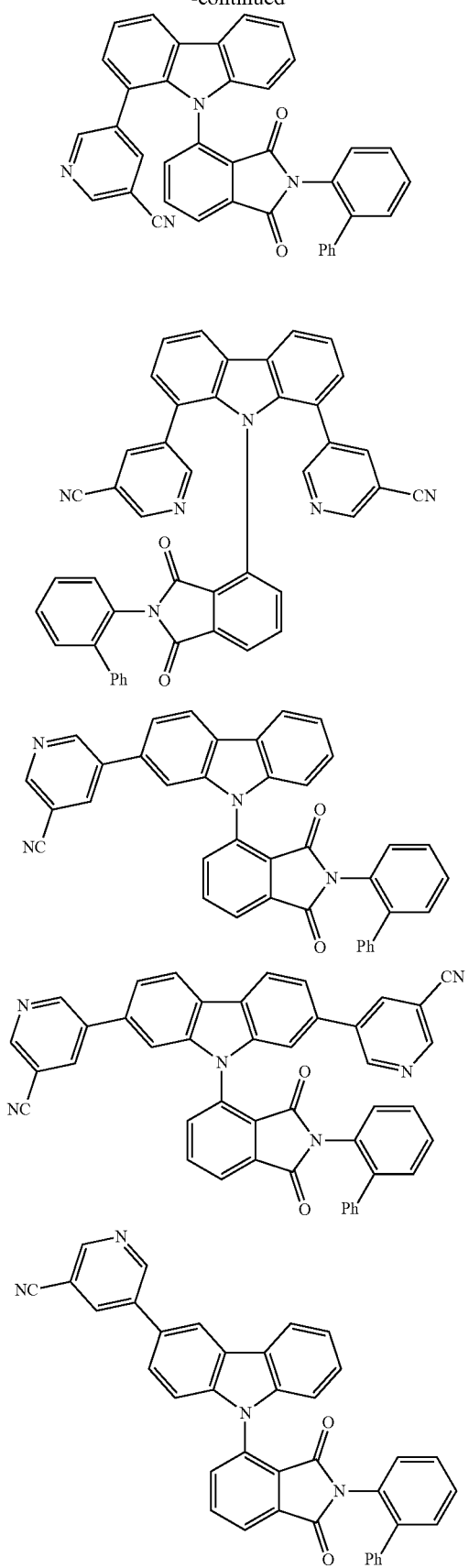
286
-continued
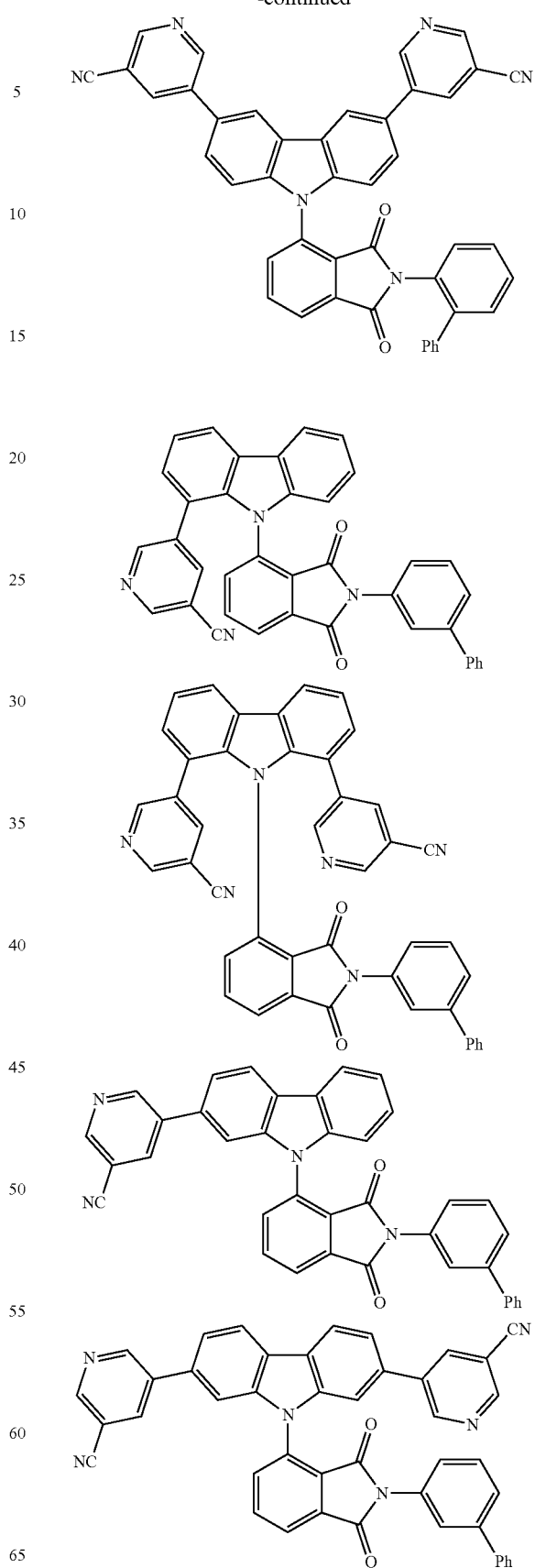

287
-continued
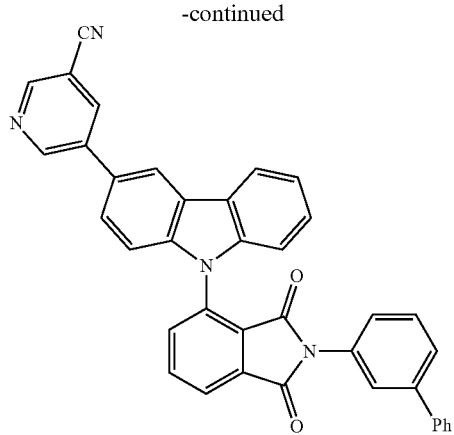
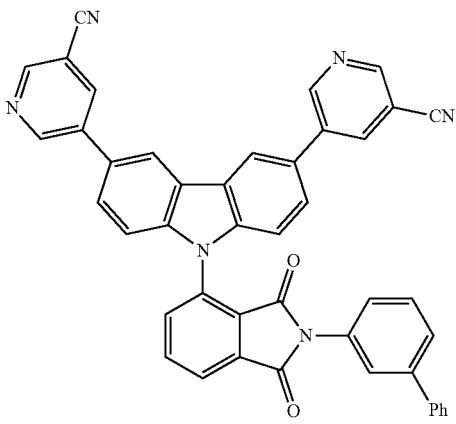
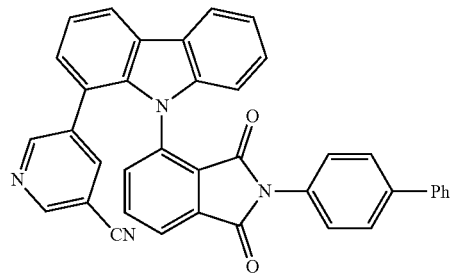
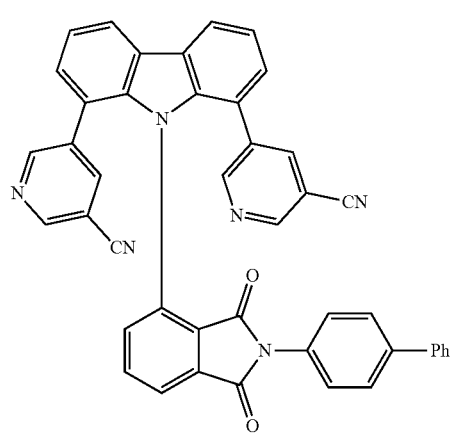
288
-continued
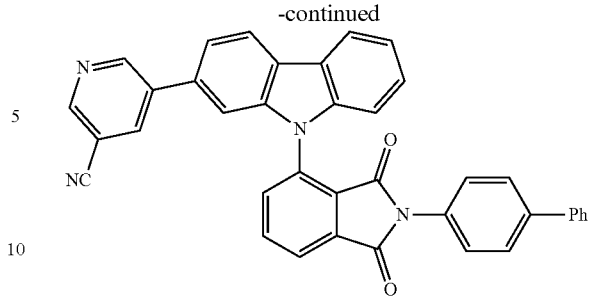
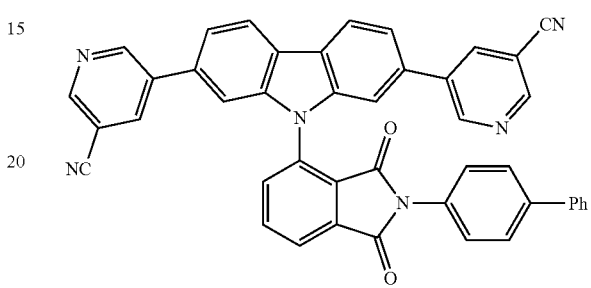
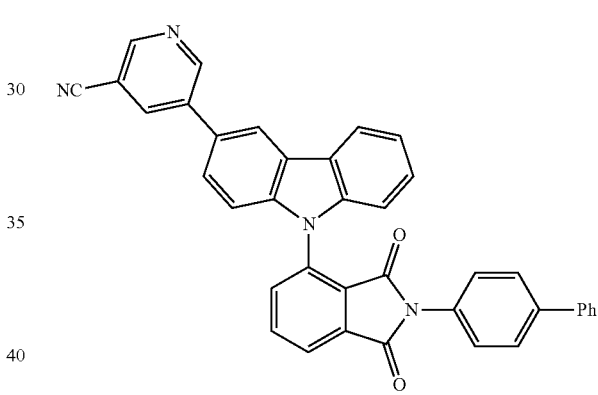
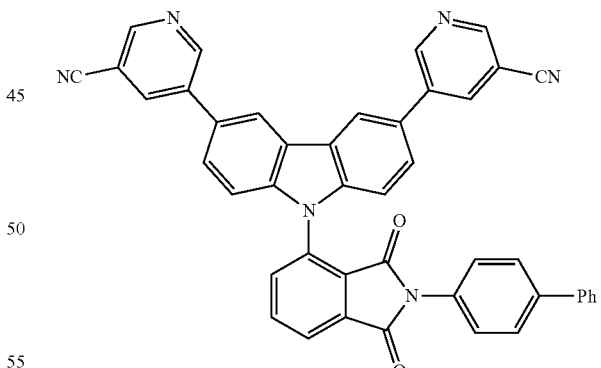
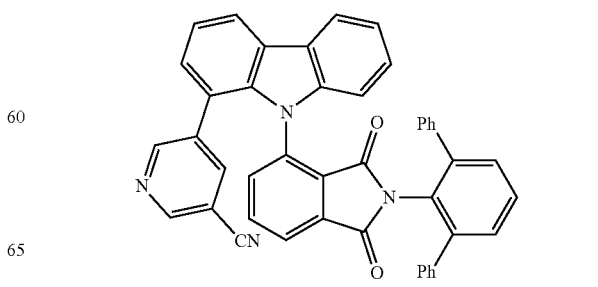

289
-continued
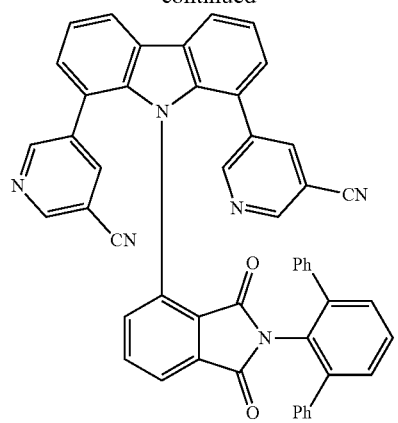
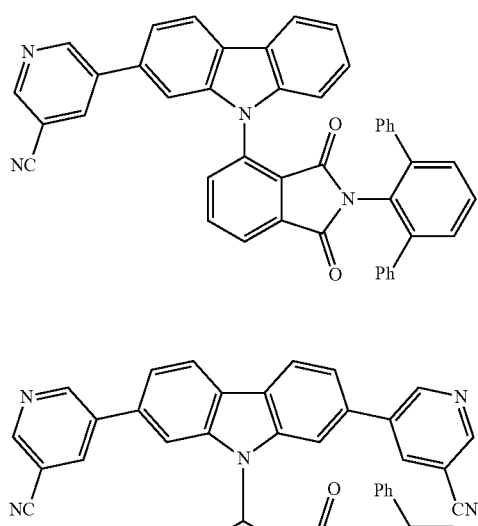
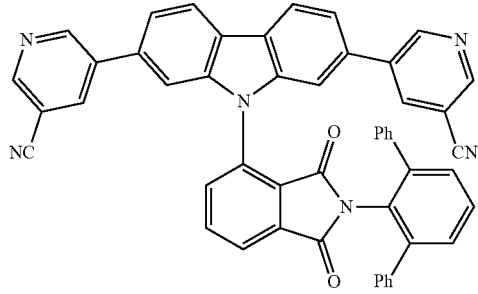
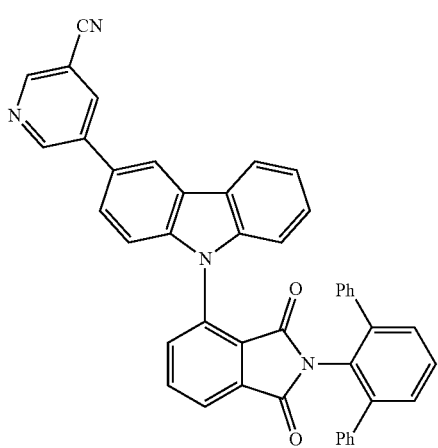
290
-continued
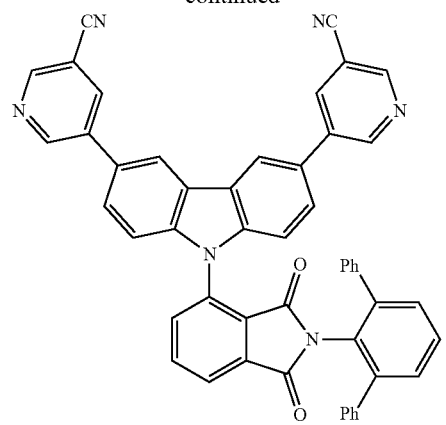
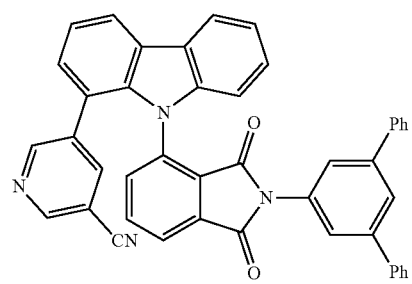
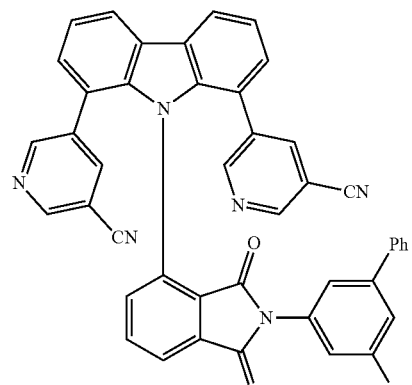
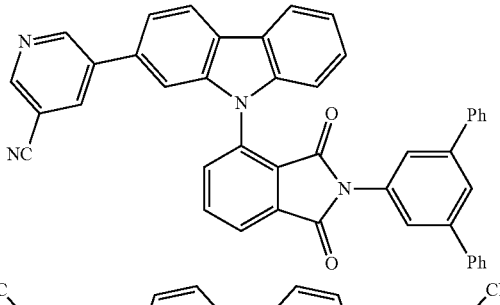
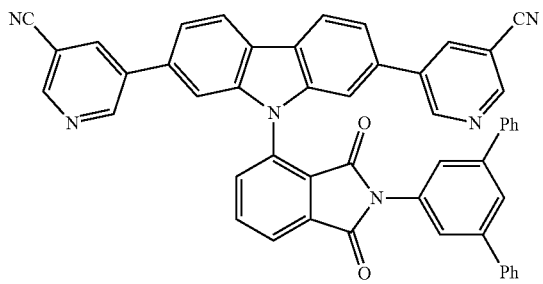

291
-continued
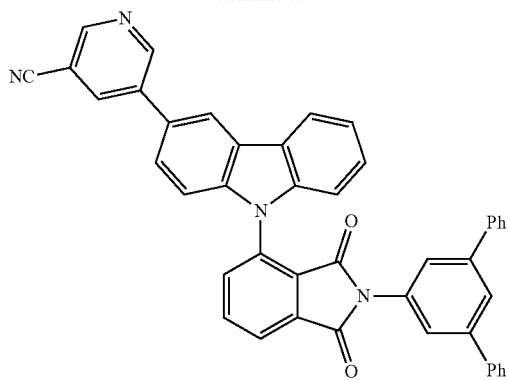
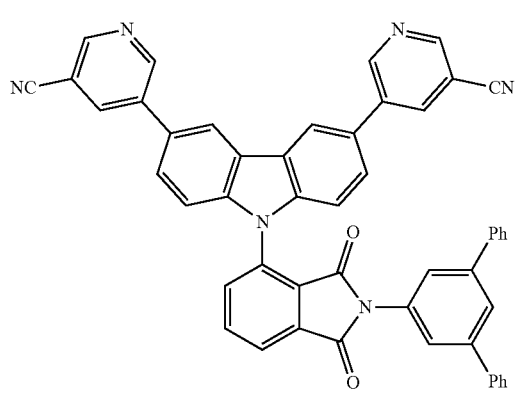
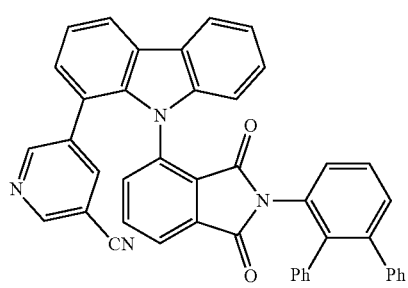
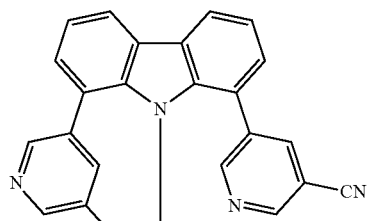
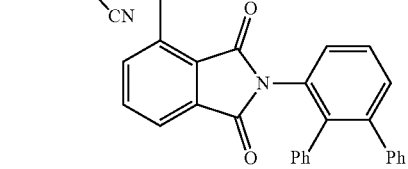
292
-continued
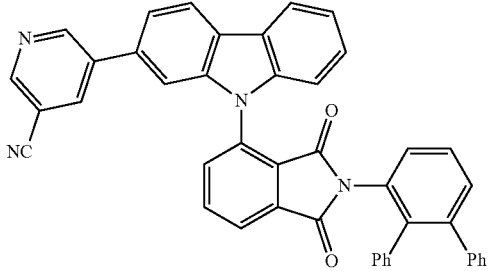
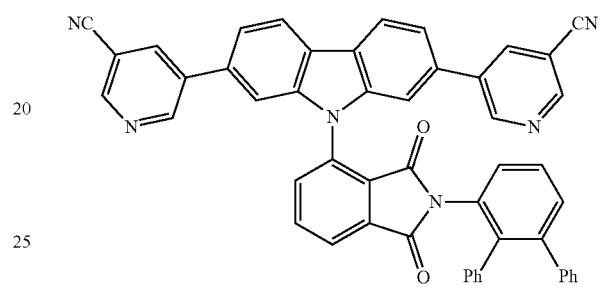
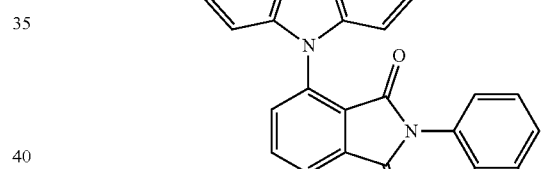
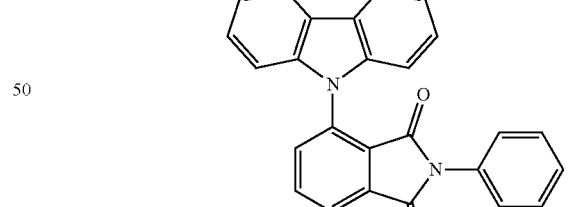
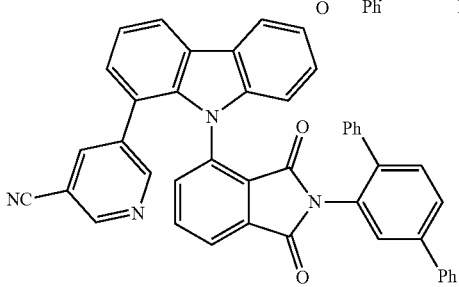

-continued
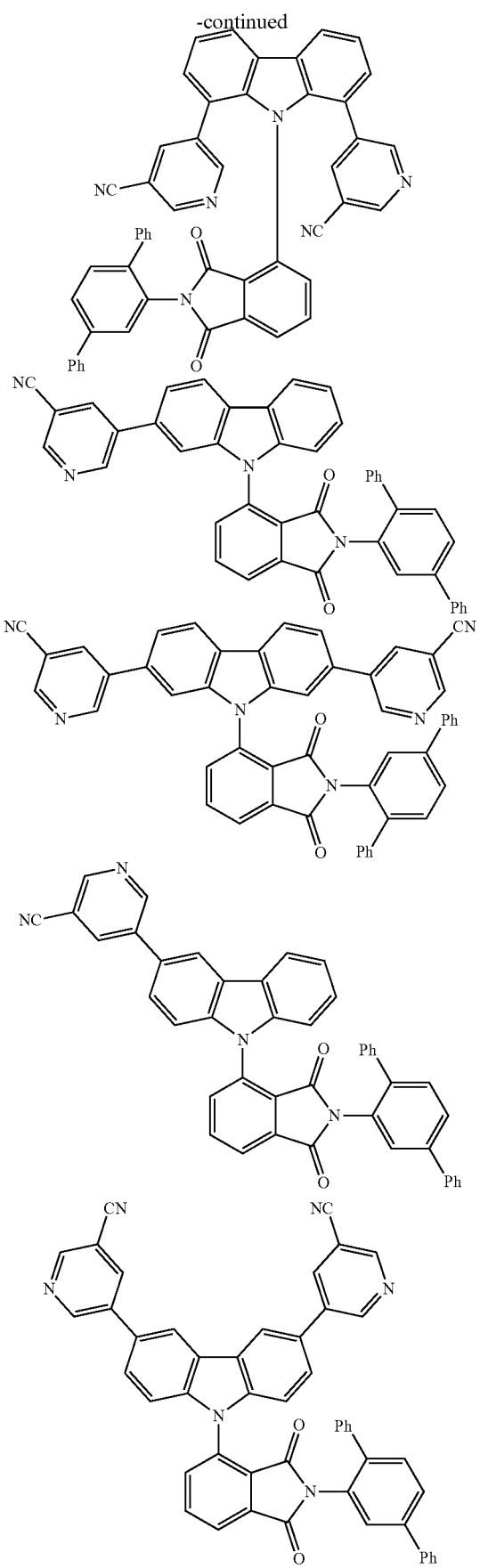
-continued
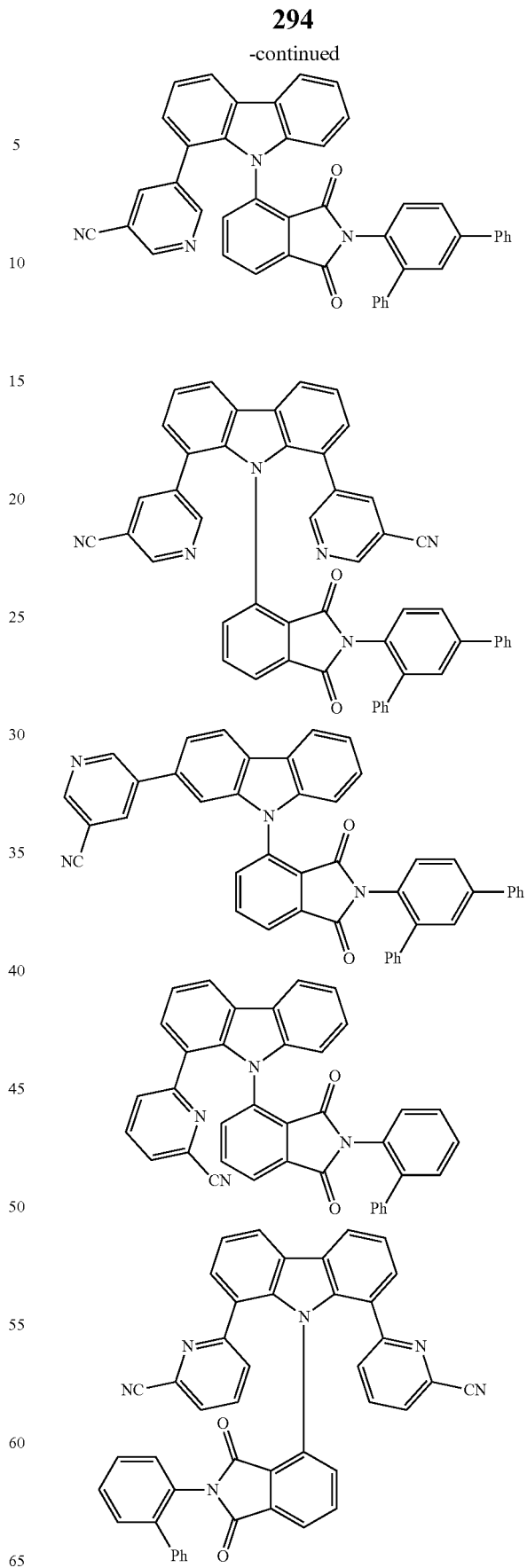

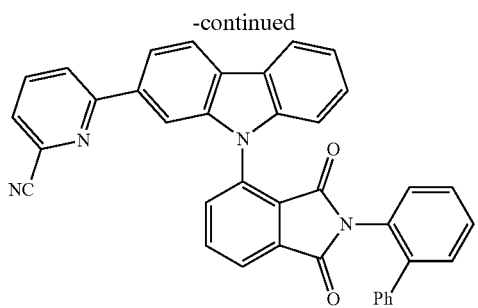
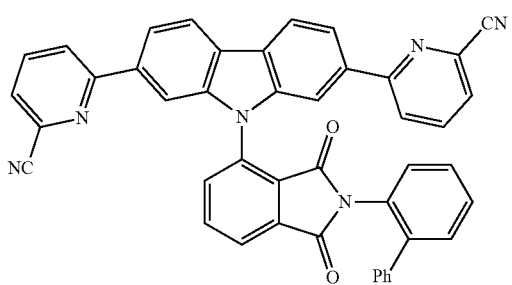
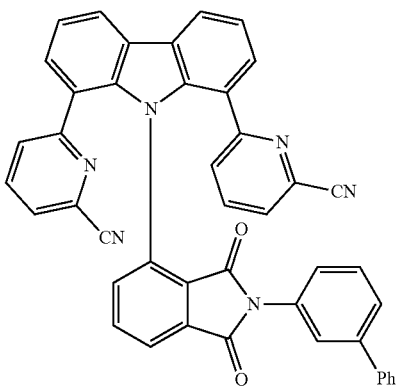
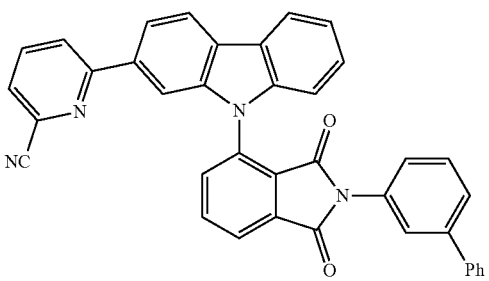
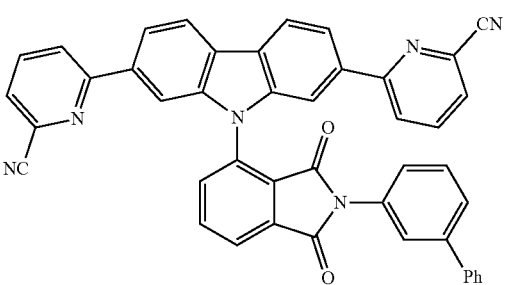
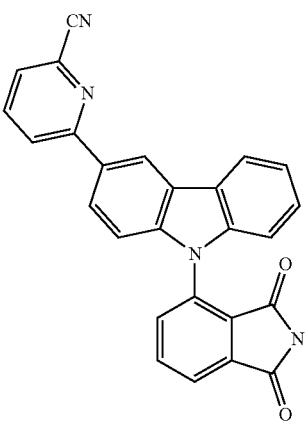

297
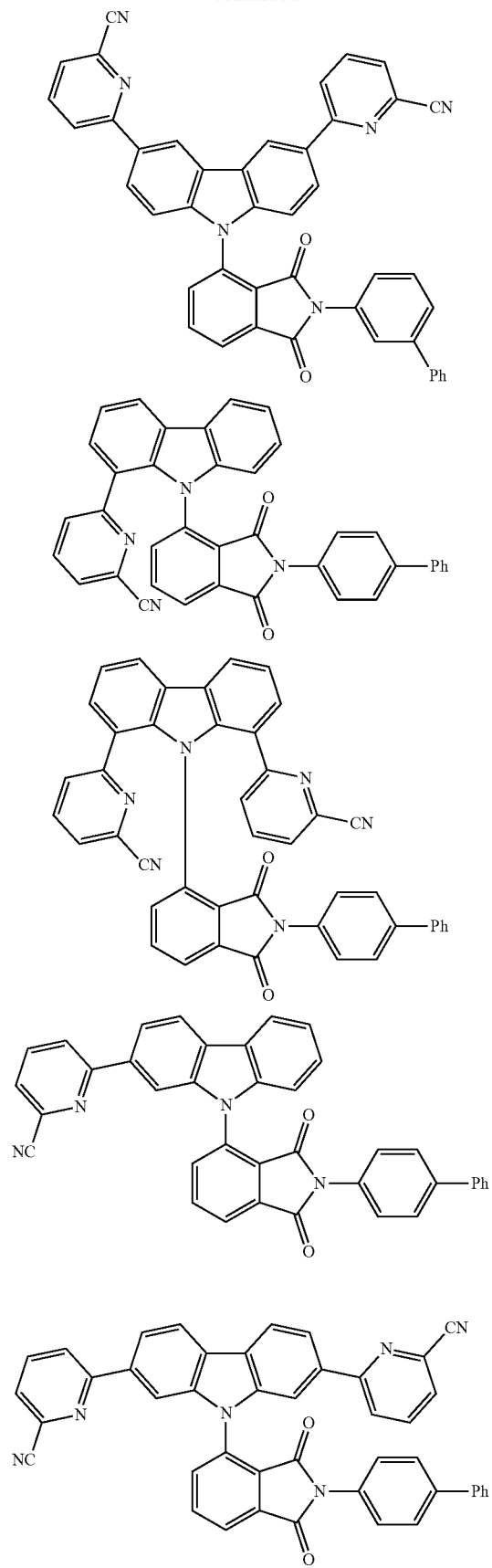
298
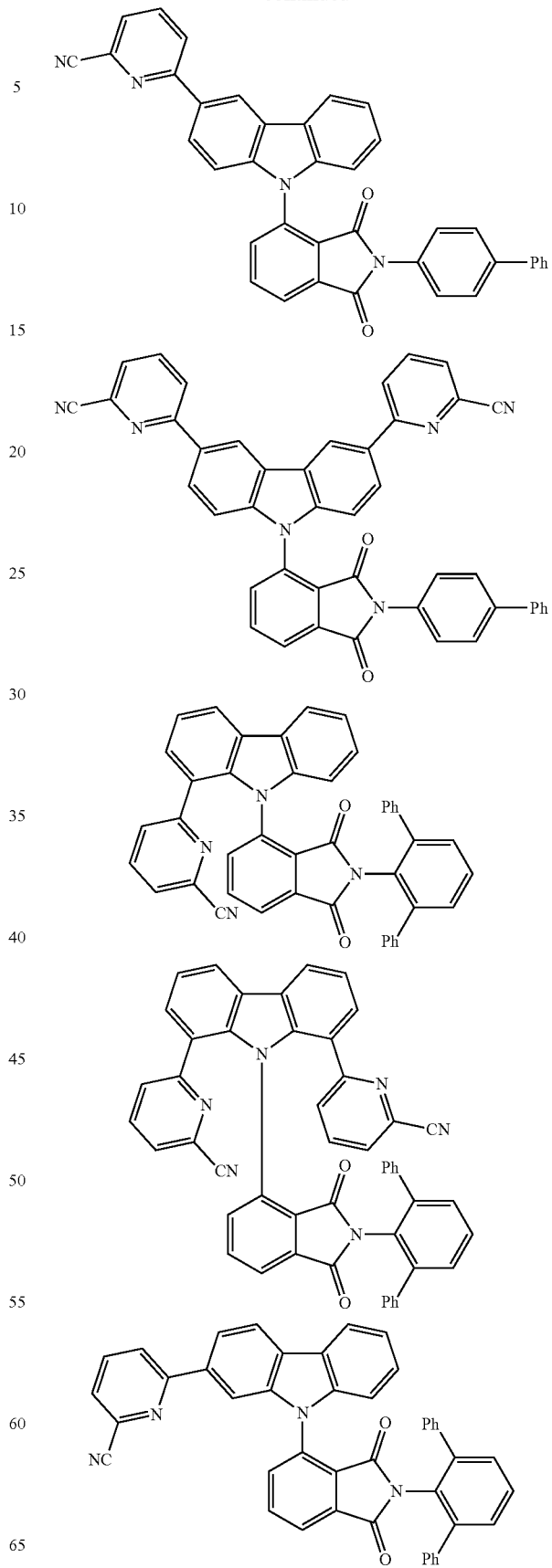

299
-continued
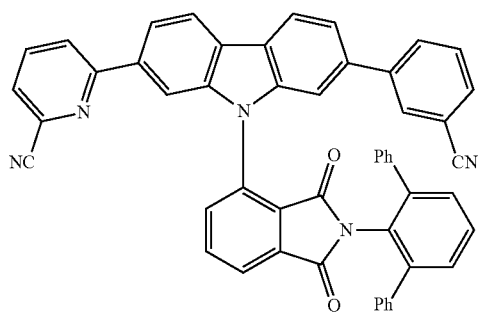
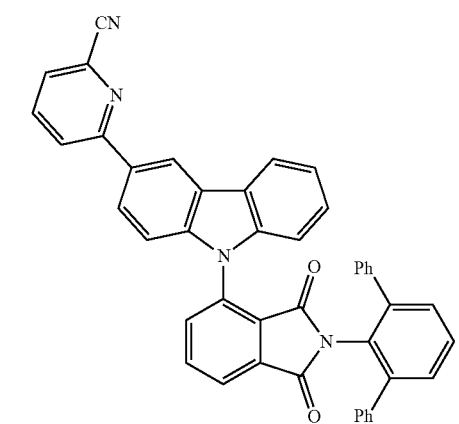
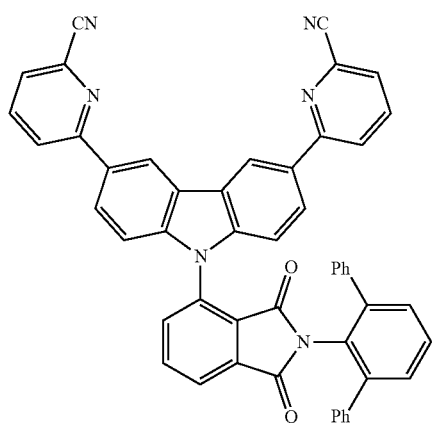
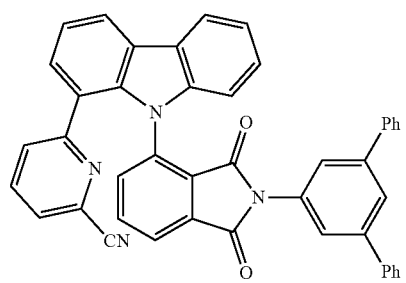
300
-continued
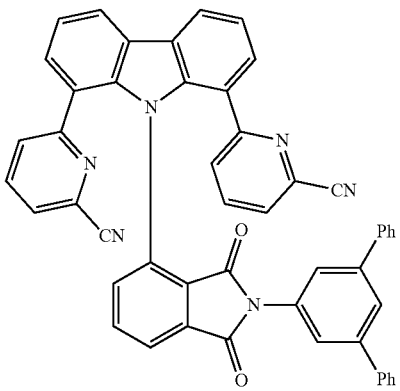
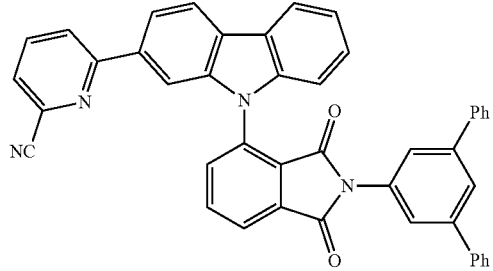
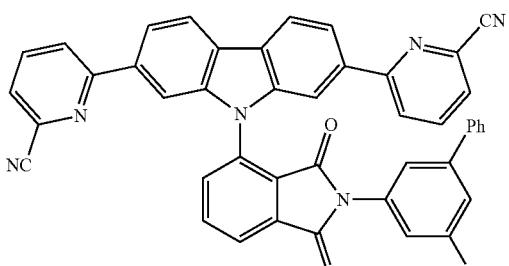
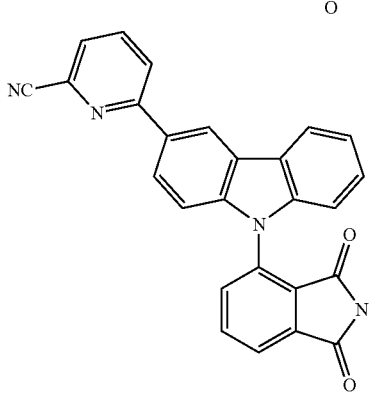
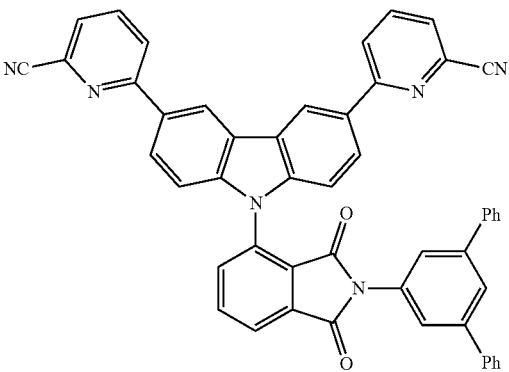

301
-continued
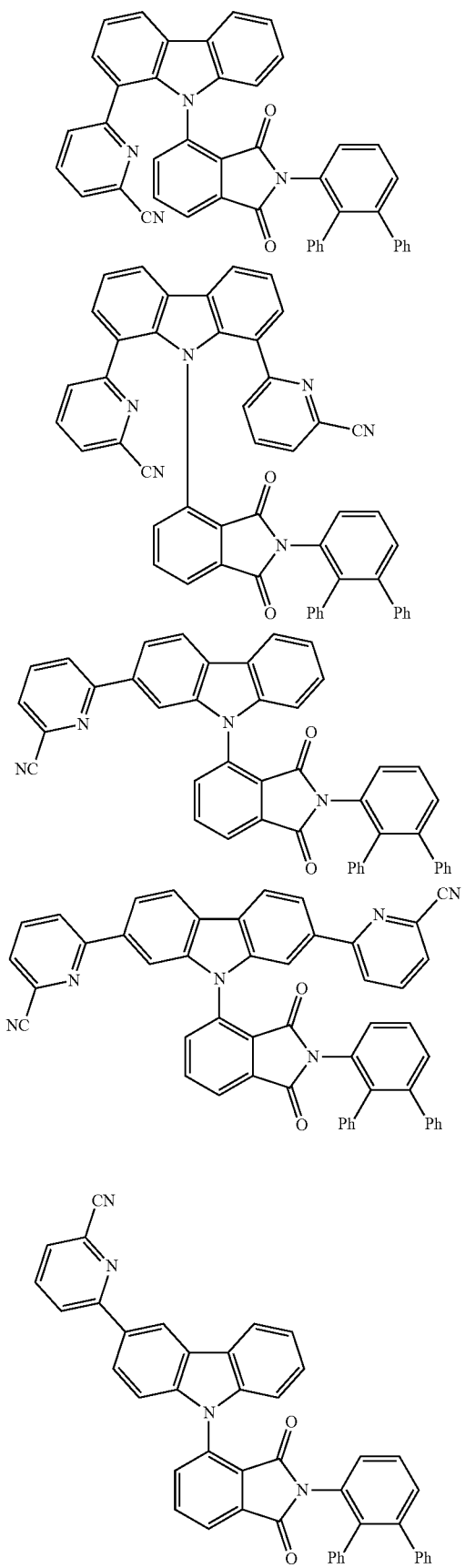
302
-continued
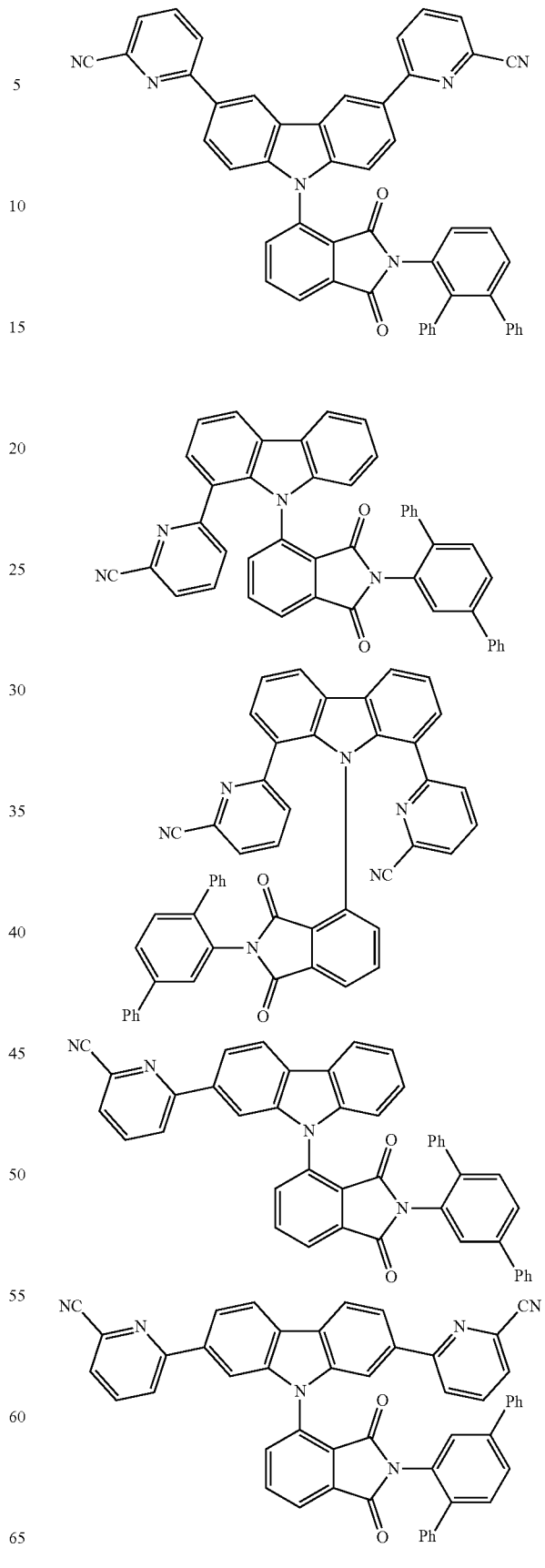

303
-continued
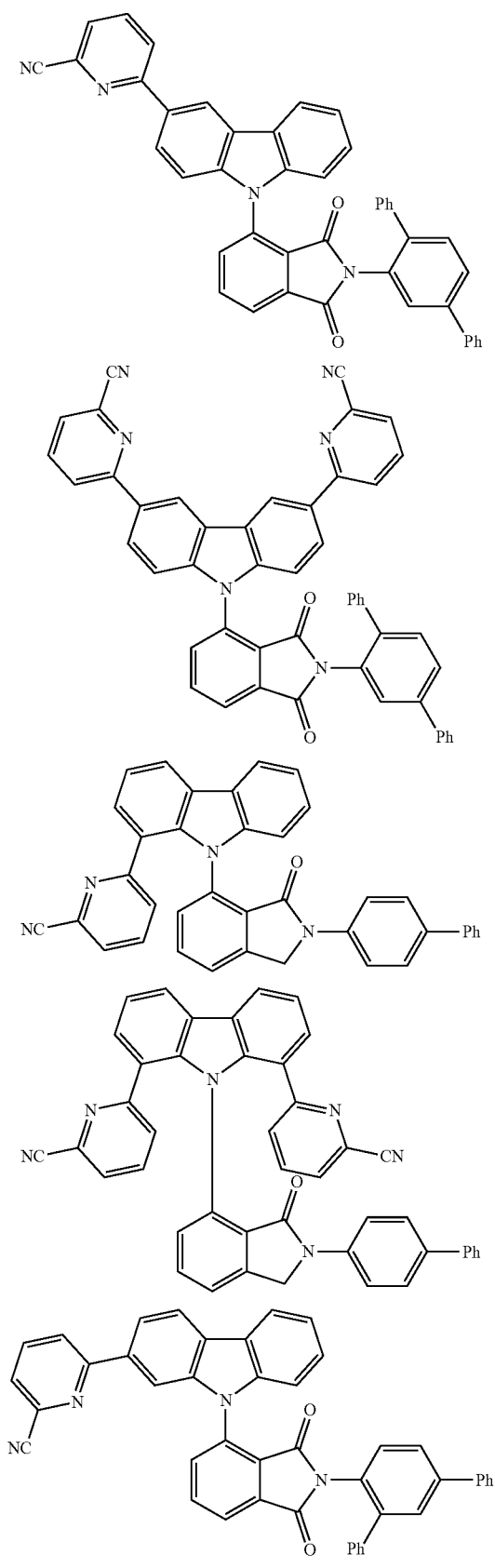
304
-continued
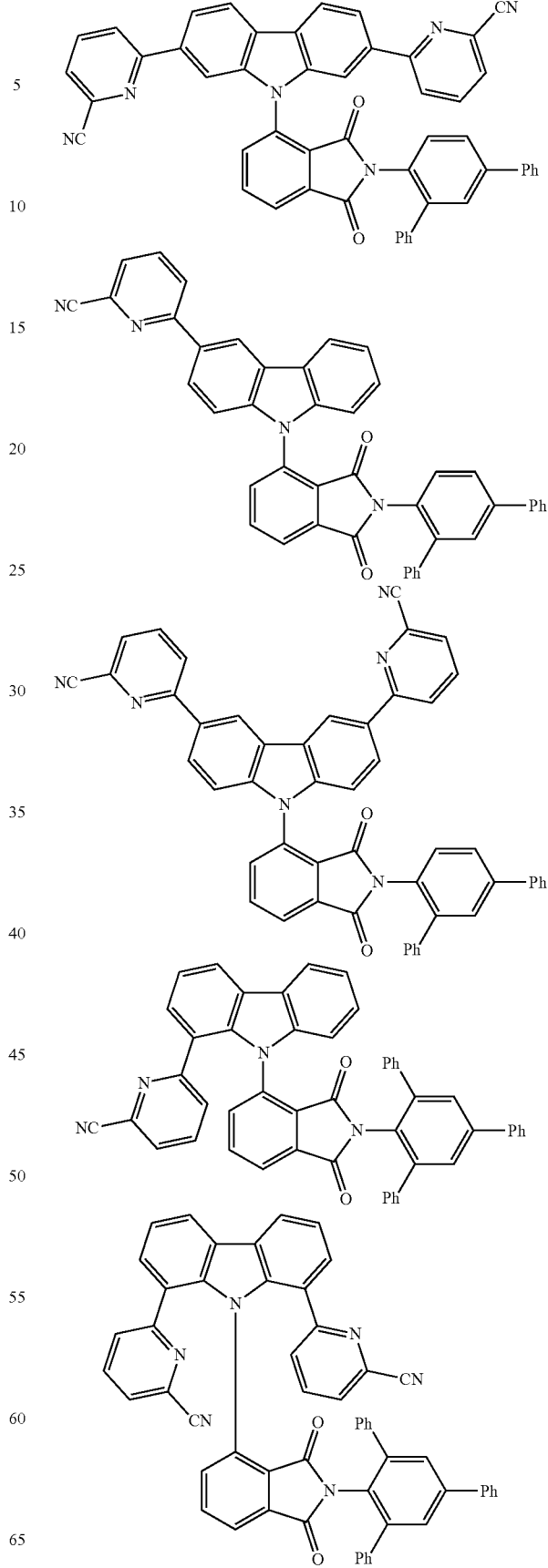

305
-continued
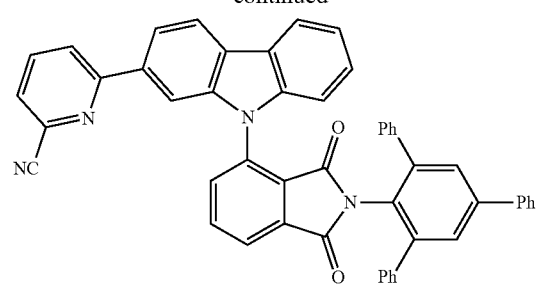
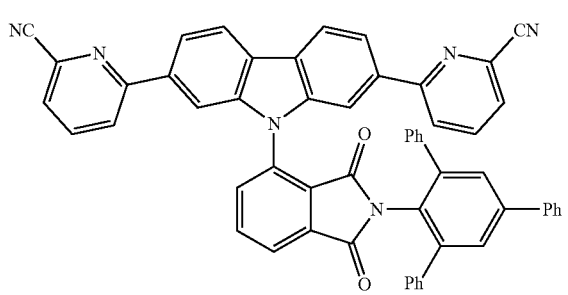
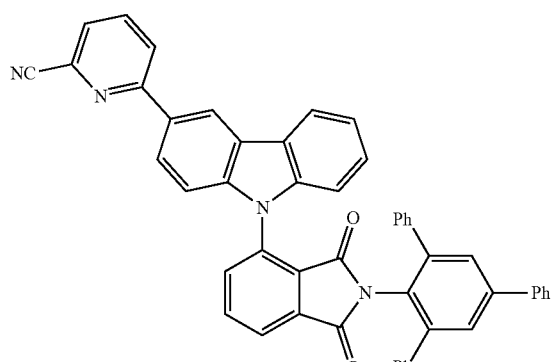
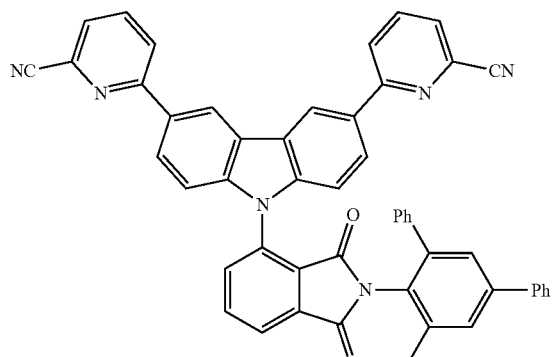
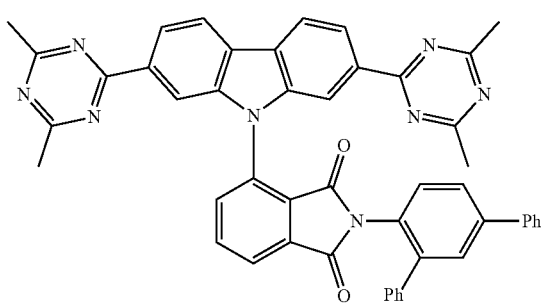
306
-continued
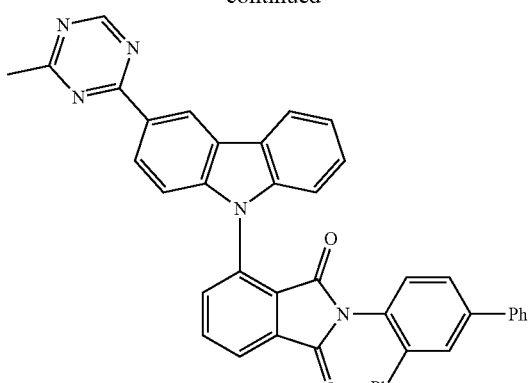
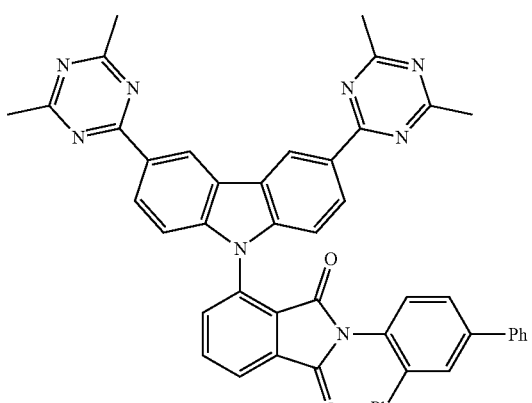
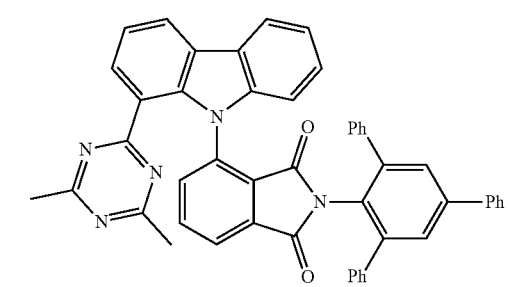
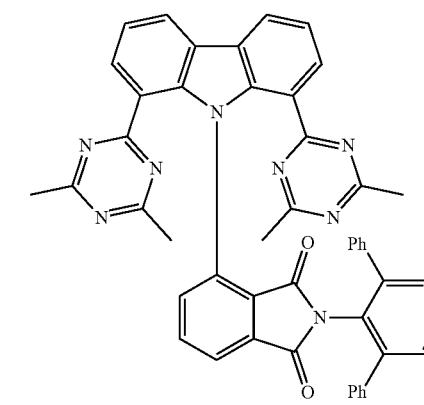

307
-continued
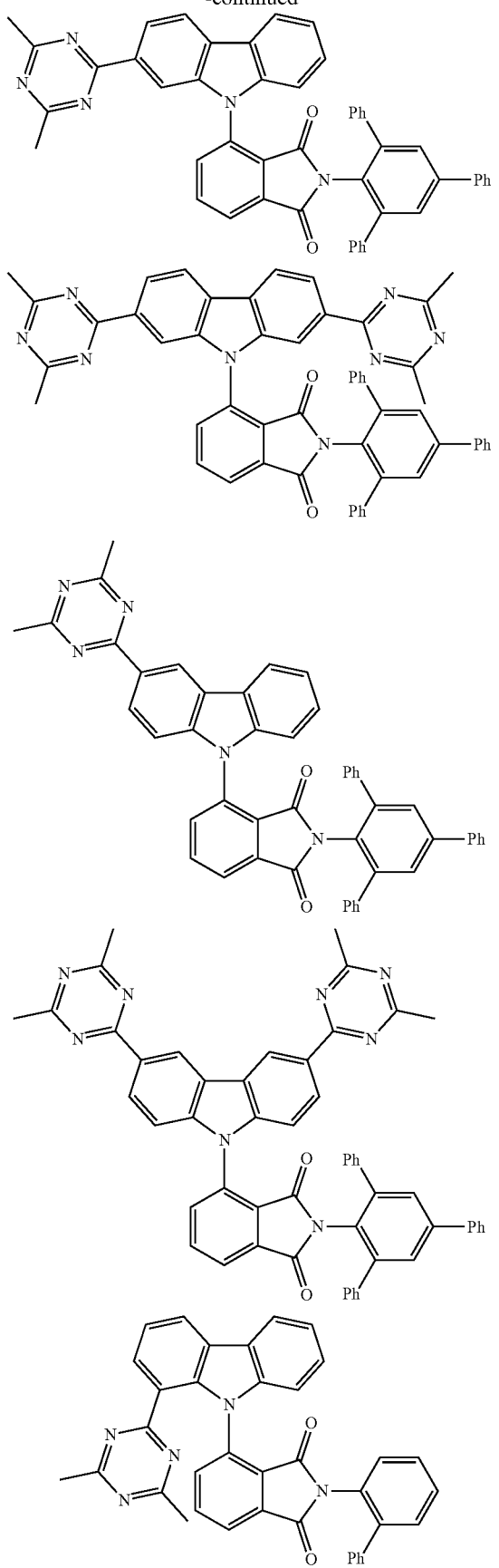
308
-continued
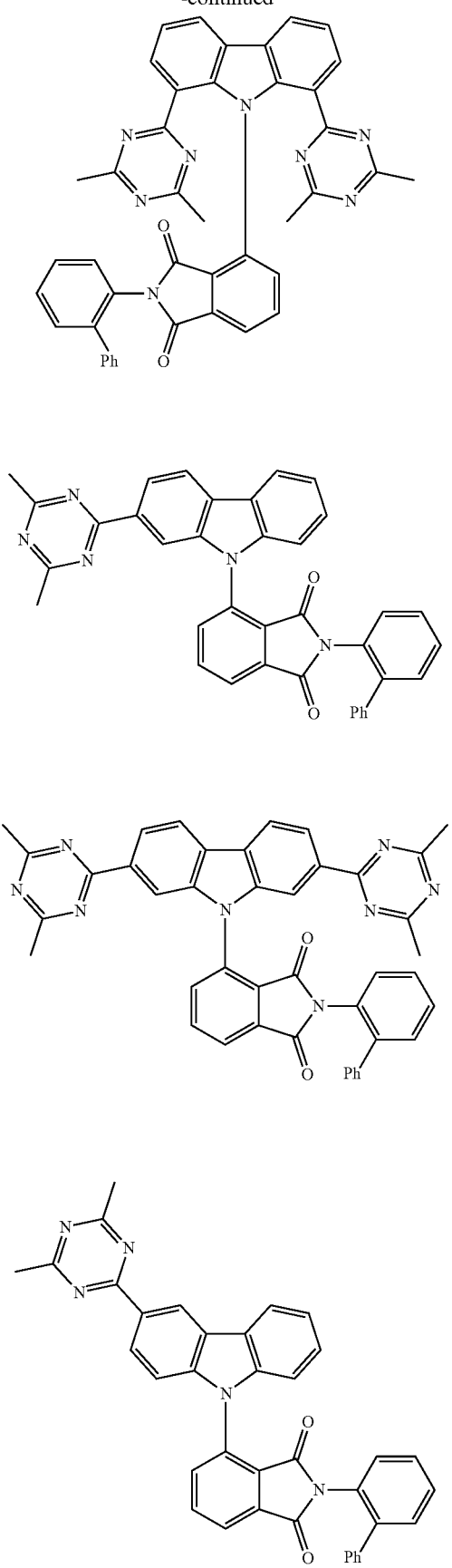

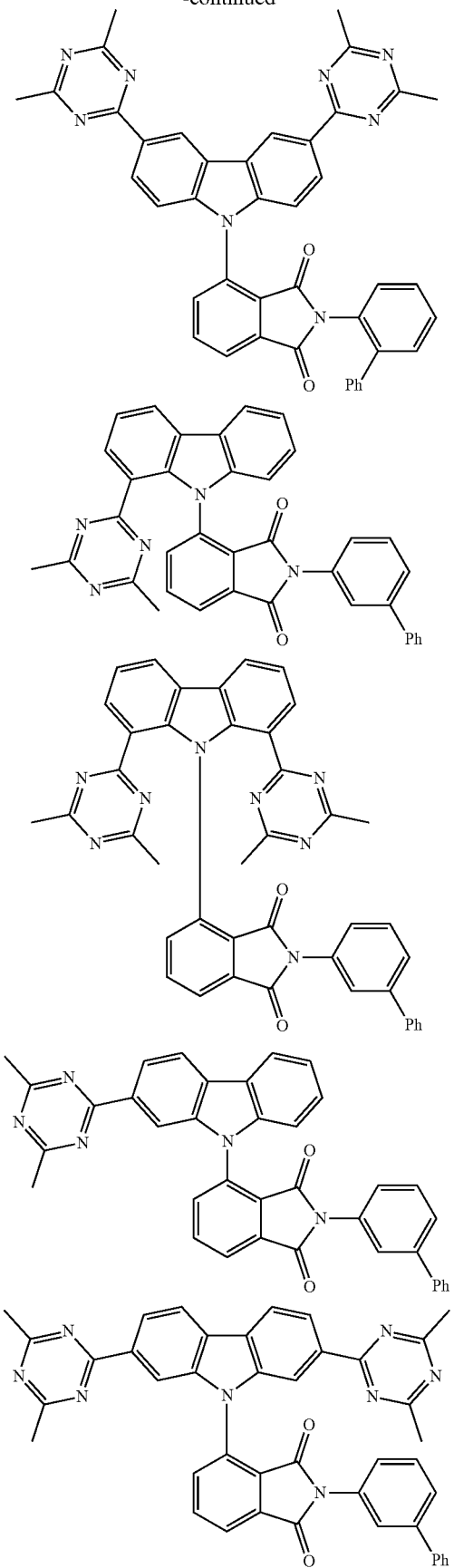

311
-continued
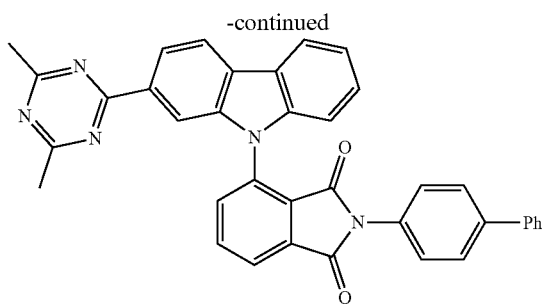
312
-continued
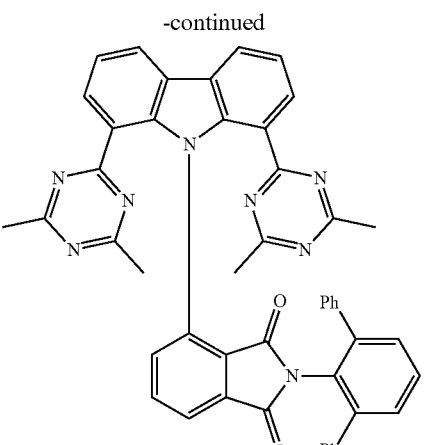
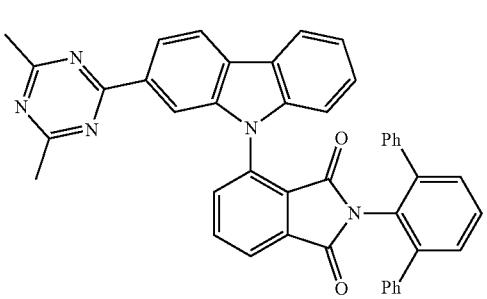
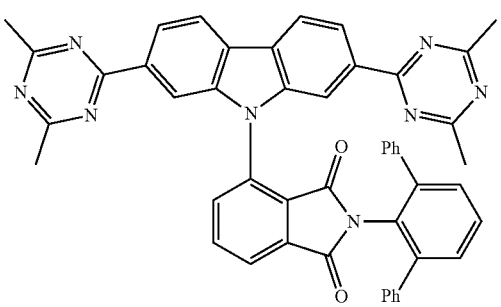
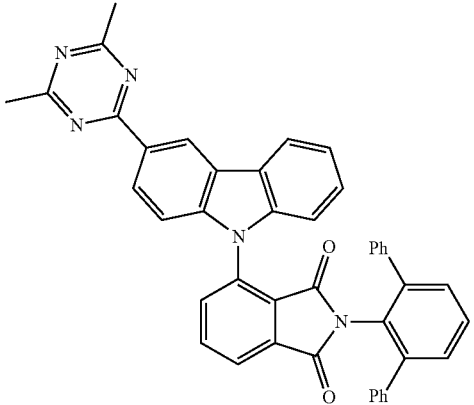

313
-continued
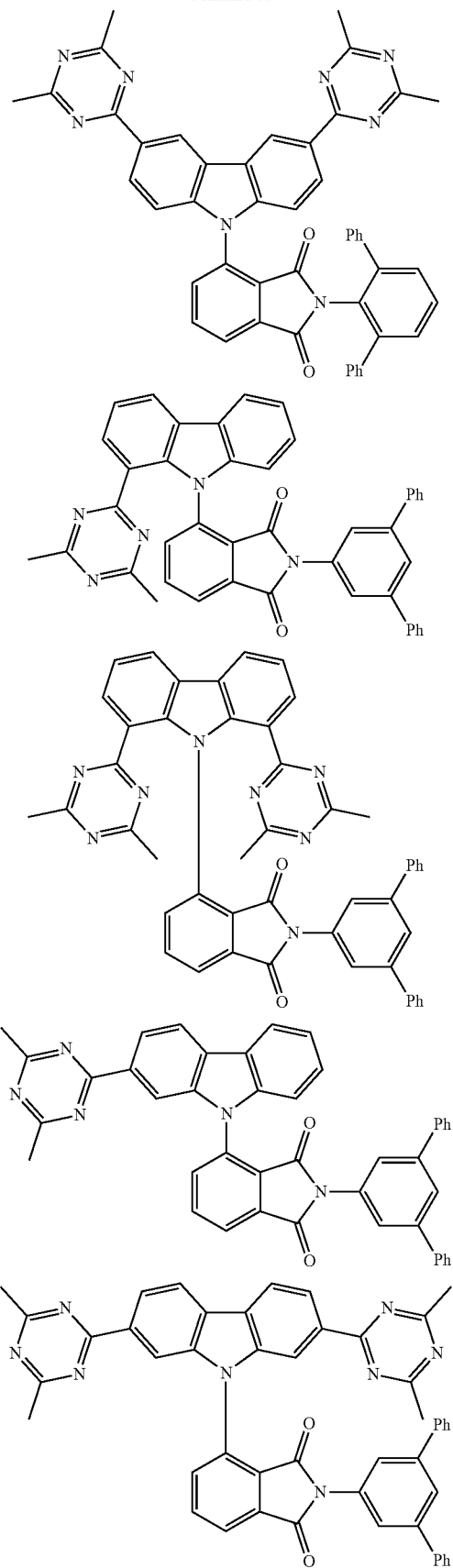
314
-continued
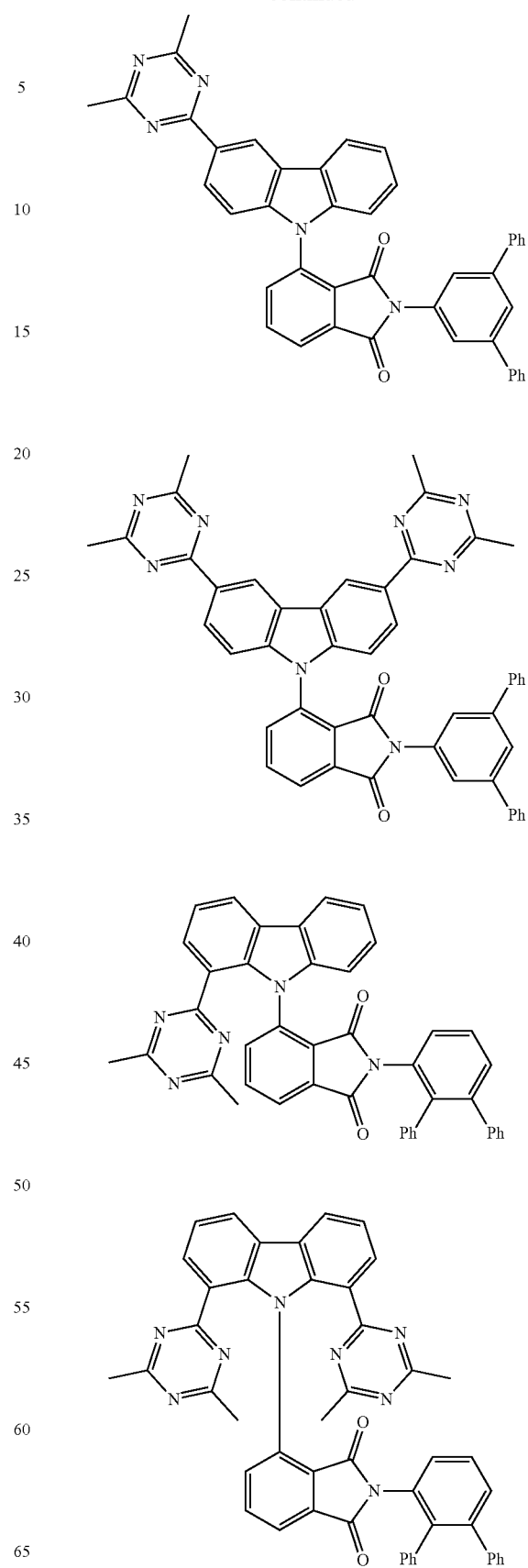

315
-continued
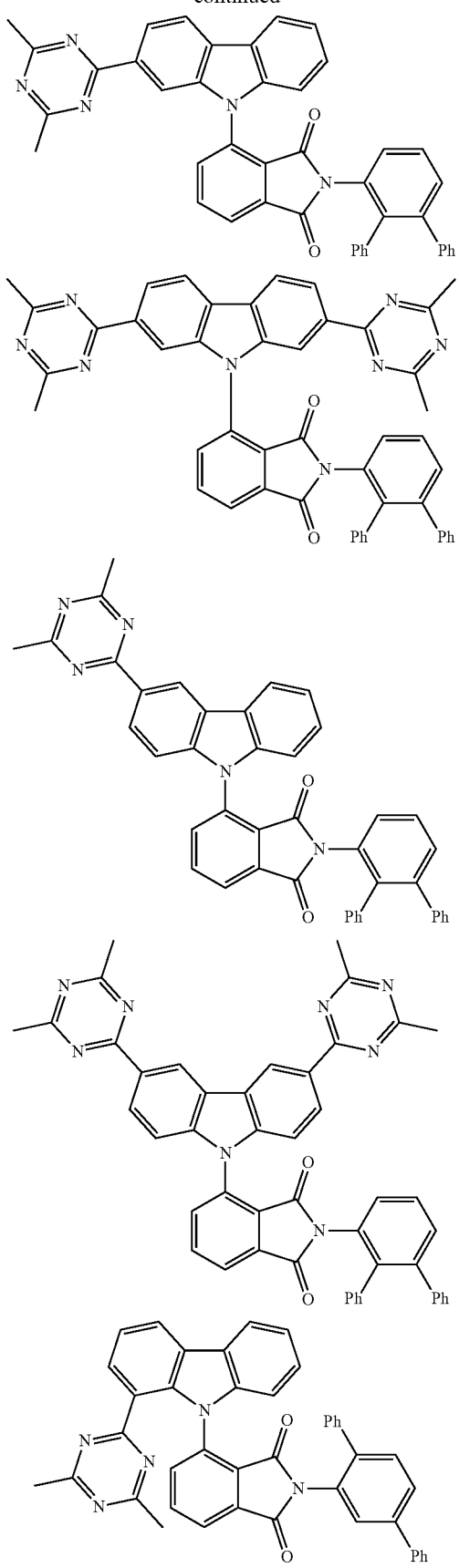
316
-continued
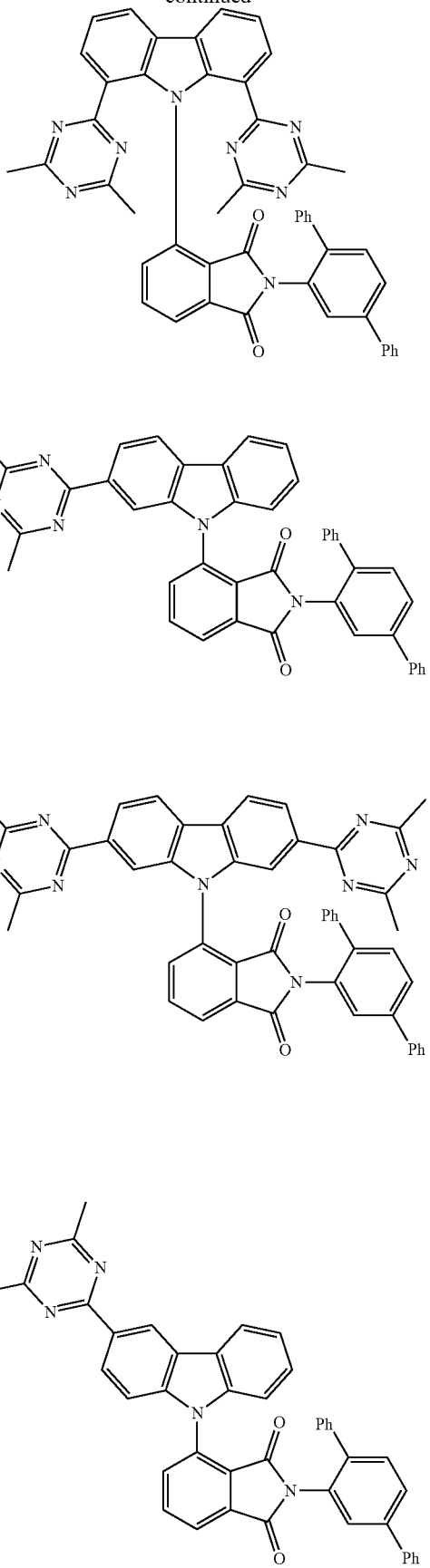

317
-continued
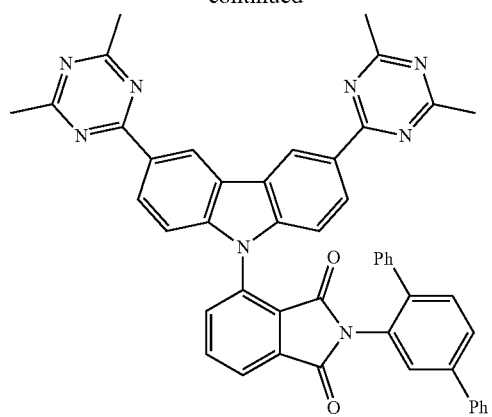
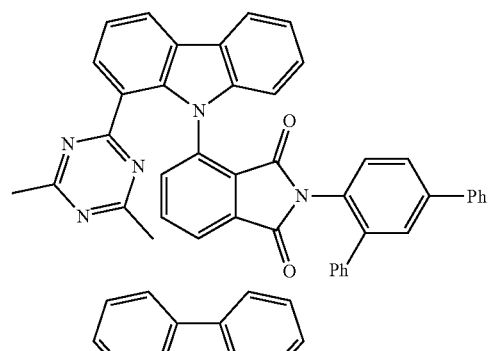
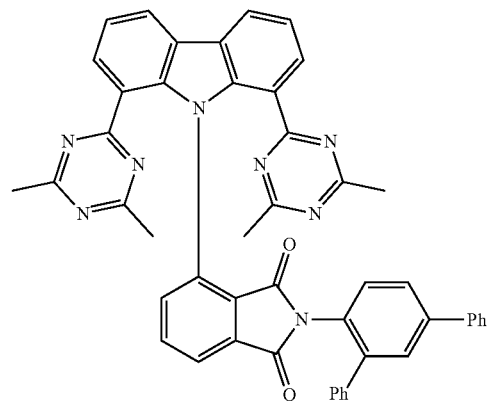
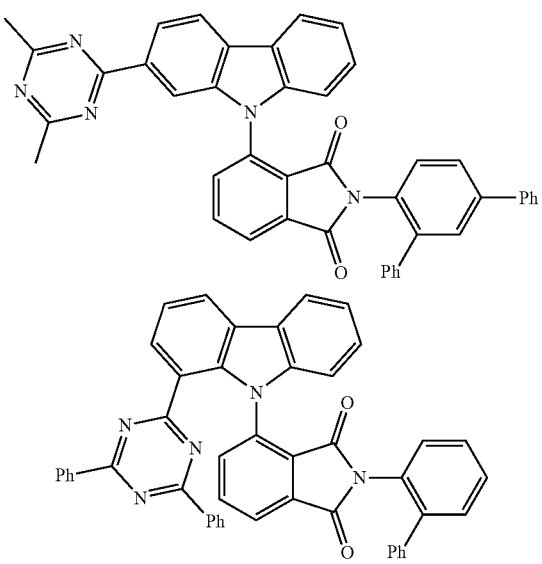
318
-continued
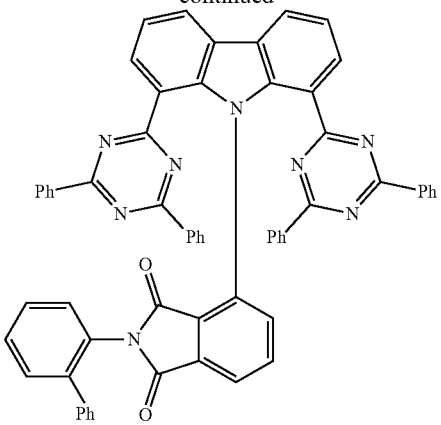
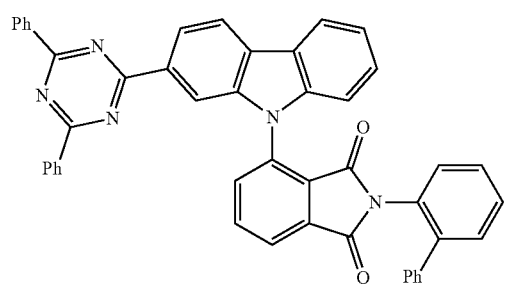
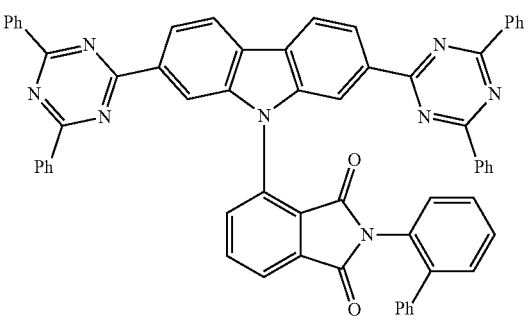
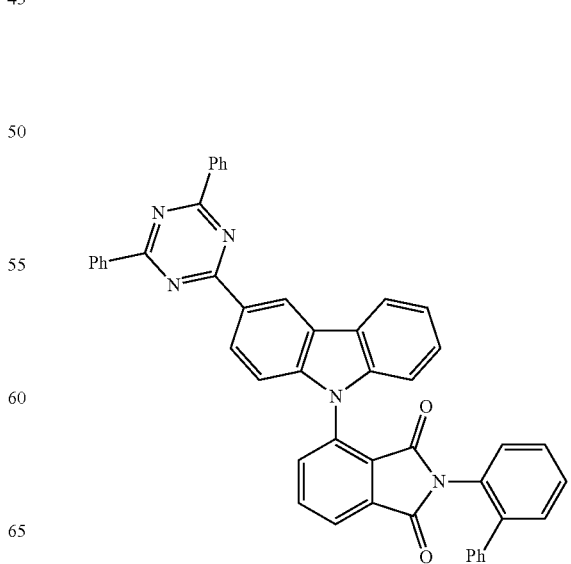

-continued
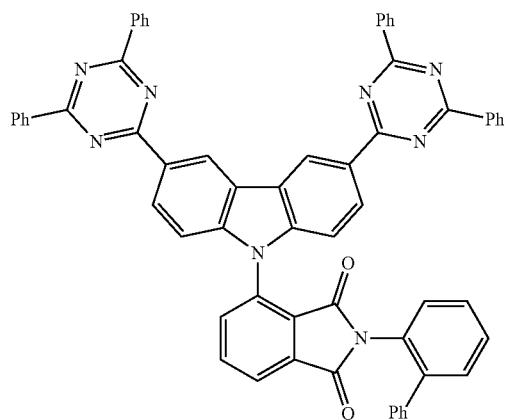
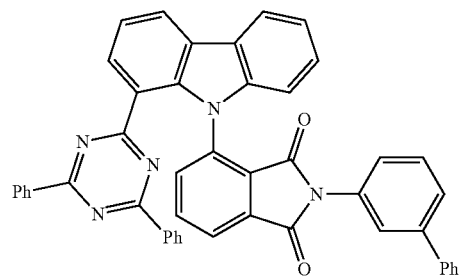
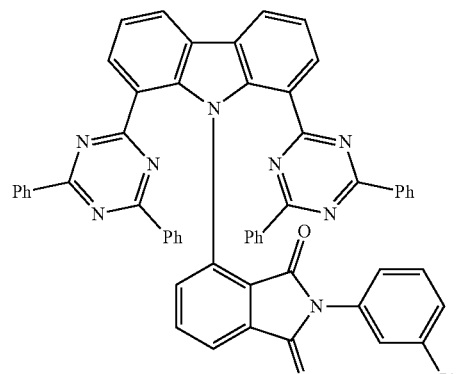
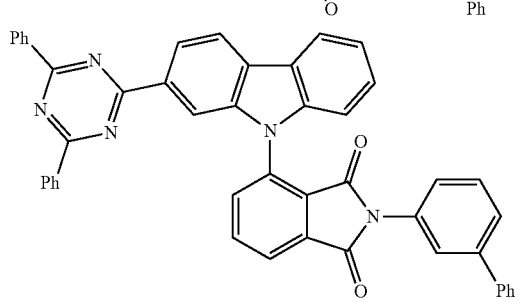
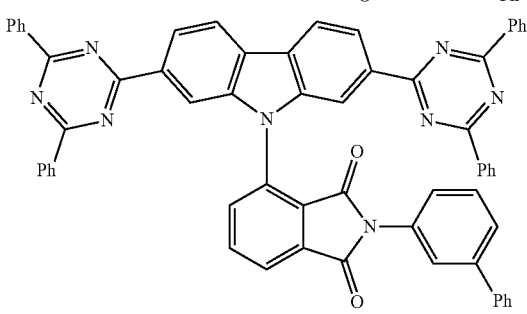
-continued
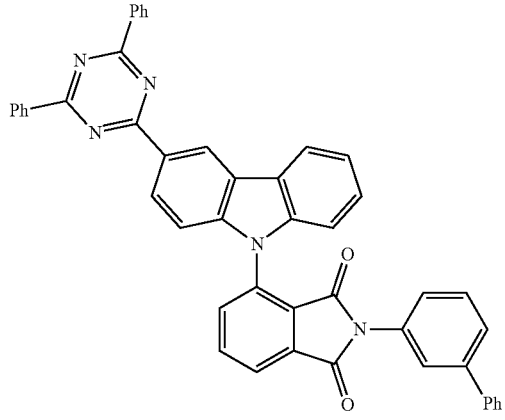
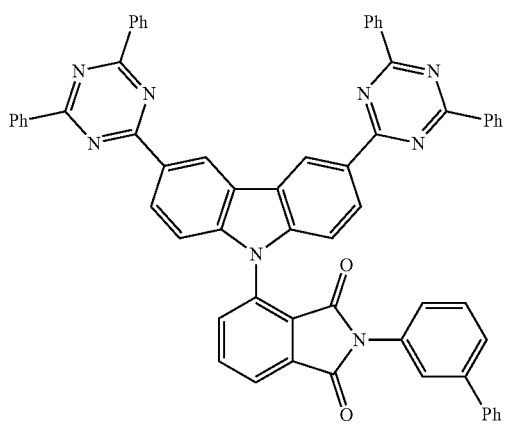
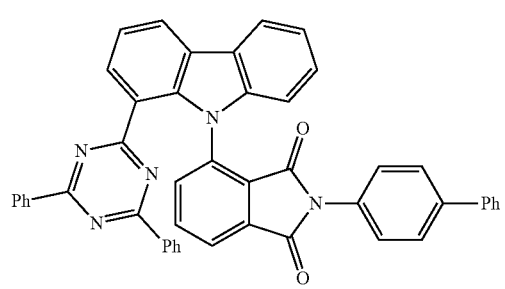
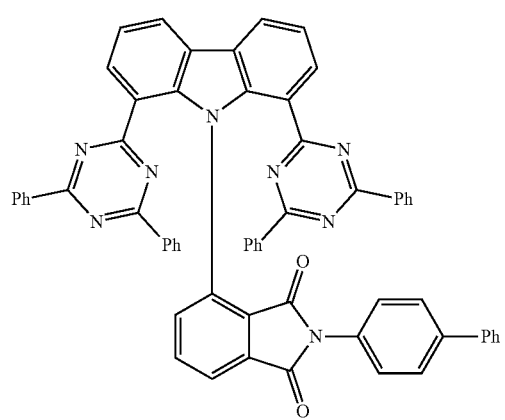

321
-continued
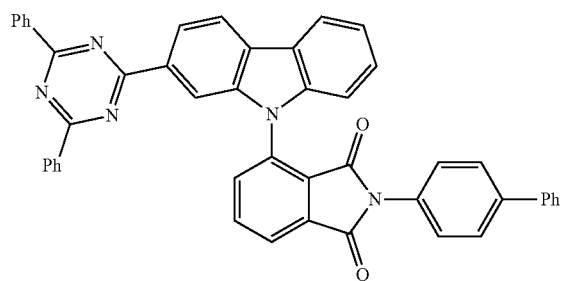
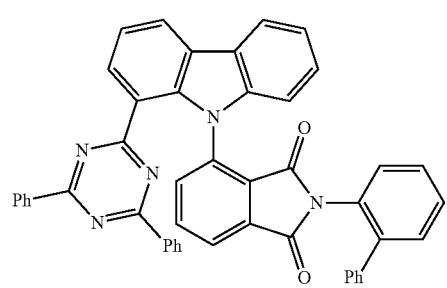
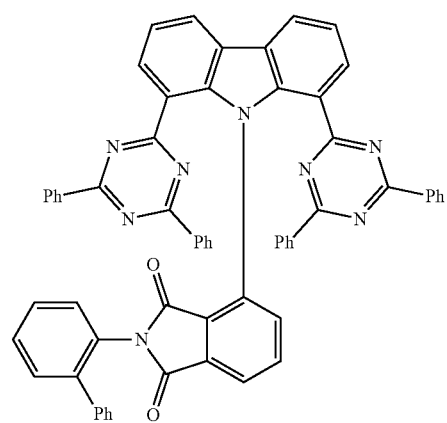
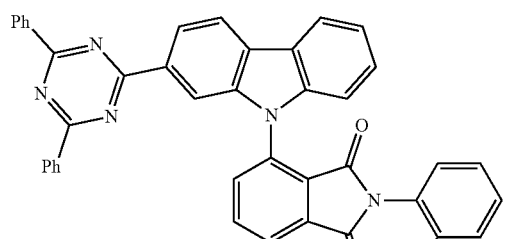
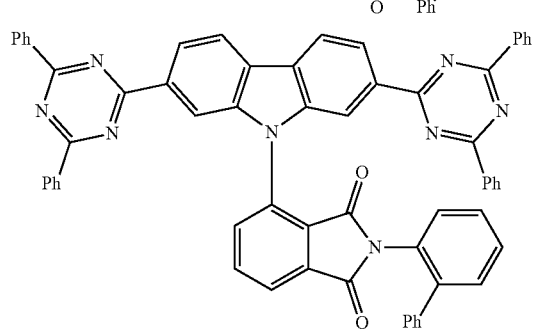
322
-continued
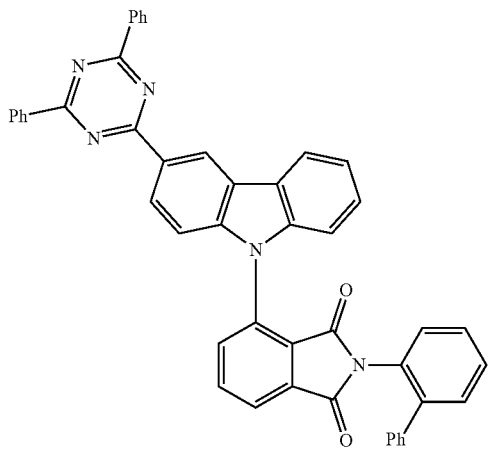
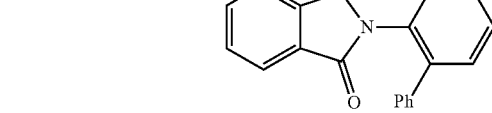
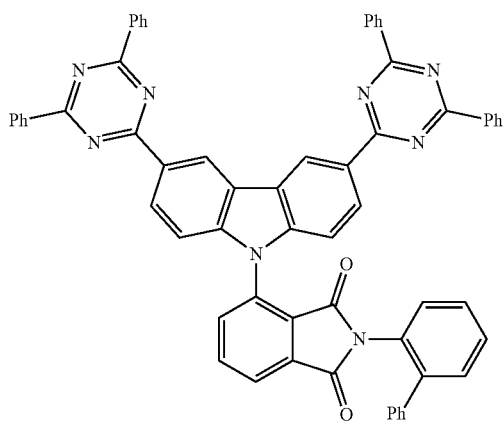
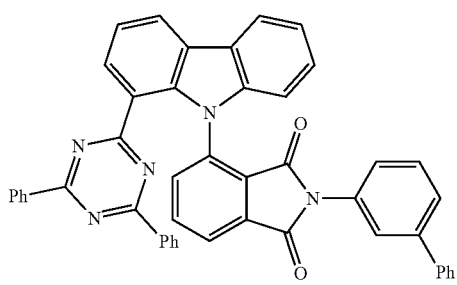
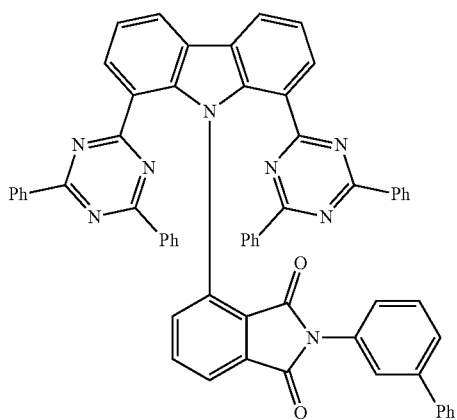

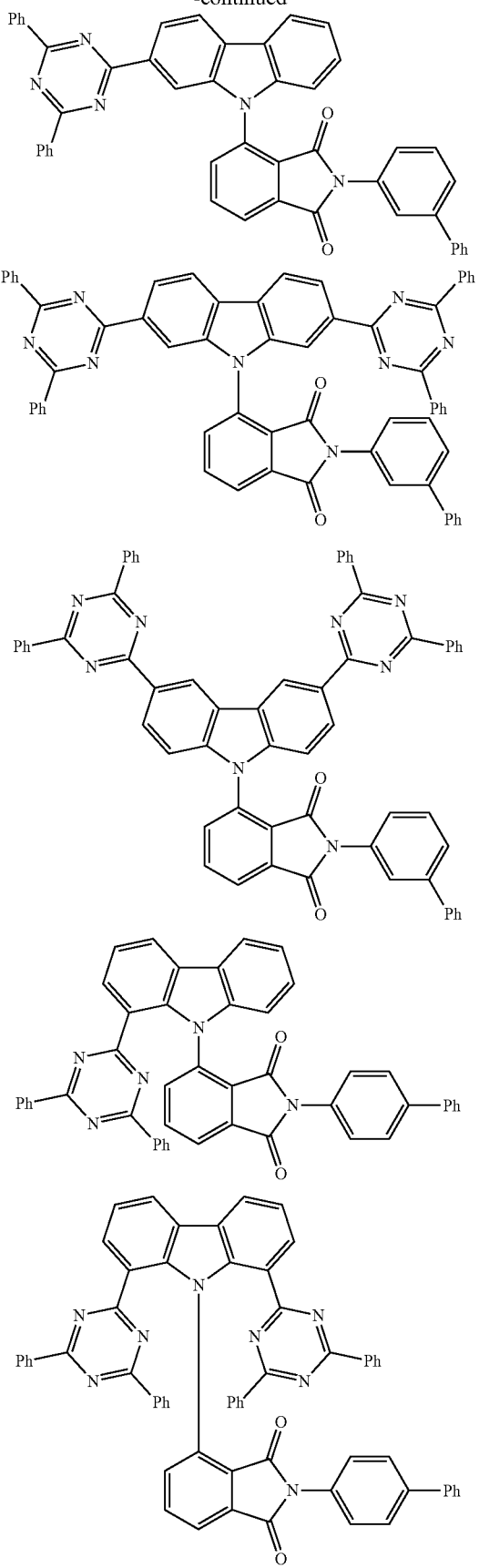
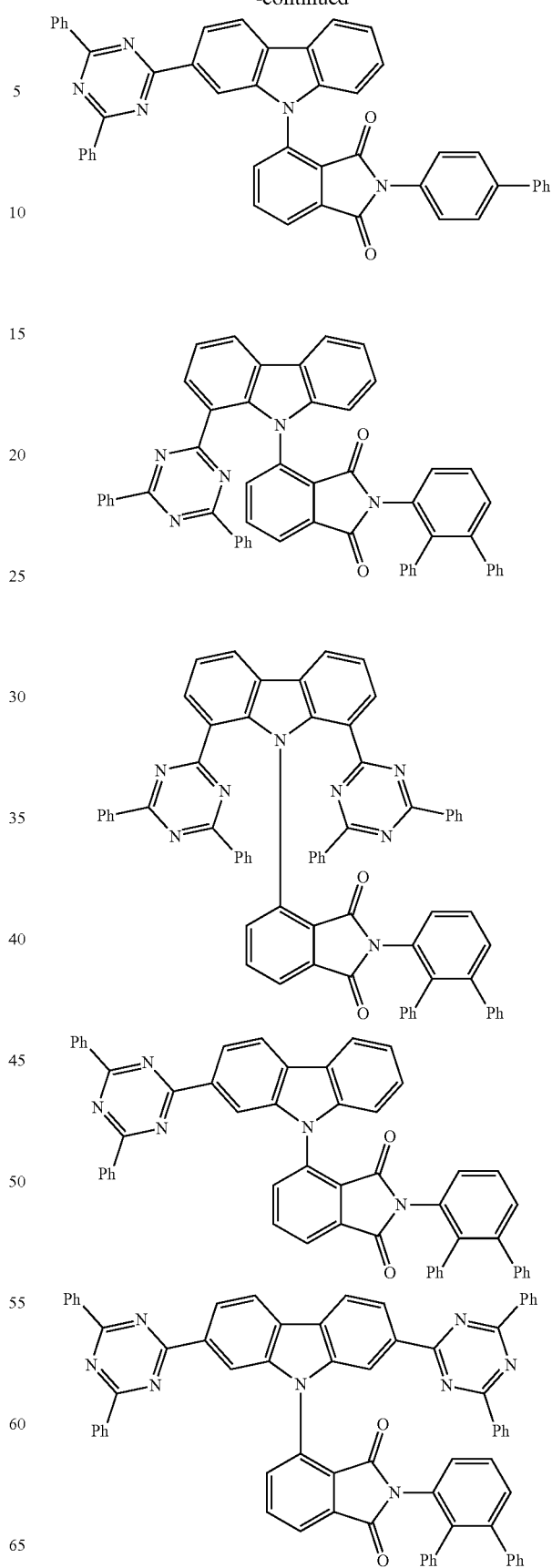

325
-continued
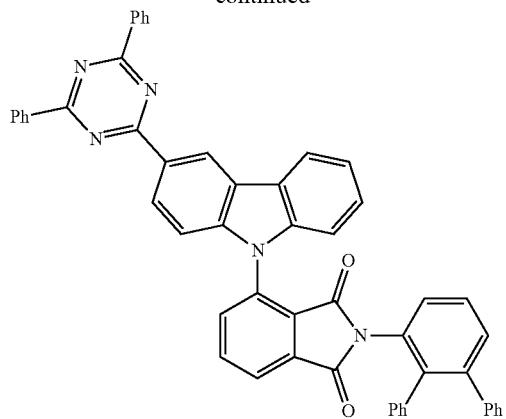
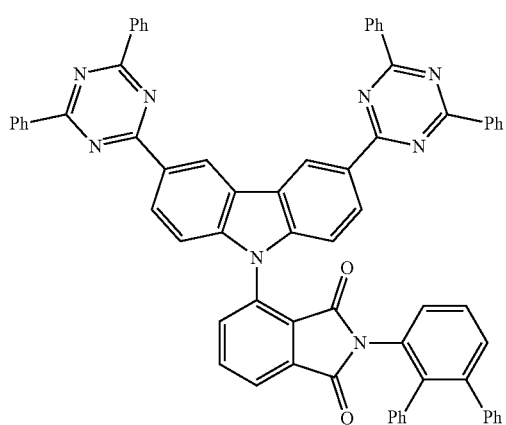
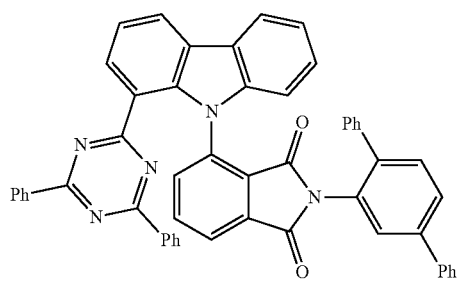
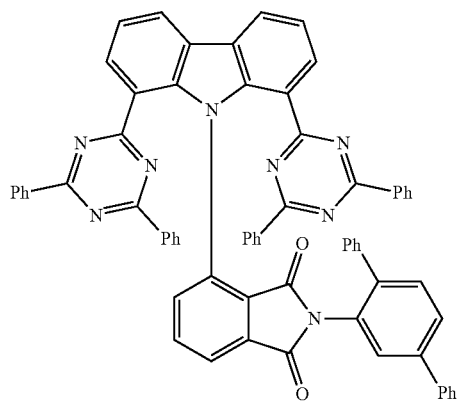
326
-continued
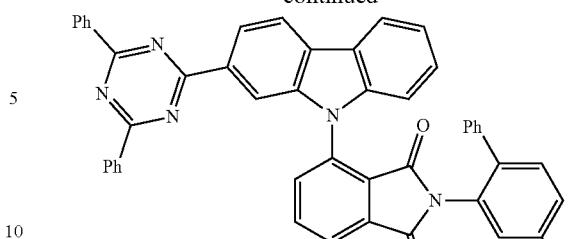
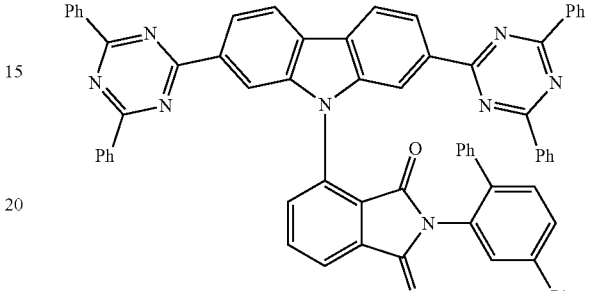
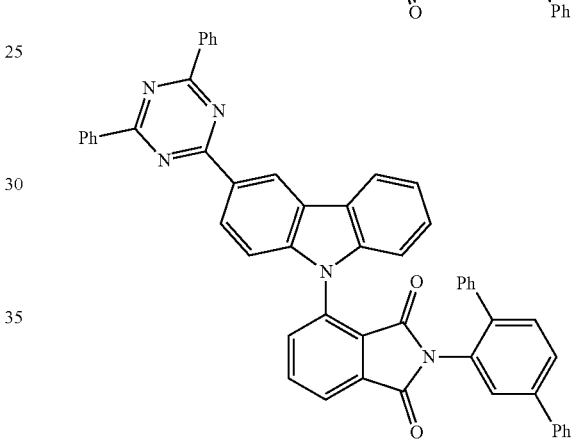
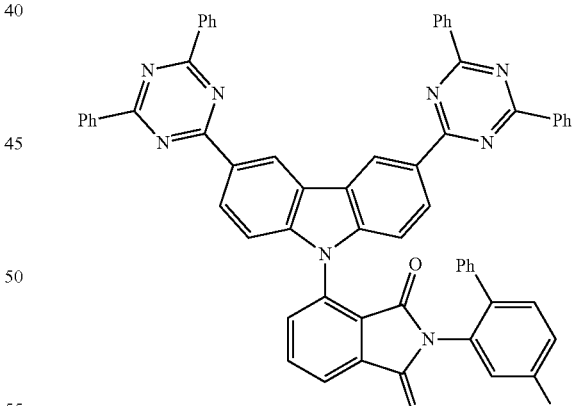
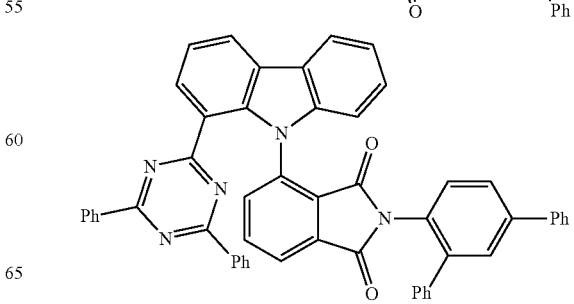

327
-continued
328
-continued
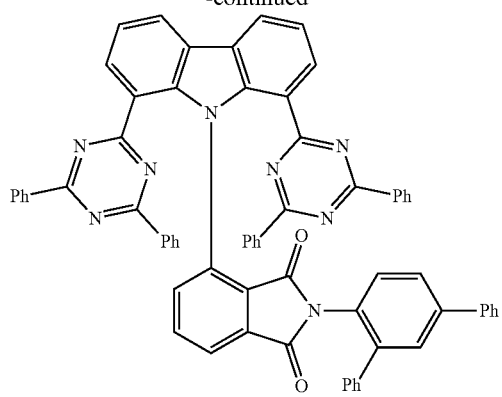
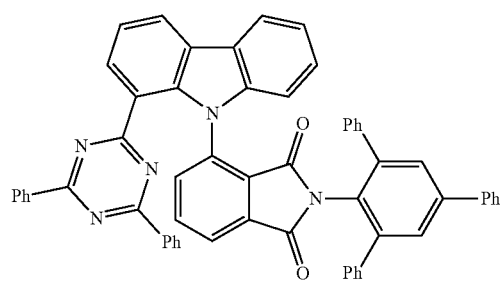
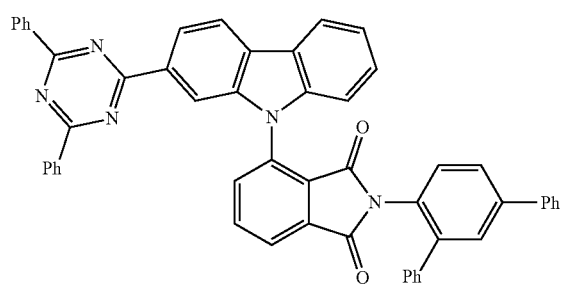
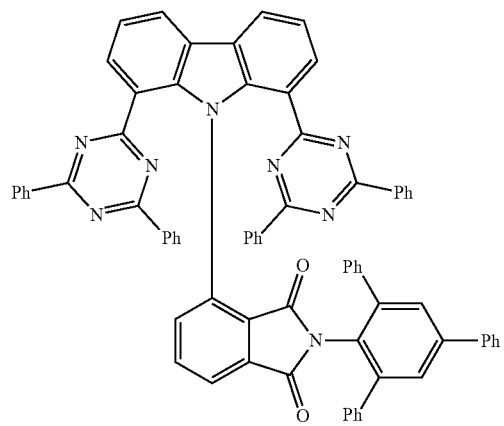
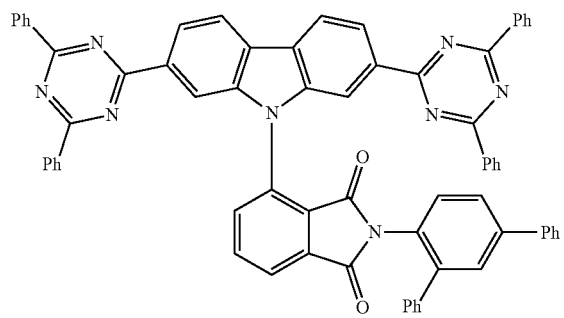
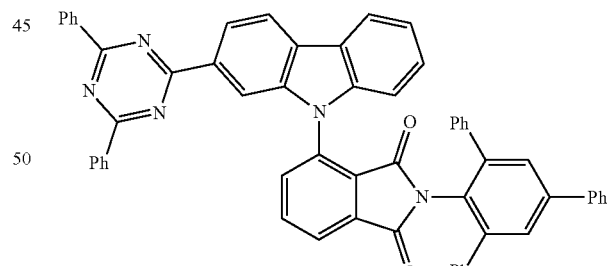
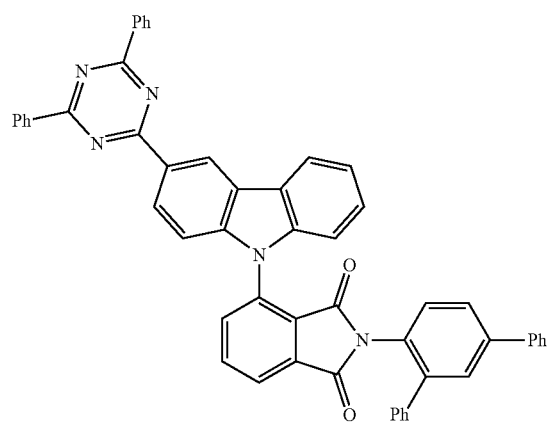
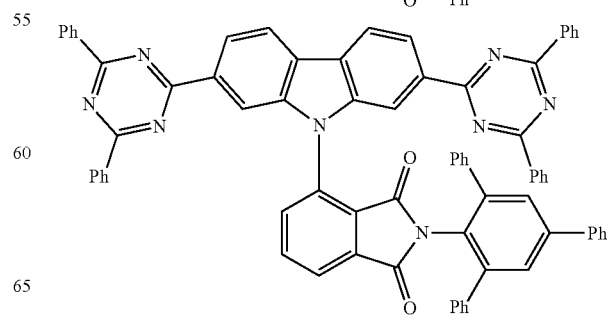

329

-continued

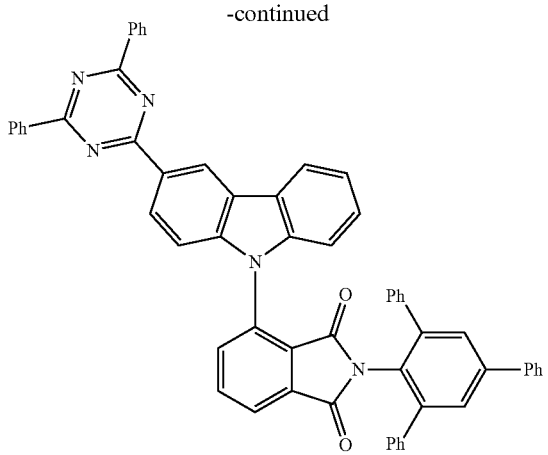

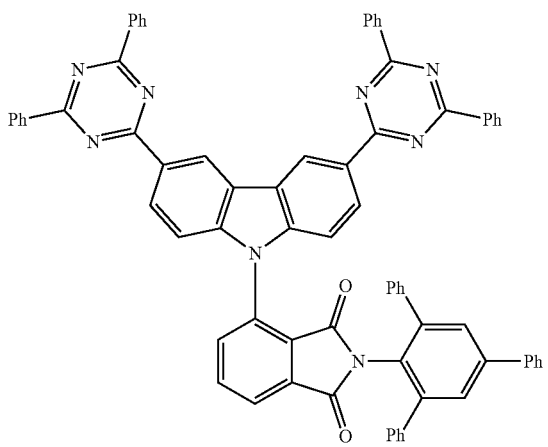

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

The invention claimed is:

1. An organic molecule comprising:

a first chemical unit comprising a structure of the Formula A1:

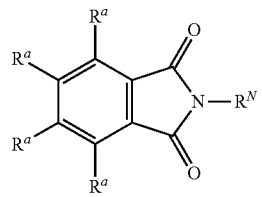

Formula A1 one second chemical unit comprising a structure of the Formula D1:

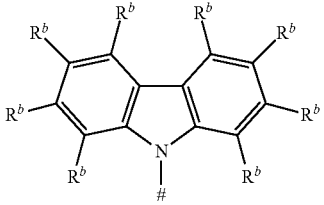

Formula D1 with
# = point of attachment of the second chemical unit to the first chemical unit;
$R^N$ comprises a structure of the Formula N1:

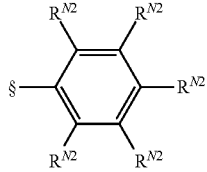

Formula N1 with
§ = point of attachment of the chemical unit of Formula N1 to the first chemical unit;
$R^{N2}$ is the same or different at each instance and is H, phenyl or naphthyl;
one $R^a$ is a point of attachment of the first chemical unit to the second chemical unit and the other $R^a$s are H;
$R^b$ at each instance is independently selected from the group consisting of H, deuterium, $CF_3$, $C(=O)R^1$, CN, carbazolyl which is unsubstituted or substituted by one or more $R^2$, $Si(R^4)_3$, an alkyl group which is unsubstituted or substituted by one or more $R^2$, an aryl group which is unsubstituted or substituted by one or more $R^2$, and a heteroaryl group which is unsubstituted or substituted by one or more $R^2$;
$R^1$ independently at each instance is an aryl group which is unsubstituted or substituted by one or more $R^3$;
$R^2$ at each instance is independently selected from the group consisting of $CF_3$, $C(=O)R^1$, CN, an alkyl group which is unsubstituted or substituted by one or more $R^3$, an aryl group which is unsubstituted or substituted by one or more $R^3$, and a heteroaryl group which is unsubstituted or substituted by one or more $R^3$;
$R^3$ at each instance is independently selected from the group consisting of an unsubstituted alkyl group, an unsubstituted aryl group and an unsubstituted heteroaryl group;
$R^4$ at each instance is independently selected from the group consisting of an aryl group which is unsubstituted or substituted by one or more $R^3$, and a heteroaryl group which is unsubstituted or substituted by one or more $R^3$;
where two or more of the $R^1$, $R^2$ and $R^3$ substituents together optionally form a monocyclic, polycyclic, aliphatic, aromatic and/or benzofused ring system;
wherein not less than one and not more than three $R^{N2}$ is phenyl or naphthyl, and wherein at least one of the $R^{N2}$ which is phenyl or naphthyl is in the ortho position relative to the point of attachment of the chemical unit of Formula N1 to the first chemical unit.

2. The organic molecule according to claim 1, wherein the organic molecule is represented by Formula A2:

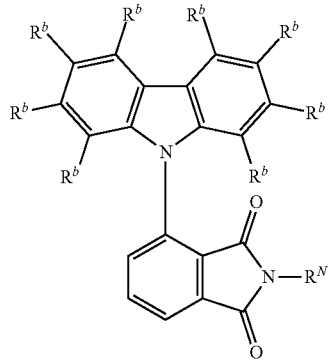

Formula A2 where $R^b$ and $R^N$ have the aforestated meanings.

3. The organic molecule according to claim 1, wherein the organic molecule is represented by Formula A3:

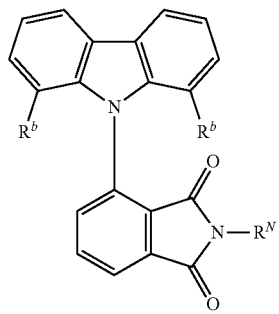

Formula A3 where $R^b$ and $R^N$ have the aforestated meanings.

4. The organic molecule according to claim 1, wherein the organic molecule is represented by Formula A4:

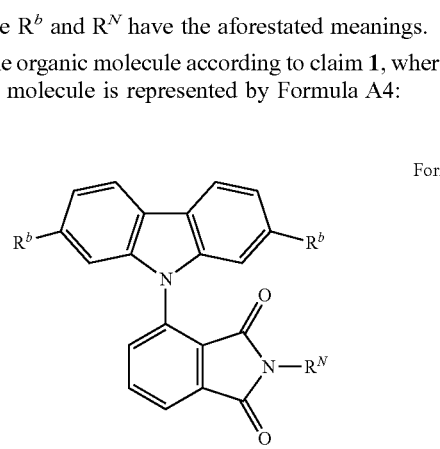

Formula A4 where $R^b$ and $R^N$ have the aforestated meanings.

5. The organic molecule according to claim 1, wherein the organic molecule is represented by Formula A5:

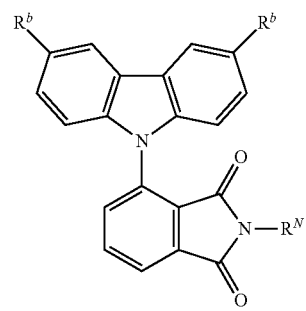

Formula A5 where $R^b$ and $R^N$ have the aforestated meanings.

6. The organic molecule according to claim 1, where $R^N$ is the same or different at each instance and is selected from one of the following structures:

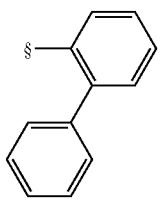

O1

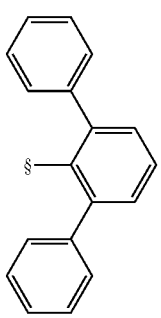

O4

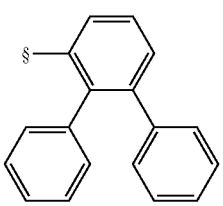

O6

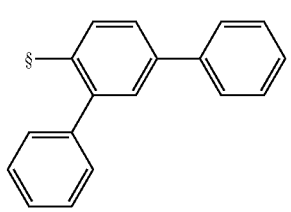

O8

-continued

O9

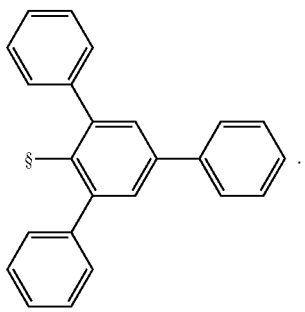

7. The organic molecule according to claim 1, where $R^N$ is represented by the structure P3:

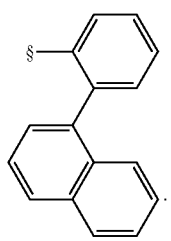

P3

8. The organic molecule according to claim 1, where $R^b$ is the same or different at each instance and is selected from the group consisting of H, deuterium, methyl, i-propyl, t-butyl, $CF_3$, CN, a phenyl group which is unsubstituted or substituted by one or more $R^6$, a pyridine group which is unsubstituted or substituted by one or more $R^6$, a pyrimidine group which is unsubstituted or substituted by one or more $R^6$, a pyrazine group which is unsubstituted or substituted by one or more $R^6$, and a triazine group which is unsubstituted or substituted by one or more $R^6$, where $R^6$ is the same or different at each instance and is selected from the group consisting of deuterium, methyl, i-propyl, t-butyl, $CF_3$, CN and phenyl.

9. A composition comprising:
 (a) at least one organic molecule according to claim 1 as an emitter and/or a host;
 (b) one or more emitter and/or host materials different from the at least one organic molecule according to claim 1.

10. An optoelectronic device comprising the organic molecule according to claim 1.

11. The optoelectronic device according to claim 10, wherein the optoelectronic device is an organic light-emitting diode, a light-emitting electrochemical cell, an organic light-emitting sensor, an organic diode, an organic solar cell, an organic transistor, an organic field-effect transistor, an organic laser or a down-conversion element.

12. The optoelectronic device according to claim 10, wherein the organic molecule is one of an emitter and a host in the optoelectronic device.

13. The optoelectronic device according to claim 12, wherein a proportion of the organic molecule in the emitter or the host is in the range of 1% to 80%.

14. The optoelectronic device according to claim 10, comprising:
 a substrate;
 an anode;
 a cathode, wherein the anode or the cathode is applied to the substrate; and
 at least one light-emitting layer disposed between the anode and the cathode and which comprises the organic molecule.

15. An optoelectronic device comprising the organic molecule according to claim 2.

16. The optoelectronic device according to claim 15, wherein the organic molecule is one of an emitter and a host in the optoelectronic device.

17. An optoelectronic device comprising the composition according to claim 9.

18. The optoelectronic device according to claim 17, comprising:
 a substrate;
 an anode;
 a cathode, wherein the anode or the cathode is disposed on the substrate, and
 at least one light-emitting layer disposed between the anode and the cathode and which comprises the composition.

19. The optoelectronic device according to claim 17, wherein the composition is one of an emitter and a host in the optoelectronic device.

20. A process for producing an optoelectronic component, comprising processing of the organic molecule according to claim 1 by an evaporation process or from a solution.

* * * * *